(12) United States Patent
Pons et al.

(10) Patent No.: US 12,343,377 B2
(45) Date of Patent: Jul. 1, 2025

(54) COMBINATION THERAPIES COMPRISING A HYPOMETHYLATION AGENT FOR TREATING CANCER

(71) Applicant: ALX Oncology Inc., Burlingame, CA (US)

(72) Inventors: Jaume Pons, San Francisco, CA (US); Hong Wan, Foster City, CA (US); Sophia Randolph, Chico, CA (US)

(73) Assignee: ALX Oncology Inc., South San Francisco, CA (US)

( * ) Notice: Subject to any disclaimer, the term of this patent is extended or adjusted under 35 U.S.C. 154(b) by 668 days.

(21) Appl. No.: 17/334,151

(22) Filed: May 28, 2021

(65) Prior Publication Data

US 2022/0401516 A1 Dec. 22, 2022

Related U.S. Application Data

(60) Provisional application No. 63/145,925, filed on Feb. 4, 2021, provisional application No. 63/114,959, filed on Nov. 17, 2020, provisional application No. 63/109,083, filed on Nov. 3, 2020, provisional application No. 63/106,285, filed on Oct. 27, 2020, provisional application No. 63/033,074, filed on Jun. 1, 2020.

(51) Int. Cl.
| | | |
|---|---|---|
| *A61K 38/17* | (2006.01) | |
| *A61K 31/122* | (2006.01) | |
| *A61K 31/352* | (2006.01) | |
| *A61K 31/405* | (2006.01) | |
| *A61K 31/513* | (2006.01) | |
| *A61K 31/635* | (2006.01) | |
| *A61K 31/706* | (2006.01) | |
| *A61K 31/7068* | (2006.01) | |
| *A61K 47/64* | (2017.01) | |
| *A61P 35/02* | (2006.01) | |

(52) U.S. Cl.
CPC ........ *A61K 38/1774* (2013.01); *A61K 31/122* (2013.01); *A61K 31/352* (2013.01); *A61K 31/405* (2013.01); *A61K 31/513* (2013.01); *A61K 31/635* (2013.01); *A61K 31/706* (2013.01); *A61K 31/7068* (2013.01); *A61K 47/6425* (2017.08); *A61P 35/02* (2018.01)

(58) Field of Classification Search
CPC .............. A61K 38/1774; A61K 31/122; A61K 31/352; A61K 31/405; A61K 31/513; A61K 31/635; A61K 31/706; A61K 31/7068; A61K 47/6425; A61K 31/496; A61K 38/177; A61K 45/00; A61K 45/06; A61P 35/02; A61P 35/00
See application file for complete search history.

(56) References Cited

U.S. PATENT DOCUMENTS

| | | |
|---|---|---|
| 9,845,345 B2 | 12/2017 | Ring et al. |
| 9,944,911 B2 | 4/2018 | Ring et al. |
| 10,259,859 B2 | 4/2019 | Pons et al. |
| 10,696,730 B2 | 6/2020 | Pons et al. |
| 11,208,459 B2 | 12/2021 | Pons et al. |
| 11,208,481 B2 | 12/2021 | Ring et al. |
| 11,613,564 B2 | 3/2023 | Pons et al. |
| 11,639,376 B2 | 5/2023 | Pons et al. |
| 12,098,214 B2 | 9/2024 | Wan et al. |
| 2015/0071905 A1 | 3/2015 | Ring et al. |
| 2015/0329616 A1 | 11/2015 | Uger et al. |
| 2016/0186150 A1 | 6/2016 | Deming et al. |
| 2017/0107270 A1 | 4/2017 | Pons et al. |
| 2018/0037652 A1 | 2/2018 | Liu et al. |
| 2018/0105600 A1 | 4/2018 | Pons et al. |
| 2018/0141986 A1 | 5/2018 | Tian et al. |
| 2018/0155405 A1 | 6/2018 | Ring et al. |
| 2018/0195054 A1 | 7/2018 | Ring et al. |
| 2018/0312563 A1 | 11/2018 | Uger et al. |
| 2018/0312587 A1 | 11/2018 | Van Eenennaam et al. |
| 2018/0371435 A1 | 12/2018 | Deming et al. |
| 2020/0239543 A1 | 7/2020 | Pons et al. |
| 2020/0263154 A1 | 8/2020 | Deming et al. |
| 2020/0392199 A1 | 12/2020 | Pons et al. |
| 2020/0400662 A1 | 12/2020 | Wan et al. |
| 2021/0070838 A1 | 3/2021 | Pons et al. |
| 2021/0154269 A1 | 5/2021 | Wan et al. |
| 2021/0388329 A1 | 12/2021 | Deming et al. |
| 2022/0064293 A1 | 3/2022 | Ring et al. |
| 2022/0196651 A1 | 6/2022 | Pons et al. |
| 2022/0213166 A1 | 7/2022 | Pons et al. |

(Continued)

FOREIGN PATENT DOCUMENTS

| | | |
|---|---|---|
| CN | 104136037 A | 11/2014 |
| CN | 108350048 A | 7/2018 |

(Continued)

OTHER PUBLICATIONS

Pollyea et al. (Blood Advances, 3(24): 4326-4335, 2019).*
Wei et al. (Blood, 134 (Suplement_1) : 568, 2019).*
Molica et al. (Am J Hematol., 94: 1254-1265, 2019).*
Astx727, Oral Decitabine and Cedazuridine (ASTX727), DNA methyltransferase (DNMT) inhibitor (Hematological Malignancies), retrieved Sep. 13, 2021 from <https://astx.com/research-development/clinical-pipeline/oral-decitabine-and-cedazuridine-astx727-hematological-malignancies/>, 1 page.
Casara et al. (2018). "S55746 is a novel orally active BCL-2 selective and potent inhibitor that impairs hematological tumor growth," Oncotarget. 9(28): 20075-20088.

(Continued)

*Primary Examiner* — Nelson B Moseley, II
(74) *Attorney, Agent, or Firm* — MORRISON & FOERSTER LLP

(57) ABSTRACT

Provided are methods of treating cancer (e.g., a hematological cancer such as myelodysplastic syndrome) that comprise administering a polypeptide (e.g. a fusion polypeptide) that comprises a SIRPα D1 domain variant and an Fc domain variant in combination with a hypomethylating agent (e.g., azacitidine). Also provided are related kits.

17 Claims, 18 Drawing Sheets
Specification includes a Sequence Listing.

(56) References Cited

U.S. PATENT DOCUMENTS

| | | |
|---|---|---|
| 2022/0242928 A1 | 8/2022 | Pons et al. |
| 2022/0363779 A1 | 11/2022 | Wan et al. |
| 2022/0401516 A1 | 12/2022 | Pons et al. |
| 2023/0218719 A1 | 7/2023 | Wan et al. |
| 2023/0340433 A1 | 10/2023 | Deming et al. |
| 2024/0075101 A1 | 3/2024 | Wan et al. |
| 2024/0132567 A1 | 4/2024 | Pons et al. |
| 2024/0343778 A1 | 10/2024 | Pons et al. |

FOREIGN PATENT DOCUMENTS

| | | | |
|---|---|---|---|
| EP | 3287470 A1 | 2/2018 | |
| WO | WO-2013109752 A1 | 7/2013 | |
| WO | WO-2014094122 A1 | 6/2014 | |
| WO | WO-2016023040 A1 | 2/2016 | |
| WO | WO-2016063233 A1 | 4/2016 | |
| WO | WO-2016187226 A1 | 11/2016 | |
| WO | WO 2017/027422 * | 2/2017 | ............. C07K 14/47 |
| WO | WO-2017027422 A1 | 2/2017 | |
| WO | WO-2017068164 A1 | 4/2017 | |
| WO | WO-2017177333 A1 | 10/2017 | |
| WO | WO-2017178653 A2 | 10/2017 | |
| WO | WO-2018057669 A1 | 3/2018 | |
| WO | WO-2018081897 A1 | 5/2018 | |
| WO | WO-2018081898 A1 | 5/2018 | |
| WO | WO-2018107058 A1 | 6/2018 | |
| WO | WO-2018149938 A1 | 8/2018 | |
| WO | WO-2018176132 A1 | 10/2018 | |
| WO | WO-2018210795 A1 | 11/2018 | |
| WO | WO-2019023347 A1 | 1/2019 | |
| WO | WO-2020047326 A2 | 3/2020 | |
| WO | WO-2020243338 A1 | 12/2020 | |
| WO | WO-2020247820 A1 | 12/2020 | |
| WO | WO-2021076908 A1 | 4/2021 | |
| WO | WO-2021108693 A1 | 6/2021 | |
| WO | WO-2021247430 A1 | 12/2021 | |
| WO | WO-2022010806 A1 | 1/2022 | |
| WO | WO-2022120286 A1 | 6/2022 | |
| WO | WO-2022241157 A1 | 11/2022 | |

OTHER PUBLICATIONS

Chao et al. (2010). "Anti-CD47 antibody synergizes with rituximab to promote phagocytosis and eradicate non-Hodgkin lymphoma," Cell, 142(5):699-713.

Chao et al. (2011). "Extranodal dissemination of non-Hodgkin lymphoma requires CD47 and is inhibited by anti-CD47 antibody therapy," Blood 118(18):4890-4901.

Cheson et al. (2000). "Report of an international working group to standardize response criteria for myelodysplastic syndromes," Blood, 96:3671-3674.

Cheson et al. (2006). "Clinical application and proposal for modification of the International Working Group (IWG) response criteria in myelodysplasia," Blood, 108:419-425.

Chow et al. (2020). "A phase I study of ALX148, a CD47 blocker, in combination with standard anticancer antibodies and chemotherapy regimens in patients with advanced malignancy," Journal of Clinical Oncology, 38:15_suppl, 3056-3056.

DACOGEN Label, Highlights of Prescribing Information, 2010, FDA, retrieved Sep. 13, 2021 from <www.accessdata.fda.gov/drugsatfda_docs/label/2010/021790s006lbl.pdf>.

Dacogen Product Information, 2021, EMA, retrieved retrieved Sep. 14, 2021 from <www.ema.europa.eu/en/documents/product-information/dacogen-epar-product-information_en.pdf>, 29 pages.

Datta et al. (2012). "Novel Insights into the Molecular Mechanism of Action of DNA Hypomethylating Agents: Role of Protein Kinase C δ in Decitabine-Induced Degradation of DNA Methyltransferase 1," Genes cancer, 3(1):71-81.

Diesch et al. (2016). "A clinical-molecular update on azanucleoside-based therapy for the treatment of hematologic cancers," Clin Epigenetics, 8:71.

Dinardo et al. (2019). "Venetoclax combined with decitabine or azacitidine in treatment-naive, elderly patients with acute myeloid leukemia," Blood, 133(1):7-17.

Duchmann, et al. (2019). "Clinical update on hypomethylating agents," Int J Hematol 110, 161-169.

ECOG Performance Status, retrieved Sep. 13, 2021 from <ecog-acrin.org/resources/ecog-performance-status>, 1 page.

Edris et al. (2012). "Antibody therapy targeting the CD47 protein is effective in a model of aggressive metastatic leiomyosarcoma," Proc Natl Acad Sci U S A, 109(17):6656-61.

Feng et al.(2018). "Combination Treatment with 5F9 and Azacitidine Enhances Phagocytic Elimination of Acute Myeloid Leukemia," Meeting Report, Blood (2018) 132 (Supplement 1): 2729.

Gabrilovich et al. (2012). "Coordinated regulation of myeloid cells by tumours," Nat Rev Immunol. 12(4):253-68.

Galli et al. (2015). "CD47 protein expression in acute myeloid leukemia: A tissue microarray-based analysis," Leuk Res, 39(7):749-56.

Goto et al. (2014). "Efficacy of anti-CD47 antibody-mediated phagocytosis with macrophages against primary effusion lymphoma," Eur J. Cancer, 50(10):1836-1846.

Greenberg et al. (2012). "Revised international prognostic scoring system for myelodysplastic syndromes," Blood, 120 (12):2454-2465.

Husain et al. (2018). "Expanding the Boundaries of Biotherapeutics with Bispecific Antibodies," Biodrugs 32(5): 441-464.

Jiang et al. (2013). "CD47 is expressed abnormally on hematopoietic cells in myelodysplastic syndrome," Leukemia Research, 37(8):907-910.

Kabat (1991). Sequences of proteins of immunological interest, 5th ed. U.S. Dept. of Health and Human Services, Public Health Service, National Institutes of Health: Bethesda, MD, 12 pages.

Kauder et al. (2018). "ALX148 blocks CD47 and enhances innate and adaptive antitumor immunity with a favorable safety profile," PLoS One, 13(8): e0201832.

Kim et al. (2012). "Anti-CD47 antibodies promote phagocytosis and inhibit the growth of human myeloma cells," Leukemia 26:2538-2545.

Kim et al. (2020). "ALX148, a CD47 Blocker, in Combination with Rituximab in Patients with Relapsed/Refractory (R/R) Non-Hodgkin Lymphoma," Abstract # EP1247, 25th Congress of the European Hematology Association, Poster.

Majeti et al. (2009). "CD47 is an adverse prognostic factor and therapeutic antibody target on human acute myeloid leukemia stem cells," Cell, 138(2):286-99.

Miller et al. (2019). "Quantitative high-throughput screening assays for the discovery and development of SIRPα-CD47 interaction inhibitors," PLoS One 14(7): e0218897.

Murata et al. (2018). "Anti-human SIRPα antibody is a new tool for cancer immunotherapy," Cancer Sci, 109(5):1300-1308.

Oldenborg (2013). "CD47: A Cell Surface Glycoprotein Which Regulates Multiple Functions of Hematopoietic Cells in Health and Disease," ISRN Hematol, Article ID 614619, 19 pages.

Petrova et al. (2017). "TTI-621 (SIRPαFc): A CD47-Blocking Innate Immune Checkpoint Inhibitor with Broad Antitumor Activity and Minimal Erythrocyte Binding," Clin Cancer Res, 23:1086-1079.

Ring et al. (2017). "Anti-SIRPα antibody immunotherapy enhances neutrophil and macrophage antitumor activity," PNAS USA, 114(49): E10578-E10585.

Russ et al. (2018). "Blocking "don't eat me" signal of CD47-SIRPα in hematological malignancies, an in-depth review," Blood Rev, 32(6):480-489, S0268-960X(17)30093-0.

Sasikumar et al. "Abstract B007: Potent antitumor activity of a novel and orally available small-molecule antagonist targeting the CD47/SIRPα pathway" CR-NCI-EORTC International Conference: Molecular Targets and Cancer Therapeutics; Oct. 26-30, 2017, Philadelphia, PA; Mol Cancer Ther, Published Jan. 1, 2018, (17) (1 Supplement) B007.

Sato et al. (2017). "DNA Hypomethylating Drugs in Cancer Therapy," Cold Spring Harb Perspect Med, 7:a026948.

Schanz et al. (2012). "New comprehensive cytogenetic scoring system for primary myelodysplastic syndromes (MDS) and oligoblastic

(56) References Cited

OTHER PUBLICATIONS acute myeloid leukemia after MDS derived from an international database merge," J Clin Oncol, 30(8): 820-829.
Spiess et al. (2015). "Alternative molecular formats and therapeutic applications for bispecific antibodies," Molecular Immunology 67(2): 95-106.
Tse et al. (2008). "ABT-263: a potent and orally bioavailable Bcl-2 family inhibitor," Cancer Res, 68(9): 3421-3429.
U.S. Appl. No. 16/886,559, filed May 28, 2020 for Pons et al. (Copy not submitted herewith pursuant to the waiver of 37 C.F.R. § 1.98(a)(2)(iii) issued by the Office Sep. 21, 2004).
U.S. Appl. No. 16/894,468, filed Jun. 5, 2020 for Hong et al. (Copy not submitted herewith pursuant to the waiver of 37 C.F.R. § 1.98(a)(2)(iii) issued by the Office Sep. 21, 2004).
U.S. Appl. No. 17/105,353, filed Nov. 25, 2020 for Wan et al. (Copy not submitted herewith pursuant to the waiver of 37 C.F.R. § 1.98(a)(2)(iii) issued by the Office Sep. 21, 2004).
U.S. Appl. No. 17/164,716, filed Feb. 1, 2021 for Deming et al. (Copy not submitted herewith pursuant to the waiver of 37 C.F.R. § 1.98(a)(2)(iii) issued by the Office Sep. 21, 2004).
Venclyxto Label, Highlights of Prescribing Information, 2016, FDA, retrieved Feb. 8, 2021 from <www.accessdata.fda.gov/drugsatfda_docs/label/2016/208573s000lbl.pdf>, 25 pages.
Venclyxto Product Information, 2020, EMA, retrieved Feb. 8, 2021 from <www.ema.europa.eu/en/medicines/human/EPAR/venclyxto#product-information-section>, 6 pages.
VIDAZA Label, Highlights of Prescribing Information, 2008, FDA, retrieved Sep. 13, 2021 from <www.accessdata.fda.gov/drugsatfda_docs/label/2008/050794s011lbl.pdf>.
Vidaza Product Information, 2021, EMA, retrieved retrieved Sep. 14, 2021 from retrieved Sep. 13, 2021 from <www.ema.Europa.eu/en/documents/product-information/vidaza-epar-product-information_en.pdf>, 35 pages.
Weiskopf et al. (2017.) "Cancer immunotherapy targeting the CD47/SIRPα axis," European Journal of Cancer, vol. 76, pp. 100-109.
Yanigata et al. (2017). "Anti-SIRPα antibodies as a potential new tool for cancer immunotherapy," JCI Insight, 2:e89140.
Zhang et al. (2018). "Disrupting CD47-SIRPa axis alone or combined with autophagy depletion for the therapy of glioblastoma," Carcinogenesis, 39: 689-699.
Zhao et al. (epub Oct. 31, 2011). "CD47-signal regulatory protein-α (SIRPα) interactions form a barrier for antibody-mediated tumor cell destruction," Proc Natl Acad Sci USA. 108(45):18342-18347.
International Search Report and written opinion mailed on Sep. 30, 2021, for PCT Application No. PCT/US2021/034967, filed on May 28, 2021, 12 pages.
International Preliminary Report on Patentability mailed on Dec. 6, 2022, for PCT Application No. PCT/US2021/034967, filed on May 28, 2021, 8 pages.
U.S. Appl. No. 18/185,255, filed Mar. 16, 2023 for Pons et al., titled "Constructs Having a Sirp-Alpha Domain or Variant Thereof," (Copy not submitted herewith pursuant to the waiver of 37 C.F.R. § 1.98(a)(2)(iii) issued by the Office Sep. 21, 2004).
U.S. Appl. No. 18/342,331, filed Jun. 27, 2023 for Wan et al., titled "Combination Therapies for Treating Cancer," (Copy not submitted herewith pursuant to the waiver of 37 C.F.R. § 1.98(a)(2)(iii) issued by the Office Sep. 21, 2004).
U.S. Appl. No. 18/452,972, filed Aug. 21, 2023 for Pons et al., titled "Methods of Treating Cancer," (Copy not submitted herewith pursuant to the waiver of 37 C.F.R. § 1.98(a)(2)(iii) issued by the Office Sep. 21, 2004).
U.S. Appl. No. 18/540,092, filed Dec. 14, 2023 for Pons et al., titled "Constructs Having a Sirp-Alpha Domain or Variant Thereof," (Copy not submitted herewith pursuant to the waiver of 37 C.F.R. § 1.98(a)(2)(iii) issued by the Office Sep. 21, 2004).
U.S. Appl. No. 18/441,339, filed Feb. 14, 2024 for Deming et al., titled " Sirp-Alpha Variant Constructs and Uses Thereof," (Copy not submitted herewith pursuant to the waiver of 37 C.F.R. § 1.98(a)(2)(iii) issued by the Office Sep. 21, 2004).
Chao et al. (2020). "Therapeutic Targeting of the Macrophage Immune Checkpoint CD47 in Myeloid Malignancies," Front. Oncol., 9:1380, 9 pages.
Uger et al. (2019). "Blockade of the CD47-SIRPα axis: a promising approach for cancer immunotherapy," Expert Opinion on Biological Therapy, 20(1):5-8.
U.S. Appl. No. 18/970,690, filed Dec. 5, 2024 for Ring et al. (Copy not submitted herewith pursuant to the waiver of 37 C.F.R. § 1.98(a)(2)(iii) issued by the Office Sep. 21, 2004).

\* cited by examiner

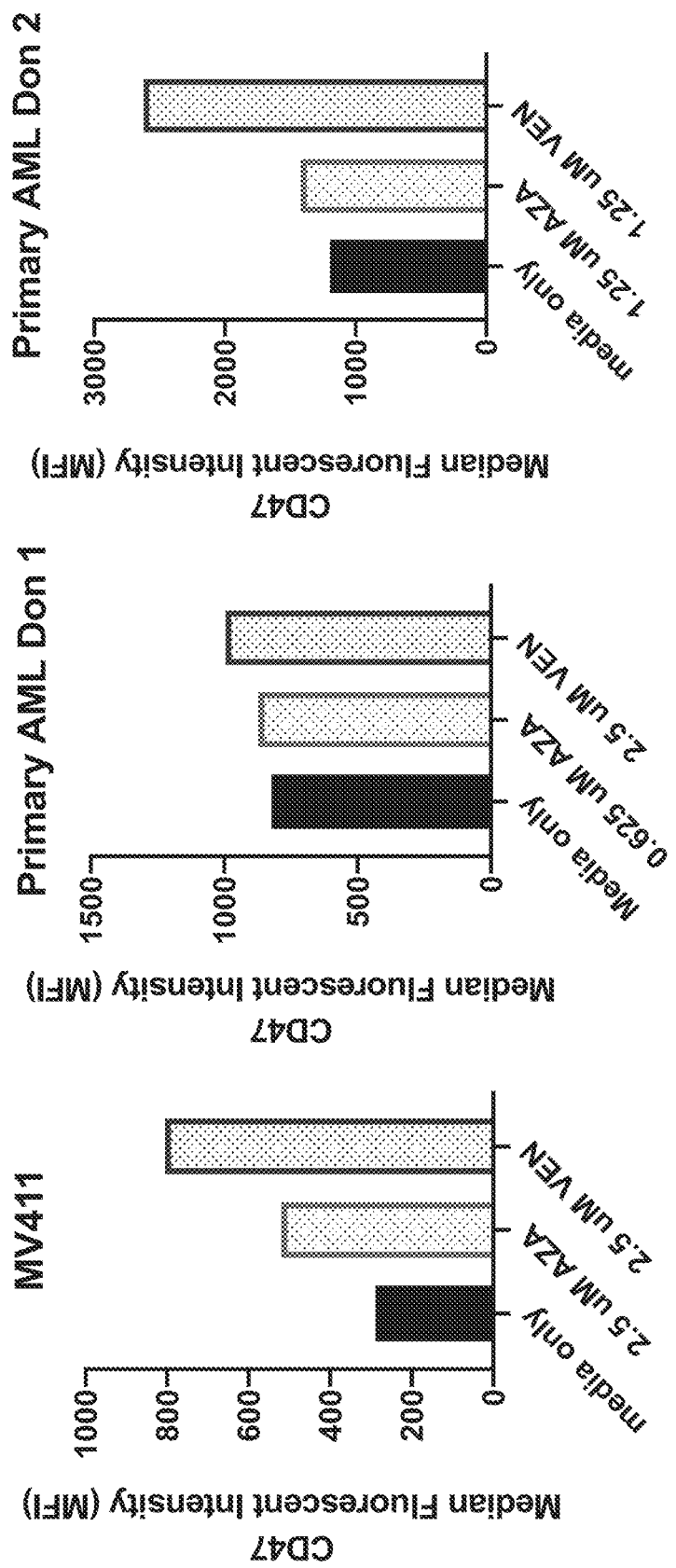

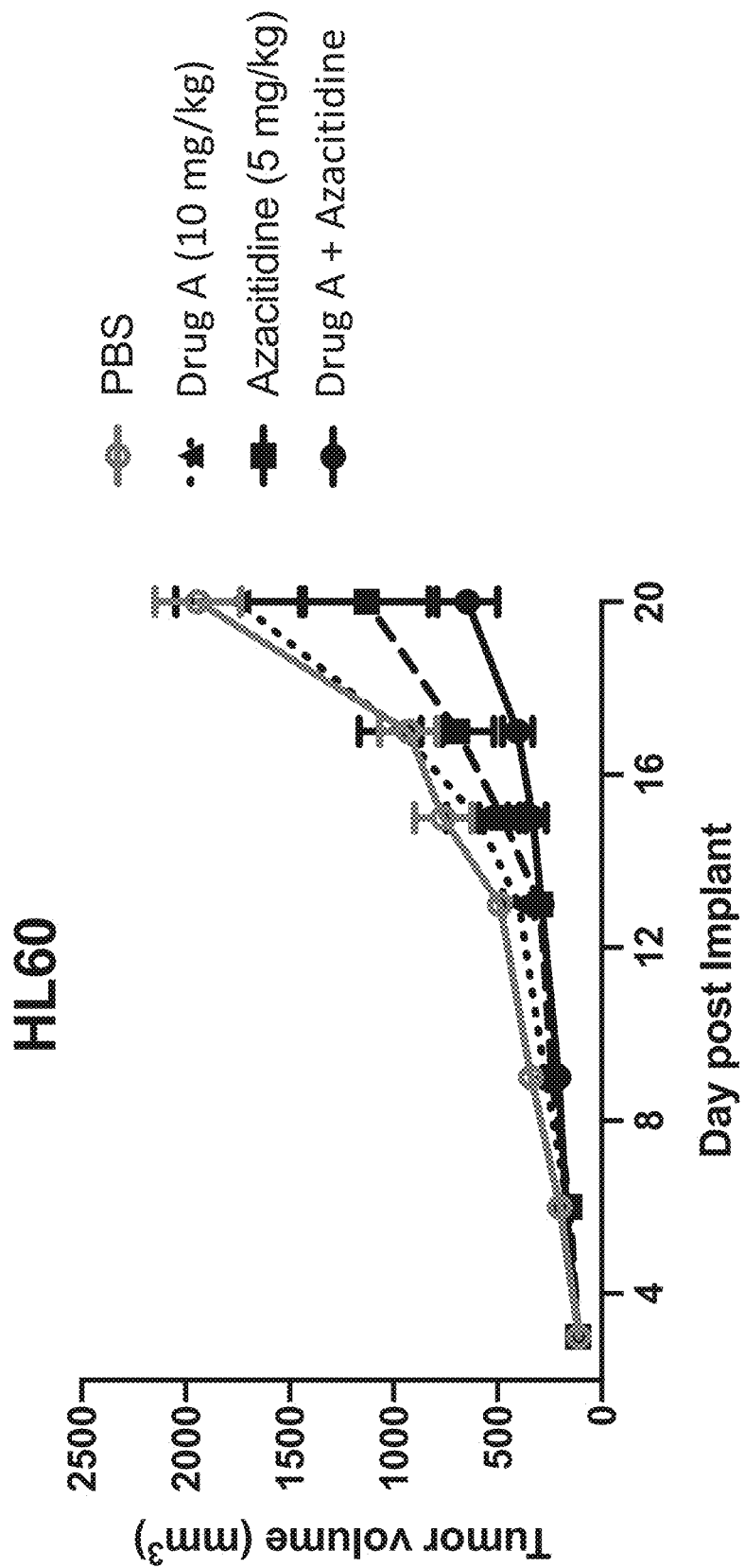

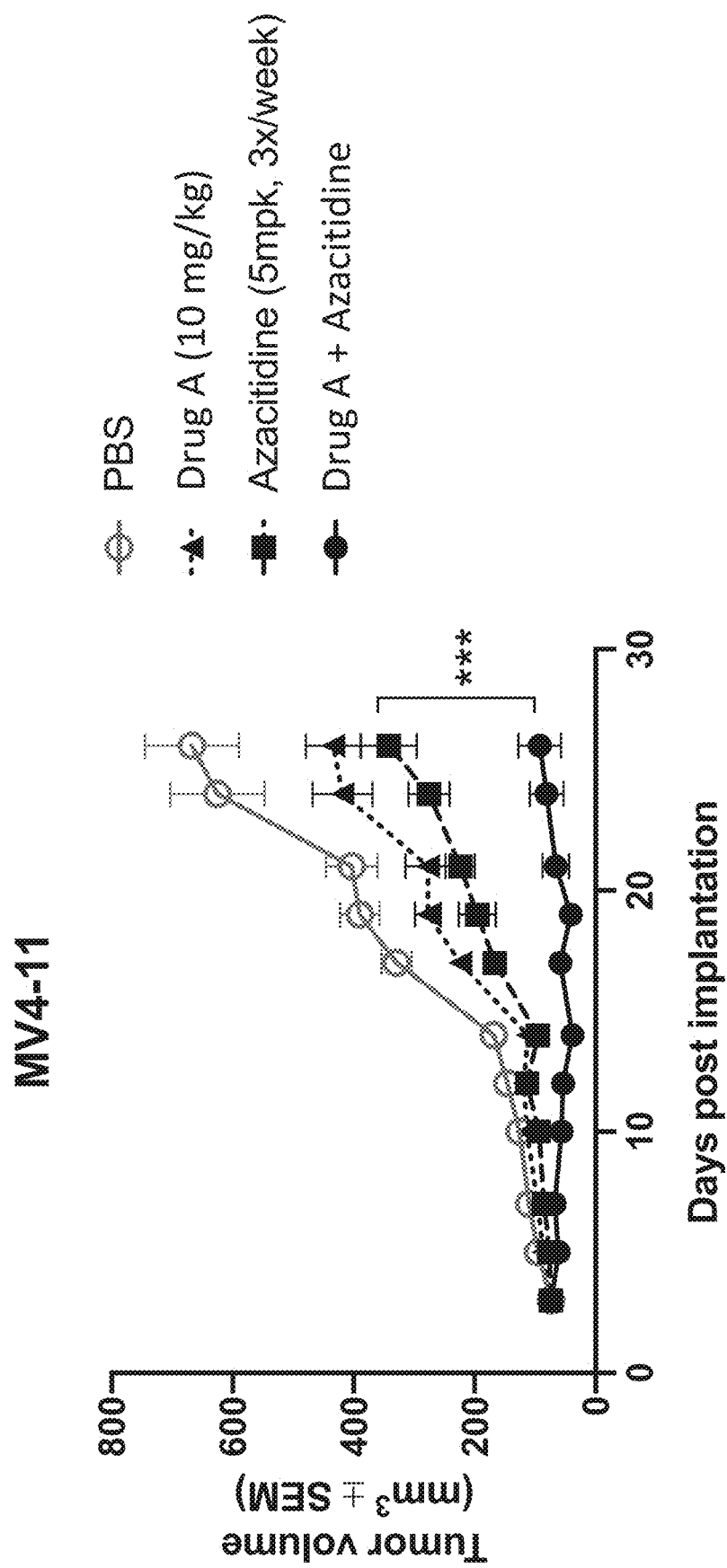

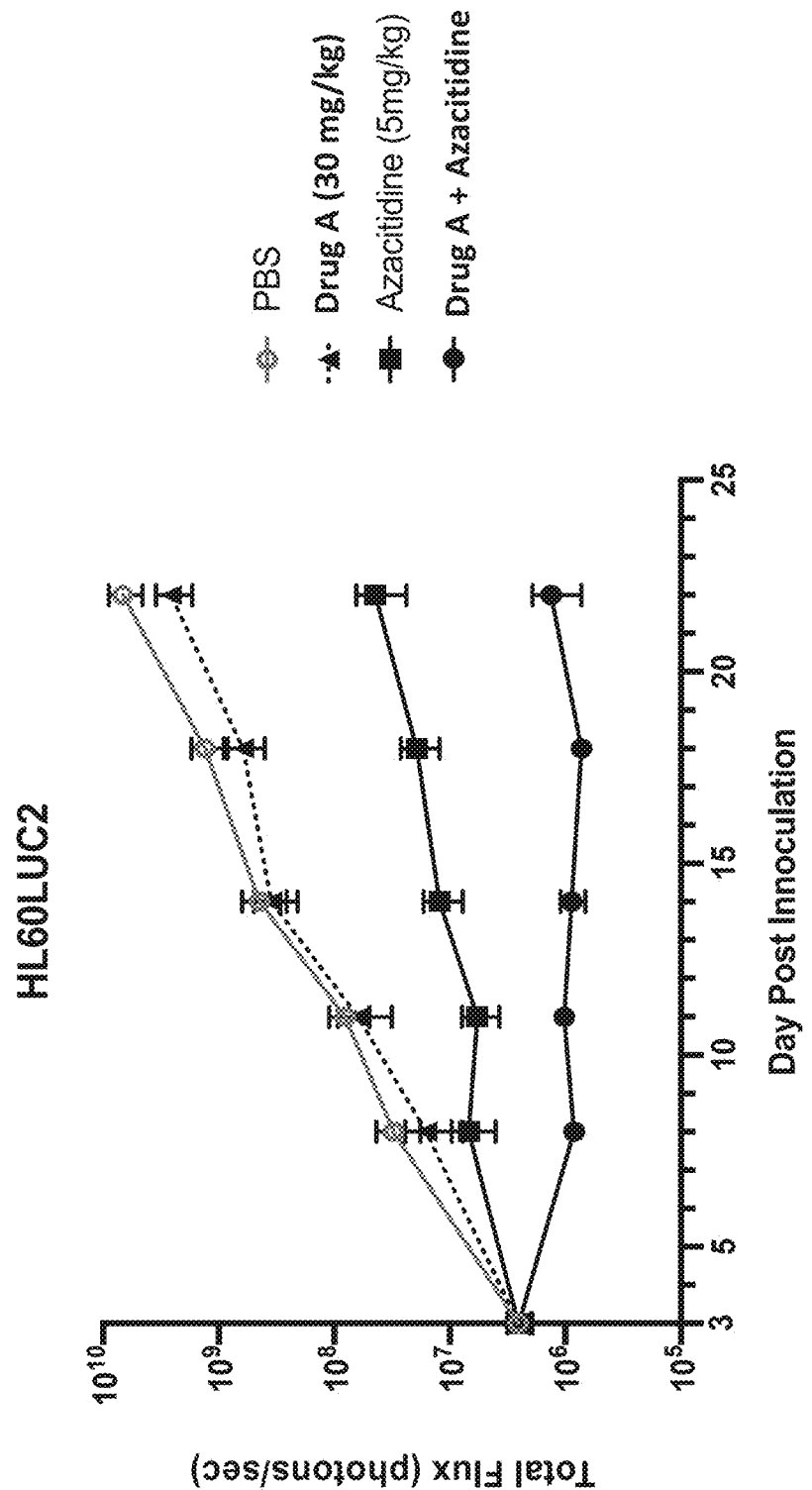

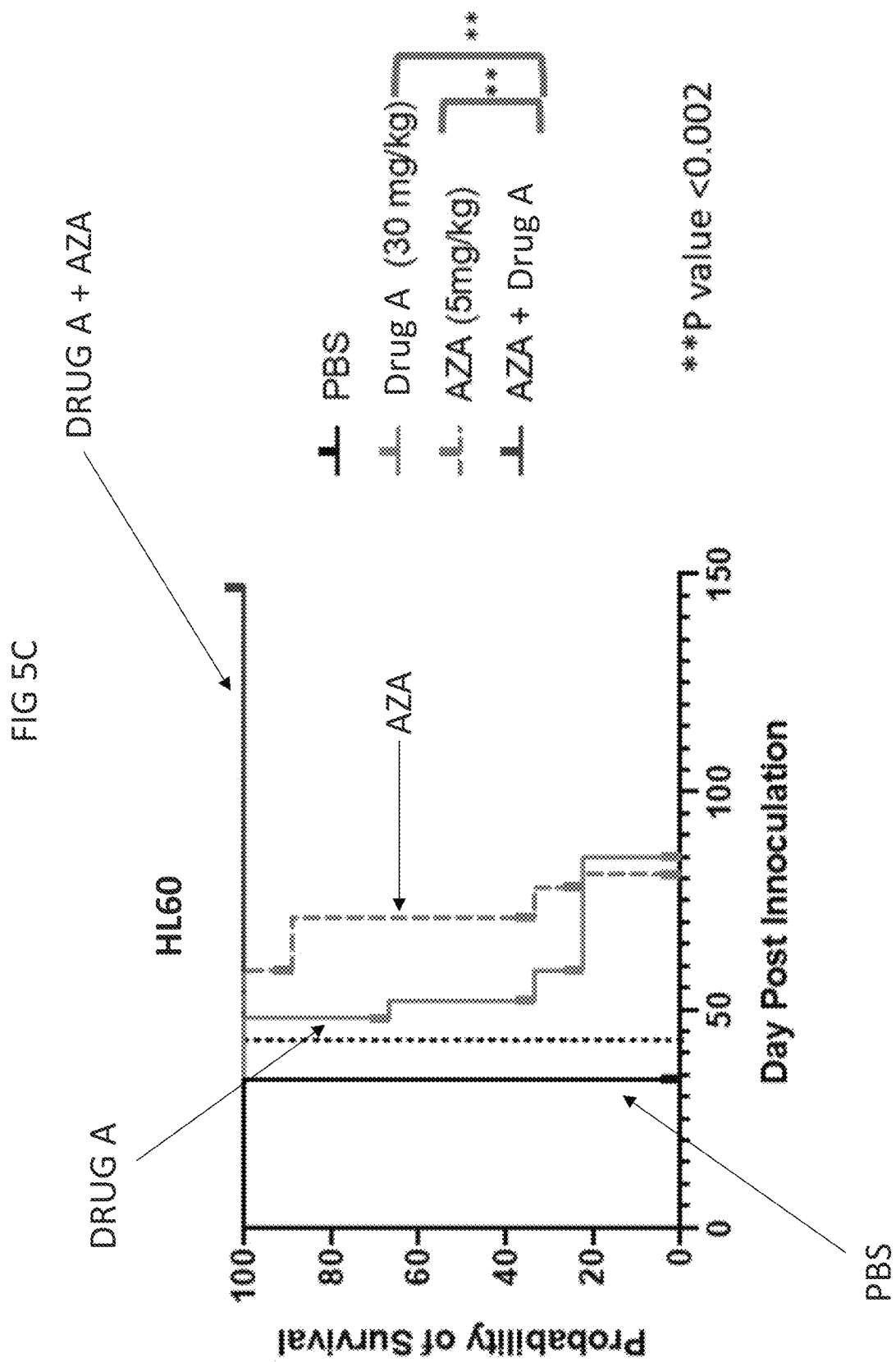

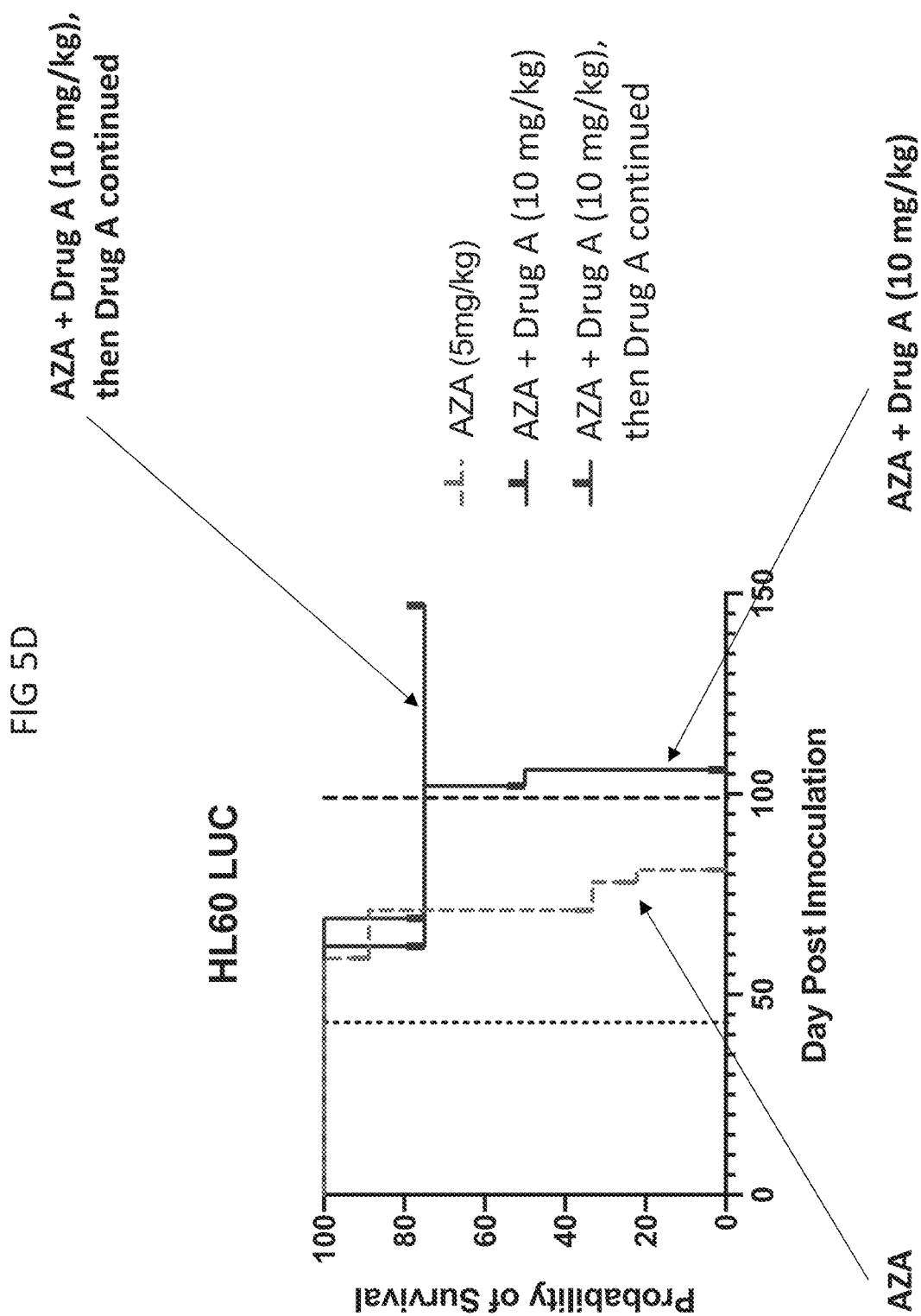

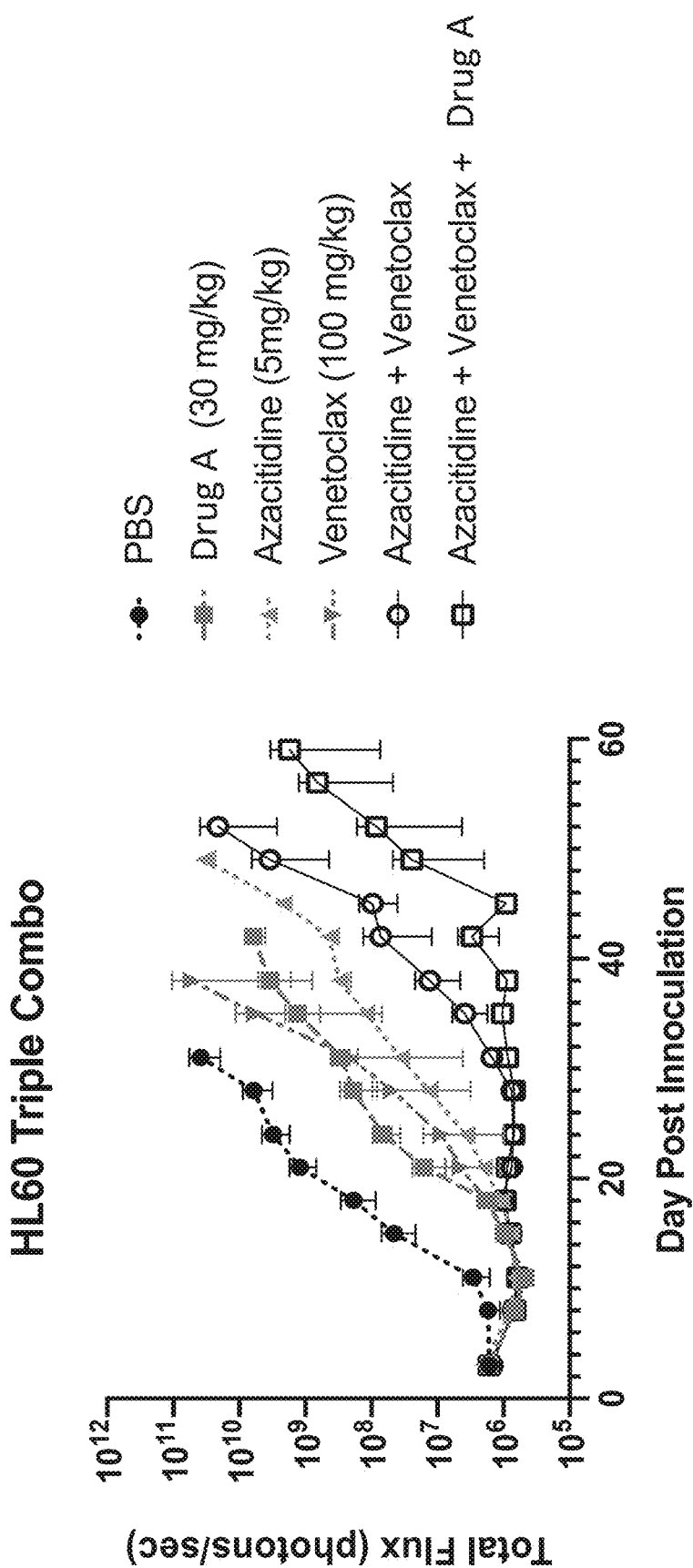

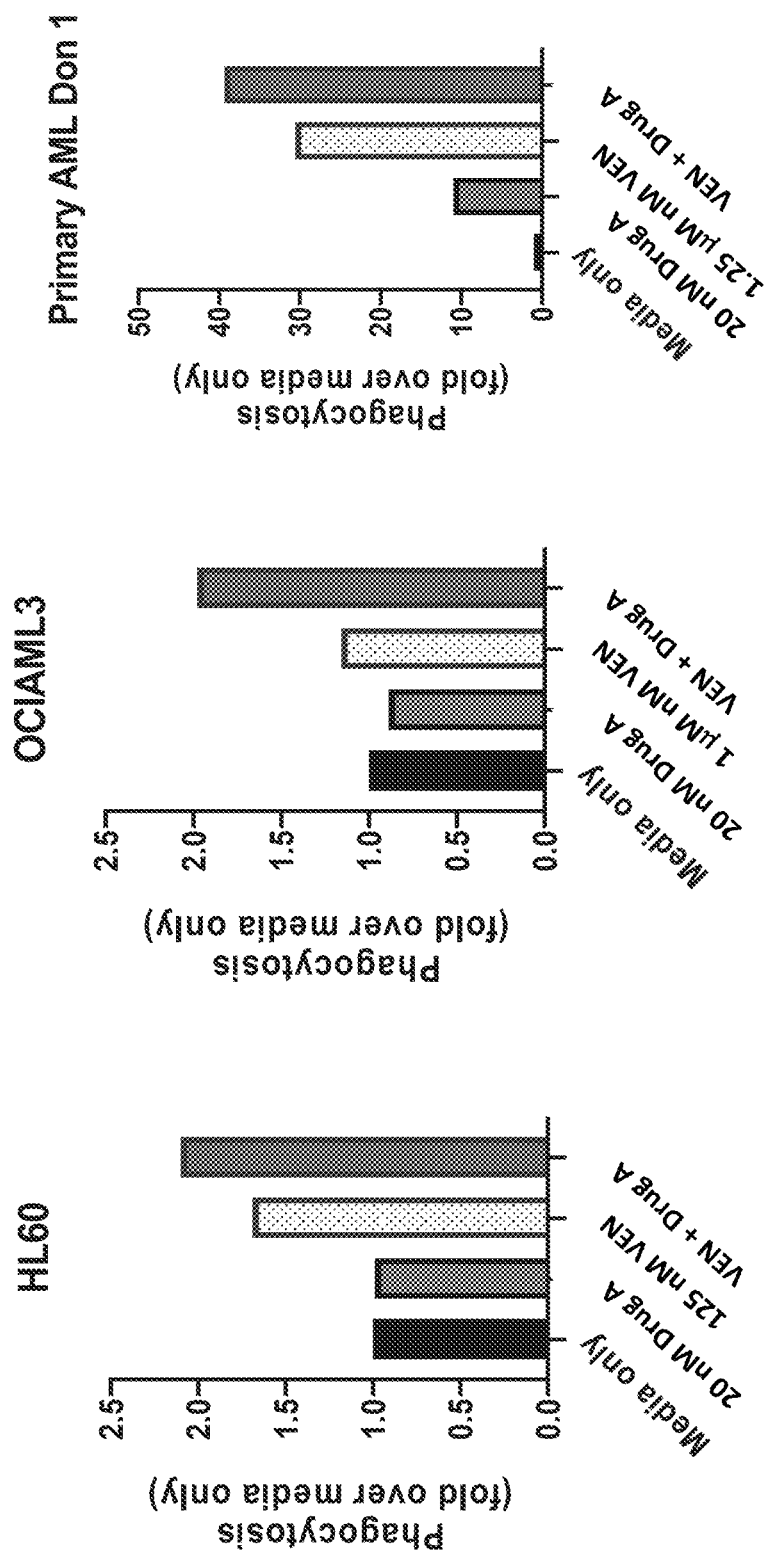

US 12,343,377 B2

COMBINATION THERAPIES COMPRISING A HYPOMETHYLATION AGENT FOR TREATING CANCER

CROSS REFERENCE TO RELATED APPLICATIONS

This application claims the priority benefit of U.S. Provisional Application 63/033,074, filed Jun. 1, 2020; U.S. Provisional Application 63/106,285, filed Oct. 27, 2020; U.S. Provisional Application 63/109,083, filed Nov. 3, 2020; U.S. Provisional Application 63/114,959, filed Nov. 17, 2020; and U.S. Provisional Application 63/145,925, filed Feb. 4, 2021, the contents of each of which are incorporated herein by reference in their entirety

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757972001200SEQLIST.TXT, date recorded: May 28, 2021, size: 297 KB)

FIELD OF THE INVENTION

The present invention relates to methods of treating cancer that comprise administering an agent that blocks the interaction between CD47 (e.g., hCD47) and SIRPα (e.g., hSIRPα) to an individual in need thereof in combination with a hypomethylation agent (e.g., azacitidine).

BACKGROUND

Many cancers have a poor prognosis, even when treated with available therapeutics. For example, there are approximately 70,000 people living with diagnosed myelodysplastic syndrome (MDS) in the U.S. Patients with MDS have a wide range of expected outcomes that can be estimated from their Revised International Prognostic Scoring System, or IPSS-R, risk category. Patients with very low IPSS-R have an median overall survival of 8.8 years, whereas those with very high IPSS-R have an median overall survival of under ten months. For patients with higher-risk MDS (intermediate, high and very high IPSS-R), standard of care treatments include stem cell transplant (SCT), high and low-intensity chemotherapy regimens and hypomethylating agents (or HMAs). SCT is the only therapy that is potentially curative; however, the procedure is difficult to tolerate, especially for older patients, and has a non-relapse mortality rate of approximately 40% at 200 days for all patients with MDS.

Since nearly 75% of patients are diagnosed at age 70 or older, balancing a patient's age at prognosis with potential treatment-related impact on quality of life is important in considering treatment options. Regardless of age, treatment goals for patients with MDS are a balance of improved survival, symptom alleviation and quality of life. There is a need in the art for new treatments to provide additional therapeutic options and improve outcomes for patients with myelodysplastic syndrome (MDS), including patients with higher risk MDS.

Tumor cells may manipulate the myeloid compartment to evade the anti-tumor host immune response (Gabrilovich et al., Nat Rev Immunol (2012) 12(4):253-68). For example, while CD47 expressed on the surface of normal cells binds SIRPα on macrophages and provides a "don't eat me" signal, tumor cells have also been found to overexpress CD47 to evade the macrophage component of immune surveillance (Oldenborg, ISRN Hematol (2013) 614619).

Macrophage-mediated destruction of cancer cells is optimized by the simultaneous disruption of "don't eat me" signals (e.g., CD47-SIRPα) and the activation of "eat me" signals. Neither component alone is sufficient to trigger maximal phagocytic reaction against tumor cells. As described above, CD47 provides a fundamental "don't eat me" signal through its interaction with SIRPα on macrophages. The pro-phagocytic "eat me" signal can be provided to the same macrophages by binding to their activating Fc gamma receptors. For example, the pro-phagocytic "eat me" signal can be provided by binding of the Fc domain of anti-tumor antibodies to Fc receptors on macrophages. Pro-phagocytic signaling can also be provided by other stimuli, such as the binding of the protein calreticulin on the surface of the tumor cells to the LRP receptor on macrophages.

In myelodysplastic syndromes (MDS) and acute myeloid leukemia (AML), overexpression and abnormal expression of CD47 has been reported on the dysplastic cell and is suggested to have an inverse correlation with survival (Majeti et al. 2009; Jiang et al. 2013; Galli et al. 2015).

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

In some embodiments, provided is a method of treating cancer (e.g., myelodysplastic syndrome (MDS) or acute myeloid leukemia (AML)) in an individual, comprising administering to the individual an effective amount of: (a) a fusion polypeptide comprising a SIRPα D1 domain variant and an Fc domain variant, and (b) a hypomethylating agent; wherein the C-terminus of the SIRPα D1 domain variant of the fusion polypeptide is linked to the N-terminus of the Fc-domain variant. In some embodiments, provided is a method of treating cancer (e.g., AML) in an individual, comprising administering to the individual an effective amount of: (a) a fusion polypeptide comprising a SIRPα D1 domain variant and an Fc domain variant, and (b) a hypomethylating agent; wherein the C-terminus of the SIRPα D1 domain variant of the fusion polypeptide is linked to the N-terminus of the Fc-domain variant. In some embodiments, the SIRPα D1 domain variant of the fusion polypeptide comprises the amino acid sequence of SEQ ID NO: 81 or SEQ ID NO: 85; and the Fc domain variant of the fusion polypeptide is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the cancer is myelodysplastic syndrome (MDS). In some embodiments, the MDS is higher risk MDS. In some embodiments, the individual has received prior therapy for MDS. In some embodiments, the individual has not received prior therapy for MDS. In some embodiments, treatment for MDS comprises an induction phase and a maintenance phase, wherein the induction phase comprises administering (a) the fusion polypeptide comprising a SIRPα D1 domain variant and an Fc domain variant, and (b) the hypomethylating agent, and wherein the maintenance phase comprises administering the fusion polypeptide comprising a SIRPα D1 domain variant and an Fc domain variant without the hypomethylating agent. In some embodiments, the cancer is acute myeloid leukemia (AML). In some embodiments, the fusion polypeptide is administered at a dose up to about 60 mg/kg. In some embodiments, fusion polypeptide is administered at a dose of about 60 mg/kg once every four weeks (q4w). In some embodiments, the cancer is acute myeloid leukemia (AML). In some embodiments, the individual has subcytologically or histologically confirmed diagnosis of relapsed/refractory or newly diagnosed AML per WHO 2016 classification. In some embodiments, the individual has AML that is relapsed/refractory or that is previously untreated in patients not considered suitable for intensive induction therapy. In some embodiments, the individual has AML that is relapsed/refractory after prior treatment with a HMA-based regimen. In some embodiments, the individual has previously untreated AML and is not considered a suitable candidate for intensive induction therapy. In some embodiments, the individual has adequate renal and liver function. In some embodiments, the individual is ≥18 years old. In some embodiments, the individual has adequate performance status. In some embodiments, the individual has not undergone prior allo-hematopoietic stem cell transplantation (HSCT). In some embodiments, the individual is least 3 months post-HCST, without uncontrolled graft-versus-host disease (GVHD). In some embodiments, the individual has not undergone prior allo-HSCT. In some embodiments, the individual does not have newly diagnosed AML with favorable risk cytogenetics such as t(8; 21), inv(16), or t(16; 16) as per the National Comprehensive Cancer Network (NCCN) guidelines version 3, 2019 for AML. In some embodiments, the individual does not have acute promyelocytic leukemia (APL). In some embodiments, the individual has not undergone prior treatment with any anti-CD47 or anti-SIRPα (signal regulatory protein alpha) agent. In some embodiments, the individual does not have known active viral infections, including hepatitis B and C, human immunodeficiency virus (HIV), acquired immunodeficiency syndrome (AIDS) related illness, or sars-cov-2 (severe acute respiratory syndrome coronavirus 2). In some embodiments, the fusion polypeptide is administered at a dose up to about 60 mg/kg. In some embodiments, fusion polypeptide is administered at a dose of about 60 mg/kg once every four weeks (q4w).

In some embodiments, the hypomethylating agent is azacitidine, decitabine, 5-fluoro-2'-deoxycytidine, zebularine, CP-4200, RG108, nanaomycin A, guadecitabine, RX-3117, EPI01, antroquinonol, CC-486, or ASTX727. In some embodiments, the hypomethylating agent is azacitidine. In some embodiments, the azacitidine is administered to the individual in one or more 28-day cycles, and wherein the azacitidine is administered to the individual at a dose of 75 mg/m² daily for 7 days of every 28 day cycle. In some embodiments, the azacitidine is administered to the in one or more 28-day cycles, and wherein the azacitidine is administered to the individual during each 28-day cycle at a dose of 75 mg/m² daily for 5 days, followed by 2 days without azacitidine administration, and then administered to the individual at a dose of 75 mg/m² for 2 additional days. In some embodiments, the azacitidine is administered intravenously or subcutaneously.

In some embodiments, the Bcl-2 inhibitor is venetoclax, ABT-737, navitoclax, BCL201, or AZD-0466. In some embodiments, the Bcl-2 inhibitor is venetoclax. In some embodiments, the venetoclax is administered at a dose of 100 mg on day 1, at a dose of 200 mg on day 2, and at a dose of 400 mg every day following day 2. In some embodiments, the venetoclax is administered at a dose of 100 mg on day 1, at a dose of 200 mg on day 2, and at a dose of 400 mg on day 3, and at a dose of 600 mg every day following day 3. In some embodiments, the venetoclax is administered orally.

In some embodiments, provided is a method of treating cancer in an individual, comprising administering to the individual an effective amount of a fusion polypeptide comprising a SIRPα D1 domain variant and an Fc domain variant, wherein the C-terminus of the SIRPα D1 domain variant is fused to the N-terminus of the Fc domain variant, and wherein the fusion polypeptide is administered at a dose of up to about 60 mg/kg. In some embodiments, the fusion polypeptide is administered at a dose of about 60 mg/kg. In some embodiments, wherein the fusion polypeptide is administered at a dose of about 60 mg/kg once every 4 weeks (q4w). In some embodiments, the fusion polypeptide is administered at a dose of about 45 mg/kg. In some embodiments, the fusion polypeptide is administered at a dose of about 45 mg/kg once every 3 weeks (q3w). In some embodiments, the cancer is a hematological cancer. In some embodiments, the cancer is a solid tumor.

In some embodiments, the SIRPα D1 domain variant of the fusion polypeptide comprises the amino acid sequence of SEQ ID NO: 81 or SEQ ID NO: 85; and the Fc domain variant of the fusion polypeptide is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat.

In some embodiments of any of the methods provided herein, the SIRPα D1 domain variant comprises the amino acid sequence of SEQ ID NO: 85. In some embodiments, the SIRPα D1 domain variant comprises the amino acid sequence of SEQ ID NO: 81. In some embodiments, the Fc domain variant is a human IgG1 Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the fusion polypeptide comprises the amino acid sequence of SEQ ID NO: 136. In some embodiments, the fusion polypeptide comprises the amino acid sequence of SEQ ID NO: 135. In some embodiments, the fusion polypeptide forms a homodimer. In some embodiments, the fusion polypeptide is administered intravenously. In some embodiments, the individual is a human.

In some embodiments, provided is a kit comprising a fusion polypeptide in a pharmaceutically acceptable carrier, for use in combination with azacitidine for treating cancer in an individual in need thereof, wherein the fusion polypeptide comprises a SIRPα D1 domain variant and an Fc domain variant, wherein the C-terminus of the SIRPα D1 domain variant is fused to the N-terminus of the Fc domain variant, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the individual is human. In some embodiments, the cancer is myelodysplastic syndrome (MDS) or acute myeloid leukemia (AML). In some embodiments, the cancer is MDS. In some embodiments, the MDS is higher risk MDS.

In some embodiments, provided is a kit comprising a fusion polypeptide in a pharmaceutically acceptable carrier, for use in combination with azacitidine and venetoclax for treating cancer in an individual in need thereof, wherein the fusion polypeptide comprises a SIRPα D1 domain variant and an Fc domain variant, wherein the C-terminus of the SIRPα D1 domain variant is fused to the N-terminus of the Fc domain variant, wherein the SIRPα D1 domain variant comprises the amino acid sequence of SEQ ID NO: 81 or SEQ ID NO: 85; wherein the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat; and wherein the individual is human. In some embodiments, the cancer is AML.

In some embodiments, the kit further comprises instructions for administering azacitidine by IV infusion or subcutaneously in one or more 28-day cycles, wherein the azacitidine is administered to the individual at a dose of 75 mg/m$^2$ daily for 7 days of each 28-day cycle. In some embodiments, the kit further comprises instructions for administering azacitidine by IV infusion or subcutaneously in one or more 28-day cycles, wherein the azacitidine is administered to the individual during each 28 day cycle at a dose of 75 mg/m$^2$ daily for 5 days, followed by 2 days without azacitidine administration, and then administered to the individual at a dose of 75 mg/m$^2$ for 2 additional days.

In some embodiments, the kit further comprises instructions for administering venetoclax orally at a dose of 100 mg on Day 1, 200 mg on Day 2, and 400 mg on every day following Day 2. In some embodiments, the kit further comprises instructions for administering venetoclax orally at a dose of 100 mg on Day 1, 200 mg on Day 2, and 400 mg on Day 3, and 600 mg on every day following Day 3.

In some embodiments of the kits, the SIRPα D1 domain variant comprises the amino acid sequence of SEQ ID NO: 85. In some embodiments, the SIRPα D1 domain variant comprises the amino acid sequence of SEQ ID NO: 81. In some embodiments, the Fc domain variant is a human IgG1 Fc region comprising L234A, L235A, G237A, and N297A mutations, wherein numbering is according to the EU index of Kabat. In some embodiments, the Fc domain variant comprises the amino acid sequence of SEQ ID NO: 91. In some embodiments, the fusion polypeptide comprises the amino acid sequence of SEQ ID NO: 136. In some embodiments, the fusion polypeptide comprises the amino acid sequence of SEQ ID NO: 135. In some embodiments, the fusion polypeptide forms a homodimer. In some embodiments, the kit further comprises instructions for administering the fusion polypeptide to the individual at a dose of up to 60 mg/kg. In some embodiments, the kit further comprises instructions for administering the fusion polypeptide to the individual at a dose of 60 mg/kg once every four weeks (q4w). In some embodiments, the kit further comprises instructions for administering the fusion polypeptide by IV infusion.

DESCRIPTION OF THE FIGURES

FIG. 3C provides the results of in vitro experiments that were performed to assess the effect of azacitidine or venetoclax on the expression of CD47 on the surface of MV4-11 human acute myeloid leukemia cell lines and primary AML blasts from 2 human donors.

FIG. 4A provides results of experiments that were performed to assess the effects of Drug A, azacitidine, and Drug A+azacitidine on tumor growth in mice bearing HL60 tumor xenografts. FIG. 4C provides results of experiments that were performed to assess the effects of Drug A, azacitidine, and Drug A+azacitidine on tumor growth in mice bearing MV4-11 tumor xenografts.

FIG. 5A provides results from experiments that were performed to assess the effects of Drug A, azacitidine, and Drug A+azacitidine on tumor growth in mice engrafted with HL60-LUC2 at a concentration of 7.5E6 cells/mouse via tail vein injection. FIG. 5C provides results of experiments that were performed to assess the effects of Drug A, azacitidine, or Drug A+azacitidine on tumor growth in mice engrafted with HL60-LUC2 up to study termination on Day 147. FIG. 5D provides results of experiments that were performed to assess the effects of Drug A monotherapy (e.g., maintenance therapy) on tumor growth in mice engrafted with HL60-LUC2 who had already received 14 doses of Drug A+azacitidine (e.g., induction therapy).

FIG. 6A provides results of experiments that were performed to assess the effects of Drug A, azacitidine, venetoclax, azacitidine+venetoclax, or Drug A+azacitidine+venetoclax on tumor growth in mice engrafted with HL60-LUC2 at a concentration of $10\times10^6$ cells/mouse via tail vein injection.

FIG. 7B provides results of experiments that were performed to assess the effects of Drug A, venetoclax, and Drug A+venetoclax on the phagocytosis of AML cells by human monocyte-derived macrophages.

DETAILED DESCRIPTION

Figure 1A:
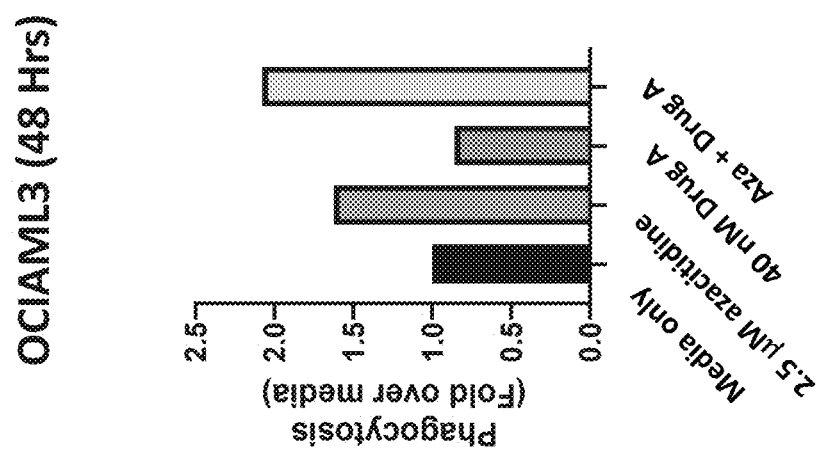
FIG. 1A provides results of experiments that were performed to assess the effects of Drug A, azacitidine, and Drug A+azacitidine on the phagocytosis of human HL60 cells by macrophages.

The following description sets forth exemplary methods, parameters and the like. It should be recognized, however, that such description is not intended as a limitation on the scope of the present disclosure but is instead provided as a description of exemplary embodiments.

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description or the claims, such terms are intended to be inclusive in a manner similar to the term "comprising."

As used herein, the terms "treatment", "treating", and the like, refer to administering an agent, or carrying out a procedure, for the purposes of obtaining an effect. In some embodiments, the effect is prophylactic in terms of completely or partially preventing a disease or symptom thereof. In some embodiments, the effect is therapeutic in terms of affecting a partial or complete cure for a disease or symptoms of the disease.

As used herein, the term "linker" refers to a linkage between two elements, e.g., protein domains. In some embodiments, a linker can be a covalent bond or a spacer. The term "spacer" refers to a moiety (e.g., a polyethylene glycol (PEG) polymer) or an amino acid sequence (e.g., a 1-200 amino acid sequence) occurring between two polypeptides or polypeptide domains to provide space or flexibility (or both space and flexibility) between the two polypeptides or polypeptide domains. In some embodiments, an amino acid spacer is part of the primary sequence of a polypeptide (e.g., joined to the spaced polypeptides or polypeptide domains via the polypeptide backbone).

As used herein, the term "effective amount" refers to an amount of a polypeptide or a pharmaceutical composition containing a polypeptide described herein, e.g., a polypeptide having a SIRPα D1 domain or variant thereof, that is sufficient and effective in achieving a desired therapeutic effect in treating a patient having a disease, such as a cancer, e.g., solid tumor or hematological cancer. In some embodiments, an effective amount of polypeptide will avoid adverse side effects.

As used herein, the term "pharmaceutical composition" refers to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with the polypeptide. In some embodiments, the pharmaceutical composition is in tablet or capsule form for oral administration or in aqueous form for intravenous or subcutaneous administration, for example by injection.

As used herein, the terms "subject," "individual," and "patient" are used interchangeably to refer to a vertebrate, for example, a mammal. Mammals include, but are not limited to, murines, simians, humans, farm animals, sport animals, and pets. Tissues, cells, and their progeny of a biological entity obtained in vivo or cultured in vitro are also encompassed. None of the terms entail supervision of a medical professional.

As used herein, the term "affinity" or "binding affinity" refers to the strength of the binding interaction between two molecules. Generally, binding affinity refers to the strength of the sum total of non-covalent interactions between a molecule and its binding partner, such as a SIRPα D1 domain variant and CD47. Unless indicated otherwise, binding affinity refers to intrinsic binding affinity, which reflects a 1:1 interaction between members of a binding pair. The binding affinity between two molecules is commonly described by the dissociation constant (KD) or the association constant (KA). Two molecules that have low binding affinity for each other generally bind slowly, tend to dissociate easily, and exhibit a large KD. Two molecules that have high affinity for each other generally bind readily, tend to remain bound longer, and exhibit a small KD. In some embodiments, the KD of two interacting molecules is determined using known methods and techniques, e.g., surface plasmon resonance (SPR). KD can be calculated as the ratio of koff/kon.

As used herein, the term "$K_D$ less than" refers to a numerically smaller $K_D$ value and an increasing binding affinity relative to the recited KD value. As used herein, the term "KD greater than" refers to a numerically larger KD value and a decreasing binding affinity relative to the recited KD value.

As used herein, "in conjunction with" refers to administration of one treatment modality in addition to another treatment modality. As such, "in conjunction with" refers to administration of one treatment modality before, during, or after administration of the other treatment modality to the individual.

Overview

Provided herein are methods of treating cancer (e.g., a myeloid cancer such as myelodysplastic syndrome ("MDS") in an individual (e.g., a human individual) that comprise administering to the individual an effective amount of (a) an agent that blocks the interaction between CD47 (e.g., hCD47) and SIRPα (e.g., hSIRPα) and (b) a hypomethylating agent. In some embodiments, provided are methods of treating acute myeloid leukemia ("AML").

In some embodiments, the agent that blocks the interaction between CD47 (e.g., hCD47) and SIRPα (e.g., hSIRPα) is a small molecule inhibitor of the CD47-SIRPα pathway (e.g., RRX-001 and others). See, e.g., Miller et al. (2019) "Quantitative high-throughput screening assays for the discovery and development of SIRPα-CD47 interaction inhibitors." *PLoS ONE* 14(7): e0218897 and Sasikumar et al. ACR-NCI-EORTC International Conference: Molecular Targets and Cancer Therapeutics; October 26-30, 2017; Philadelphia, PA; Abstract B007.

In some embodiments, the agent that blocks the interaction between CD47 (e.g., hCD47) and SIRPα (e.g., hSIRPα) binds CD47 (e.g., hCD47). In some embodiments, the agent binds CD47 (e.g., hCD47) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the agent that binds CD47 (e.g., hCD47) exhibits at least about 50% CD47 receptor occupancy (e.g., at least about any one of 50%, 55%, 60%, 65%, 70%, 75%, 80%, 85%, 90%, 95%, 99%, or about 100%) in a human subject. In some embodiments, the agent that binds CD47 (e.g., hCD47) has an EC50 of about 80 ng/ml or less, e.g., about any one of 75, 70, 65, 60, 55, 50, 45, 40, 35, 30, 25, 20, 15, 10, or 5 ng/ml. In some embodiments, the agent that binds CD47 (e.g., hCD47) is an anti-CD47 antibody (e.g., a therapeutic anti-CD47 antibody) or an antigen-binding fragment thereof. In some embodiments, the antigen binding fragment is a Fab, a Fab', a Fab'-SH, an F(ab')2, an Fv, an scFv, a one-armed antibody, or a diabody. In some embodiments, the anti-CD47 antibody is a monospecific antibody. In some embodiments, the anti-CD47 antibody is a multispecific (e.g., bispecific) antibody. In some embodiments the term "anti-CD47 antibody" encompasses antibody-based constructs (such as multispecific constructs) including, without limitation triomabs, DARTs (i.e., dual-affinity re-targeting antibodies), TandAbs (i.e., tandem diabodies), tandem scFvs, CrossMabs, DNLs (i.e., dock and lock antibodies), DVD-Ig (i.e., dual variable domain immunoglobulins), tetravalent bispecific IgGs, nanobodies, dual targeting domains, and ART-Igs (i.e., asymmetric reengineering technology-immunoglobulins). Additional details regarding exemplary antibody constructs (both monospecific and multispecific) are provided in Husain et al. (2018) *Biodrugs* 32(5): 441-464 and Spiess et al. (2015) *Molecular Immunology* 67(2): 95-106. In some embodiments, the anti-CD47 antibody is Hu5F9-G4, B6H12.2, BRIC126, CC-90002, SRF231, or IBI188 (from Innovent Biologics) (see, e.g., Zhao et al. (2011), *PNAS USA* 108:18342-18347; Chao et al. (2010) *Cell* 142:699-713, Kim et al. (2012) *Leukemia* 26:2538-2545; Chao et al. (2011) *Blood* 118:4890-4891; Goto et al. (2014) *Eur J. Cancer* 50:1836-1846; and Edris et al. (2012) *PNAS USA* 109:6656-61 for additional information about these anti-CD47 antibodies).

In some embodiments, the agent that blocks the interaction between CD47 (e.g., hCD47) and SIRPα (e.g., hSIRPα) binds SIRPα (e.g., hSIRPα). In some embodiments, the agent binds SIRPα (e.g., hSIRPα) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the agent that binds SIRPα (e.g., hSIRPα) exhibits at least about 50% SIRPα receptor occupancy (e.g., at least about any one of 50%, 55%, 60%, 65%, 70%, 75%, 80%, 85%, 90%, 95%, 99%, or about 100%) in a human subject. In some embodiments, the agent that binds SIRPα (e.g., hSIRPα) has an EC50 of about 80 ng/ml or less, e.g., about any one of 75, 70, 65, 60, 55, 50, 45, 40, 35, 30, 25, 20, 15, 10, or 5 ng/ml. In some embodiments, the agent that binds SIRPα (e.g., hSIRPα) is an anti-SIRPα antibody (e.g., a therapeutic anti-SIRPα antibody) or an antigen-binding fragment thereof. In some embodiments, the antigen binding fragment is a Fab, a Fab', a Fab'-SH, an F(ab')2, an Fv, an scFv, a one-armed antibody, or a diabody. In some embodiments, the anti-SIRPα antibody is a monospecific antibody or monospecific antibody construct (including, but not limited to those described above). In some embodiments, the anti-SIRPα antibody is a multispecific (e.g., bispecific) antibody or a multispecific antibody construct (including, but not limited to those described above). In some embodiments, the anti-SIRPα antibody is KWAR23, SE12C3, 040, or MY-1 (see, e.g., Ring et al. (2017) *PNAS USA* 114(49): E10578-E10585); Murata et al. (2018) Cancer Sci 109(5):1300-1308; and Yanigata et al. (2017) JCI Insight 2:e89140 for additional information about these anti-SIRPα antibodies). In some embodiments, the anti-SIRPα antibody is an antibody described in WO 2018/057669; US-2018-0105600-A1; US20180312587; WO2018107058; WO2019023347; US20180037652; WO2018170795; WO2017178653; WO2018149938; WO2017068164; and WO2016063233, the contents of which are incorporated herein by reference in their entireties.

In some embodiments, the agent that blocks the interaction between CD47 (e.g., hCD47) and SIRPα (e.g., hSIRPα) is an anti-SIRPβ antibody or an anti-SIRPγ antibody (e.g., an anti-SIRPβ antibody or anti-SIRPγ antibody that is capable of binding SIRPα), or an antigen-binding fragment thereof. In some embodiments, the agent is an antibody (or antigen binding fragment thereof) that is capable of bind two or more of SIRPα, SIRPβ, and SIRPγ. In some embodiments, such antibody binds SIRPα (e.g., hSIRPα) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the antibody exhibits at least about 50% SIRPα receptor occupancy (e.g., at least about any one of 50%, 55%, 60%, 65%, 70%, 75%, 80%, 85%, 90%, 95%, 99%, or about 100%) in a human subject. In some embodiments, the antibody has an EC50 of about 80 ng/ml or less, e.g., about any one of 75, 70, 65, 60, 55, 50, 45, 40, 35, 30, 25, 20, 15, 10, or 5 ng/ml. In some embodiments, the antigen binding fragment is a Fab, a Fab', a Fab'-SH, an F(ab')2, an Fv, an scFv, a one-armed antibody, or a diabody. In some embodiments, the antibody is a monospecific antibody or monospecific antibody construct (including, but not limited to those described above). In some embodiments, the antibody is a multispecific (e.g., bispecific) antibody or a multispecific antibody construct (including, but not limited to those described above).

In some embodiments, the agent that blocks the interaction between CD47 (e.g., hCD47) and SIRPα (e.g., hSIRPα) is a fusion polypeptide comprising a moiety that binds CD47. In some embodiments, the fusion polypeptide comprises an antibody Fc region and a moiety that binds CD47. In some embodiments, the portion of the fusion polypeptide that binds CD47 (e.g., hCD47) binds CD47 (e.g., hCD47) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the fusion polypeptide exhibits at least about 50% CD47 receptor occupancy (e.g., at least about any one of 50%, 55%, 60%, 65%, 70%, 75%, 80%, 85%, 90%, 95%, 99%, or about 100%) in a human subject. In some embodiments, the fusion polypeptide has an EC50 of about 80 ng/ml or less, e.g., about any one of 75, 70, 65, 60, 55, 50, 45, 40, 35, 30, 25, 20, 15, 10, or 5 ng/ml. In some embodiments, the fusion polypeptide comprises WT human antibody Fc region. In some embodiments, the fusion polypeptide comprises an Fc variant (e.g., a variant of a WT human antibody Fc region) that exhibits reduced (e.g., such as ablated) effector function as compared to a WT Fc region. Exemplary Fc variants are described in WO 2017/027422 and US 2017/0107270, the contents of which are incorporated herein by reference in their entireties. In some embodiments, moiety that binds CD47 (e.g., hCD47) is a WT SIRPα (e.g., hSIRPα), or a WT SIRPγ (e.g., hSIRPγ). In some embodiments, moiety that binds CD47 (e.g., hCD47) is a CD47-binding fragment (e.g., d1 domain) of a WT SIRPα (e.g., hSIRPα), or a WT SIRPγ (e.g., hSIRPT). In some embodiments, the moiety that binds CD47 (e.g., hCD47) is a SIRPα variant, a SIRPγ variant, a SIRPβ variant, or a CD47-binding fragment thereof (e.g., the d1 domain). Exemplary SIRPγ variants, SIRPβ1 variant, and SIRPβ2 variants are described in, e.g., WO 2013/109752; US 2015/0071905; U.S. Pat. No. 9,944,911; WO 2016/023040; WO 2017/027422; US 2017/0107270; U.S. Pat. Nos. 10,259,859; 9,845,345; WO2016187226; US20180155405; WO2017177333; WO2014094122; US2015329616; US20180312563; WO2018176132; WO2018081898; WO2018081897; PCT/US2019/048921; US20180141986A1; and EP3287470A1, the contents of which are incorporated herein by reference in their entireties.

In some embodiments, the agent that blocks the interaction between CD47 (e.g., hCD47) and SIRPα (e.g., hSIRPα) is a fusion polypeptide comprising an antibody Fc region and a SIRPα variant. In some embodiments, the SIRPα variant binds CD47 (e.g., hCD47) with a $K_D$ of about 10 nM or better (such as at least about any one of 9 nM, 8 nM, 7 nM, 6 nM, 5 nM, 3 nM, 2 nM, 1 nM, 750 pM, 500 pM, 250 pM, 200 pM, 100 pM, 50 pM, 25 pM, 20 pM 10 pM or less than 10 pM). In some embodiments, the fusion polypeptide exhibits at least about 50% CD47 receptor occupancy (e.g., at least about any one of 50%, 55%, 60%, 65%, 70%, 75%, 80%, 85%, 90%, 95%, 99%, or about 100%) in a human subject. In some embodiments, the fusion polypeptide has an EC50 of about 80 ng/ml or less, e.g., about any one of 75, 70, 65, 60, 55, 50, 45, 40, 35, 30, 25, 20, 15, 10, or 5 ng/ml. In some embodiments, the fusion polypeptide comprises WT human antibody Fc region. In some embodiments, the fusion polypeptide comprises an Fc variant (e.g., a variant of a WT human antibody Fc region) that exhibits reduced (e.g., such as ablated) effector function as compared to a WT Fc region, such as those described in the references cited herein. In some embodiments, the fusion polypeptide comprises a SIRPα variant described in WO 2013/109752; US 2015/0071905; WO 2016/023040; WO 2017/027422; US 2017/0107270; U.S. Pat. Nos. 10,259,859; 9,845,345; WO2016187226; US20180155405; WO2017177333; WO2014094122; US2015329616; US20180312563; WO2018176132; WO2018081898; WO2018081897; US20180141986A1; and EP3287470A1, the contents of which are incorporated herein by reference in their entireties. In some embodiments, the fusion polypeptide comprising an antibody Fc region and a SIRPα variant is TTI-621, TTI-622, or IMM01 (see, e.g., Petrova et al. (2017) Clin Cancer Res 23:1086-1079; Russ et al. (2018) Blood Rev S0268-960X(17)30093-0; Zhang, X, Chen, W, Fan, J et al. Disrupting CD47-SIRPα axis alone or combined with autophagy depletion for the therapy of glioblastoma. Carcinogenesis 2018; 39: 689-99).

In some embodiments, the agent that blocks the interaction between CD47 (e.g., hCD47) and SIRPα (e.g., hSIRPα) is a fusion polypeptide comprising a SIRPα D1 domain variant (e.g., a SIRPα D1 domain variant described herein) and an Fc domain variant (e.g., an Fe domain variant described herein).

Further details regarding the methods of treatment with polypeptides comprising a SIRPα D1 domain variant and an Fc domain variant are described below. See also WO 2017/027422 and U.S. Pat. No. 10,259,859, the contents of each of which are incorporated by reference herein in their entireties.

Also provided herein are methods of treating cancer in an individual that comprise administering to the individual an effective amount of a polypeptide (e.g., fusion polypeptide) comprising a SIRPα D1 domain variant and an Fc domain variant, wherein the polypeptide is administered at a dose of about 60 mg/kg once every four weeks (q4w). Also provided herein are methods of treating cancer in an individual that comprise administering to the individual an effective amount of a polypeptide (e.g., fusion polypeptide) comprising a SIRPα D1 domain variant and an Fc domain variant, wherein the polypeptide is administered at a dose of about 45 mg/kg once every three weeks (q3w). In some embodiments, the fusion polypeptide is administered in combination with at least one additional anti-cancer agent.

Signal-Regulatory Protein α (SIRPα) D1 Domain and Variants Thereof

Disclosed herein, in some embodiments, are polypeptides comprising a signal-regulatory protein α (SIRP-α) D1 variant comprising a SIRPα D1 domain, or a fragment thereof, that comprises an amino acid mutation at residue 80 relative to a wild-type SIRPα D1 domain (e.g., a wild-type SIRPα D1 domain set forth in SEQ ID NO: 1 or 2); and at least one additional amino acid mutation relative to a wild-type SIRPα D1 domain (e.g., a wild-type SIRPα D1 domain set forth in SEQ ID NO: 1 or 2) at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc domain variants, wherein an Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Signal-regulatory protein α ("SIRP-α" or "SIRP-alpha") is a transmembrane glycoprotein belonging to the Ig superfamily that is widely expressed on the membrane of myeloid cells. SIRPα interacts with CD47, a protein broadly expressed on many cell types in the body. The interaction of SIRPα with CD47 prevents engulfment of "self" cells, which can otherwise be recognized by the immune system. It has been observed that high CD47 expression on tumor cells can act, in acute myeloid leukemia and several solid tumor cancers, as a negative prognostic factor for survival.

Native SIRPα comprises 3 highly homologous immunoglobulin (Ig)-like extracellular domains—D1, D2, and D3. The SIRPα D1 domain ("D1 domain") refers to the membrane distal, extracellular domain of SIRPα and mediates binding of SIRPα to CD47. As used herein, the term "SIRPα polypeptide" refers to any SIRPα polypeptide or fragment thereof that is capable of binding to CD47. There are at least ten variants of wild-type human SIRPα. Table 1 shows the amino acid sequences of the D1 domains of the naturally occurring wild-type human SIRPα D1 domain variants (SEQ ID NOs: 1and 2). In some embodiments, a SIRPα polypeptide comprises a SIRPα D1 domain. In some embodiments, a SIRPα polypeptide comprises a wild-type D1 domain, such as those provided in SEQ ID NOs: 1 and 2. In some embodiments, a SIRPα polypeptide includes a D2 or D3 domain (or both a D2 and a D3 domain) (see Table 3) of a wild-type human SIRPα.

comprises one or more amino acid substitutions, insertions, additions, or deletions relative to a wild-type D1 domain shown in SEQ ID NOs: 1 and 2. Table 2 lists exemplary amino acid substitutions in each SIRPα D1 domain variant (SEQ ID NOs: 13-14). In some embodiments, the SIRPα D1 domain polypeptide or SIRPα D1 domain variant comprises a fragment of the D1 domain. In some embodiments, the SIRPα polypeptide fragment or SIRPα D1 domain variant fragment comprises an amino acid sequence of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. In some embodiments, the SIRPα D1 domain fragments retain the ability to bind to CD47.

In some embodiments, a polypeptide of the disclosure comprising a SIRPα D1 domain variant binds with higher binding affinity to CD47 than a wild-type human SIRPα D1 domain. In some embodiments, the SIRPα D1 domain variant binds to human CD47 with at least 1-fold (e.g., at least 1.5-fold, 2-fold, 2.5-fold, 3-fold, 3.5-fold, 4-fold, 5-fold or greater than 5-fold) affinity than the affinity of a naturally occurring D1 domain. In some embodiments, the SIRPα D1 domain variant binds to human CD47 with at least 1-fold (e.g., at least 10-fold, 100-fold, 1000-fold or greater than 1000-fold) affinity than the affinity of a naturally occurring D1 domain.

As used herein, the term "optimized affinity" or "optimized binding affinity" refers to an optimized strength of the binding interaction between a polypeptide disclosed herein,

TABLE 1

Sequences of Wild-Type SIRPα D1 Domains

| SEQ ID NO: | Description | Amino Acid Sequence |
|---|---|---|
| 1 | Wild-type D1 domain variant 1 | EEELQVIQPDKSVLVAAGETATLRCTATSLIPVGPIQ WFRGAGPGRELIYNQKEGHFPRVTTVSDLTKRNNM DFSIRIGNITPADAGTYYCVKFRKGSPDDVEFKSGAG TELSVRAKPS |
| 2 | Wild-type D1 domain variant 2 | EEELQVIQPDKSVSVAAGESAILHCTVTSLIPVGPIQW FRGAGPARELIYNQKEGHFPRVTTVSESTKRENMDF SISISNITPADAGTYYCVKFRKGSPDTEFKSGAGTELS VRAKPS |
| 11 | Wild-type pan-D1 domain | EEX$_1$LQVIQPDKX$_2$VX$_3$VAAGEX$_4$AX$_5$LX$_6$CTX$_7$TSLIP VGPIQWFRGAGPX$_8$RELIYNQKEGHFPRVTTVSX$_9$X$_{10}$ TKRX$_{11}$NMDFX$_{12}$IX$_{13}$IX$_{14}$NITPADAGTYYCVKFRKGS X$_{15}$X$_{16}$DX$_{17}$EFKSGAGTELSVRX$_{18}$KPS |
| | Amino acid substitutions relative to SEQ ID NO: 11 | X$_1$ is E or G; X$_2$ is S or F; X$_3$ is L or S; X$_4$ is T or S; X$_5$ is T or I; X$_6$ is R, H, or L; X$_7$ is A or V; X$_8$ is G or A; X$_9$ is D or E; X$_{10}$ is L or S; X$_{11}$ is N or E or D; X$_{12}$ is S or P; X$_{13}$ is R or S; X$_{14}$ is G or S; X$_{15}$ is P or absent; X$_{16}$ is D or P; X$_{17}$ is V or T; and X$_{18}$ is A or G |

As used herein, the term "SIRPα D1 domain variant" refers to a polypeptide comprising a SIRPα D1 domain or a CD47-binding portion of a SIRPα polypeptide that has a higher affinity to CD47 than wild-type SIRPα. A SIRPα D1 domain variant comprises at least one amino acid substitution, deletion, or insertion (or a combination thereof) relative to a wild-type SIRPα.

In some embodiments, SIRPα D1 domain variants disclosed herein comprise a SIRPα D1 domain or variant thereof. In some embodiments, a SIRPα D1 domain variant including a SIRPα D1 domain variant, and CD47. For example, in some embodiments, the polypeptide binds primarily or with higher affinity to CD47 on cancer cells and does not substantially bind or binds with lower affinity to CD47 on non-cancer cells. In some embodiments, the binding affinity between the polypeptide and CD47 is optimized such that the interaction does not cause clinically relevant toxicity or decreases toxicity compared to a variant which binds with maximal affinity. In some embodiments, in order to achieve an optimized binding affinity between a polypeptide provided herein and CD47, the polypeptide including a SIRPα D1 domain variant is developed to have a lower binding affinity to CD47 than which is maximally achievable. In some embodiments, the SIRPα D1 domain variants disclosed herein cross react with rodent, non-human primate (NIP), and human CD47.

As used herein, the term "immunogenicity" refers to the property of a protein (e.g., a therapeutic protein) which causes an immune response in the host as though it is a foreign antigen. The immunogenicity of a protein can be assayed in vitro in a variety of different ways, such as through in vitro T-cell proliferation assays.

As used herein, the term "minimal immunogenicity" refers to an immunogenicity of a protein (e.g., a therapeutic protein) that has been modified, e.g., through amino acid substitutions, to be lower (e.g., at least 10%, 25%, 50%, or 100% lower) than the immunogenicity before the amino acid substitutions are introduced (e.g., an unmodified protein). In some embodiments, a protein (e.g., a therapeutic protein) is modified to have minimal immunogenicity and causes no or very little host immune response even though it is a foreign antigen.

In some embodiments, the SIRPα D1 domain variant demonstrates minimal immunogenicity. In some embodiments, a SIRPα polypeptide of the disclosure administered to a subject has the same amino acid sequence as that of the SIRPα polypeptide in a biological sample of the subject, except for amino acid changes which increase affinity of the SIRPα D1 domain variant. In some embodiments, the polypeptide variants disclosed herein do not cause acute anemia in rodent or non-human primates (NHP) studies.

Table 2 lists specific amino acid substitutions in a SIRPα D1 domain variant relative to each D1 domain sequence. In some embodiments, a SIRPα D1 domain variant includes one or more (e.g., two, three, four, five, six, seven, eight, nine, ten, eleven, twelve, thirteen, fourteen or more) of the substitutions listed in Table 2. In some embodiments, a SIRPα D1 domain variant includes at most fourteen amino acid substitutions relative to a wild-type D1 domain. In some embodiments, a SIRPα D1 domain variant includes at most ten amino acid substitutions relative to a wild-type D1 domain. In some embodiments, a SIRPα D1 domain variant includes at most seven amino acid substitutions relative to a wild-type D1 domain. In some embodiments, a SIRPα D1 domain variant of the disclosure has at least 90% (e.g., at least 92%, 95%, 97% or greater than 97%) amino acid sequence identity to a sequence of a wild-type D1 domain.

In some embodiments, a SIRPα D1 domain variant is a chimeric SIRPα D1 domain variant that includes a portion of two or more wild-type D1 domains or variants thereof (e.g., a portion of one wild-type D1 domain or variant thereof and a portion of another wild-type D1 domain or variant thereof). In some embodiments, a chimeric SIRPα D1 domain variant includes at least two portions (e.g., three, four, five or more portions) of wild-type D1 domains or variants thereof, wherein each of the portions is from a different wild-type D1 domain. In some embodiments, a chimeric SIRPα D1 domain variant further includes one or more amino acid substitutions listed in Table 2.

TABLE 2

Amino Acid Substitutions in a SIRPα D1 Domain Variant

| SEQ ID NO: | Description | Amino Acid Sequence |
|---|---|---|
| 13 | D1 domain v1 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRIGNITPADAGTYYCX$_{12}$KX$_{13}$RKGSPDDVE X$_{14}$KSGAGTELSVRAKPS |
| — | Amino acid substitutions relative to SEQ ID NO: 13 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = V, I; X$_{13}$ = F, L, V; X$_{14}$ = F, V |
| 14 | D1 domain v2 | EEEX$_1$QX$_2$IQPDKSVSVAAGESX$_3$ILHCTX$_4$TSLX$_5$PVGPI QWFRGAGPARX$_6$LIYNQX$_7$X$_8$GX$_9$FPRVTTVSEX$_{10}$TX$_{11}$R ENMDFSISISNITPADAGTYYCX$_{12}$KX$_{13}$RKGSPDTEX$_{14}$K SGAGTELSVRAKPS |
| — | Amino acid substitutions relative to SEQ ID NO: 14 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = V, I; X$_{13}$ = F, L, V; X$_{14}$ = F, V |
| 23 | Pan D1 domain | EEX$_1$X$_2$QX$_3$IQPDKX$_4$VX$_5$VAAGEX$_6$X$_7$X$_8$LX$_9$CTX$_{10}$TSLX$_{11}$ PVGPIQWFRGAGPX$_{12}$RX$_{13}$LIYNQX$_{14}$X$_{15}$GX$_{16}$FPRVTT VSX$_{17}$X$_{18}$TX$_{19}$RX$_{20}$NMDFX$_{21}$IX$_{22}$IX$_{23}$NITPADAGTYYCX$_{24}$ KX$_{25}$RKGSPDX$_{26}$X$_{27}$EX$_{28}$KSGAGTELSVRX$_{29}$KPS |
| — | Amino acid substitutions relative to SEQ ID NO: 23 | X$_1$ = E, G; X$_2$ = L, I, V; X$_3$ = V, L, I; X$_4$ = S, F; X$_5$ = L, S; X$_6$ = S, T; X$_7$ = A, V; X$_8$ = I, T; X$_9$ = H, R; X$_{10}$ = A, V, I, L; X$_{11}$ = I, T, S, F; X$_{12}$ = A, G; X$_{13}$ = E, V, L; X$_{14}$ = K, R; X$_{15}$ = E, Q; X$_{16}$ = H, P, R; X$_{17}$ = D, E; X$_{18}$ = S, L, T, G; X$_{19}$ = K, R; X$_{20}$ = E, D; X$_{21}$ = S, P; X$_{22}$ = S, R; X$_{23}$ = S, G; X$_{24}$ = V, I; X$_{25}$ = F, L, V; X$_{26}$ = D or absent; X$_{27}$ = T, V; X$_{28}$ = F, V; and X$_{29}$ = A, G | peptide variants disclosed herein lower the risk of side effects compared to anti-CD47 antibodies or wild-type SIRPα. In some embodiments, the polypeptide variants disclosed herein lower the risk of anemia compared to anti-CD47 antibodies or wild-type SIRPα. In some embodi- In some embodiments, a polypeptide comprises a SIRPα D1 domain variant that comprises a sequence of EEEX$_1$QX$_2$IQPDKSVLVAAGETX$_3$TLRCTX$_4$TSLX$_5$PV-GPIQWFRGAGPGRX$_6$LIYNQX$_7$X$_8$G X$_9$FPRVTTV SDX$_{10}$TX$_{11}$RNNMFSJRIGNJTPADAGTYYCX$_{12}$KX$_{13}$ RKGSPDDVEX$_{14}$KSGA GTELSVRAKPS (SEQ ID NO: 13), wherein X$_1$ is L, I, or V; X$_2$ is V, L, or, I; X$_3$ is A or V; X$_4$ is A, I, or L; X$_5$ is I, T, S, or F; X$_6$ is E, V, or L; X$_7$ is K or R; X$_8$ is E or Q; X$_9$ is H, P, or R; X$_{10}$ is L, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 1.

In some embodiments, a polypeptide comprises a SIRPα D1 domain variant that comprises the sequence of SEQ TD NOs: 13, wherein X$_1$ is L, I, or V. In any of the aforementioned embodiments, X$_2$ is V, L, or, IL In some embodiments, X$_3$ is A or V. In some embodiments, X$_4$ is A, I, or L. In some embodiments, X$_5$ is I, T, S, or F. In some embodiments, X$_6$ is E, V, or L. In some embodiments, X$_7$ is K or R. In some embodiments, X$_8$ is E or Q. In some embodiments, X$_9$ is H, P, or R. In some embodiments, X$_{10}$ is L, T, or G. In some embodiments, X$_{11}$ is K or R. In some embodiments, X$_{12}$ is V or I. In some embodiments, X$_{13}$ is F, L, V. In some embodiments, X$_{14}$ is F or V. In some embodiments, the polypeptide of this aspect of the disclosure includes no more than six amino acid substitutions relative to the wild-type SIRPα D1 domain that comprises the sequence of SEQ ID NO: 1.

In some embodiments, the polypeptide binds CD47 with at least 10-fold greater binding affinity than the wild-type SIRPα D1 domain that comprises the sequence of SEQ ID NO: 1. In some embodiments, the polypeptide binds CD47 with at least 100-fold greater binding affinity than the wild-type SIRPα D1 domain that comprises the sequence of SEQ ID NO: 1. In some embodiments, the polypeptide binds CD47 with at least 1000-fold greater binding affinity than the wild-type SIRPα D1 domain that comprises the sequence of SEQ ID NO: 1. In some embodiments, a SIRPα D1 domain variant polypeptide or fragment thereof binds to CD47 with a KD less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a KD between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant that comprises a sequence of: EEEX$_1$QX$_2$IQPDKSVSVAAGESX$_3$ILHCTX$_4$TSLX$_5$PV-GPIQWFRGAGPARX$_6$LIYNQX$_7$X$_8$G X$_9$FPRVTTVSEX$_{10}$TX$_{11}$RENMDFSISISNITPADAGT-YYCX$_{12}$KX$_{13}$RKGSPDTEX$_{14}$KSGAGT ELSVRAKPS (SEQ ID NO: 14), wherein X$_1$ is L, I, or V; X$_2$ is V, L, or, I; X$_3$ is A or V; X$_4$ is V, I, or L; X$_5$ is I, T, S, or F; X$_6$ is E, V, or L; X$_7$ is K or R; X$_8$ is E or Q; X$_9$ is H, P, or R; X$_{10}$ is S, T, or G; X$_{11}$ is K or R; X$_{12}$ is V or I; X$_{13}$ is F, L, or V; and X$_{14}$ is F or V; and wherein the variant comprises at least one amino acid substitution relative to a wild-type SIRPα D1 domain that comprises the sequence of SEQ ID NO: 2.

In some embodiments in this aspect of the disclosure, the polypeptide comprises the sequence of SEQ ID NO: 14, wherein X$_1$ is L, I, or V. In some embodiments, X$_2$ is V, L, or, I. In some embodiments, X$_3$ is A or V. In some embodiments, X$_4$ is V, I, or L. In some embodiments, X$_5$ is I, T, S, or F. In some embodiments, X$_6$ is E, V, or L. In some embodiments, X$_7$ is K or R. In some embodiments, X$_8$ is E or Q. In some embodiments, X$_9$ is H, P, or R. In some embodiments, X$_{10}$ is S, T, or G. In some embodiments, X$_{11}$ is K or R. In some embodiments, X$_{12}$ is V or I. In some embodiments, X$_{13}$ is F, L, or V. In some embodiments, X$_{14}$ is F or V. In some embodiments, the polypeptide of this aspect of the disclosure includes no more than six amino acid substitutions relative to the wild-type SIRPα D1 domain that comprises the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, a SIRPα D1 domain variant polypeptide or fragment thereof binds to CD47 with a K$_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a K$_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEX$_1$X$_2$QX$_3$IQPDKX$_4$VX$_5$VAAGEX$_6$X$_7$X$_8$LX$_9$CTX$_{10}$-TSLX$_{11}$PVGPIQWFRGAGPX$_{12}$RX$_{13}$LIY NQX$_{14}$X$_{15}$GX$_{16}$FPRVTTVSX$_{17}$X$_{18}$TX$_{19}$RX$_{20}$NMDFX$_{21}$-IX$_{22}$IX$_{23}$NITPADAGTYYCX$_{24}$KX$_{25}$RK GSPDX$_{26}$X$_{27}$EX$_{28}$KSGAGTELSVRX$_{29}$KPS (SEQ ID NO: 23), wherein X$_1$ is E or G; X$_2$ is L, I, or V; X$_3$ is V, L, or, I; X$_4$ is S or F; X$_5$ is L or S; X$_6$ is S or T; X$_7$ is A or V; X$_8$ is I or T; X$_9$ is H or R; X$_{10}$ is A, V, I, or L; X$_{11}$ is I, T, S, or F; X$_{12}$ is A or G; X$_{13}$ is E, V, or L; X$_{14}$ is K or R; X$_{15}$ is E or Q; X$_{16}$ is H, P, or R; X$_{17}$ is D or E; X$_{18}$ is S, L, T, or G; X$_{19}$ is K or R; X$_{20}$ is E or D; X$_{21}$ is S or P; X$_{22}$ is S or R; X$_{23}$ is S or G; X$_{24}$ is V or I; X$_{25}$ is F, L, V; X$_{26}$ is D or absent; X$_{27}$ is T or V; X$_{28}$ is F or V; and X$_{29}$ is A or G; and wherein the variant comprises at least one amino acid substitution relative to a wild-type SIRPα D1 domain having the sequence of SEQ ID NO: 1 or 2.

In any of the aforementioned embodiments in this aspect of the disclosure, X$_2$ is L, I, or V. In any of the aforementioned embodiments, X$_3$ is V, L, or, I. In embodiments, X$_4$ is S or F. In some embodiments, X$_5$ is L or S. In some embodiments, X$_6$ is S or T. In some embodiments, X$_7$ is A or V. In some embodiments, X$_8$ is I or T. In some embodiments, X$_9$ is H or R. In some embodiments, X$_{10}$ is A, V, I, or L. In some embodiments, X$_{11}$ is I, T, S, or F. In some embodiments, X$_{12}$ is A or G. In some embodiments, X$_{13}$ is E, V, or L. In some embodiments, X$_{14}$ is K or R. In some embodiments, X$_{15}$ is E or Q. In some embodiments, X$_{16}$ is H, P, or R. In some embodiments, X$_{17}$ is D or E. In some embodiments, X$_{18}$ is S, L, T, or G. In some embodiments, X$_{19}$ is K or R. In some embodiments, X$_{20}$ is E or D. In some embodiments, X$_{21}$ is S or P. In some embodiments, X$_{22}$ is S or R. In some embodiments, X$_{23}$ is S or G. In some embodiments, X$_{24}$ is V or I. In some embodiments, X$_{25}$ is F, L, V. In some embodiments, X$_{26}$ is D or absent. In some embodiments, X$_{27}$ is T or V. In some embodiments, X$_{28}$ is F or V. In some embodiments, X$_{29}$ is A or G. In some embodiments, the polypeptide of this aspect of the disclosure includes no more than six amino acid substitutions relative to the wild-type SIRPα D1 domain having the sequence of SEQ ID NO: 1 or 2.

In some embodiments, the polypeptide binds CD47 with at least 10-fold greater binding affinity than the wild-type SIRPα D1 domain having the sequence of SEQ ID NO: 1 or 2. In some embodiments, the polypeptide binds CD47 with at least 100-fold greater binding affinity than the wild-type SIRPα D1 domain having the sequence of SEQ ID NO: 1 or 2. In some embodiments, the polypeptide binds CD47 with at least 1000-fold greater binding affinity than the wild-type SIRPα D1 domain having the sequence of SEQ ID NO: 1 or 2. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide of the disclosure including a SIRPα D1 domain variant further comprises a D2 domain having the sequence of SEQ ID NO: 24, a D3 domain having the sequence of SEQ ID NO: 25, or a D2 domain having the sequence of SEQ ID NO: 24 and a D3 domain having the sequence of SEQ ID NO: 25 of a wild-type human SIRPα as shown in Table 3. In some embodiments, the SIRPα D1 domain variant further comprises a fragment or variant of a D2 domain or a fragment or variant of a D3 domain. In some embodiments, the SIRPα D1 domain variant further comprises a fragment or variant of a D2 domain and a fragment or variant of a D3 domain.

In some embodiments, a SIRPα D1 domain variant is joined to a D2 or D3 domain by way of a linker. In some embodiments, a SIRPα D1 domain variant is joined to a D2 and D3 domain by way of a linker.

TABLE 3

Amino Acid Sequences of SIRPα D2 and D3 Domains

| SEQ ID NO: | Description | Amino Acid Sequence |
|---|---|---|
| 24 | SIRPα D2 domain | APVVSGPAARATPQHTVSFTCESHGF SPRDITLKWFKNGNELSDFQTNVDPV GESVSYSIHSTAKVVLTREDVHSQVI CEVAHVTLQGDPLRGTANLSETIR |
| 25 | SIRPα D3 domain | VPPTLEVTQQPVRAENQVNVTCQVRK FYPQRLQLTWLENGNVSRTETASTVT ENKDGTYNWMSWLLVNVSAHRDDVKL TCQVEHDGQPAVSKSHDLKVS |

In some embodiments, a polypeptide of the disclosure including a SIRPα D1 domain variant is attached to an Fc domain variant in order to improve the pharmacokinetic properties of the polypeptide, e.g., increase serum half-life. In some embodiments, a SIRPα D1 domain variant is attached to an Fc domain variant that is unable to dimerism. In some embodiments, Fc domain variants serve to increase the serum half-life of the polypeptides described herein. In some embodiments, a polypeptide of the disclosure including a SIRPα D1 domain variant does not include the sequence of any one of SEQ ID NOs: 26-36 shown in Table 4.

TABLE 4

| SEQ ID NO: | AMINO ACID SEQUENCE |
|---|---|
| 26 | EEELQVIQPDKSVSVAAGESAILHCTITSLIPVGPIQWFRGAGPARELIYNQRE GHFPRVTTVSETTRRENMDFSISISNITPADAGTYYCVKFRKGSPDTEVKSGA GTELSVRAKPS |
| 27 | EEEVQVIQPDKSVSVAAGESAILHCTLTSLIPVGPIQWFRGAGPARVLIYNQRQ GHFPRVTTVSEGTRRENMDFSISISNITPADAGTYYCIKFRKGSPDTEFKSGAG TELSVRAKPS |
| 28 | EEEVQIIQPDKSVSVAAGESVILHCTITSLTPVGPIQWFRGAGPARLLIYNQRE GPFPRVTTVSETTRRENMDFSISISNITPADAGTYYCVKLRKGSPDTEFKSGAG TELSVRAKPS |
| 29 | EEELQIIQPDKSVSVAAGESAILHCTITSLSPVGPIQWFRGAGPARVLIYNQRQ GPFPRVTTVSEGTKRENMDFSISISNITPADAGTYYCIKLRKGSPDTEFKSGAG TELSVRAKPS |
| 30 | EEEIQVIQPDKSVSVAAGESVIIHCTVTSLFPVGPIQWFRGAGPARVLIYNQRQ GRFPRVTTVSEGTKRENMDFSISISNITPADAGTYYCVKVRKGSPDTEVKSGA GTELSVRAKPS |
| 31 | EEEVQIIQPDKSVSVAAGESIILHCTVTSLFPVGPIQWFRGAGPARVLIYNQRE GRFPRVTTVSEGTRRENMDFSISISNITPADAGTYYCIKLRKGSPDTEFKSGAG TELSVRAKPS |
| 32 | EEEVQLIQPDKSVSVAAGESAILHCTVTSLFPVGPIQWFRGAGPARVLIYNQR EGPFPRVTTVSEGTKRENMDFSISISNITPADAGTYYCIKFRKGSPDTEVKSGA GTELSVRAKPS |
| 33 | EEELQIIQPDKSVLVAAGETATLRCTITSLFPVGPIQWFRGAGPGRVLIYNQRQ GPFPRVTTVSDTTKRNNMDFSIRIGNITPADAGTYYCIKFRKGSPDDVEFKSG AGTELSVRAKPS |
| 34 | EEELQIIQPDKSVSVAAGESAILHCTITSLFPVGPIQWFRGAGPARLLIYNQRQ GPFPRVTTVSETTKRENMDFSISISNITPADAGTYYCVKFRKGSPDTEFKSGAG TELSVRAKPS |

TABLE 4-continued

| SEQ ID NO: | AMINO ACID SEQUENCE |
|---|---|
| 35 | EEEVQIIQPDKSVSVAAGESAILHCTITSLFPVGPIQWFRGAGPARVLIYNQKQ GPFPRVTTISETTRRENMDFSISISNITPADAGTYYCIKFRKGSPDTEFKSGAGT ELSVRAKPS |
| 36 | EEELQIIQPDKSVSVAAGESAILHCTITSLTPVGPIQWFRGAGPARVLIYNQRQ GPFPRVTTVSEGTRRENMDFSISISNITPADAGTYYCIKFRKGSPDTEVKSGAG TELSVRAKPS |

In some embodiments, the polypeptides and polypeptide constructs described herein are utilized in vitro for binding assays, such as immune assays. For example, in some embodiments, the polypeptides and polypeptide constructs described herein are utilized in liquid phase or bound to a solid phase carrier. In some embodiments, polypeptides utilized for immunoassays are detectably labeled in various ways.

In some embodiments, polypeptides and polypeptide constructs described herein are bound to various carriers and used to detect the presence of specific antigen expressing cells. Examples of carriers include glass, polystyrene, polypropylene, polyethylene, dextran, nylon, amylases, natural and modified celluloses, polyacrylamides, agaroses, and magnetite. The nature of the carrier can be either soluble or insoluble.

Various different labels and methods of labeling are known. Examples of labels include enzymes, radioisotopes, fluorescent compounds, colloidal metals, chemiluminescent compounds, and bio-luminescent compounds. Various techniques for binding labels to polypeptides disclosed herein are available.

In some embodiments, the polypeptides are coupled to low molecular weight haptens. These haptens are then specifically detected by means of a second reaction. For example, in some embodiments, the hapten biotin is used with avidin or the haptens dinitrophenyl, pyridoxal, or fluorescein are detected with specific anti-hapten antibodies (e.g., anti-dinitrophenyl antibodies, anti-pyridoxal antibodies, and anti-fluorescein antibodies respectively).

SIRPα D1 Domain Variants with Altered Glycosylation Patterns

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain (e.g., a wild-type SIRPα D1 domain set forth in SEQ ID NO: 1 or 2); and at least one additional amino acid mutation relative to a wild-type SIRPα D1 domain (e.g., a wild-type SIRPα D1 domain set forth in SEQ ID NO: 1 or 2) at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc domain variant, wherein an Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, a polypeptide in a composition disclosed herein comprises a SIRPα D1 domain variant that has reduced or minimal glycosylation. The D1 domain of SEQ ID NOs: 1 and 2 in Table 1 each contains a single potential N-linked glycosylation site at amino acid N80 in the sequence N80ITP. Expression of a SIRPα D1 domain in Chinese Hamster Ovary (CHO) cells results in a major band of 16 kDa (non-glycosylated) and a minor band of higher molecular weight that was removed by Endo Hf. Endo Hf is a recombinant protein fusion of Endoglycosidase H and maltose binding protein. Endo Hf cleaves within the chitobiose core of high mannose and some hybrid oligosaccharides from N-linked glycoproteins. This implies that a proline at amino acid position 83 can reduce the efficiency of glycosylation, leading to a protein with different degrees of glycosylation and therefore heterogeneity. For drug development, heterogeneity can give rise to challenges in process development. Therefore, to investigate the possibility of generating homogenous, non-glycosylated forms of SIRPα D1 domain variants, in some embodiments, amino acid N80 of a SIRPα D1 variant is mutated to Ala. In some embodiments, to make a non-glycosylated, SIRPα D1 domain variant, amino acid N80 in a SIRPα D1 domain variant is replaced by any amino acid, including any naturally and non-naturally occurring amino acid, e.g., N80A and N80Q. In some embodiments, a SIRPα D1 domain variant comprises an N80A mutation and at least 1 additional mutation (e.g., at least 2, 3, 4, 5, 6, 7, 8, 9, or 10 additional mutations or more). In some embodiments, the additional mutation is in the CD47 binding site. In some embodiments, the additional mutation is in the hydrophobic core of the D1 domain.

In some embodiments, a polypeptide in a composition disclosed herein includes a SIRPα D1 domain variant that has increased glycosylation relative to a wild-type SIRPα D1 domain. Another option to increase homogeneity of the final product is to enhance the efficiency of glycosylation at amino acid N80 and generate SIRPα D1 domain variants with increased glycosylation relative to a wild-type. In some embodiments, the amino acid P83 in the sequence NITP83 affects the degree of glycosylation at amino acid N80. In some embodiments, changing P83 to any amino acid increases the efficiency of glycosylation at N80. In some embodiments, amino acid P83 in a SIRPα D1 domain variant is replaced by any amino acid, including naturally and non-naturally amino acids, e.g., P83V, P83A, P83I, and P83L. In some embodiments, a polypeptide of the disclosure is expressed in a cell that is optimized not to glycosylate proteins that are expressed by such cell, for example by genetic engineering of the cell line (e.g., genetically engineered yeast or mammalian host) or modifications of cell culture conditions such as addition of kifunensine or by using a naturally non-glycosylating host such as a prokaryote (*E. coli*, etc.).

Table 5 lists specific amino acid substitutions in a SIRPα D1 domain variant relative to each D1 domain variant sequence. In some embodiments, a SIRPα D1 domain variant includes one or more (e.g., two, three, four, five, six, seven, eight, nine, ten, eleven, twelve, thirteen, fourteen or more) of the substitutions listed in Table 5. In some embodiments, the SIRPα D1 domain variants are not glycosylated or are minimally glycosylated. In some embodiments, the SIRPα D1 domain variants are fully glycosylated or almost fully glycosylated. In some embodiments, a SIRPα D1 domain variant includes at most fourteen amino acid substitutions relative to a wild-type D1 domain. In some embodiments, a SIRPα D1 domain variant includes at most ten amino acid substitutions relative to a wild-type D1 domain. In some embodiments, a SIRPα D1 domain variant includes at most seven amino acid substitutions relative to a wild-type D1 domain. In some embodiments, a SIRPα D1 domain variant of the disclosure has at least 90% (e.g., at least 92%, 95%, 97% or greater than 97%) amino acid sequence identity to a sequence of a wild-type D1 domain.

In some embodiments, a SIRPα D1 domain variant is a chimeric SIRPα D1 domain variant that includes a portion of two or more wild-type D1 domains or variants thereof (e.g., a portion of one wild-type D1 domain or variant thereof and a portion of another wild-type D1 domain or variant thereof). In some embodiments, a chimeric SIRPα D1 domain variant includes at least two portions (e.g., three, four, five or more portions) of wild-type D1 domains or variants thereof, wherein each of the portions is from a different wild-type D1 domain. In some embodiments, a chimeric SIRPα D1 domain variant further includes one or more amino acid substitutions listed in Table 5.

TABLE 5

Amino Acid Substitutions in a SIRPα D1 Domain Variant

| SEQ ID NO: | Description | Amino Acid Sequence |
|---|---|---|
| 37 | D1 domain v1 | EEEX$_1$QX$_2$IQPDKSVLVAAGETX$_3$TLRCTX$_4$TSLX$_5$PVGP IQWFRGAGPGRX$_6$LIYNQX$_7$X$_8$GX$_9$FPRVTTVSDX$_{10}$TX$_{11}$ RNNMDFSIRIGX$_{12}$ITX$_{13}$ADAGTYYCX$_{14}$KX$_{15}$RKGSPDD VEX$_{16}$KSGAGTELSVRAKPS |
| — | Amino acid substitutions relative to SEQ ID NO: 37 | X$_1$ = L, I, V; X$_2$ = V, L, I; X$_3$ = A, V; X$_4$ = A, I, L; X$_5$ = I, T, S, F; X$_6$ = E, V, L; X$_7$ = K, R; X$_8$ = E, Q; X$_9$ = H, P, R; X$_{10}$ = L, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 38 | D1 domain v2 | EEEX$_1$QX$_2$IQPDKSVSVAAGESX$_3$ILHCTX$_4$TSLX$_5$PVGPI QWFRGAGPARX$_6$LIYNQX$_7$X$_8$GX$_9$FPRVTTVSEX$_{10}$TX$_{11}$R ENMDFSISISX$_{12}$ITX$_{13}$ADAGTYYCX$_{14}$KX$_{15}$RKGSPDTEX$_{16}$ KSGAGTELSVRAKPS |
| — | Amino acid substitutions relative to SEQ ID NO: 38 | X$_1$ = L, I, V; X$_2$ = V, L, I; X$_3$ = A, V; X$_4$ = V, I, L; X$_5$ = I, T, S, F; X$_6$ = E, V, L; X$_7$ = K, R; X$_8$ = E, Q; X$_9$ = H, P, R; X$_{10}$ = S, T, G; X$_{11}$ = K, R; X$_{12}$ = N, A, C, D, E, F, G, H, I, K, L, M, P, Q, R, S, T, V, W, Y; X$_{13}$ = P, A, C, D, E, F, G, H, I, K, L, M, N, Q, R, S, T, V, W, Y; X$_{14}$ = V, I; X$_{15}$ = F, L, V; X$_{16}$ = F, V |
| 47 | Pan D1 domain | EEX$_1$X$_2$QX$_3$IQPDKX$_4$VX$_5$VAAGEX$_6$X$_7$X$_8$LX$_9$CTX$_{10}$TSLX$_{11}$ PVGPIQWFRGAGPX$_{12}$RX$_{13}$LIYNQX$_{14}$X$_{15}$GX$_{16}$FPRVTT VSX$_{17}$X$_{18}$TX$_{19}$RX$_{20}$NMDFX$_{21}$IX$_{22}$IX$_{23}$X$_{24}$ITX$_{25}$ADAGTYY CX$_{26}$KX$_{27}$RKGSPDX$_{28}$X$_{29}$EX$_{30}$KSGAGTELSVRX$_{31}$KPS |
| — | Amino acid substitutions relative to SEQ ID NO: 47 | X$_1$ = E, G; X$_2$ = L, I, V; X$_3$ = V, L, I; X$_4$ = S, F; X$_5$ = L, S; X$_6$ = S, T; X$_7$ = A, V; X$_8$ = I, T; X$_9$ = H, R, L; X$_{10}$ = A, V, I, L; X$_{11}$ = I, T, S, F; X$_{12}$ = A, G; X$_{13}$ = E, V, L; X$_{14}$ = K, R; X$_{15}$ = E, Q; X$_{16}$ = H, P, R; X$_{17}$ = D, E; X$_{18}$ = S, L, T, G; X$_{19}$ = K, R; X$_{20}$ = E, N; X$_{21}$ = S, P; X$_{22}$ = S, R; X$_{23}$ = S, G; X$_{24}$ = any amino acid; X$_{25}$ = any amino acid; X$_{26}$ = V, I; X$_{27}$ = F, L, V; X$_{28}$ = D or absent; X$_{29}$ = T, V; X$_{30}$ = F, V; and X$_{31}$ = A, G |
| 48 | Pan D1 domain | EEELQX$_1$IQPDKSVX$_2$VAAGEX$_3$AX$_4$LX$_5$CTX$_6$TSLX$_7$PV GPIQWFRGAGPX$_8$RX$_9$LIYNQX$_{10}$X$_{11}$GX$_{12}$FPRVTTVSX$_{13}$ X$_{14}$TKRX$_{15}$NMDFSIX$_{16}$IX$_{17}$X$_{18}$ITPADAGTYYCX$_{19}$KFRK GX$_{20}$X$_{21}$X$_{22}$DX$_{23}$EFKSGAGTELSVRAKPS |
| — | Amino acid substitutions relative to SEQ ID NO: 48 | X$_1$ = V, I; X$_2$ = L, S; X$_3$ = T, S; X$_4$ = T, I; X$_5$ = R, H; X$_6$ = A, V, I; X$_7$ = I, R, Y, K, F; X$_8$ = G, A; X$_9$ = E, V; X$_{10}$ = K, R; X$_{11}$ = E, D, Q; X$_{12}$ = H, P; X$_{13}$ = D, E; X$_{14}$ = S, L, T; X$_{15}$ = N, E; X$_{16}$ = R, S; X$_{17}$ = G, S; X$_{18}$ = N, A; X$_{19}$ = V, I; X$_{20}$ = S, I, M; X$_{21}$ = P or absent; X$_{22}$ = D, P; and X$_{23}$ = V, T |
| 49 | Pan D1 domain | EEELQX$_1$IQPDKSVLVAAGETATLRCTX$_2$TSLX$_3$PVGPIQ WFRGAGPGRX$_4$LIYNQX$_5$X$_6$GX$_7$FPRVTTVSDX$_8$TKRNN MDFSIRIGX$_9$ITPADAGTYYCX$_{10}$KFRKGSPDDVEFKSG AGTELSVRAKPS |

TABLE 5-continued

Amino Acid Substitutions in a SIRPα D1 Domain Variant

| SEQ ID NO: | Description | Amino Acid Sequence |
|---|---|---|
| — | Amino acid substitutions relative to SEQ ID NO: 49 | $X_1$ = V, I, L; $X_2$ = A, I, V, L; $X_3$ = I, F, S, T; $X_4$ = E, V, L; $X_5$ = K, R; $X_6$ = E, Q; $X_7$ = H, P, R; $X_8$ = L, T, S, G; $X_9$ = A; and $X_{10}$ = V, I |
| 50 | Pan D1 domain | EEELQX$_1$IQPDKSVSVAAGESAILHCTX$_2$TSLX$_3$PVGPIQ WFRGAGPARX$_4$LIYNQX$_5$X$_6$GX$_7$FPRVTTVSEX$_8$TKREN MDFSISISX$_9$ITPADAGTYYCX$_{10}$KFRKGSPDTEFKSGAG TELSVRAKPS |
| — | Amino acid substitutions relative to SEQ ID NO: 50 | $X_1$ = V, I; $X_2$ = V, I; $X_3$ = I, F; $X_4$ = E, V; $X_5$ = K, R; $X_6$ = E, Q; $X_7$ = H, P; $X_8$ = S, T; $X_9$ = N, A; and $X_{10}$ = V, I |
| 51 | Pan D1 domain | EEELQX$_1$IQPDKSVLVAAGETATLRCTX$_2$TSLX$_3$PVGPIQ WFRGAGPGRX$_4$LIYNQX$_5$EGX$_6$FPRVTTVSDX$_7$TKRNN MDFSIRIGX$_8$ITPADAGTYYCX$_9$KFRKGSPDDVEFKSGA GTELSVRAKPS |
| — | Amino acid substitutions relative to SEQ ID NO: 51 | $X_1$ = V, I; $X_2$ = A, I; $X_3$ = I, F; $X_4$ = E, V; $X_5$ = K, R; $X_6$ = H, P; $X_7$ = L, T; $X_8$ = N, A; and $X_9$ = V, I |
| 52 | Pan D1 domain | EEELQX$_1$IQPDKSVLVAAGETATLRCTX$_2$TSLX$_3$PVGPIQ WFRGAGPGRELIYNQX$_4$EGX$_5$FPRVTTVSDX$_6$TKRNNM DFSIRIGX$_7$ITPADAGTYYCVKFRKGSPDDVEFKSGAGT ELSVRAKPS |
| — | Amino acid substitutions relative to SEQ ID NO: 52 | $X_1$ = V, L, I; $X_2$ = A, I, L; $X_3$ = I, T, S, F; $X_4$ = K, R; $X_5$ = H, P, R; $X_6$ = L, T, G; and $X_7$ = N, A |
| 212 | Pan D1 domain | EEELQX$_1$IQPDKSVSVAAGESAILHCTX$_2$TSLX$_3$PVGPIQ WFRGAGPARELIYNQX$_4$EGX$_5$FPRVTTVSEX$_6$TKRENM DFSISISX$_7$ITPADAGTYYCVKFRKGSPDTEFKSGAGTE LSVRAKPS |
| — | Amino acid substitutions relative to SEQ ID NO: 212 | $X_1$ = V, L, I; $X_2$ = V, I, L; $X_3$ = I, T, S, F; $X_4$ = K, R; $X_5$ = H, P, R; $X_6$ = S, T, G; and $X_7$ = N, A |
| 218 | Pan D1 domain | EEELQX$_1$IQPDKSVLVAAGETATLRCTX$_2$TSLX$_3$PVGPIQ WFRGAGPGRX$_4$LIYNQX$_5$X$_6$GX$_7$FPRVTTVSDX$_8$TKRNN MDFSIRIGX$_9$X$_{10}$X$_{11}$X$_{12}$ADAGTYYCX$_{13}$KFRKGSPDDVE FKSGAGTELSVRAKPS |
| — | Amino acid substitutions relative to SEQ ID NO: 218 | $X_1$ = V, L, or I; $X_2$ = A, V, L, or I; $X_3$ = I, S, T, or F; $X_4$ = E, L, or V; $X_5$ = K or R; $X_6$ = E or Q; $X_7$ = H, R or P; $X_8$ = S, G, L or T; $X_9$ = any amino acid; $X_{10}$ = any amino acid; $X_{11}$ = any amino acid; $X_{12}$ = any amino acid; and $X_{13}$ = V or I |
| 219 | Pan D1 domain | EEELQX$_1$IQPDKSVLVAAGETATLRCTX$_2$TSLX$_3$PVGPIQ WFRGAGPGRX$_4$LIYNQX$_5$X$_6$GX$_7$FPRVTTVSDX$_8$TKRNN MDFSIRIGX$_9$ITX$_{10}$ADAGTYYCX$_{11}$KFRKGSPDDVEFKS GAGTELSVRAKPS |
| — | Amino acid substitutions relative to SEQ ID NO: 219 | $X_1$ = V, L or I; $X_2$ = A, V, L, or I; $X_3$ = I, S, T or F; $X_4$ = E, L, or V; $X_5$ = K or R; $X_6$ = E or Q; $X_7$ = H, R or P; $X_8$ = S, G, L, or T; $X_9$ = N, $X_{10}$ = any amino acid other than P; and $X_{11}$ = V or I |

In some embodiments, a polypeptide includes a SIRPα-D1 domain variant having a sequence of: EEEX$_1$QX$_2$IQPDKSVLVAAGETX$_3$TLRCTX$_4$TSLX$_5$PV-GPIQWFRGAGPGRX$_6$LIYNQX$_7$X$_8$GX$_9$FPRVTTVSDX$_{10}$TX$_{11}$iRNNMDJFSIRIGX$_{12}$ITX$_{13}$-ADAGTYYCX$_{14}$KX$_{15}$RKGSPDDVEX$_{16}$KS GAG-TELSVRAKPS (SEQ ID NO: 37), wherein $X_1$ is L, I, or V; $X_2$ is V, L, or, I; $X_3$ is A or V; $X_4$ is A, I, or L; $X_5$ is I, T, S, or F; $X_6$ is E, V, or L; $X_7$ is K or R; $X_8$ is E or Q; $X_9$ is H, P, or R; $X_{10}$ is L, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D1 domain having the sequence of SEQ ID NO: 1.

In some embodiments in this aspect of the disclosure, a polypeptide includes a SIRPα D1 domain variant having a sequence of SEQ ID NO: 37, wherein $X_1$ is L, I, or V. In some embodiments, $X_2$ is V, L, or, I. In some embodiments, $X_3$ is A or V. In some embodiments, $X_4$ is A, I, or L. In some embodiments, $X_5$ is I, T, S, or F. In some embodiments, $X_6$ is E, V, or L. In some embodiments, $X_7$ is K or R. In some embodiments, $X_8$ is E or Q. In some embodiments, $X_9$ is H, P, or R. In some embodiments, $X_{10}$ is L, T, or G. In some embodiments, $X_{11}$ is K or R. In some embodiments, $X_{12}$ is N, A, C, D, E, F, G, H, I, K, L, M, P, Q, R, S, T, V, W, or Y. In some embodiments, $X_{13}$ is P, A, C, D, E, F, G, H, I, K, L, M, N, Q, R, S, T, V, W, or Y. In some embodiments, $X_{14}$ is V or I. In some embodiments, $X_{15}$ is F, L, V. In some embodiments, $X_{16}$ is F or V.

In some embodiments, a polypeptide provided herein includes no more than ten amino acid substitutions relative to the wild-type SIRPα D1 domain having the sequence of SEQ ID NO: 1. In some embodiments, the polypeptide provided herein includes no more than seven amino acid substitutions relative to the wild-type SIRPα D1 domain having the sequence of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NO: 1. In some embodiments, the polypeptide binds CD47 with at least 1000-fold greater binding affinity than the wild-type SIRPα D1 domain having the sequence of SEQ ID NO: 1. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEEX$_1$QX$_2$IQPDKSVSVAAGESX$_3$ILHCTX$_4$TSLX$_5$PV-GPIQWFRGAGPARX$_6$LIYNQX$_7$X$_8$G X$_9$FPRVTTVSEX$_{10}$TX$_{11}$RENMDFSISISX$_{12}$ITX$_{13}$ADA-GTYYCX$_{14}$KX$_{15}$RKGSPDTEX$_{16}$KSGA GTELSVRAKPS (SEQ ID NO: 38), wherein $X_1$ is L, I, or V; $X_2$ is V, L, or, I; $X_3$ is A or V; $X_4$ is V, I, or L; $X_5$ is I, T, S, or F; $X_6$ is E, V, or L; $X_7$ is K or R; $X_8$ is E or Q; $X_9$ is H, P, or R; $X_{10}$ is S, T, or G; $X_{11}$ is K or R; $X_{12}$ is N, A, C, D, E, F, G, H, I, K, L, M, P, Q, R, S, T, V, W, or Y; $X_{13}$ is P, A, C, D, E, F, G, H, I, K, L, M, N, Q, R, S, T, V, W, or Y; $X_{14}$ is V or I; $X_{15}$ is F, L, or V; and $X_{16}$ is F or V; and wherein the variant comprises at least one amino acid substitution relative to a wild-type SIRPα D1 domain having the sequence of SEQ ID NO: 2.

In some embodiments in this aspect of the disclosure, a polypeptide includes a SIRPα D1 domain variant having a sequence of SEQ ID NO: 38, wherein $X_1$ is L, I, or V. In some embodiments, $X_2$ is V, L, or, I. In some embodiments, $X_3$ is A or V. In some embodiments, $X_4$ is V, I, or L. In some embodiments, $X_5$ is I, T, S, or F. In some embodiments, $X_6$ is E, V, or L. In some embodiments, $X_7$ is K or R. In some embodiments, $X_8$ is E or Q. In some embodiments, $X_9$ is H, P, or R. In some embodiments, $X_{10}$ is S, T, or G. In some embodiments, $X_{11}$ is K or R. In some embodiments, $X_{12}$ is N, A, C, D, E, F, G, H, I, K, L, M, P, Q, R, S, T, V, W, or Y. In some embodiments, $X_{13}$ is P, A, C, D, E, F, G, H, I, K, L, M, N, Q, R, S, T, V, W, or Y. In some embodiments, $X_{14}$ is V or I. In some embodiments, $X_{15}$ is F, L, or V. In some embodiments, $X_{16}$ is F or V.

In some embodiments, a polypeptide includes a SIRPα D1 domain variant having no more than ten amino acid substitutions relative to the wild-type SIRPα D1 domain having the sequence of SEQ ID NO: 2. In some embodiments, a polypeptide includes a SIRPα D1 domain variant having no more than seven amino acid substitutions relative to the wild-type SIRPα D1 domain having the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEX$_1$X$_2$QX$_3$IQPDKX$_4$VX$_5$VAAGEX$_6$X$_7$X$_8$LX$_9$CTX$_{10}$ TSLX$_{11}$PVGPIQWFRGAGPX$_{12}$RX$_{13}$LIY NQX$_{14}$X$_{15}$GX$_{16}$FPRVTTVSX$_{17}$X$_{18}$TX$_{19}$RX$_{20}$NMDFX$_{21}$ IX$_{22}$IX$_{23}$X$_{24}$ITX$_{25}$ADAGTYYCX$_{26}$KX$_{27}$RKGSPDX$_{28}$X$_{29}$ EX$_{30}$KSGAGTELSVRX$_{31}$KPS (SEQ ID NO: 47), wherein $X_1$ is E or G; $X_2$ is L, I, or V; $X_3$ is V, L, or, I; $X_4$ is S or F; $X_5$ is L or S; $X_6$ is S or T; $X_7$ is A or V; $X_8$ is I or T; $X_9$ is H, R, or L; $X_{10}$ is A, V, I, or L; $X_{11}$ is I, T, S, or F; $X_{12}$ is A or G; $X_{13}$ is E, V, or L; $X_{14}$ is K or R; $X_{15}$ is E or Q; $X_{16}$ is H, P, or R; $X_{17}$ is D or E; $X_{18}$ is S, L, T, or G; $X_{19}$ is K or R; $X_{20}$ is E or N; $X_{21}$ is S or P; $X_{22}$ is S or R; $X_{23}$ is S or G; $X_{24}$ is any amino acid; $X_{25}$ is any amino acid; $X_{26}$ is V or I; $X_{27}$ is F, L, V; $X_{28}$ is D or absent; $X_{29}$ is T or V; $X_{30}$ is F or V; and $X_{31}$ is A or G; and wherein the variant comprises at least one amino acid substitution relative to a wild-type SIRPα D1 domain having the sequence of SEQ ID NO: 1 or 2.

In some embodiments, the polypeptide comprises the sequence of SEQ ID NO: 47, wherein $X_1$ is E or G. In any of the aforementioned embodiments in this aspect of the disclosure, $X_2$ is L, I, or V. In any of the aforementioned embodiments, $X_3$ is V, L, or, I. In any of the aforementioned embodiments, $X_4$ is S or F. In any of the aforementioned embodiments, $X_5$ is L or S. In any of the aforementioned embodiments, $X_6$ is S or T. In any of the aforementioned embodiments, $X_7$ is A or V. In any of the aforementioned embodiments, $X_8$ is I or T. In any of the aforementioned embodiments, $X_9$ is H or R. In any of the aforementioned embodiments, $X_{10}$ is A, V, I, or L. In any of the aforementioned embodiments, $X_{11}$ is I, T, S, or F. In any of the aforementioned embodiments, $X_{12}$ is A or G. In any of the aforementioned embodiments, $X_{13}$ is E, V, or L. In any of the aforementioned embodiments, $X_{14}$ is K or R. In any of the aforementioned embodiments, $X_{15}$ is E or Q. In any of the aforementioned embodiments, $X_{16}$ is H, P, or R. In any of the aforementioned embodiments, $X_{17}$ is D or E. In any of the aforementioned embodiments, $X_{18}$ is S, L, T, or G. In any of the aforementioned embodiments, $X_{19}$ is K or R. In any of the aforementioned embodiments, $X_{20}$ is E or N. In any of the aforementioned embodiments, $X_{21}$ is S or P. In any of the aforementioned embodiments, $X_{22}$ is S or R. In any of the aforementioned embodiments, $X_{23}$ is S or G. In any of the aforementioned embodiments, $X_{24}$ is N, A, C, D, E, F, G, H, I, K, L, M, P, Q, R, S, T, V, W, or Y. In any of the aforementioned embodiments, $X_{25}$ is P, A, C, D, E, F, G, H, I, K, L, M, N, Q, R, S, T, V, W, or Y. In any of the aforementioned embodiments, $X_{26}$ is V or I. In any of the aforementioned embodiments, $X_{27}$ is F, L, V. In any of the aforementioned embodiments, $X_{28}$ is D or absent. In any of the aforementioned embodiments, $X_{29}$ is T or V. In any of the aforementioned embodiments, $X_{30}$ is F or V. In any of the aforementioned embodiments, $X_{31}$ is A or G.

In some embodiments, the polypeptide of this aspect of the disclosure includes no more than ten amino acid substitutions relative to the wild-type SIRPα D1 domain having the sequence of SEQ ID NO: 1 or 2. In some embodiments, the polypeptide of this aspect of the disclosure includes no more than seven amino acid substitutions relative to the wild-type SIRPα D1 domain having the sequence of SEQ ID NO: 1 or 2.

In some embodiments, the polypeptide binds CD47 with at least 10-fold greater binding affinity than the wild-type SIRPα D1 domain having the sequence of SEQ ID NO: 1 or 2. In some embodiments, the polypeptide binds CD47 with at least 100-fold greater binding affinity than the wild-type SIRPα D1 domain having the sequence of SEQ ID NO: 1 or 2. In some embodiments, the polypeptide binds CD47 with at least 1000-fold greater binding affinity than the wild-type SIRPα D1 domain having the sequence of SEQ ID NO: 1 or 2. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, a polypeptide includes a SIRPα D1 domain variant having a sequence of: EEELQX$_1$IQPDKSVX$_2$VAAGEX$_3$AX$_4$LX$_5$CTX$_6$TSLX$_7$PVGPIQWFRGAGPX$_8$RX$_9$LIYNQX$_{10}$X$_{11}$GX$_{12}$FPRVTTVSX$_{13}$X$_{14}$TKRX$_{15}$NMDFSIX$_{16}$IX$_{17}$X$_{18}$ITPADAGTYYCX$_{19}$KFRKGX$_{20}$X$_{21}$X$_{22}$DX$_{23}$EFKSGAGTELSVRAKPS (SEQ ID NO: 48), wherein $X_1$ is V or I; $X_2$ is L or S; $X_3$ is T or S; $X_4$ is T or I; $X_5$ is R or H; $X_6$ is A, V, or I; $X_7$ is I, R, Y, K or F; $X_8$ is G or A; $X_9$ is E or V; $X_{10}$ is K or R; $X_{11}$ is E, D or Q; $X_{12}$ is H or P; $X_{13}$ is D or E; $X_{14}$ is S, L or T; $X_{15}$ is N or E; $X_{16}$ is R or S; $X_{17}$ is G or S; $X_{18}$ is N or A; $X_{19}$ is V or I; $X_{20}$ is S, I or M; $X_{21}$ is P or absent; $X_{22}$ is D or P; and $X_{23}$ is V or T, or a fragment thereof.

In another aspect, the disclosure features a polypeptide including a SIRPα D1 domain variant having a sequence of: EEELQX$_1$IQPDKSVLVAAGETATLRCTX$_2$TSLX$_3$PVGPIQWFRGAGPGRX$_4$LIYNQX$_5$X$_6$GX$_7$FPRVTTVSDX$_8$TKRNNMIDFSIRIGX$_9$ITPADAGTYYCX$_{10}$KFRKGSPDDVEFKSGAGTELSV RAKPS (SEQ ID NO: 49), wherein $X_1$ is V, L, or I; $X_2$ is A, I, V, or L; $X_3$ is I, F, S, or T; $X_4$ is E, V, or L; $X_5$ is K or R; $X_6$ is E or Q; $X_7$ is H, P, or R; $X_8$ is L, T, S, or G; $X_9$ is A; and $X_{10}$ is V or I; and wherein the variant comprises at least one amino acid substitution relative to a wild-type SIRPα D1 domain having the sequence of SEQ ID NO: 1.

In some embodiments, the polypeptide comprises the sequence of SEQ ID NO: 49, wherein $X_1$ is V, L or I. In any of the aforementioned embodiments in this aspect of the disclosure, $X_2$ is A, I, V, or L. In any of the aforementioned embodiments, $X_3$ is I, F, S, or T. In any of the aforementioned embodiments, $X_4$ is E, V, or L. In any of the aforementioned embodiments, $X_5$ is K or R. In any of the aforementioned embodiments, $X_6$ is E or Q. In any of the aforementioned embodiments, $X_7$ is H, P, or R. In any of the aforementioned embodiments, $X_8$ is L, T, S or G. In any of the aforementioned embodiments, $X_9$ is A. In any of the aforementioned embodiments, $X_{10}$ is V or I.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 49, wherein each of $X_1$, $X_2$, $X_3$, $X_4$, $X_5$, $X_6$, $X_7$, $X_8$, $X_9$, and $X_{10}$ are not a wild-type amino acid.

In some embodiments, the polypeptide of this aspect of the disclosure includes no more than ten amino acid substitutions relative to the wild-type SIRPα D1 domain having the sequence of any one of SEQ ID NO: 1. In some embodiments, the polypeptide of this aspect of the disclosure includes no more than seven amino acid substitutions relative to the wild-type SIRPα D1 domain having the sequence of any one of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NO: 1. In some embodiments, the polypeptide binds CD47 with at least 1000-fold greater binding affinity than the wild-type SIRPα D1 domain having the sequence of SEQ ID NO: 1. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVSVAAGESAILHCTX$_2$TSLX$_3$PVGPIQWFRGAGPARX$_4$LIYNQX$_5$X$_6$GX$_7$FPRVTTVSEX$_8$TKRENMDFSISISX$_9$ITPADAGTYYCX$_{10}$KFRKGSPDTEFKSGAGTELSVR AKPS, (SEQ ID NO: 50), wherein $X_1$ is V or I; $X_2$ is V or I; $X_3$ is I or F; $X_4$ is E or V; $X_5$ is K or R; $X_6$ is E or Q; $X_7$ is H or P; $X_8$ is S or T; $X_9$ is N or A; and $X_{10}$ V or I; and wherein the variant comprises at least one amino acid substitution relative to a wild-type SIRPα D1 domain having the sequence of SEQ ID NO: 2.

In some embodiments, the polypeptide comprises the sequence of SEQ ID NO: 50, wherein $X_1$ is V or I. In any of the aforementioned embodiments in this aspect of the disclosure, $X_2$ is V or I. In any of the aforementioned embodiments, $X_3$ is I or F. In any of the aforementioned embodiments, $X_4$ is E or V. In any of the aforementioned embodiments, $X_5$ is K or R. In any of the aforementioned embodiments, $X_6$ is E or Q. In any of the aforementioned embodiments, $X_7$ is H or P. In any of the aforementioned embodiments, $X_8$ is S or R. In any of the aforementioned embodiments, $X_9$ is N or A. In any of the aforementioned embodiments, $X_{10}$ is V or I.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 50, wherein each of $X_1$, $X_2$, $X_3$, $X_4$, $X_5$, $X_6$, $X_7$, $X_8$, $X_9$, and $X_{10}$ is not a wild-type amino acid.

In some embodiments, the polypeptide of this aspect of the disclosure includes no more than ten amino acid substitutions relative to the wild-type SIRPα D1 domain having the sequence of SEQ ID NO: 2. In some embodiments, the polypeptide of this aspect of the disclosure includes no more than seven amino acid substitutions relative to the wild-type SIRPα D1 domain having the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVLVAAGETATLRCTX$_2$TSLX$_3$PVGPIQWFRGAGPGRX$_4$LIYNQX$_5$EGX$_6$FPRVTTVSDX$_7$TKRNNMIDFSIRIGX$_8$ITPADAGTYYCX$_9$KFRKGSPDDVEFKSGAGTELSVRAKPS (SEQ ID NO: 51), wherein $X_1$ is V or I; $X_2$ is A or I; $X_3$ is I or F; $X_4$ is E or V; $X_5$ is K or R; $X_6$ is H or P; $X_7$ is L or T; $X_8$ is N or A; and $X_9$ is V or I; and wherein the variant comprises at least one amino acid substitution relative to a wild-type SIRPα D1 domain having the sequence of SEQ ID NO: 1.

In some embodiments, the polypeptide comprises the sequence of SEQ ID NO: 51, wherein $X_1$ is V or I. In any of the aforementioned embodiments in this aspect of the disclosure, $X_2$ is A or I. In any of the aforementioned embodiments, $X_3$ is I or F. In any of the aforementioned embodiments, $X_4$ is E or V. In any of the aforementioned embodiments, $X_5$ is K or R. In any of the aforementioned embodiments, $X_6$ is H or P. In any of the aforementioned embodiments, $X_7$ is L or T. In any of the aforementioned embodiments, $X_8$ is N or A. In any of the aforementioned embodiments, $X_9$ is V or I. In some embodiments, $X_4$ is not V.

In some embodiments, the polypeptide comprises the sequence of SEQ ID NO: 51, wherein $X_8$ is A. In any of the aforementioned embodiments in this aspect of the disclosure, $X_8$ is A and $X_1$ is V or I. In any of the aforementioned embodiments in this aspect of the disclosure, $X_8$ is A and $X_2$ is A or I. In any of the aforementioned embodiments, $X_8$ is A and $X_3$ is I or F. In any of the aforementioned embodiments, $X_8$ is A and $X_4$ is E or V. In some embodiments, $X_4$ is not V. In any of the aforementioned embodiments, $X_8$ is A and $X_5$ is K or R. In any of the aforementioned embodiments, $X_8$ is A and $X_6$ is H or P. In any of the aforementioned embodiments, $X_8$ is A and $X_7$ is A or V. In any of the aforementioned embodiments, $X_8$ is A and $X_9$ is V or I.

In some embodiments, the polypeptide comprises the sequence of SEQ ID NO: 51, wherein $X_8$ is A. In any of the aforementioned embodiments in this aspect of the disclosure, $X_8$ is A and $X_1$ is I. In any of the aforementioned embodiments in this aspect of the disclosure, $X_8$ is A and $X_2$ is I. In any of the aforementioned embodiments, $X_8$ is A and $X_3$ is F. In any of the aforementioned embodiments, $X_8$ is A and $X_4$ is V. In any of the aforementioned embodiments, $X_8$ is A and $X_5$ is R. In any of the aforementioned embodiments, $X_8$ is A and $X_6$ is P. In any of the aforementioned embodiments, $X_8$ is A and $X_7$ is T. In any of the aforementioned embodiments, $X_8$ is A and $X_9$ is I.

In some embodiments, the polypeptide comprises a SIRPα D1 domain variant that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 51, wherein each of $X_1$, $X_2$, $X_3$, $X_4$, $X_5$, $X_6$, $X_7$, $X_8$, and $X_9$ is not a wild-type amino acid.

In some embodiments, the polypeptide of this aspect of the disclosure comprises no more than ten amino acid substitutions relative to the wild-type SIRPα D1 domain having the sequence of SEQ ID NO: 1. In some embodiments, the polypeptide of this aspect of the disclosure comprises no more than seven amino acid substitutions relative to the wild-type SIRPα D1 domain having the sequence of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NOs: 1. In some embodiments, the polypeptide binds CD47 with at least 1000-fold greater binding affinity than the wild-type SIRPα D1 domain having the sequence of SEQ ID NO: 1. In some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVLVAAGETATLRCTX$_2$TSLX$_3$PVGP- IQWFRGAGPGRELIYNQX$_4$EGX$_5$F PRVTTVSDX$_6$TKRNNMDFSIRIGX$_7$ITPADAGTYYC-VKFRKGSPDDVEFKSGAGTEL SVR AKPS (SEQ ID NO: 222), wherein X$_1$ is V, L, or I; X$_2$ is A, I, or L; X$_3$ is I, T, S, or F; X$_4$ is K or R; X$_5$ is H or P; X$_6$ is L, T, or G; X$_7$ is N or A; and wherein the variant comprises at least one amino acid substitution relative to a wild-type SIRPα D1 domain having a sequence according to SEQ ID NO: 1.

In some embodiments, the polypeptide comprises the sequence of SEQ ID NO: 222, wherein X$_1$ is V, L, or I. In any of the aforementioned embodiments in this aspect of the disclosure, X$_2$ is A, I, or L. In any of the aforementioned embodiments, X$_3$ is I, T, S, or F. In any of the aforementioned embodiments, X$_4$ is K or R. In any of the aforementioned embodiments, X$_5$ is H or P. In any of the aforementioned embodiments, X$_6$ is L, T, or G. In any of the aforementioned embodiments, X$_7$ is N or A.

In some embodiments, the polypeptide comprises the sequence of SEQ ID NO: 222, wherein X$_1$ is V or I. In any of the aforementioned embodiments in this aspect of the disclosure, X$_2$ is A or I. In any of the aforementioned embodiments, X$_3$ is I or F. In any of the aforementioned embodiments, X$_4$ is K or R. In any of the aforementioned embodiments, X$_5$ is H or P. In any of the aforementioned embodiments, X$_6$ is L or T. In any of the aforementioned embodiments, X$_7$ is N or A.

In some embodiments, the polypeptide comprises the sequence of SEQ ID NO: 222, wherein X$_7$ is A. In any of the aforementioned embodiments in this aspect of the disclosure, X$_7$ is A and X$_1$ is V or I. In any of the aforementioned embodiments in this aspect of the disclosure, X$_7$ is A and X$_2$ is A or I. In any of the aforementioned embodiments, X$_7$ is A and X$_3$ is I or F. In any of the aforementioned embodiments, X$_7$ is A and X$_4$ is K or R. In any of the aforementioned embodiments, X$_7$ is A and X$_5$ is H or P. In any of the aforementioned embodiments, X$_7$ is A and X$_6$ is L or T.

In some embodiments, the polypeptide comprises the sequence of SEQ ID NO: 222, wherein X$_7$ is A. In any of the aforementioned embodiments in this aspect of the disclosure, X$_7$ is A and X$_1$ is I. In any of the aforementioned embodiments in this aspect of the disclosure, X$_7$ is A and X$_2$ is I. In any of the aforementioned embodiments, X$_7$ is A and X$_3$ is F. In any of the aforementioned embodiments, X$_7$ is A and X$_4$ is R. In any of the aforementioned embodiments, X$_7$ is A and X$_5$ is P. In any of the aforementioned embodiments, X$_7$ is A and X$_6$ is T.

In some embodiments, the polypeptide comprises a SIRPα D1 domain that comprises at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 222, wherein each of X$_1$, X$_2$, X$_3$, X$_4$, X$_5$, X$_6$, and X$_7$ is not a wild-type amino acid.

In some embodiments, the polypeptide of this aspect of the disclosure includes no more than ten amino acid substitutions relative to the wild-type SIRPα D1 domain having the sequence of SEQ ID NO: 1. In some embodiments, the polypeptide of this aspect of the disclosure includes no more than seven amino acid substitutions relative to the wild-type SIRPα D1 domain having the sequence of SEQ ID NO: 1.

In some embodiments, the polypeptide binds CD47 with at least 10-fold greater binding affinity than the wild-type SIRPα D1 domain having the sequence of SEQ ID NO: 1. In some embodiments, the polypeptide binds CD47 with at least 100-fold greater binding affinity than the wild-type SIRPα D1 domain having the sequence of SEQ ID NO: 1. In some embodiments, the polypeptide binds CD47 with at least 1000-fold greater binding affinity than the wild-type SIRPα D1 domain having the sequence of SEQ ID NO: 1. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRPα D1 domain variant polypeptides and fragments thereof bind to CD47 with a higher affinity than a SIRPα polypeptide binds to CD47. For example, in some embodiments, a SIRPα D1 domain variant polypeptide or fragment thereof binds to CD47 with a $K_D$ less than $1\times10^{-8}$ M, less than $5\times10^{-9}$ M, less than $1\times10^{-9}$ M, less than $5\times10^{-10}$ M, less than $1\times10^{-10}$ M or less than $1\times10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In another aspect, the disclosure features a polypeptide including a SIRPα D1 domain variant having a sequence of: EEELQX$_1$IQPDKSVSVAAGESAILHCTX$_2$TSLX$_3$PVGP-IQWFRGAGPARELIYNQX$_4$EGX$_5$FP RVTTVSEX$_6$TKRENMDFSISISX$_7$ITPADAGTYYCV-KFRKGSPDTEFKSGAGTEL SVRAKP S (SEQ ID NO: 212), wherein X$_1$ is V, L, or I; X$_2$ is V, I, or L; X$_3$ is I, T, S, or F; X$_4$ is K or R; X$_5$ is H, P, or R; X$_6$ is S, T, of G; X$_7$ is N or A; and wherein the variant comprises at least one amino acid substitution relative to a wild-type SIRPα D1 domain having the sequence of SEQ ID NO: 2.

In some embodiments, the polypeptide comprises the sequence of SEQ ID NO: 212, wherein X$_1$ is V, L, or I. In any of the aforementioned embodiments in this aspect of the disclosure, X$_2$ is V, I, or L. In any of the aforementioned embodiments, X$_3$ is I, T, S, or F. In any of the aforementioned embodiments, X$_4$ is K or R. In any of the aforementioned embodiments, X$_5$ is H or P. In any of the aforementioned embodiments, X$_6$ is S, T, or G. In any of the aforementioned embodiments, X$_7$ is N or A.

In some embodiments, the polypeptide comprises the sequence of SEQ ID NO: 212, wherein X$_1$ is V or I. In any of the aforementioned embodiments in this aspect of the disclosure, X$_2$ is V or I. In any of the aforementioned embodiments, X$_3$ is I or F. In any of the aforementioned embodiments, X$_4$ is K or R. In any of the aforementioned embodiments, X$_5$ is H or P. In any of the aforementioned embodiments, X$_6$ is S or T. In any of the aforementioned embodiments, X$_7$ is N or A.

In some embodiments, the polypeptide comprises the sequence of SEQ ID NO: 212, wherein X$_7$ is A. In any of the aforementioned embodiments in this aspect of the disclosure, X$_7$ is A and X$_1$ is V or I. In any of the aforementioned embodiments in this aspect of the disclosure, X$_7$ is A and X$_2$ is V or I. In any of the aforementioned embodiments, X$_7$ is A and X$_3$ is I or F. In any of the aforementioned embodiments, X$_7$ is A and X$_4$ is K or R. In any of the aforementioned embodiments, X$_7$ is A and X$_5$ is H or P. In any of the aforementioned embodiments, X$_7$ is A and X$_6$ is S or T.

In some embodiments, the polypeptide comprises the sequence of SEQ ID NO: 212, wherein X$_7$ is A. In any of the aforementioned embodiments in this aspect of the disclosure, X$_7$ is A and X$_1$ is I. In any of the aforementioned embodiments in this aspect of the disclosure, $X_7$ is A and $X_2$ is I. In any of the aforementioned embodiments, $X_7$ is A and $X_3$ is F. In any of the aforementioned embodiments, $X_7$ is A and $X_4$ is R. In any of the aforementioned embodiments, $X_7$ is A and $X_5$ is P. In any of the aforementioned embodiments, $X_7$ is A and $X_6$ is T.

In some embodiments, the polypeptide comprises a SIRPα D1 domain having at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NO: 212, wherein each of $X_1$, $X_2$, $X_3$, $X_4$, $X_5$, $X_6$, and $X_7$ is not a wild-type amino acid.

In some embodiments, the polypeptide of this aspect of the disclosure includes no more than ten amino acid substitutions relative to the wild-type SIRPα D1 domain having the sequence of SEQ ID NO: 2. In some embodiments, the polypeptide of this aspect of the disclosure includes no more than seven amino acid substitutions relative to the wild-type SIRPα D1 domain having the sequence of SEQ ID NO: 2.

In some embodiments, the polypeptide binds CD47 with at least 10-fold greater binding affinity than the wild-type SIRPα D1 domain having the sequence of SEQ ID NO: 2. In some embodiments, the polypeptide binds CD47 with at least 100-fold greater binding affinity than the wild-type SIRPα D1 domain having the sequence of SEQ ID NO: 2. In some embodiments, the polypeptide binds CD47 with at least 1000-fold greater binding affinity than the wild-type SIRPα D1 domain having the sequence of SEQ ID NO: 2. In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRPα D1 domain variant polypeptides and fragments thereof bind to CD47 with a higher affinity than a SIRPα polypeptide binds to CD47. For example, in some embodiments, a SIRPα D1 domain variant polypeptide or fragment thereof binds to CD47 with a $K_D$ less than $1 \times 10^{-8}$ M, less than $5 \times 10^{-9}$ M, less than $1 \times 10^{-9}$ M, less $5 \times 10^{-10}$ M, less than $1 \times 10^{-10}$ M or less than $1 \times 10^{-11}$ M. In some embodiments, a SIRPα D1 domain variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

Described herein, in some embodiments, is a polypeptide comprising a SIRPα D1 domain variant having a sequence according to: EEELQX$_1$IQPDKSVLVAAGETATLR-CTX$_2$TSLX$_3$P TABLE 6-continued SIRPα Variant Polypeptides

| SEQ ID NO: | Amino Acid Sequence |
|---|---|
| 54 | EEELQVIQPDKSVSVAAGESAILHCTVTSLFPVGPIQWFRGAGPARELIYNQR<br>QGPFPRVTTVSESTKRENMDFSISISNITPADAGTYYCVKFRKGSPDTEFKSGA<br>GTELSVRAKPS |
| 55 | EEELQVIQPDKSVSVAAGESAILHCTITSLFPVGPIQWFRGAGPARVLIYNQRQ<br>GPFPRVTTVSETTKRENMDFSISISNITPADAGTYYCIKFRKGSPDTEFKSGAG<br>TELSVRAKPS |
| 56 | EEELQIIQPDKSVSVAAGESAILHCTVTSLFPVGPIQWFRGAGPARVLIYNQRQ<br>GPFPRVTTVSETTKRENMDFSISISNITPADAGTYYCIKFRKGSPDTEFKSGAG<br>TELSVRAKPS |
| 57 | EEELQIIQPDKSVSVAAGESAILHCTITSLIPVGPIQWFRGAGPARVLIYNQRQG<br>PFPRVTTVSETTKRENMDFSISISNITPADAGTYYCIKFRKGSPDTEFKSGAGT<br>ELSVRAKPS |
| 58 | EEELQIIQPDKSVSVAAGESAILHCTITSLFPVGPIQWFRGAGPARELIYNQRQ<br>GPFPRVTTVSETTKRENMDFSISISNITPADAGTYYCIKFRKGSPDTEFKSGAG<br>TELSVRAKPS |
| 59 | EEELQIIQPDKSVSVAAGESAILHCTITSLFPVGPIQWFRGAGPARVLIYNQKQ<br>GPFPRVTTVSETTKRENMDFSISISNITPADAGTYYCIKFRKGSPDTEFKSGAG<br>TELSVRAKPS |
| 60 | EEELQIIQPDKSVSVAAGESAILHCTITSLFPVGPIQWFRGAGPARVLIYNQRE<br>GPFPRVTTVSETTKRENMDFSISISNITPADAGTYYCIKFRKGSPDTEFKSGAG<br>TELSVRAKPS |
| 61 | EEELQIIQPDKSVSVAAGESAILHCTITSLFPVGPIQWFRGAGPARVLIYNQRQ<br>GHFPRVTTVSETTKRENMDFSISISNITPADAGTYYCIKFRKGSPDTEFKSGAG<br>TELSVRAKPS |
| 62 | EEELQIIQPDKSVSVAAGESAILHCTITSLFPVGPIQWFRGAGPARVLIYNQRQ<br>GPFPRVTTVSESTKRENMDFSISISNITPADAGTYYCIKFRKGSPDTEFKSGAG<br>TELSVRAKPS |
| 63 | EEELQIIQPDKSVSVAAGESAILHCTITSLFPVGPIQWFRGAGPARVLIYNQRQ<br>GPFPRVTTVSETTKRENMDFSISISNITPADAGTYYCVKFRKGSPDTEFKSGAG<br>TELSVRAKPS |
| 64 | EEELQVIQPDKSVSVAAGESAILHCTVTSLIPVGPIQWFRGAGPARELIYNQRE<br>GPFPRVTTVSESTKRENMDFSISISNITPADAGTYYCVKFRKGSPDTEFKSGAG<br>TELSVRAKPS |
| 65 | EEELQVIQPDKSVSVAAGESAILHCTVTSLFPVGPIQWFRGAGPARELIYNQR<br>EGPFPRVTTVSESTKRENMDFSISISNITPADAGTYYCVKFRKGSPDTEFKSGA<br>GTELSVRAKPS |
| 66 | EEELQVIQPDKSVSVAAGESAILHCTITSLFPVGPIQWFRGAGPARELIYNQRE<br>GPFPRVTTVSESTKRENMDFSISISNITPADAGTYYCVKFRKGSPDTEFKSGAG<br>TELSVRAKPS |
| 67 | EEELQVIQPDKSVSVAAGESAILHCTITSLFPVGPIQWFRGAGPARELIYNQRE<br>GPFPRVTTVSETTKRENMDFSISISNITPADAGTYYCVKFRKGSPDTEFKSGAG<br>TELSVRAKPS |
| 68 | EEELQIIQPDKSVSVAAGESAILHCTITSLFPVGPIQWFRGAGPARELIYNQREG<br>PFPRVTTVSESTKRENMDFSISISNITPADAGTYYCVKFRKGSPDTEFKSGAGT<br>ELSVRAKPS |
| 69 | EEELQVIQPDKSVSVAAGESAILHCTITSLIPVGPIQWFRGAGPARELIYNQRE<br>GPFPRVTTVSESTKRENMDFSISISNITPADAGTYYCVKFRKGSPDTEFKSGAG<br>TELSVRAKPS |
| 70 | EEELQIIQPDKSVSVAAGESAILHCTITSLFPVGPIQWFRGAGPARELIYNQREG<br>PFPRVTTVSETTKRENMDFSISISNITPADAGTYYCVKFRKGSPDTEFKSGAGT<br>ELSVRAKPS |
| 71 | EEELQVIQPDKSVLVAAGETATLRCTATSLFPVGPIQWFRGAGPGRELIYNQR<br>QGPFPRVTTVSDLTKRNNMDFSIRIGNITPADAGTYYCVKFRKGSPDDVEFKS<br>GAGTELSVRAKPS |
| 72 | EEELQIIQPDKSVLVAAGETATLRCTITSLFPVGPIQWFRGAGPGRELIYNQRE<br>GPFPRVTTVSDLTKRNNMDFSIRIGNITPADAGTYYCVKFRKGSPDDVEFKSG<br>AGTELSVRAKPS |

TABLE 6-continued

SIRPα Variant Polypeptides

| SEQ ID NO: | Amino Acid Sequence |
|---|---|
| 73 | EEELQVIQPDKSVLVAAGETATLRCTITSLFPVGPIQWFRGAGPGRELIYNQRE<br>GPFPRVTTVSDTTKRNNMDFSIRIGNITPADAGTYYCVKFRKGSPDDVEFKSG<br>AGTELSVRAKPS |
| 74 | EEELQIIQPDKSVLVAAGETATLRCTITSLFPVGPIQWFRGAGPGRELIYNQRE<br>GPFPRVTTVSDTTKRNNMDFSIRIGNITPADAGTYYCVKFRKGSPDDVEFKSG<br>AGTELSVRAKPS |
| 75 | EEELQVIQPDKSVLVAAGETATLRCTITSLFPVGPIQWFRGAGPGRELIYNQRE<br>GPFPRVTTVSDLTKRNNMDFSIRIGNITPADAGTYYCVKFRKGSPDDVEFKSG<br>AGTELSVRAKPS |
| 76 | EEELQVIQPDKSVLVAAGETATLRCTATSLFPVGPIQWFRGAGPGRELIYNQR<br>EGPFPRVTTVSDLTKRNNMDFSIRIGNITPADAGTYYCVKFRKGSPDDVEFKS<br>GAGTELSVRAKPS |
| 77 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPS |
| 78 | EEELQIIQPDKSVLVAAGETATLRCTITSLFPVGPIQWFRGAGPGRVLIYNQRQ<br>GPFPRVTTVSDTTKRNNMDFSIRIGAITPADAGTYYCIKFRKGSPDDVEFKSG<br>AGTELSVRAKPS |
| 79 | EEELQVIQPDKSVLVAAGETATLRCTATSLFPVGPIQWFRGAGPGRELIYNQR<br>QGPFPRVTTVSDLTKRNNMDFSIRIGAITPADAGTYYCVKFRKGSPDDVEFKS<br>GAGTELSVRAKPS |
| 80 | EEELQIIQPDKSVLVAAGETATLRCTITSLFPVGPIQWFRGAGPGRVLIYNQRE<br>GPFPRVTTVSDTTKRNNMDFSIRIGAITPADAGTYYCIKFRKGSPDDVEFKSG<br>AGTELSVRAKPS |
| 81 | EEELQVIQPDKSVLVAAGETATLRCTATSLFPVGPIQWFRGAGPGRELIYNQR<br>EGPFPRVTTVSDLTKRNNMDFSIRIGAITPADAGTYYCVKFRKGSPDDVEFKS<br>GAGTELSVRAKPS |
| 82 | EEELQVIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPS |
| 83 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPS |
| 84 | EEELQVIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |
| 85 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |
| 86 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPS |
| 87 | EEELQVIQPDKSVLVAAGETATLRCTATSLIPVGPIQWFRGAGPGRELIYNQK<br>EGHFPRVTTVSDLTKRNNMDFSIRIGNITPADAGTYYCVKFRKGSPDDVEFKS<br>GAGTELSVRAKPS |
| 195 | EEELQIIQPDKSVLVAAGETATLRCTMTSLFPVGPIQWFRGAGPGRELIYNQR<br>EGPFPRVTTVSDTTKRNNMDFSIRIGAITPADAGTYYCVKFRKGSPDDVEFKS<br>GAGTELSVRAKPS |
| 196 | EEELQIIQPDKSVLVAAGETATLRCTITSLKPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |
| 197 | EEELQIIQPDKSVLVAAGETATLRCTITSLRPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |
| 198 | EEELQIIQPDKSVLVAAGETATLRCTITSLYPVGPIQWFRGAGPGRELIYNQRE<br>GPFPRVTTVSDTTKRNNMDFSIRIGAITPADAGTYYCVKFRKGSPDDVEFKSG<br>AGTELSVRAKPS |

TABLE 6-continued

SIRPα Variant Polypeptides

| SEQ ID NO: | Amino Acid Sequence |
|---|---|
| 199 | EEELQIIQPDKSVLVAAGETATLRCTITSLFPVGPIQWFRGAGPGRELIYNQRD GPFPRVTTVSDTTKRNNMDFSIRIGAITPADAGTYYCVKFRKGSPDDVEFKSG AGTELSVRAKPS |
| 200 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGIPDDVEFKSG AGTELSVRAKPS |
| 201 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGNIPDDVEFKS GAGTELSVRAKPS |
| 202 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDVEFKSGA GTELSVRAKPS |
| 203 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSSEPDVEFKS GAGTELSVRAKPS |
| 204 | EEELQIIQPDKSVLVAAGETATLRCTITSLRPVGPIQWFRGAGPGRELIYNQRD GPFPRVTTVSDTTKRNNMDFSIRIGAITPADAGTYYCVKFRKGSPDDVEFKSG AGTELSVRAKPS |
| 205 | EEELQIIQPDKSVLVAAGETATLRCTITSLRPVGPIQWFRGAGPGRELIYNQRE GPFPRVTTVSDTTKRNNMDFSIRIGAITPADAGTYYCVKFRKGIPDDVEFKSG AGTELSVRAKPS |
| 206 | EEELQIIQPDKSVLVAAGETATLRCTITSLRPVGPIQWFRGAGPGRELIYNQRD GPFPRVTTVSDTTKRNNMDFSIRIGAITPADAGTYYCVKFRKGIPDDVEFKSG AGTELSVRAKPS |
| 207 | EEELQIIQPDKSVLVAAGETATLRCTITSLYPVGPIQWFRGAGPGRELIYNQRD GPFPRVTTVSDTTKRNNMDFSIRIGAITPADAGTYYCVKFRKGSPDDVEFKSG AGTELSVRAKPS |
| 208 | EEELQIIQPDKSVLVAAGETATLRCTITSLYPVGPIQWFRGAGPGRELIYNQRE GPFPRVTTVSDTTKRNNMDFSIRIGAITPADAGTYYCVKFRKGIPDDVEFKSG AGTELSVRAKPS |
| 209 | EEELQIIQPDKSVLVAAGETATLRCTITSLYPVGPIQWFRGAGPGRELIYNQRD GPFPRVTTVSDTTKRNNMDFSIRIGAITPADAGTYYCVKFRKGIPDDVEFKSG AGTELSVRAKPS |
| 210 | EEELQIIQPDKSVLVAAGETATLRCTITSLFPVGPIQWFRGAGPGRELIYNQRD GPFPRVTTVSDTTKRNNMDFSIRIGAITPADAGTYYCVKFRKGIPDDVEFKSG AGTELSVRAKPS |
| 213 | EEELQVIQPDKSVLVAAGETATLRCTATSLFPVGPIQWFRGAGPGRELIYNQR QGPFPRVTTVSDLTKRNNMDFSIRIGNITVADAGTYYCVKFRKGSPDDVEFKS GAGTELSVRAKPS |

In some embodiments, the polypeptide comprises a SIRPα D1 domain variant that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 6.

In some embodiments, the polypeptide comprises a SIRPα D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to SEQ ID NOs: 80, 81, or 85 in Table 6.

Fc Domain Variants and Fusion Polypeptides Comprising Same

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain (e.g., a wild-type SIRPα D1 domain set forth in SEQ ID NO: 1 or 2); and at least one additional amino acid mutation relative to a wild-type SIRPα D1 domain (e.g., a wild-type SIRPα D1 domain set forth in SEQ ID NO: 1 or 2) at a residue selected from the group consisting of: residue 6, residue 27, residue 31, residue 47, residue 53, residue 54, residue 56, residue 66, and residue 92.

Also disclosed herein, in some embodiments, are Fc domain variant dimers, wherein the Fc domain variant dimer comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

Antibodies that target cell surface antigens can trigger immunostimulatory and effector functions that are associated with Fc receptor (FcR) engagement on immune cells.

There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, a SIRPα D1 polypeptide construct comprises a non-naturally occurring SIRPα D1 domain variant linked to an Fc domain variant which forms an Fc domain having ablated or reduced effector function.

In some embodiments, a Fc domain variant refers to a polypeptide chain that includes second and third antibody constant domains (e.g., CH2 and CH3). In some embodiments, an Fc domain variant also includes a hinge domain. In some embodiments, the Fc domain variant is of any immunoglobulin antibody isotype, including IgG, IgE, IgM, IgA, and IgD. Additionally, in some embodiments, an Fc domain variant is of any IgG subtype (e.g., IgG1, IgG2, IgG2a, IgG2b, IgG2c, IgG3, and IgG4). In some embodiments, an Fc domain variant comprises as many as ten amino acid modifications (e.g., insertions, deletions and/or substitutions) relative to a wild-type Fc domain monomer sequence (e.g., 1-10, 1-8, 1-6, 1-4 amino acid substitutions, additions or insertions, deletions, or combinations thereof) that alter the interaction between an Fc domain and an Fc receptor.

As used herein, the term "Fc domain dimer" refers to a dimer of two Fc domains. In a wild-type Fc domain dimer, two wild-type Fc domains dimerism by the interaction between the two CH3 antibody constant domains, as well as one or more disulfide bonds that form between the hinge domains of the two dimerized Fc domains.

As used herein, the term "Fc domain dimer variant" comprises at least one Fc domain variant. In some embodiments, an Fc domain dimer variant comprises Fc domain variants that are mutated to lack effector functions, for example a "dead Fc domain dimer variant." In some embodiments, each of the Fc domains in an Fc domain dimer variant includes amino acid substitutions in the CH2 antibody constant domain to reduce the interaction or binding between the Fc domain dimer variant and an Fc receptor, such as an Fcγ receptor (FcγR), an Fcα receptor (FcαR), or an Fcε (FcεR).

In some embodiments, a SIRPα D1 domain variant (e.g., any of the variants described in Tables 2, 5, and 6) is fused to an Fc domain variant of an immunoglobulin or a fragment of an Fc domain variant. In some embodiments, an Fc domain variant of an immunoglobulin or a fragment of an Fc domain variant is capable of forming an Fc domain dimer with another Fc domain variant. In some embodiments, an Fc domain variant of an immunoglobulin or a fragment of an Fc domain variant is not capable of forming an Fc domain dimer with another Fc domain variant. In some embodiments, an Fc domain variant or a fragment of an Fc domain variant is fused to a polypeptide of the disclosure to increase serum half-life of the polypeptide. In some embodiments, an Fc domain variant or a fragment of an Fc domain variant fused to a polypeptide of the disclosure dimerizes with a second Fc domain variant to form an Fc domain dimer variant which binds an Fc receptor, or alternatively, an Fc domain variant binds to an Fc receptor. In some embodiments, an Fc domain variant or a fragment of the Fc domain variant fused to a polypeptide to increase serum half-life of the polypeptide does not induce any immune system-related response.

In some embodiments, a SIRPα polypeptide or construct provided herein includes a SIRPα D1 domain or variant thereof joined to a first Fc domain variant and an antibody variable domain joined to a second Fc domain variant, in which the first and second Fc domain variants combine to form an Fc domain dimer variant (e.g., a heterodimeric Fc domain dimer variant). An Fc domain dimer is the protein structure that is found at the C-terminus of an immunoglobulin. An Fc domain dimer includes two Fc domains that are dimerized by the interaction between the CH3 antibody constant domains. A wild-type Fc domain dimer forms the minimum structure that binds to an Fc receptor, e.g., FcγRI, FcγRIIa, FcγRIIb, FcγRIIIa, FcγRIIIb, and FcγRIV.

The Fc domain dimer is not involved directly in binding an antibody to its target, but can be involved in various effector functions, such as participation of the antibody in antibody-dependent cellular toxicity. In some embodiments, the Fc domain in a SIRPα polypeptide or construct of the disclosure comprises amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. In some embodiments, the SIRPα polypeptides or constructs of the disclosure are characterized by decreased binding (e.g., minimal binding or absence of binding) to a human Fc receptor and decreased binding (e.g., minimal binding or absence of binding) to complement protein C1q. In some embodiments, the SIRPα constructs of the disclosure are characterized by decreased binding (e.g., minimal binding or absence of binding) to human FcγRI, FcγRIIA, FcγRIIB, FcγRIIIB, or any combinations thereof, and C1q. To alter or reduce an antibody-dependent effector function, such as ADCC, CDC, ADCP, or any combinations thereof, in some embodiments, the Fc domains in SIRPα constructs of the disclosure are of the IgG class and comprise one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda, MD (1991))).

In some embodiments, polypeptide constructs comprising a non-native Fc region described herein exhibit reduced or ablated binding to at least one of Fcγ receptors CD16a, CD32a, CD32b, CD32c, and CD64 as compared to a polypeptide construct comprising a native Fc region. In some cases, the polypeptide constructs described herein exhibit reduced or ablated binding to CD16a, CD32a, CD32b, CD32c, and CD64 Fcγ receptors.

CDC refers to a form of cytotoxicity in which the complement cascade is activated by the complement component C1q binding to antibody Fc domains. In some embodiments, polypeptide constructs comprising a non-native Fc region described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising a non-native Fc region as described herein exhibit reduced CDC as compared to a polypeptide construct comprising a wild-type Fc region. In some embodiments, polypeptide constructs comprising a non-native Fc region as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising a non-natural Fc domain variants or Fc domain dimer variants as described herein exhibit negligible CDC as compared to a polypeptide construct comprising a wild-type Fc region.

In some embodiments, the Fc domain variants or Fc domain dimer variants described herein are minimally glycosylated or have reduced glycosylation relative to a wild-type sequence. In some embodiments, deglycosylation is accomplished with a mutation of N297A, or by mutating N297 to any amino acid which is not N. In some embodiments, deglycosylation is accomplished by disrupting the motif N-Xaa1-Xaa2-Xaa3, wherein N=asparagine; Xaa1=any amino acid except P (proline); Xaa2=T (threonine), S (serine) or C (cysteine); and Xaa3=any amino acid except P (proline). In one embodiment, the N-Xaa1-Xaa2-Xaa3 motif refers to residues 297-300 as designated according to Kabat et al., 1991. In some embodiments, a mutation to any one or more of N, Xaa1, Xaa2, or Xaa3 results in deglycosylation of the Fc domain variant or Fc domain dimer variant.

In some embodiments, variants of antibody IgG constant regions (e.g., Fc domain variants or Fc domain dimer variants) possess a reduced capacity to specifically bind Fcγ receptors or have a reduced capacity to induce phagocytosis. In some embodiments, variants of antibody IgG constant regions (e.g., Fc domain variants or Fc domain dimer variants) possess a reduced capacity to specifically bind Fcγ receptors and have a reduced capacity to induce phagocytosis. For example, in some embodiments, an Fc domain variant is mutated to lack effector functions, typical of a "dead" Fc domain variant. For example, in some embodiments, an Fc domain variant includes specific amino acid substitutions that are known to minimize the interaction between the Fc domain dimer and an Fcγ receptor. In some embodiments, an Fc domain variant is from an IgG1 antibody and includes one or more of amino acid substitutions L234A, L235A, G237A, and N297A (as designated according to the EU numbering system per Kabat et al., 1991). In some embodiments, one or more additional mutations are included in such IgG1 Fc domain variant. Non-limiting examples of such additional mutations for human IgG1 Fc domain variants include E318A and K322A. In some instances, a human IgG1 Fc domain variant has up to 12, 11, 10, 9, 8, 7, 6, 5 or 4 or fewer mutations in total as compared to wild-type human IgG1 sequence. In some embodiments, one or more additional deletions are included in such IgG1 Fc domain variant. For example, in some embodiments, the C-terminal lysine of the Fc domain IgG1 heavy chain constant region provided in SEQ ID NO: 88 in Table 7 is deleted, for example to increase the homogeneity of the polypeptide when the polypeptide is produced in bacterial or mammalian cells. In some instances, a human IgG1 Fc domain variant has up to 12, 11, 10, 9, 8, 7, 6, 5 or 4 or fewer deletions in total as compared to wild-type human IgG1 sequence (see, e.g., SEQ ID NO: 161 below). In some embodiments, a IgG1 Fc domain variant has a sequence according to any one of SEQ ID NO: 135, SEQ ID NO: 136 or SEQ ID NO: 137.

SEQ ID NO: 161:
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPG

In some embodiments, an Fc domain variant is from an IgG2 or IgG4 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc domain variant comprises a human IgG2 Fc domain sequence comprising one or more of A330S, P331S and N297A amino acid substitutions (as designated according to the EU numbering system per Kabat, et al. (1991). In some embodiments, one or more additional mutations are included in such IgG2 Fc domain variants. Non-limiting examples of such additional mutations for human IgG2 Fc domain variant include V234A, G237A, P238S, V309L and H268A (as designated according to the EU numbering system per Kabat et al. (1991)). In some instances, a human IgG2 Fc domain variant has up to 12, 11, 10, 9, 8, 7, 6, 5, 4, 3 or fewer mutations in total as compared to wild-type human IgG2 sequence. In some embodiments, one or more additional deletions are included in such IgG2 Fc domain variant. For example, in some embodiments, the C-terminal lysine of the Fc domain IgG2 heavy chain constant region provided in SEQ ID NO: 89 in Table 7 is deleted, for example to increase the homogeneity of the polypeptide when the polypeptide is produced in bacterial or mammalian cells. In some instances, a human IgG2 Fc domain variant has up to 12, 11, 10, 9, 8, 7, 6, 5 or 4 or fewer deletions in total as compared to wild-type human IgG2 sequence (see, e.g., SEQ ID NO: 162 below).

SEQ ID NO: 162:
ERKCCVECPPCPAPPVAGPSVFLFPPKPKDTLMISRTPEVTCVVVDVSHE

DPEVQFNWYVDGVEVHNAKTKPREEQFNSTFRVVSVLTVVHQDWLNGKEY

KCKVSNKGLPAPIEKTISKTKGQPREPQVYTLPPSREEMTKNQVSLTCLV

KGFYPSDIAVEWESNGQPENNYKTTPPMLDSDGSFFLYSKLTVDKSRWQQ

GNVFSCSVMHEALHNHYTQKSLSLSPG

When the Fc domain variant is an IgG4 Fc domain variant, in some embodiments, such Fc domain variant comprises a S228P mutation (as designated according to Kabat, et al. (1991)). In some instances, a human IgG4 Fc domain variant has up to 12, 11, 10, 9, 8, 7, 6, 5, 4, 3, 2 or 1 mutation(s) in total as compared to wild-type human IgG4 sequence. In some embodiments, the Fc domain variant comprises a human IgG4 Fc sequence comprising one or more of S228P, E233P, F234V, L235A, and delG236 amino acid substitutions (as designated according to the EU numbering system per Kabat, et al. (1991). In some embodiments, the Fc domain variant comprises a human IgG4 Fc sequence comprising one or more of S228P, E233P, F234V, L235A, delG236, and N297A amino acid substitutions (as designated according to the EU numbering system per Kabat, et al. (1991).

In some embodiments, the Fc domain variant includes at least one of the mutations L234A, L235A, G237A or N297A of an IgG1 Fc region or at least one of the mutations A330S, P331S or N297A of an IgG2 Fc region. In some embodiments, the Fc domain variant includes at least two of the mutations L234A, L235A, G237A or N297A of an IgG1 Fc region or at least two of the mutations A330S, P331S or N297A of an IgG2 Fc region. In some embodiments, the Fc domain variant includes at least three of the mutations L234A, L235A, G237A or N297A of an IgG1 Fc region or consists of the mutations A330S, P331S and N297A of an IgG2 Fc region. In some embodiments, the Fc domain variant consists of the mutations L234A, L235A, G237A and N297A.

In some embodiments, the Fc domain variant exhibits reduced binding to an Fc receptor of the subject compared to the wild-type human IgG Fc region. In some embodiments, the Fc domain variant exhibits ablated binding to an Fc receptor of the subject compared to the wild-type human IgG Fc region. In some embodiments, the Fc domain variant exhibits a reduction of phagocytosis compared to the wild-type human IgG Fc region. In some embodiments, the Fc domain variant exhibits ablated phagocytosis compared to the wild-type human IgG Fc region.

SEQ ID NO: 88 and SEQ ID NO: 89 provide amino acid sequences of Fc domain IgG1 and IgG2 heavy chain constant regions. In some embodiments, an Fc domain variant is any variant of SEQ ID NOs: 90-95 as shown in Table 7.

TABLE 7

Amino Acid Sequences of Fc Domain Variants

| SEQ ID NO: | AMINO ACID SEQUENCE |
|---|---|
| 88 | EPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQG NVFSCSVMHEALHNHYTQKSLSLSPGK |
| 89 | STKGPSVFPLAPCSRSTSESTAALGCLVKDYFPEPVTVSWNSGALTSGVHTFP AVLQSSGLYSLSSVVTVPSSSLGTQTYTCNVDHKPSNTKVDKTVERKCCVE CPPCPAPPVAGPSVFLFPPKPKDTLMISRTPEVTCVVVDVSHEDPEVQFNWY VDGVEVHNAKTKPREEQFNSTFRVVSVLTVVHQDWLNGKEYKCKVSNKGL PAPIEKTISKTKGQPREPQVYTLPPSREEMTKNQVSLTCLVKGFYPSDIAVEW ESNGQPENNYKTTPPMLDSDGSFFLYSKLTVDKSRWQQGNVFSCSVMHEAL HNHYTQKSLSLSPGK |
| 90 | DKTHTCPPCPAPEAAGAPSVFLFPPKPKDTLMISRTPEVTCVVVDVSHEDPE VKFNWYVDGVEVHNAKTKPREEQYASTYRVVSVLTVLHQDWLNGKEYKC KVSNKALPAPIEKTISKAKGQPREPQVYTLPPSREEMTKNQVSLTCLVKGFY PSDIAVEWESNGQPENNYKTTPPVLDSDGSFFLYSKLTVDKSRWQQGNVFS CSVMHEALHNHYTQKSLSLSPGK |
| 91 | DKTHTCPPCPAPEAAGAPSVFLFPPKPKDTLMISRTPEVTCVVVDVSHEDPE VKFNWYVDGVEVHNAKTKPREEQYASTYRVVSVLTVLHQDWLNGKEYKC KVSNKALPAPIEKTISKAKGQPREPQVYTLPPSREEMTKNQVSLTCLVKGFY PSDIAVEWESNGQPENNYKTTPPVLDSDGSFFLYSKLTVDKSRWQQGNVFS CSVMHEALHNHYTQKSLSLSPG |
| 92 | VECPPCPAPPVAGPSVFLFPPKPKDTLMISRTPEVTCVVVDVSHEDPEVQFN WYVDGVEVHNAKTKPREEQFASTFRVVSVLTVVHQDWLNGKEYKCKVSN KGLPSSIEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVM HEALHNHYTQKSLSLSPGK |
| 93 | VECPPCPAPPVAGPSVFLFPPKPKDTLMISRTPEVTCVVVDVSHEDPEVQFN WYVDGVEVHNAKTKPREEQFASTFRVVSVLTVVHQDWLNGKEYKCKVSN KGLPSSIEKTISKTKGQPREPQVYTLPPSREEMTKNQVSLTCLVKGFYPSDIA VEWESNGQPENNYKTTPPMLDSDGSFFLYSKLTVDKSRWQQGNVFSCSVM HEALHNHYTQKSLSLSPG |
| 94 | ERKSSVECPPCPAPPVAGPSVFLFPPKPKDTLMISRTPEVTCVVVDVSHEDPE VQFNWYVDGVEVHNAKTKPREEQFASTFRVVSVLTVVHQDWLNGKEYKC KVSNKGLPSSIEKTISKTKGQPREPQVYTLPPSREEMTKNQVSLTCLVKGFYP SDIAVEWESNGQPENNYKTTPPMLDSDGSFFLYSKLTVDKSRWQQGNVFSC SVMHEALHNHYTQKSLSLSPGK |
| 95 | ERKSSVECPPCPAPPVAGPSVFLFPPKPKDTLMISRTPEVTCVVVDVSHEDPE VQFNWYVDGVEVEINAKTKPREEQFASTFRVVSVLTVVHQDWLNGKEYKC KVSNKGLPSSIEKTISKTKGQPREPQVYTLPPSREEMTKNQVSLTCLVKGFYP SDIAVEWESNGQPENNYKTTPPMLDSDGSFFLYSKLTVDKSRWQQGNVFSC SVMHEALHNHYTQKSLSLSPG |

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc domain variant or Fc domain dimer variant as described herein exhibit reduced ADCC or ADCP as compared to a polypeptide construct comprising a wild-type Fc region. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, polypeptide constructs comprising an Fc domain variant or Fc domain dimer variant as described herein exhibit ablated ADCC or ADCP as compared to a polypeptide construct comprising a wild-type Fc region.

Complement-directed cytotoxicity, which is also referred to herein as CDC, refers to a form of cytotoxicity in which the complement cascade is activated by the complement component C1q binding to antibody Fc domains. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising an Fc domain variant or Fc domain dimer variant as described herein exhibit reduced CDC as compared to a polypeptide construct comprising a wild-type Fc region. In some embodiments, polypeptide constructs comprising an Fc domain variant or Fc domain dimer variant as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, polypeptide constructs comprising an Fc domain variant or Fc domain dimer variant as described herein exhibit negligible CDC as compared to a polypeptide construct comprising a wild-type Fc region.

Fc domain variants or Fc domain dimer variants herein include those that exhibit reduced binding to an Fcγ receptor compared to the wild-type human IgG Fc region. For example, in some embodiments, an Fc domain variant or Fc domain dimer variant exhibits binding to an Fcγ receptor that is less than the binding exhibited by a wild-type human IgG Fc region to an Fcγ receptor, as described in the Examples. In some instances, an Fc domain variant or Fc domain dimer variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptor, e.g., CD16a, CD32a, CD32b, CD32c, or CD64.

In some instances, the Fc domain variants or Fc domain dimer variants disclosed herein exhibit a reduction of phagocytosis compared to its wild-type human IgG Fc region. Such Fc domain variants or Fc domain dimer variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc domain variant or Fc domain dimer variant exhibits ablated phagocytosis compared to its wild-type human IgG Fc region.

In some embodiments, the Fc domain variants or Fc domain dimer variants disclosed herein are coupled to one or more fusion partners. In some cases the fusion partner is a therapeutic moiety. In some cases, the fusion partner is selected to enable targeting of an expressed protein, purification, screening, display, and the like. In some embodiments, the fusion partner also affects the degree of binding to Fc receptors or the degree of phagocytosis reduction. As described herein, in some embodiments, when an Fc domain variant or Fc domain dimer variant is coupled to a fusion partner, it forms a polypeptide construct as described below.

In some embodiments, fusion partners are linked to the Fc domain variant or Fc domain dimer variant sequence via a linker sequence. In some embodiments, the linker sequence generally comprises a small number of amino acids, such as less than ten amino acids, although longer linkers are also utilized. In some cases, the linker has a length less than 10, 9, 8, 7, 6, or 5 amino acids or shorter. In some cases, the linker has a length of at least 10, 11, 12, 13, 14, 15, 20, 25, 30, or 35 amino acids or longer. Optionally, in some embodiments, a cleavable linker is employed.

In some embodiments, a fusion partner is a targeting or signal sequence that directs an Fc domain variant or Fc domain dimer variant protein and any associated fusion partners to a desired cellular location or to the extracellular media. In some embodiments, certain signaling sequences target a protein to be either secreted into the growth media, or into the periplasmic space, located between the inner and outer membrane of the cell. In some embodiments, a fusion partner is a sequence that encodes a peptide or protein that enables purification or screening. Such fusion partners include, but are not limited to, polyhistidine tags (His-tags) (for example His6 (SEQ ID NO: 223) and His10 (SEQ ID NO: 224)) or other tags for use with Immobilized Metal Affinity Chromatography (IMAC) systems (e.g., Ni+2 affinity columns), GST fusions, MBP fusions, Strep-tag, the BSP biotinylation target sequence of the bacterial enzyme BirA, and epitope tags which are targeted by antibodies (for example c-myc tags, flag-tags, and the like).

In some embodiments, such tags are useful for purification, for screening, or both. For example, in some embodiments, an Fc domain variant or Fc domain dimer variant is purified using a His-tag by immobilizing it to a Ni+2 affinity column, and then after purification the same His-tag is used to immobilize the antibody to a Ni+2 coated plate to perform an ELISA or other binding assay as described elsewhere herein. In some embodiments, a fusion partner enables the use of a selection method to screen Fc domain variants or Fc domain dimer variants as described herein.

Various fusion partners that enable a variety of selection methods are available. For example, by fusing the members of an Fc domain variant or Fc domain dimer variant library to the gene III protein, phage display can be employed. In some embodiments, fusion partners Fc domain variants or Fc domain dimer variants to be labeled. Alternatively, in some embodiments, a fusion partner binds to a specific sequence on the expression vector, enabling the fusion partner and associated Fc domain variant or Fc domain dimer variant to be linked covalently or noncovalently with the nucleic acid that encodes them.

In some embodiments, when a fusion partner is a therapeutic moiety, the therapeutic moiety is, e.g., a peptide, a protein, an antibody, a siRNA, or a small molecule. Non-limiting examples of therapeutic antibodies that are coupled to the Fc domain variants or Fc domain dimer variants of the present disclosure include, but are not limited to antibodies that recognize CD47. Non-limiting examples of therapeutic polypeptides that are coupled to the Fc domain variants or Fc domain dimer variants of the present disclosure include, but are not limited to, CD47 binding polypeptides, including SIRPα polypeptides. In such instances, the CD47 binding polypeptide is attached or fused to an Fc domain variant or Fc domain dimer variant of the disclosure. Examples of CD47 binding polypeptides include, but are not limited to, anti-CD47 antibodies or fragments thereof, and ligands of CD47 such as SIRPα or a fragment thereof. Additional examples of CD47 binding polypeptides include, but are not limited to naturally-occurring forms of SIRPα as well as mutants thereof.

In some embodiments, disclosed herein is a polypeptide comprising an Fc domain dimer variant, wherein the Fc domain dimer variant comprises two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain variants are identical (i.e., homodimer). In some embodiments, the Fc domain variants are different (i.e., heterodimer). In some embodiments, at least one of the Fc domain variant in an Fc domain dimer is a human IgG1 Fc region consisting of mutations L234A, L235A, G237A, and N297A. In some embodiments, at least one of the Fc domain variants in an Fc domain dimer is a human IgG2 Fc region consisting of mutations A330S, P331S and N297A. In some embodiments, the Fc domain dimer variant exhibits ablated or reduced binding to an Fc receptor compared to the wild-type version of the human IgG Fc region. In some embodiments, the Fc domain dimer variant exhibits ablated or reduced binding to CD16a, CD32a, CD32b, CD32c, and CD64 Fc receptors compared to the wild-type version of the human IgG Fc region. In some embodiments, the Fc domain dimer variant exhibits ablated or reduced binding to C1q compared to the wild-type version of the human IgG Fc fusion. In some embodiments, at least one of the Fc domain variants in an Fc domain dimer variant is a human IgG4 Fc region comprising mutations S228P, E233P, F234V, L235A, delG236, and N297A. In some embodiments, the Fc domain dimer variant exhibits ablated or reduced binding to an Fc receptor compared to the wild-type human IgG4 Fc region. In some embodiments, the Fc domain dimer variant exhibits ablated or reduced binding to CD16a and CD32b Fcγ receptors compared to the wild-type version of its human IgG4 Fc region. In some embodiments, the Fc domain dimer variant binds to an Fcγ receptor with a $K_D$ greater than about $5 \times 10^{-6}$ M.

In some embodiments, the Fc domain dimer variant further comprises a CD47 binding polypeptide. In some embodiments, the Fc domain dimer variant exhibits ablated or reduced binding to an Fcγ receptor compared to a wild-type version of a human IgG Fc region. In some embodiments, the CD47 binding polypeptide does not cause acute anemia in rodents and non-human primates. In some embodiments, the CD47 binding polypeptide does not cause acute anemia in humans.

In some embodiments, the CD47 binding polypeptide is a signal-regulatory protein α (SIRP-α) polypeptide or a fragment thereof. In some embodiments, the SIRPα polypeptide comprises a SIRPα D1 domain variant comprising the amino acid sequence, EEELQX1IQPDKSVLVA-AGETATLRCTX2TSLX3PVGPIQWFRGAGPGRX4LIY-NQX5EG X6FPRVTTVSDX7TKRNNMDFSIRIGX8I-TPADAGTYYCX9KFRKGSPDDVEFKSGAGTE LSVRAKPS (SEQ ID NO: 221), wherein X1 is V or I; X2 is A or I; X3 is I or F; X4 is E or V; X5 is K or R; X6 is H or P; X7 is L or T; X8 is any amino acid other than N; and X9 is V or I. In some embodiments, the SIRPα polypeptide comprises a SIRPα D1 domain variant wherein X1 is V or I; X2 is A or I; X3 is I or F; X4 is E; X5 is K or R; X6 is H or P; X7 is L or T; X8 is not N; and X9 is V.

In some embodiments, disclosed herein, is a polypeptide comprising: a SIRPα D1 domain variant, wherein the SIRPα D1 domain variant is a non-naturally occurring high affinity SIRPα D1 domain, wherein the SIRPα D1 domain variant binds to human CD47 with an affinity that is at least 10-fold greater than the affinity of a naturally occurring D1 domain; and an Fc domain variant, wherein the Fc domain variant is linked to a second polypeptide comprising a second Fc domain variant to form an Fc domain dimer variant, wherein the Fc domain dimer variant has ablated or reduced effector function. In some embodiments, the non-naturally occurring high affinity SIRPα D1 domain comprises an amino acid mutation at residue 80.

In some embodiments, disclosed herein, is a SIRPα D1 domain variant, wherein the SIRPα D1 domain variant binds CD47 from a first species with a KD less than 250 nM; and wherein the SIRPα D1 domain variant binds CD47 from a second species with a KD less than 250 nM; and the KD for CD47 from the first species and the KD for CD47 from the second species are within 100 fold of each other; wherein the first species and the second species are selected from the group consisting of: human, rodent, and non-human primate. In some embodiments, the SIRPα D1 domain variant binds CD47 from at least 3 different species. In some embodiments, the non-human primate is cynomolgus monkey.

In some embodiments, disclosed herein, is a polypeptide comprising (a) a SIRPα D1 domain that binds human CD47 with a KD less than 250 nM; and (b) an Fc domain or variant thereof linked to the N-terminus or the C-terminus of the SIRPα D1 domain, wherein the polypeptide does not cause acute anemia in rodents and non-human primates. In some embodiments, the polypeptide is a non-naturally occurring variant of a human SIRP-α. In some embodiments, administration of the polypeptide in vivo results in hemoglobin reduction by less than 50% during the first week after administration. In some embodiments, administration of the polypeptide in humans results in hemoglobin reduction by less than 50% during the first week after administration. In some embodiments, the polypeptide further comprises at least one Fc domain dimer variant, wherein the Fc domain dimer variant comprises an Fc domain variant selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A. In some embodiments, the Fc domain variant is a human IgG1 Fc region consisting of mutations L234A, L235A, G237A, and N297A. In some embodiments, the Fc domain variant is a human IgG2 Fc region consisting of mutations A330S, P331S and N297A.

The SIRPα constructs of the disclosure include a SIRPα domain or variant thereof that has its C-terminus joined to the N-terminus of an Fc domain or variant thereof by way of a linker using conventional genetic or chemical means, e.g., chemical conjugation. In some embodiments, a linker (e.g., a spacer) is inserted between the polypeptide and the Fc domain or variant thereof. In some embodiments, a polypeptide of the disclosure including a SIRPα D1 domain variant is fused to an Fc domain variant that is incapable of forming a dimer. In some embodiments, a polypeptide of the disclosure is fused to an Fc domain or variant thereof that is capable of forming a dimer, e.g., a heterodimer, with another Fc domain or variant thereof. In some embodiments, a polypeptide of the invention is fused to an Fc domain or variant thereof and this fusion protein forms a homodimer. In some embodiments, a polypeptide of the disclosure is fused to a first Fc domain or variant thereof and a different protein or peptide (e.g., an antibody variable region) is fused to a second Fc domain or variant thereof. In some embodiments, a SIRPα D1 domain or variant thereof is joined to a first Fc domain or variant thereof and a therapeutic protein (e.g., a cytokine, an interleukin, an antigen, a steroid, an anti-inflammatory agent, or an immunomodulatory agent) is joined to a second Fc domain or variant thereof. In some embodiments, the first and second Fc domains or variants thereof form a heterodimer.

Without the limiting the foregoing, in some embodiments, a SIRPα D1 domain variant polypeptide (e.g., any of the variants described in Tables 2, 5, and 6) is fused to an Fc polypeptide or Fc variant polypeptide, such as an Fc domain or variant thereof. Examples of polypeptides comprising a SIRPα D1 domain variant polypeptide and a fused Fc domain variant polypeptide include, but are not limited to, SEQ ID NOS: 96-137, 214, and 216 shown in Table 8.

TABLE 8

Polypeptides Comprising SIRPα D1 Domain Variants Fused to Fc Domain Variants

| SEQ ID NO: | Amino Acid Sequence |
|---|---|
| 96 | EEELQIIQPDKSVLVAAGETATLRCTITSLFPVGPIQWFRGAGPGRVLIYNQRQGPFPRVTTVSDTTKRNNMDFSIRIGNITPADAGTYYCIKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 97 | EEELQVIQPDKSVLVAAGETATLRCTATSLFPVGPIQWFRGAGPGRELIYNQRQGPFPRVTTVSDLTKRNNMDFSIRIGNITPADAGTYYCVKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 98 | EEELQIIQPDKSVLVAAGETATLRCTITSLFPVGPIQWFRGAGPGRVLIYNQRQGPFPRVTTVSDTTKRNNMDFSIRIGAITPADAGTYYCIKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALEINHYTQKSLSLSPGK |
| 99 | EEELQVIQPDKSVLVAAGETATLRCTATSLFPVGPIQWFRGAGPGRELIYNQRQGPFPRVTTVSDLTKRNNMDFSIRIGAITPADAGTYYCVKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 100 | EEELQVIQPDKSVLVAAGETATLRCTATSLFPVGPIQWFRGAGPGRELIYNQREGPFPRVTTVSDLTKRNNMDFSIRIGAITPADAGTYYCVKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 101 | EEELQVIQPDKSVLVAAGETATLRCTITSLFPVGPIQWFRGAGPGRELIYNQREGPFPRVTTVSDLTKRNNMDFSIRIGAITPADAGTYYCVKFRKGSPDDVEFKSGAGTELSVRAKPSDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 102 | EEELQIIQPDKSVLVAAGETATLRCTITSLFPVGPIQWFRGAGPGRELIYNQREGPFPRVTTVSDLTKRNNMDFSIRIGAITPADAGTYYCVKFRKGSPDDVEFKSGAGTELSVRAKPSDKTHTCPPCPAPEAAGAPSVFLFPPKPKDTLMISRTPEVTC |

TABLE 8-continued

Polypeptides Comprising SIRPα D1 Domain Variants
Fused to Fc Domain Variants

| SEQ ID NO: | Amino Acid Sequence |
|---|---|
|  | VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALHNHYTQKSLSLSPGK |
| 103 | EEELQVIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALHNHYTQKSLSLSPGK |
| 104 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSDKTHTCPPCPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALHNHYTQKSLSLSPGK |
| 105 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSVECPPCPAPPVAGPSVFLFPPKPKDTLMISRTPEVTCVVVD<br>VSHEDPEVQFNWYVDGVEVHNAKTKPREEQFASTFRVVSVLTVVHQDWLN<br>GKEYKCKVSNKGLPSSIEKTISKTKGQPREPQVYTLPPSREEMTKNQVSLTCL<br>VKGFYPSDIAVEWESNGQPENNYKTTPPMLDSDGSFFLYSKLTVDKSRWQQ<br>GNVFSCSVMHEALHNHYTQKSLSLSPGK |
| 106 | EEELQVIQPDKSVLVAAGETATLRCTATSLFPVGPIQWFRGAGPGRELIYNQR<br>QGPFPRVTTVSDLTKRNNMDFSIRIGNITPADAGTYYCVKFRKGSPDDVEFKS<br>GAGTELSVRAKPSVECPPCPAPPVAGPSVFLFPPKPKDTLMISRTPEVTCVVV<br>DVSHEDPEVQFNWYVDGVEVHNAKTKPREEQFASTFRVVSVLTVVHQDWL<br>NGKEYKCKVSNKGLPSSIEKTISKTKGQPREPQVYTLPPSREEMTKNQVSLTC<br>LVKGFYPSDIAVEWESNGQPENNYKTTPPMLDSDGSFFLYSKLTVDKSRWQ<br>QGNVESCSVMHEALHNHYTQKSLSLSPGK |
| 107 | EEELQIIQPDKSVLVAAGETATLRCTITSLFPVGPIQWFRGAGPGRVLIYNQRQ<br>GPFPRVTTVSDTTKRNNMDFSIRIGAITPADAGTYYCIKFRKGSPDDVEFKSG<br>AGTELSVRAKPSVECPPCPAPPVAGPSVFLFPPKPKDTLMISRTPEVTCVVVD<br>VSHEDPEVQFNWYVDGVEVHNAKTKPREEQFASTFRVVSVLTVVHQDWLN<br>GKEYKCKVSNKGLPSSIEKTISKTKGQPREPQVYTLPPSREEMTKNQVSLTCL<br>VKGFYPSDIAVEWESNGQPENNYKTTPPMLDSDGSFFLYSKLTVDKSRWQQ<br>GNVFSCSVMHEALHNHYTQKSLSLSPGK |
| 108 | EEELQVIQPDKSVLVAAGETATLRCTATSLFPVGPIQWFRGAGPGRELIYNQR<br>QGPFPRVTTVSDLTKRNNMDFSIRIGAITPADAGTYYCVKFRKGSPDDVEFKS<br>GAGTELSVRAKPSVECPPCPAPPVAGPSVFLFPPKPKDTLMISRTPEVTCVVV<br>DVSHEDPEVQFNWYVDGVEVEINAKTKPREEQFASTFRVVSVLTVVHQDWL<br>NGKEYKCKVSNKGLPSSIEKTISKTKGQPREPQVYTLPPSREEMTKNQVSLTC<br>LVKGFYPSDIAVEWESNGQPENNYKTTPPMLDSDGSFFLYSKLTVDKSRWQ<br>QGNVFSCSVMHEALHNHYTQKSLSLSPGK |
| 109 | EEELQVIQPDKSVLVAAGETATLRCTATSLFPVGPIQWFRGAGPGRELIYNQR<br>EGPFPRVTTVSDLTKRNNMDFSIRIGAITPADAGTYYCVKFRKGSPDDVEFKS<br>GAGTELSVRAKPSVECPPCPAPPVAGPSVFLFPPKPKDTLMISRTPEVTCVVV<br>DVSHEDPEVQFNWYVDGVEVEINAKTKPREEQFASTFRVVSVLTVVHQDWL<br>NGKEYKCKVSNKGLPSSIEKTISKTKGQPREPQVYTLPPSREEMTKNQVSLTC<br>LVKGFYPSDIAVEWESNGQPENNYKTTPPMLDSDGSFFLYSKLTVDKSRWQ<br>QGNVFSCSVMHEALHNHYTQKSLSLSPGK |
| 110 | EEELQVIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPSVECPPCPAPPVAGPSVFLFPPKPKDTLMISRTPEVTCVVVD<br>VSHEDPEVQFNWYVDGVEVHNAKTKPREEQFASTFRVVSVLTVVHQDWLN<br>GKEYKCKVSNKGLPSSIEKTISKTKGQPREPQVYTLPPSREEMTKNQVSLTCL<br>VKGFYPSDIAVEWESNGQPENNYKTTPPMLDSDGSFFLYSKLTVDKSRWQQ<br>GNVFSCSVMHEALHNHYTQKSLSLSPGK |
| 111 | EEELQIIQPDKSVLVAAGETATLRCTITSLFPVGPIQWFRGAGPGRELIYNQRE<br>GPFPRVTTVSDLTKRNNMDFSIRIGAITPADAGTYYCVKFRKGSPDDVEFKSG<br>AGTELSVRAKPSVECPPCPAPPVAGPSVFLFPPKPKDTLMISRTPEVTCVVVD<br>VSHEDPEVQFNWYVDGVEVHNAKTKPREEQFASTFRVVSVLTVVHQDWLN |

TABLE 8-continued

Polypeptides Comprising SIRPα D1 Domain Variants Fused to Fc Domain Variants

| SEQ ID NO: | Amino Acid Sequence |
|---|---|
| | GKEYKCKVSNKGLPSSIEKTISKTKGQPREPQVYTLPPSREEMTKNQVSLTCL
VKGFYPSDIAVEWESNGQPENNYKTTPPMLDSDGSFFLYSKLTVDKSRWQQ
GNVFSCSVMHEALHNHYTQKSLSLSPGK |
| 112 | EEELQVIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKSG
AGTELSVRAKPSVECPPCPAPPVAGPSVFLFPPKPKDTLMISRTPEVTCVVVD
VSHEDPEVQFNWYVDGVEVHNAKTKPREEQFASTFRVVSVLTVVHQDWLN
GKEYKCKVSNKGLPSSIEKTISKTKGQPREPQVYTLPPSREEMTKNQVSLTCL
VKGFYPSDIAVEWESNGQPENNYKTTPPMLDSDGSFFLYSKLTVDKSRWQQ
GNVFSCSVMHEALHNHYTQKSLSLSPGK |
| 113 | EEELQIIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKSG
AGTELSVRAKPSVECPPCPAPPVAGPSVFLFPPKPKDTLMISRTPEVTCVVVD
VSHEDPEVQFNWYVDGVEVHNAKTKPREEQFASTFRVVSVLTVVHQDWLN
GKEYKCKVSNKGLPSSIEKTISKTKGQPREPQVYTLPPSREEMTKNQVSLTCL
VKGFYPSDIAVEWESNGQPENNYKTTPPMLDSDGSFFLYSKLTVDKSRWQQ
GNVFSCSVMHEALHNHYTQKSLSLSPGK |
| 114 | EEELQIIQPDKSVLVAAGETATLRCTITSLFPVGPIQWFRGAGPGRVLIYNQRQ
GPFPRVTTVSDTTKRNNMDFSIRIGNITPADAGTYYCIKFRKGSPDDVEFKSG
AGTELSVRAKPSERKSSVECPPCPAPPVAGPSVFLFPPKPKDTLMISRTPEVTC
VVVDVSHEDPEVQFNWYVDGVEVHNAKTKPREEQFASTFRVVSVLTVVHQ
DWLNGKEYKCKVSNKGLPSSIEKTISKTKGQPREPQVYTLPPSREEMTKNQV
SLTCLVKGFYPSDIAVEWESNGQPENNYKTTPPMLDSDGSFFLYSKLTVDKS
RWQQGNVFSCSVMHEALHNHYTQKSLSLSPGK |
| 115 | EEELQVIQPDKSVLVAAGETATLRCTATSLFPVGPIQWFRGAGPGRELIYNQR
QGPFPRVTTVSDLTKRNNMDFSIRIGNITPADAGTYYCVKFRKGSPDDVEFKS
GAGTELSVRAKPSERKSSVECPPCPAPPVAGPSVFLFPPKPKDTLMISRTPEVT
CVVVDVSHEDPEVQFNWYVDGVEVHNAKTKPREEQFASTFRVVSVLTVVH
QDWLNGKEYKCKVSNKGLPSSIEKTISKTKGQPREPQVYTLPPSREEMTKNQ
VSLTCLVKGFYPSDIAVEWESNGQPENNYKTTPPMLDSDGSFFLYSKLTVDK
SRWQQGNVFSCSVMHEALHNHYTQKSLSLSPGK |
| 116 | EEELQIIQPDKSVLVAAGETATLRCTITSLFPVGPIQWFRGAGPGRVLIYNQRQ
GPFPRVTTVSDTTKRNNMDFSIRIGAITPADAGTYYCIKFRKGSPDDVEFKSG
AGTELSVRAKPSERKSSVECPPCPAPPVAGPSVFLFPPKPKDTLMISRTPEVTC
VVVDVSHEDPEVQFNWYVDGVEVHNAKTKPREEQFASTFRVVSVLTVVHQ
DWLNGKEYKCKVSNKGLPSSIEKTISKTKGQPREPQVYTLPPSREEMTKNQV
SLTCLVKGFYPSDIAVEWESNGQPENNYKTTPPMLDSDGSFFLYSKLTVDKS
RWQQGNVFSCSVMHEALHNHYTQKSLSLSPGK |
| 117 | EEELQVIQPDKSVLVAAGETATLRCTATSLFPVGPIQWFRGAGPGRELIYNQR
QGPFPRVTTVSDLTKRNNMDFSIRIGAITPADAGTYYCVKFRKGSPDDVEFKS
GAGTELSVRAKPSERKSSVECPPCPAPPVAGPSVFLFPPKPKDTLMISRTPEVT
CVVVDVSHEDPEVQFNWYVDGVEVHNAKTKPREEQFASTFRVVSVLTVVH
QDWLNGKEYKCKVSNKGLPSSIEKTISKTKGQPREPQVYTLPPSREEMTKNQ
VSLTCLVKGFYPSDIAVEWESNGQPENNYKTTPPMLDSDGSFFLYSKLTVDK
SRWQQGNVFSCSVMHEALHNHYTQKSLSLSPGK |
| 118 | EEELQVIQPDKSVLVAAGETATLRCTATSLFPVGPIQWFRGAGPGRELIYNQR
EGPFPRVTTVSDLTKRNNMDFSIRIGAITPADAGTYYCVKFRKGSPDDVEFKS
GAGTELSVRAKPSERKSSVECPPCPAPPVAGPSVFLFPPKPKDTLMISRTPEVT
CVVVDVSHEDPEVQFNWYVDGVEVHNAKTKPREEQFASTFRVVSVLTVVH
QDWLNGKEYKCKVSNKGLPSSIEKTISKTKGQPREPQVYTLPPSREEMTKNQ
VSLTCLVKGFYPSDIAVEWESNGQPENNYKTTPPMLDSDGSFFLYSKLTVDK
SRWQQGNVFSCSVMHEALHNHYTQKSLSLSPGK |
| 119 | EEELQVIQPDKSVLVAAGETATLRCTITSLFPVGPIQWFRGAGPGRELIYNQRE
GPFPRVTTVSDLTKRNNMDFSIRIGAITPADAGTYYCVKFRKGSPDDVEFKSG
AGTELSVRAKPSERKSSVECPPCPAPPVAGPSVFLFPPKPKDTLMISRTPEVTC
VVVDVSHEDPEVQFNWYVDGVEVHNAKTKPREEQFASTFRVVSVLTVVHQ
DWLNGKEYKCKVSNKGLPSSIEKTISKTKGQPREPQVYTLPPSREEMTKNQV
SLTCLVKGFYPSDIAVEWESNGQPENNYKTTPPMLDSDGSFFLYSKLTVDKS
RWQQGNVFSCSVMHEALHNHYTQKSLSLSPGK |
| 120 | EEELQIIQPDKSVLVAAGETATLRCTITSLFPVGPIQWFRGAGPGRELIYNQRE
GPFPRVTTVSDLTKRNNMDFSIRIGAITPADAGTYYCVKFRKGSPDDVEFKSG
AGTELSVRAKPSERKSSVECPPCPAPPVAGPSVFLFPPKPKDTLMISRTPEVTC
VVVDVSHEDPEVQFNWYVDGVEVHNAKTKPREEQFASTFRVVSVLTVVHQ
DWLNGKEYKCKVSNKGLPSSIEKTISKTKGQPREPQVYTLPPSREEMTKNQV
SLTCLVKGFYPSDIAVEWESNGQPENNYKTTPPMLDSDGSFFLYSKLTVDKS
RWQQGNVFSCSVMHEALHNHYTQKSLSLSPGK |

TABLE 8-continued

Polypeptides Comprising SIRPα D1 Domain Variants
Fused to Fc Domain Variants

| SEQ ID NO: | Amino Acid Sequence |
|---|---|
| 121 | EEELQVIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSERKSSVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 122 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSERKSSVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 123 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPELLGGPSVFLFPPKPKDTLMISRTPEVTCV<br>VVDVSHEDPEVKFNWYVDGVEVEINAKTKPREEQYNSTYRVVSVLTVLHQD<br>WLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSR<br>WQQGNVFSCSVMHEALHNHYTQKSLSLSPGK |
| 124 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPEEAAGAPSVFLFPPKPKDTLMISRTPEVTC<br>VVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSR<br>WQQGNVFSCSVMHEALHNHYTQKSLSLSPGK |
| 125 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPELLGGPSVFLFPPKPKDTLMISRTPEVTCV<br>VVDVSHEDPEVKFNWYVDGVEVEINAKTKPREEQYASTYRVVSVLTVLHQD<br>WLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSR<br>WQQGNVESCSVMHEALEINHYTQKSLSLSPGK |
| 126 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQWNYVDGVEVHNAKTKPREEQFNSTFRVVSVLTVVHQ<br>DWLNGKEYKCKVSNKGLPAPIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 127 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFNSTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 128 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPAPIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 129 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSERKCCVECPPCPAPPVAGPSVFLFPPKPKDTLMISRTPEVTC<br>VVVDVSHEDPEVQFNWYVDGVEVHNAKTKPREEQFASTFRVVSVLTVVHQ<br>DWLNGKEYKCKVSNKGLPSSIEKTISKTKGQPREPQVYTLPPSREEMTKNQV<br>SLTCLVKGFYPSDIAVEWESNGQPENNYKTTPPMLDSDGSFFLYSKLTVDKS<br>RWQQGNVFSCSVMHEALHNHYTQKSLSLSPGK |
| 130 | EEELQVIQPDKSVSVAAGESAILHCTVTSLIPVGPIQWFRGAGPARELIYNQKE<br>GHFPRVTTVSESTKRENMDFSISISNITPADAGTYYCVKFRKGSPDTEFKSGA |

TABLE 8-continued

Polypeptides Comprising SIRPα D1 Domain Variants
Fused to Fc Domain Variants

| SEQ ID NO: | Amino Acid Sequence |
|---|---|
| | GTELSVRAKPSESKYGPPCPSCPAPEFLGGPSVFLFPPKPKDTLMISRTPEVTC
VVVDVSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSR
WQEGNVFSCSVMHEALHNHYTQKSLSLSLGK |
| 131 | EEELQIIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKSG
AGTELSVRAKPSESKYGPPCPPCPAPEFLGGPSVFLFPPKPKDTLMISRTPEVT
CVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRLTVDKS
RWQEGNVFSCSVMHEALEINHYTQKSLSLSLGK |
| 132 | EEELQIIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKSG
AGTELSVRAKPSESKYGPPCPPCPAPEFEGGPSVFLFPPKPKDTLMISRTPEVT
CVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRLTVDKS
RWQEGNVFSCSVMHEALHNHYTQKSLSLSLGK |
| 133 | EEELQIIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKSG
AGTELSVRAKPSESKYGPPCPPCPAPPVAGPSVFLFPPKPKDTLMISRTPEVTC
VVVDVSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSR
WQEGNVFSCSVMHEALEINHYTQKSLSLSLGK |
| 134 | EEELQIIQPDKSVLVAAGETATLRCTITSLFPVGPIQWFRGAGPGRVLIYNQRQ
GPFPRVTTVSDTTKRNNMDFSIRIGNITPADAGTYYCIKFRKGSPDDVEFKSG
AGTELSVRAKPSAAAPPCPPCPAPEFLGGPSVFLFPPKPKDTLMISRTPEVTCV
VVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSR
WQEGNVFSCSVMHEALEINHYTQKSLSLSPGK |
| 135 | EEELQVIQPDKSVLVAAGETATLRCTATSLFPVGPIQWFRGAGPGRELIYNQR
EGPFPRVTTVSDLTKRNNMDFSIRIGAITPADAGTYYCVKFRKGSPDDVEFKS
GAGTELSVRAKPSDKTHTCPPCPAPEAAGAPSVFLFPPKPKDTLMISRTPEVT
CVVVDVSHEDPEVKFNWYVDGVEVHNAKTKPREEQYASTYRVVSVLTVLH
QDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKS
RWQQGNVFSCSVMHEALHNHYTQKSLSLSPG |
| 136 | EEELQIIQPDKSVLVAAGETATLRCTITSLFPVGPIQWFRGAGPGRELIYNQRE
GPFPRVTTVSDTTKRNNMDFSIRIGAITPADAGTYYCVKFRKGSPDDVEFKSG
AGTELSVRAKPSDKTHTCPPCPAPEAAGAPSVFLFPPKPKDTLMISRTPEVTC
VVVDVSHEDPEVKFNWYVDGVEVHNAKTKPREEQYASTYRVVSVLTVLHQ
DWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSR
WQQGNVFSCSVMHEALHNHYTQKSLSLSPG |
| 137 | EEELQIIQPDKSVLVAAGETATLRCTITSLFPVGPIQWFRGAGPGRVLIYNQRE
GPFPRVTTVSDTTKRNNMDFSIRIGAITPADAGTYYCIKFRKGSPDDVEFKSG
AGTELSVRAKPSDKTHTCPPCPAPEAAGAPSVFLFPPKPKDTLMISRTPEVTC
VVVDVSHEDPEVKFNWYVDGVEVHNAKTKPREEQYASTYRVVSVLTVLHQ
DWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSR
WQQGNVFSCSVMHEALHNHYTQKSLSLSPG |
| 211 | EEELQIIQPDKSVLVAAGETATLRCTITSLRPVGPIQWFRGAGPGRELIYNQRD
GPFPRVTTVSDTTKRNNMDFSIRIGAITPADAGTYYCVKFRKGIPDDVEFKSG
AGTELSVRAKPSDKTHTCPPCPAPEAAGAPSVFLFPPKPKDTLMISRTPEVTC
VVVDVSHEDPEVKFNWYVDGVEVHNAKTKPREEQYASTYRVVSVLTVLHQ
DWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSR
WQQGNVFSCSVMHEALHNHYTQKSLSLSPG |
| 214 | EEELQVIQPDKSVLVAAGETATLRCTATSLFPVGPIQWFRGAGPGRELIYNQR
EGPFPRVTTVSDLTKRNNMDFSIRIGAITPADAGTYYCVKFRKGSPDDVEFKS
GAGTELSVRAKPSERKSSVECPPCPAPPVAGPSVFLFPPKPKDTLMISRTPEVT
CVVVDVSHEDPEVQFNWYVDGVEVHNAKTKPREEQFASTFRVVSVLTVVH
QDWLNGKEYKCKVSNKGLPSSIEKTISKTKGQPREPQVYTLPPSREEMTKNQ |

TABLE 8-continued

Polypeptides Comprising SIRPα D1 Domain Variants Fused to Fc Domain Variants

| SEQ ID NO: | Amino Acid Sequence |
|---|---|
|  | VSLTCLVKGFYPSDIAVEWESNGQPENNYKTTPPMLDSDGSFFLYSKLTVDK<br>SRWQQGNVFSCSVMHEALEINHYTQKSLSLSPG |
| 216 | EEELQIIQPDKSVLVAAGETATLRCTITSLFPVGPIQWFRGAGPGRVLIYNQRQ<br>GPFPRVTTVSDTTKRNNMDFSIRIGNITPADAGTYYCIKFRKGSPDDVEFKSG<br>AGTELSVRAKPSDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQD<br>WLNGKEYKCKVSNKALPAPIEKTISKAKGQPREPQVYTLPPSREEMTKNQVS<br>LTCLVKGFYPSDIAVEWESNGQPENNYKTTPPVLDSDGSFFLYSKLTVDKSR<br>WQQGNVFSCSVMHEALHNHYTQKSLSLSPGK |
| 217 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKSG<br>AGTELSVRAKPSEKTHTCPECPAPEAAGAPSVFLFPPKPKDTLMISRTPEVTC<br>VVVDVSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMTKNQV<br>SLTCEVKGFYPSDIAVEWESNGQPENNYKTTPPVLDSDGSFFLYSKLTVDKSR<br>WQQGNVFSCSVMHEALHNHYTQKSLSLSPGK |

In some embodiments, the polypeptide comprises a SIRPα D1 variant domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 8.

In some embodiments, the polypeptide comprises a SIRPα D1 domain variant that has at least 85% sequence identity (e.g., at least 86%, 87%, 88%, 89%, 90%, 91%, 92%, 93%, 94%, 9500, 9600, 97%, 980%, 9900, or 10000 sequence identity) to SEQ ID NOs: 98-104, 107-113, 116-122, or 135-137 in Table 8.

In some embodiments, the polypeptide comprises (a) a signal-regulatory protein α (SIRP-α~) D1 variant, wherein the SIRPα D1 domain variant comprises the amino acid sequence, EEX$_1$X$_2$QX$_3$IQPDKX$_4$VX$_5$VAAGEX$_6$X$_7$X$_8$-LX$_9$CTX$_{10}$TSLX$_{11}$PVGPIQWFRGAGPX$_{12}$RX$_{13}$LIY NQX$_{14}$X$_{15}$GX$_{16}$FPRVTTVSX$_{17}$X$_{18}$TX$_{19}$RX$_{20}$NMDFX$_{21}$-IX$_{22}$IX$_{23}$X$_{24}$ITX$_{25}$ADAGTYYCX$_{26}$KX$_{27}$RKGSPDX$_{28}$-X$_{29}$EX$_{30}$KSGAGTELSVRX$_{31}$KPS (SEQ ID NO: 47), wherein X$_1$ is E, or G; X$_2$ is L, I, or V; X$_3$ is V, L, or I; X$_4$ is S, or F; X$_5$ is L, or S; X$_6$ is S, or T; X$_7$ is A, or V; X$_8$ is I, or T; X$_9$ is H, R, or L; X$_{10}$ is A, V, I, or L; X$_{11}$ is I, T, S, or F; X$_{12}$ is A, or G; X$_{13}$ is E, V, or L; X$_{14}$ is K, or R; X$_{15}$ is E, or Q; X$_{16}$ is H, P, or R; X$_{17}$ is D, or E; X$_{18}$ is S, L, T, or G; X$_{19}$ is K, or R; X$_{20}$ is E, or N; X$_{21}$ is S, or P; X$_{22}$ is S, or R; X$_{23}$ is S, or G; X$_{24}$ is any amino acid; X$_{25}$ is any amino acid; X$_{26}$ is V, or I; X$_{27}$ is F, L, or V; X$_{28}$ is D or absent; X$_{29}$ is T, or V; X$_{30}$ is F, or V; and X$_{31}$ is A, or G; and wherein the SIRPα D1 domain variant comprises at least two amino acid substitutions relative to a wild-type SIRPα D1 domain having a sequence according to any one of SEQ ID NOs: 1 to 10; and (b) an Fc domain dimer variant having two Fc domain variants, wherein each Fc domain variant independently is (i) a human IgG1 Fc region comprising a N297A mutation; (ii) a human IgG1 Fc region comprising L234A, L235A, and G237A mutations; (iii) a human IgG1 Fc region comprising L234A, L235A, G237A, and N297A mutations; (iv) a human IgG2 Fc region comprising a N297A mutation; (v) a human IgG2 Fc region comprising A330S and P331S mutations; (vi) a human IgG2 Fc region comprising A330S, P331S, and N297A mutations; (vii) a human IgG4 Fc region comprising S228P, E233P, F234V, L235A, and delG236 mutations; or (viii) a human IgG4 Fc region comprising S228P, E233P, F234V, L235A, delG236, and N297A mutations.

In some embodiments, the polypeptide comprises a SIRPα D1 domain variant wherein the SIRPα D1 domain variant comprises an amino acid sequence according to SEQ ID NO: 47; an Fc domain dimer having two Fc domains, wherein one of the Fc domains is an Fc domain variant comprising a human IgG1 Fc region comprising L234A, L235A, G237A, and N297A mutations.

Dimerization of Fc Domains

In some embodiments, a SIRPα D1 domain variant polypeptide (e.g., any of the variants described in Tables 2, 5, and 6) is fused to a first Fc domain (e.g., an Fc domain variant) either at the N-terminus or at the C-terminus. In some embodiments, the first Fc domain is a variant that is incapable of forming an dimer. In some embodiments, the first Fc domain forms a dimer with a second Fc domain. In some embodiments, the first and second Fc domains comprise amino acid substitutions that promote heterodimerization between the first and second domain Fc domains.

In some embodiments, each of the two Fc domains in an Fc domain dimer includes amino acid substitutions that promote the heterodimerization of the two monomers. In some embodiments, a SIRPα construct is formed, for example, from a first subunit including a SIRPα D1 domain variant polypeptide fused to a first Fc domain and a second subunit including a second Fc domain (e.g., without a SIRPα D1 domain variant polypeptide or any other polypeptide). In some embodiments, a construct has a single SIRPα D1 domain variant polypeptide linked to an Fc domain dimer (e.g., single arm). In some embodiments, a construct has two SIRPα D1 domain variant polypeptides linked to an Fc domain dimer (e.g., double arm). In some embodiments, a SIRPα D1 domain variant having a K$_D$ of about 500 nM is particularly useful in a double arm construct. In some embodiments, a SIRPα D1 domain variant having a K$_D$ of about 50 nM is particularly useful in a double arm construct. In some embodiments, a SIRPα D1 domain variant having a K$_D$ of about 5 nM is useful in a double arm construct and a single arm construct. In some embodiments, a SIRPα D1 domain variant having a K$_D$ of about 500 pM is useful in a double arm construct and a single arm construct. In some embodiments, a SIRPα D1 domain variant having a K$_D$ of about 100 pM is useful in a double arm construct and a single arm construct. In some embodiments, a SIRPα D1 domain variant having a K$_D$ of about 50 pM is useful in a double arm construct and a single arm construct. In some embodiments, a SIRPα D1 domain variant having a $K_D$ of about 10 pM is useful in a double arm construct and a single arm construct.

In some embodiments, heterodimerization of Fc domains is promoted by introducing different, but compatible, substitutions in the two Fc domains, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain and involved in the dimerization of two Fc domains. In some embodiments, a hole in one CH3 antibody constant domain is created to accommodate a knob in another CH3 antibody constant domain, such that the knob and hole amino acids act to promote or favor the heterodimerization of the two Fc domains. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain includes the knob mutation T366W and the other Fc domain includes hole mutations T366S, L358A, and Y407V. In some embodiments, a polypeptide of the disclosure including a SIRPα D1 domain variant is fused to an Fc domain including the knob mutation T366W to limit unwanted knob-knob homodimer formation. Examples of knob-into-hole amino acid pairs are included, without limitation, in Table 9 and examples of knob-into-hole Fc domain variants and SIRPα-Fc fusions are provided in Table 10.

TABLE 9

Knob-Into-Hole Amino Acid Pairs

| First Fc Domain | Y407T | Y407A | F405A | T394S | T366S L358A Y407V | T394W Y407T | T394S |Y407A | T366W T394S |
|---|---|---|---|---|---|---|---|---|
| Second Fc Domain | T366Y | T366W | T394W | F405W | T366W | T366Y F405A | T366W F405W | F405W Y407A |

TABLE 10

Exemplary Fc Domain Variants and SIRPα D1 Domain Variant-Fc Domain Variant Fusion Polypeptides

| SEQ ID NO: | Amino Acid Sequence |
|---|---|
| 138 | EEELQIIQPDKSVLVAAGETATLRCTITSLFPVGPIQWFRGAGPGRVLIYNQR QGPFPRVTTVSDTTKRNNMDFSIRIGAITPADAGTYYCIKFRKGSPDDVEFKS GAGTELSVRAKPSDKTHTCPPCPAPEAAGAPSVFLFPPKPKDTLMISRTPEVT CVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKN QVSLWCLVKGFYPSDIAVEWESNGQPENNYKTTPPVLDSDGSFFLYSKLTV DKSRWQQGNVFSCSVMHEALHNHYTQKSLSLSPGK |
| 139 | DKTHTCPPCPAPEAAGAPSVFLFPPKPKDTLMISRTPEVTCVVVDVSHEDPEV KFNWYVDGVEVHNAKTKPREEQYASTYRVVSVLTVLHQDWLNGKEYKCK VSNKALPAPIEKTISKAKGQPREPQVYTLPPSREEMTKNQVSLSCAVKGFYPS DIAVEWESNGQPENNYKTTPPVLDSDGSFFLVSKLTVDKSRWQQGNVFSCS VMHEALHNHYTQKSLSLSPGK |
| 140 | EEELQIIQPDKSVLVAAGETATLRCTITSLFPVGPIQWFRGAGPGRVLIYNQR QGPFPRVTTVSDTTKRNNMDFSIRIGAITPADAGTYYCIKFRKGSPDDVEFKS GAGTELSVRAKPSDKTHTCPPCPAPEAAGAPSVFLFPPKPKDTLMISRTPEVT CVVVDVSHEDPEVKFNWYVDGVEVINAKTKPREEQYASTYRVVSVLTVLH QDWLNGKEYKCKVSNKALPAPIEKTISKAKGQPREPQVYTLPPSREEMTKN QVSLSCAVKGFYPSDIAVEWESNGQPENNYKTTPPVLDSDGSFFLVSKLTVD KSRWQQGNVFSCSVMHEALHNHYTQKSLSLSPGK |
| 141 | DKTHTCPPCPAPEAAGAPSVFLFPPKPKDTLMISRTPEVTCVVVDVSHEDPEV KFNWYVDGVEVHNAKTKPREEQYASTYRVVSVLTVLHQDWLNGKEYKCK VSNKALPAPIEKTISKAKGQPREPQVYTLPPSREEMTKNQVSLWCLVKGFYP SDIAVEWESNGQPENNYKTTPPVLDSDGSFFLYSKLTVDKSRWQQGNVFSC SVMHEALHNHYTQKSLSLSPGK |
| 142 | EEELQIIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKS GAGTELSVRAKPSDKTHTCPPCPAPEAAGAPSVFLFPPKPKDTLMISRTPEVT CVVVDVSHEDPEVKFNWYVDGVEVEINAKTKPREEQYASTYRVVSVLTVLH |

TABLE 10-continued

Exemplary Fc Domain Variants and SIRPα D1 Domain Variant-Fc Domain Variant Fusion Polypeptides

| SEQ ID NO: | Amino Acid Sequence |
|---|---|
|  | QDWLNGKEYKCKVSNKALPAPIEKTISKAKGQPREPQVYTLPPSREEMTKN<br>QVSLWCLVKGFYPSDIAVEWESNGQPENNYKTTPPVLDSDGSFFLYSKLTV<br>DKSRWQQGNVFSCSVMHEALHNHYTQKSLSLSPGK |
| 143 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSDKTHTCPPCPAPEAAGAPSVFLFPPKPKDTLMISRTPEVT<br>CVVVDVSHEDPEVKFNWYVDGVEVEINAKTKPREEQYASTYRVVSVLTVLH<br>QDWLNGKEYKCKVSNKALPAPIEKTISKAKGQPREPQVYTLPPSREEMTKN<br>QVSLSCAVKGFYPSDIAVEWESNGQPENNYKTTPPVLDSDGSFFLVSKLTVD<br>KSRWQQGNVFSCSVMHEALHNHYTQKSLSLSPGK |
| 144 | QVQLKQSGPGLVQPSQSLSITCTVSGESLTNYGVHWVRQSPGKGLEWLGVI<br>WSGGNTDYNTPFTSRLSINKDNSKSQVFFKMNSLQSNDTAIYYCARALTYY<br>DYEFAYWGQGTLVTVSSASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCRKTHTCPRCPAPELLGGPSVFLFPPKPKDTLMISRTP<br>EVTCVVVDVSHEDPEVKFNWYVDGVEVHNAKTKPREEQYASTYRVVSVLT<br>VLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSRL<br>TVDKSRWQQGNVFSCSVMHEALHNHYTQKSLSLSPGK |
| 145 | EEELQIIQPDKSVLVAAGETATLRCTITSLFPVGPIQWFRGAGPGRELIYNQRE<br>GPFPRVTTVSDTTKRNNMDFSIRIGAITPADAGTYYCVKFRKGSPDDVEFKS<br>GAGTELSVRAKPSEKTHTCPECPAPEAAGAPSVFLFPPKPKDTLMISRTPEVT<br>CVVVDVSHEDPEVKFNWYVDGVEVHNAKTKPREEQYASTYRVVSVLTVLH<br>QDWLNGKEYKCKVSNKALPAPIEKTISKAKGQPREPQVYTLPPSREEMTKN<br>QVSLTCEVKGFYPSDIAVEWESNGQPENNYKTTPPVLDSDGSFFLYSKLTVD<br>KSRWQQGNVFSCSVMHEALHNHYTQKSLSLSPGK |
| 146 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPSDKTHTCPPCPAPEAAGAPSVFLFPPKPKDTLMISRTPE<br>VTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSREEMT<br>KNQVSLWCLVKGFYPSDIAVEWESNGQPENNYKTTPPVLDSDGSFFLYSKL<br>TVDKSRWQQGNVFSCSVMHEALHNHYTQKSLSLSPGK |
| 147 | DKTHTCPPCPAPEAAGAPSVFLFPPKPKDTLMISRTPEVTCVVVDVSHEDPEV<br>KFNWYVDGVEVHNAKTKPREEQYNSTYRVVSVLTVLHQDWLNGKEYKCK<br>VSNKALPAPIEKTISKAKGQPREPQVYTLPPSREEMTKNQVSLSCAVKGFYPS<br>DIAVEWESNGQPENNYKTTPPVLDSDGSFFLVSKLTVDKSRWQQGNVFSCS<br>VMHEALHNHYTQKSLSLSPGK |
| 148 | EEELQVIQPDKSVLVAAGETATLRCTATSLFPVGPIQWFRGAGPGRELIYNQ<br>RQGPFPRVTTVSDLTKRNNMDFSIRIGNITPADAGTYYCVKFRKGSPDDVEF<br>KSGAGTELSVRAKPSDKTHTCPPCPAPEAAGAPSVFLFPPKPKDTLMISRTPE<br>VTCVVVDVSHEDPEVKFNWYVDGVEVEINAKTKPREEQYNSTYRVVSVLTV<br>LHQDWLNGKEYKCKVSNKALPAPIEKTISKAKGQPREPQVYTLPPSREEMT<br>KNQVSLSCAVKGFYPSDIAVEWESNGQPENNYKTTPPVLDSDGSFFLVSKLT<br>VDKSRWQQGNVFSCSVMHEALHNHYTQKSLSLSPGK |
| 149 | DKTHTCPPCPAPEAAGAPSVFLFPPKPKDTLMISRTPEVTCVVVDVSHEDPEV<br>KFNWYVDGVEVHNAKTKPREEQYNSTYRVVSVLTVLHQDWLNGKEYKCK<br>VSNKALPAPIEKTISKAKGQPREPQVYTLPPSREEMTKNQVSLWCLVKGFYP<br>SDIAVEWESNGQPENNYKTTPPVLDSDGSFFLYSKLTVDKSRWQQGNVFSC<br>SVMHEALHNHYTQKSLSLSPGK |

In addition to the knob-into-hole strategy, in some embodiments, electrostatic steering is also used to control the dimerization of Fc domains. Electrostatic steering refers to the utilization of favorable electrostatic interactions between oppositely charged amino acids in peptides, protein domains, and proteins to control the formation of higher ordered protein molecules. In particular, to control the dimerization of Fc domains using electrostatic steering, one or more amino acid residues that make up the CH3-CH3 interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In some embodiments, a negatively-charged amino acid in the interface is replaced with a positively-charged amino acid. In some embodiments, the charged amino acids are introduced to one of the interacting CH3 antibody constant domains, or both. In some embodiments, introducing charged amino acids to the interacting CH3 antibody constant domains of the two Fc domains promotes the selective formation of heterodimers of Fc domains as controlled by the electrostatic steering effects resulting from the interaction between charged amino acids. Examples of electrostatic steering amino acid pairs are included, without limitation, in Table 11.

TABLE 11

Electrostatic Steering Amino Acid Pairs

| Fc domain monomer 1 | K409D | K409D | K409E | K409E | K392D | K392D | K392E | K392E | K409D<br>K392D | K370E<br>K409D<br>K439E |
|---|---|---|---|---|---|---|---|---|---|---|
| Fc domain monomer 2 | D399K | D399R | D399K | D399R | D399K | D399R | D399K | D399R | D399K<br>D356K | D356K<br>E357K<br>D399K |

Other methods used to control the heterodimerization of Fc domains, especially in the context of constructing a bispecific antibody, are available.

In some embodiments, a first Fc domain and a second Fc domain each includes one or more of the following amino acid substitutions: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1.

In some embodiments an Fc domain comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; or (b) (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region. In some embodiments an Fc domain variant comprises: (a) one of the following amino acid substitutions relative to wild type human IgG1: T366W, T366S, L368A, Y407V, T366Y, T394W, F405W, Y349T, Y349E, Y349V, L351T, L351H, L351N, L351K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, or K409I; and (b) further comprises (i) a N297A mutation relative to a human IgG1 Fc region; (ii) a L234A, L235A, and G237A mutation relative to a human IgG1 Fc region; (iii) a L234A, L235A, G237A, and N297A mutation relative to a human IgG1 Fc region; (iv) a N297A mutation relative to a human IgG2 Fc region; (v) a A330S and P331S mutation relative to a human IgG2 Fc region; (vi) a A330S, P331S, and N297A mutation relative to a human IgG2 Fc region; (vii) a S228P, E233P, F234V, L235A, and delG236 mutation relative to a human IgG4 Fc region; or (viii) a S228P, E233P, F234V, L235A, delG236, and N297A mutation relative to a human IgG4 Fc region.

In some embodiments, the first and second Fc domains include different amino acid substitutions. In some embodiments, the first Fc domain includes T366W. In some embodiments, the second Fc domain includes T366S, L368A, and Y407V. In some embodiments, the first Fc domain includes D399K. In some embodiments, the second Fc domain includes K409D.

Linkers

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer comprising two Fc domain variants, wherein each Fc domain variant independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In the present disclosure, a linker is used to describe a linkage or connection between polypeptides or protein domains or associated non-protein moieties. In some embodiments, a linker is a linkage or connection between an Fc domain (or variant thereof) and a SIRPα D1 domain variant. In some embodiments, the linker connects the C-terminus of the SIRPα D1 domain variant and the N-terminus of the Fc domain variant, such that the two polypeptides are joined to each other in tandem series.

In some embodiments, a linker is a simple covalent bond, e.g., a peptide bond, a synthetic polymer, or any kind of bond created from a chemical reaction, e.g. chemical conjugation. When a linker is a peptide bond, in some embodiments, the carboxylic acid group at the C-terminus of one protein domain reacts with the amino group at the N-terminus of another protein domain in a condensation reaction to form a peptide bond. In some embodiments, the peptide bond is formed from synthetic means through a conventional organic chemistry reaction, or by natural production from a host cell, wherein a nucleic acid molecule encoding the DNA sequences of both proteins (e.g., an Fc domain variant and a SIRPα D1 domain variant) in tandem series can be directly transcribed and translated into a contiguous polypeptide encoding both proteins by the necessary molecular machineries (e.g., DNA polymerase and ribosome) in the host cell.

When a linker is a synthetic polymer, in some embodiments, the polymer is functionalized with reactive chemical functional groups at each end to react with the terminal amino acids at the connecting ends of two proteins.

When a linker (except peptide bond mentioned above) is made from a chemical reaction, in some embodiments, chemical functional groups (e.g., amine, carboxylic acid, ester, azide, or other functional groups), are attached synthetically to the C-terminus of one protein and the N-terminus of another protein, respectively. In some embodiments, the two functional groups then react through synthetic chemistry means to form a chemical bond, thus connecting the two proteins together.

Spacers

In the present disclosure, in some embodiments, a linker between an Fc domain monomer and a SIRPα D1 variant polypeptide of the disclosure, is an amino acid spacer including about 1-200 amino acids. Suitable peptide spacers include peptide linkers containing flexible amino acid residues such as glycine and serine. Examples of linker sequences are provided in Table 12. In some embodiments, a spacer contains motifs, e.g., multiple or repeating motifs, of GS, GG, GGS, GGG, GGGGS (SEQ ID NO: 163), GGSG (SEQ ID NO: 164), or SGGG (SEQ ID NO: 165). In some embodiments, a spacer contains 2 to 12 amino acids including motifs of GS, e.g., GS, GSGS (SEQ ID NO: 166), GSGSGS (SEQ ID NO: 167), GSGSGSGS (SEQ ID NO: 168), GSGSGSGSGS (SEQ ID NO: 169), or GSGSGSGSGSGS (SEQ ID NO: 170). In some embodiments, a spacer contains 3 to 12 amino acids including motifs of GGS, e.g., GGS, GGSGGS (SEQ ID NO: 171), GGSGGSGGS (SEQ ID NO: 172), and GGSGGSGGSGGS (SEQ ID NO: 173). In some embodiments, a spacer contains 4 to 12 amino acids including motifs of GGSG (SEQ ID NO: 164), e.g., GGSG (SEQ ID NO: 164), GGSGGGSG (SEQ ID NO: 174), or GGSGGGSGGGSG (SEQ ID NO: 175). In some embodiments, a spacer contains motifs of GGGGS (SEQ ID NO: 163), e.g., GGGGSGGGGSGGGGS (SEQ ID NO: 176). In some embodiments, a spacer contains amino acids other than glycine and serine, e.g., AAS (SEQ ID NO: 177), AAAL (SEQ ID NO: 178), AAAK (SEQ ID NO: 179), AAAR (SEQ ID NO: 180), EGKSSGSGSESKST (SEQ ID NO: 181), GSAGSAAGSGEF (SEQ ID NO: 182), AEAAAKEAAAKA (SEQ ID NO: 183), KESGSVSSE-QLAQFRSLD (SEQ ID NO: 184), GGGGAGGGG (SEQ ID NO: 185), GENLYFQSGG (SEQ ID NO: 186), SACYCELS (SEQ ID NO: 187), RSIAT (SEQ ID NO: 188), RPACKIPNDLKQKVMNH (SEQ ID NO: 189), GGSAGGSGSGSSGGSSGASGTGTAGGTGSGSGTGSG (SEQ ID NO: 190), AAANSSIDLISVPVDSR (SEQ ID NO: 191), or GGSGGGSEGGGSEGGGSEGGGSEGGGSEGGGSGGGS (SEQ ID NO: 192).

In some embodiments, a spacer contains motifs, e.g., multiple or repeating motifs, of EAAAK (SEQ ID NO: 193). In some embodiments, a spacer contains motifs, e.g., multiple or repeating motifs, of proline-rich sequences such as (XP)n, in which X is any amino acid (e.g., A, K, or E) and n is from 1-5, and PAPAP (SEQ TD NO: 194).

TABLE 12

Linker Sequences

| SEQ ID NO: | AMINO ACID SEQUENCE |
|---|---|
| 163 | GGGGS |
| 164 | GGSG |
| 165 | SGGG |
| 166 | GSGS |
| 167 | GSGSGS |
| 168 | GSGSGSGS |
| 169 | GSGSGSGSGS |
| 170 | GSGSGSGSGSGS |
| 171 | GGSGGS |
| 172 | GGSGGSGGS |
| 173 | GGSGGSGGSGGS |
| 174 | GGSGGGSG |
| 175 | GGSGGGSGGGSG |
| 176 | GGGGSGGGGSGGGGS |
| 177 | AAS |
| 178 | AAAL |
| 179 | AAAK |
| 180 | AAAR |
| 181 | EGKSSGSGSESKST |
| 182 | GSAGSAAGSGEF |
| 183 | AEAAAKEAAAKA |
| 184 | KESGSVSSEQLAQFRSLD |
| 185 | GGGGAGGGG |
| 186 | GENLYFQSGG |
| 187 | SACYCELS |
| 188 | RSIAT |
| 189 | RPACKIPNDLKQKVMNH |
| 190 | GGSAGGSGSGSSGGSSGASGTGTAGGTGSGSGTGSG |
| 191 | AAANSSIDLISVPVDSR |
| 192 | GGSGGGSEGGGSEGGGSEGGGSEGGGSEGGGSGGGS |
| 193 | EAAAK |
| 194 | PAPAP |

In some embodiments, the length of the peptide spacer and the amino acids used is adjusted depending on the two proteins involved and the degree of flexibility desired in the final protein fusion polypeptide. In some embodiments, the length of the spacer is adjusted to ensure proper protein folding and avoid aggregate formation. In some embodiments, a spacer is A or AAAL (SEQ ID NO: 178).

Vectors, Host Cells, and Protein Production

Disclosed herein, in some embodiments, are polypeptides comprising a signal-regulatory protein α (SIRP-α) D1 variant comprising a SIRPα D1 domain, or a fragment thereof, having an amino acid mutation at residue 80 relative to a wild-type SIRPα D1 domain; and at least one additional amino acid mutation relative to a wild-type SIRPα D1 domain at a residue selected from the group consisting of: residue 6, residue 27, residue 31, residue 47, residue 53, residue 54, residue 56, residue 66, and residue 92.

Also disclosed herein, in some embodiments, are polypeptides comprising an Fc variant, wherein the Fc variant comprises an Fc domain dimer having two Fc domain monomers, wherein each Fc domain monomer independently is selected from (i) a human IgG1 Fc region consisting of mutations L234A, L235A, G237A, and N297A; (ii) a human IgG2 Fc region consisting of mutations A330S, P331S and N297A; or (iii) a human IgG4 Fc region comprising mutations S228P, E233P, F234V, L235A, delG236, and N297A.

In some embodiments, the polypeptides of the disclosure are produced from a host cell. A host cell refers to a vehicle that includes the necessary cellular components, e.g., organelles, needed to express the polypeptides and fusion polypeptides described herein from their corresponding nucleic acids. In some embodiments, the nucleic acids are included in nucleic acid vectors introduced into the host cell by transformation, transfection, electroporation, calcium phosphate precipitation, direct microinjection, infection, etc. In some embodiments, the choice of nucleic acid vector depends on the host cell to be used. In some embodiments, host cells are of either prokaryotic (e.g., bacterial) or eukaryotic (e.g., mammalian) origin.

In some embodiments, a polypeptide, for example a polypeptide construct comprising a SIRPα D1 domain variant (e.g., any variant provided in Tables 2, 5, and 6) and a fusion partner such as an Fc variant are produced by culturing a host cell transformed with a nucleic acid, preferably an expression vector, containing a nucleic acid encoding the polypeptide construct (e.g., Fc variant, linker, and fusion partner) under the appropriate conditions to induce or cause expression of the polypeptide construct. In some embodiments, the conditions appropriate for expression varies with the expression vector and the host cell chosen. In some embodiments, a wide variety of appropriate host cells are used, including, but not limited to, mammalian cells, bacteria, insect cells, and yeast. For example, a variety of cell lines that find use in the present disclosure are described in the ATCC® cell line catalog, available from the American Type Culture Collection. In some embodiments, Fc domain variants of this disclosure are expressed in a cell that is optimized not to glycosylate proteins that are expressed by such cell, either by genetic engineering of the cell line or modifications of cell culture conditions such as addition of kifunensine or by using a naturally non-glycosylating host such as a prokaryote (E. coli, etc.), and in some cases, modification of the glycosylation sequence in the Fc is not be needed.

Nucleic Acid Vector Construction and Host Cells

A nucleic acid sequence encoding the amino acid sequence of a polypeptide of the disclosure can be prepared by a variety of methods. These methods include, but are not limited to, oligonucleotide-mediated (or site-directed) mutagenesis and PCR mutagenesis. In some embodiments, a nucleic acid molecule encoding a polypeptide of the disclosure is obtained using standard techniques, e.g., gene synthesis. Alternatively, a nucleic acid molecule encoding a wild-type SIRPα D1 domain is mutated to include specific amino acid substitutions using standard techniques, e.g., QuikChange™ mutagenesis. In some cases, nucleic acid molecules are synthesized using a nucleotide synthesizer or PCR techniques.

In some embodiments, the nucleic acids that encode a polypeptide construct, for example a polypeptide construct comprising a SIRPα D1 domain variant (e.g., any variant provided in Tables 2, 5, and 6) and a fusion partner such as an Fc variant are incorporated into an expression vector in order to express the protein. A variety of expression vectors can be utilized for protein expression. Expression vectors can comprise self-replicating, extra-chromosomal vectors or vectors which integrate into a host genome. A vector can also include various components or elements. For example, in some embodiments, the vector components include, but are not limited to, transcriptional and translational regulatory sequences such as a promoter sequence, a ribosomal binding site, a signal sequence, transcriptional start and stop sequences, translational start and stop sequences, 3' and 5' untranslated regions (UTRs), and enhancer or activator sequences; an origin of replication; a selection marker gene; and the nucleic acid sequence encoding the polypeptide of interest, and a transcription termination sequence. In some embodiments, expression vectors comprise a protein operably linked with control or regulatory sequences, selectable markers, any fusion partners, additional elements, or any combinations thereof. The term "operably linked" means that the nucleic acid is placed into a functional relationship with another nucleic acid sequence. Generally, these expression vectors include transcriptional and translational regulatory nucleic acid operably linked to the nucleic acid encoding the Fc variant, and are typically appropriate to the host cell used to express the protein. A selection gene or marker, such as, but not limited to, an antibiotic resistance gene or fluorescent protein gene, can be used to select for host cells containing the expression vector, for example by antibiotic or fluorescence expression. Various selection genes are available.

In some embodiments, the components or elements of a vector are optimized such that expression vectors are compatible with the host cell type. Expression vectors which find use in the present disclosure include, but are not limited to, those which enable protein expression in mammalian cells, bacteria, insect cells, yeast, and in in vitro systems.

In some embodiments, mammalian cells are used as host cells to produce polypeptides of the disclosure. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7030, and HsS78Bst cells. In some embodiments, *E. coli* cells are used as host cells to produce polypeptides of the disclosure. Examples of *E. coli* strains include, but are not limited to, *E. coli* 294 (ATCC® 31,446), *E. coli* λ 1776 (ATCC® 31,537, *E. coli* BL21 (DE3) (ATCC® BAA-1025), and *E. coli* RV308 (ATCC® 31,608).

Different host cells have characteristic and specific mechanisms for the posttranslational processing and modification of protein products (e.g., glycosylation). In some embodiments, appropriate cell lines or host systems are chosen to ensure the correct modification and processing of the polypeptide expressed. Once the vectors are introduced into host cells for protein production, host cells are cultured in conventional nutrient media modified as appropriate for inducing promoters, selecting transformants, or amplifying the genes encoding the desired sequences.

In some embodiments, a polypeptide construct, for example a polypeptide construct comprising a SIRPα D1 domain variant (e.g., any variant provided in Tables 2, 5, and 6) and a fusion partner such as an Fc variant are expressed in mammalian expression systems, including systems in which the expression constructs are introduced into the mammalian cells using virus such as retrovirus or adenovirus. In some embodiments, human, mouse, rat, hamster, or primate cells are utilized. Suitable cells also include known research cells, including but not limited to Jurkat T cells, NIH3T3, CHO, COS, and 293 cells. Alternately, in some embodiments, proteins are expressed in bacterial cells. Bacterial expression systems are well known in the art, and include *Escherichia coli* (*E. coli*), *Bacillus subtilis*, *Streptococcus cremoris*, and *Streptococcus lividans*. In some cases, polypeptide constructs comprising Fc domain variants are produced in insect cells such as but not limited to Sf9 and Sf21 cells or yeast cells such as but not limited to organisms from the genera *Saccharomyces, Pichia, Kluyveromyces, Hansenula* and *Yarrowia*. In some cases, polypeptide constructs comprising Fc domain variants are expressed in vitro using cell free translation systems. In vitro translation systems derived from both prokaryotic (e.g., *E. coli*) and eukaryotic (e.g., wheat germ, rabbit reticulocytes) cells are available and, in some embodiments, chosen based on the expression levels and functional properties of the protein of interest. For example, as appreciated by those skilled in the art, in vitro translation is required for some display technologies, for example ribosome display. In addition, in some embodiments, the Fc domain variants are produced by chemical synthesis methods such as, but not limited to, liquid-phase peptide synthesis and solid-phase peptide synthesis. In the case of in vitro transcription using a non-glycosylating system such as bacterial extracts, the Fc will not be glycosylated even in presence of the natural glycosylation site and therefore inactivation of the Fc will be equivalently obtained.

In some embodiments, a polypeptide construct includes non-natural amino acids, amino acid analogues, amino acid mimetics, or any combinations thereof that function in a manner similar to the naturally occurring amino acids. Naturally encoded amino acids generally refer to the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, e.g., an a carbon that is bound to a hydrogen, a carboxyl group, an amino group, and an R group, such as, homoserine, norleucine, methionine sulfoxide, methionine methyl sulfonium. In some embodiments, such analogs have modified R groups (such as, norleucine) or modified peptide backbones, but generally retain the same basic chemical structure as a naturally occurring amino acid.

Protein Production, Recovery, and Purification

In some embodiments, host cells used to produce polypeptides of the disclosure are grown in media suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. In some embodiments, host cells are cultured at suitable temperatures, such as from about 20° C. to about 39° C., e.g., from about 25° C. to about 37° C., preferably 37° C., and $CO_2$ levels, such as about 5% to 10%. In some embodiments, the pH of the medium is from about pH 6.8 to pH 7.4, e.g., pH 7.0, depending mainly on the host organism. If an inducible promoter is used in the expression vector, protein expression can be induced under conditions suitable for the activation of the promoter.

In some embodiments, protein recovery involves disrupting the host cell, for example by osmotic shock, sonication, or lysis. Once the cells are disrupted, cell debris is removed by centrifugation or filtration. The proteins can then be further purified. In some embodiments, a polypeptide of the disclosure is purified by various methods of protein purification, for example, by chromatography (e.g., ion exchange chromatography, affinity chromatography, and size-exclusion column chromatography), centrifugation, differential solubility, or by any other standard technique for the purification of proteins. For example, in some embodiments, the protein is isolated and purified by appropriately selecting and combining affinity columns such as Protein A column (e.g., POROS Protein A chromatography) with chromatography columns (e.g., POROS HS-50 cation exchange chromatography), filtration, ultra-filtration, de-salting and dialysis procedures. In some embodiments, a polypeptide is conjugated to marker sequences, such as a peptide to facilitate purification. An example of a marker amino acid sequence is a hexa-histidine peptide (His6-tag), which can bind to a nickel-functionalized agarose affinity column with micromolar affinity. As an alternative, a hemagglutinin "HA" tag, which corresponds to an epitope derived from the influenza hemagglutinin protein can be used.

In some embodiments, polypeptides of the disclosure, for example a polypeptide construct comprising a SIRPα D1 domain variant (e.g., any variant provided in Tables 2, 5, and 6) and a fusion partner such as an Fc variant are produced by the cells of a subject (e.g., a human), e.g., in the context of gene therapy, by administrating a vector such as a viral vector (e.g., a retroviral vector, adenoviral vector, poxviral vector (e.g., vaccinia viral vector, such as Modified Vaccinia Ankara (MVA)), adeno-associated viral vector, and alpha-viral vector) containing a nucleic acid molecule encoding a polypeptide of the disclosure. The vector, once inside a cell of the subject (e.g., by transformation, transfection, electroporation, calcium phosphate precipitation, direct microinjection, infection, etc.) can be used for the expression of a polypeptide disclosed herein. In some cases, the polypeptide is secreted from the cell. In some embodiments, if treatment of a disease or disorder is the desired outcome, no further action is required. In some embodiments, if collection of the protein is desired, blood is collected from the subject and the protein purified from the blood by various methods.

Methods of Treating Cancer

Methods of Treating Myeloid Cancer

In some embodiments, provided is a method of treating cancer (e.g., a myeloid cancer such as myelodysplastic syndrome (MDS) or acute myeloid leukemia (AML)) in an individual (e.g., a human individual) that comprises administering to the individual an effective amount of (a) an agent that blocks the interaction between CD47 (e.g., hCD47) and SIRPα (e.g., hSIRPα) and (b) a hypomethylating agent. In some embodiments, the cancer is AML. In some embodiments, the cancer is TP53-mutated AML and/or FLT3-mutated AML. In some embodiments, the cancer is MDS. In some embodiments, the method comprises an induction phase and a maintenance phase, wherein the induction phase comprises the administration of (a) the agent that blocks the interaction between CD47 (e.g., hCD47) and SIRPα (e.g., hSIRPα) and (b) the hypomethylating agent, and the maintenance phase comprises administration of the agent that blocks the interaction between CD47 (e.g., hCD47) and SIRPα (e.g., hSIRPα) without the hypomethylation agent (e.g., monotherapy with the agent that blocks the interaction between CD47 (e.g., hCD47) and SIRPα (e.g., hSIRPα)).

In some embodiments, provided is a method of treating cancer (e.g., a myeloid cancer such as myelodysplastic syndrome (MDS) or acute myeloid leukemia (AML)) in an individual (e.g., a human individual) that comprises administering to the individual an effective amount of (a) an agent that blocks the interaction between CD47 (e.g., hCD47) and SIRPα (e.g., hSIRPα), (b) a hypomethylating agent, and (c) a Bcl-2 inhibitor (e.g., a selective Bcl-2 inhibitor). In some embodiments, the cancer is AML. In some embodiments, the cancer is TP53-mutated AML and/or FLT3-mutated AML. In some embodiments, the cancer is MDS.

MDS encompasses a series of hematologic conditions characterized by chronic cytopenias (e.g., anemia, neutropenia, thrombocytopenia) accompanied by abnormal cellular maturation (myelodysplasia) and/or characteristic cytogenetic abnormalities. As a result, individuals with MDS are at risk for symptomatic anemia, infection, and bleeding, as well as progression to acute myeloid leukemia (AML), which is often refractory to standard treatment. The most common cause of death among individuals with MDS is bone marrow failure, rather than transformation to AML. In some embodiments, the MDS is higher risk MDS. In some embodiments, the MDS is considered higher risk if the individual has a Revised International Prognostic Scoring System (IPSS-R) score greater than 3. In some embodiments, the MDS is considered higher risk if the individual has a Revised International Prognostic Scoring System (IPSS-R) score greater than 3.5. The IPSS-R is a validated prognostic tool based on 5 factors: (1) the percentage of blasts (very early forms of blood cells) in the individual's bone marrow; (2) the type and number of cytogenetic abnormalities (if any); (3) the level of red blood cells (measured as hemoglobin) in the individual's blood; (4) the level of platelets in the individual's blood; and (5) the level of neutrophils in the individual's blood. Each factor is given a score, and individuals with scores≤3 are more likely to have a favorable prognostic outlook. See, e.g., Greenberg et al. (2012). "Revised international prognostic scoring system for myelodysplastic syndromes." *Blood*, 120 (12), 2454-2465; and Schanz et al. (2012). "New comprehensive cytogenetic scoring system for primary myelodysplastic syndromes (MDS) and oligoblastic acute myeloid leukemia after MDS derived from an international database merge." *J Clin Oncol*, 30 (8), 820-829 for further details regarding the IPSS-R and how scores are calculated to determine an individual's MDS risk status. In some embodiments, the individual has an IPSS-R score of about 3 or greater or about 3.5 or greater. In some embodiments, the individual has an IPSS-R score of less than about 3 or less than about 3.5. In some embodiments, the individual has received prior treatment for MDS. Current standard treatments for MDS include, e.g., hematopoietic stem cell-transplantation and azacitidine. In some embodiments, the individual has not received prior treatment for MDS.

AML is a form of cancer that is characterized by infiltration of the bone marrow, blood, and other tissues by proliferative, clonal, abnormally differentiated, and occasionally poorly differentiated cells of the hematopoietic system. It is one of the most common forms of acute leukemia among adults. Every year doctors diagnose an estimated 19,520 people in the United States with AML. An estimated 10,670 deaths occur on a yearly basis because of the disease. In some embodiments, the individual has subcytologically or histologically confirmed diagnosis of relapsed/refractory or newly diagnosed AML per WHO 2016 classification. In some embodiments, the individual has AML that is relapsed/refractory or that is previously untreated in patients not considered suitable for intensive induction therapy. In some embodiments, the individual has AML that is relapsed/refractory after prior treatment with a HMA-based regimen. In some embodiments, the individual has previously untreated AML and is not considered a suitable candidate for intensive induction therapy. In some embodiments, the individual has adequate renal and liver function. In some embodiments, the individual is ≥18 years old. In some embodiments, the individual has adequate performance status. In some embodiments, the individual has not undergone prior allo-HSCT. In some embodiments, the individual is least 3 months post-HCST, without uncontrolled graft-versus-host disease (GVHD). In some embodiments, the individual has not undergone prior allo-HSCT. In some embodiments, the individual does not have newly diagnosed AML with favorable risk cytogenetics such as t(8; 21), inv(16), or t(16; 16) as per the NCCN guidelines version 3, 2019 for AML. In some embodiments, the individual does not have acute promyelocytic leukemia (APL). In some embodiments, the individual has not undergone prior treatment with any anti-CD47 or anti-SIRPα (signal regulatory protein alpha) agent. In some embodiments, the individual does not have known active viral infections, including hepatitis B and C, human immunodeficiency virus (HIV), acquired immunodeficiency syndrome (AIDS) related illness, or sars-cov-2 (severe acute respiratory syndrome coronavirus 2).

In some embodiments, the agent that blocks the interaction between CD47 and SIRPα is a polypeptide (e.g., fusion polypeptide) comprising a SIRPα D1 domain variant (e.g., a SIRPα D1 domain variant described herein) and an Fc domain variant (e.g., an Fc domain variant described herein). In some embodiments, the C-terminus of the SIRPα D1 domain variant of the fusion polypeptide (e.g., a SIRPα D1 domain variant described herein) is fused to the N-terminus of the Fc domain variant. In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat (e.g., wherein the C-terminus of the SIRPα D1 domain variant is fused to the N-terminus of the Fc domain variant). In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer.

Hypomethylating Agents

Hypomethylating agents are a class of anticancer drugs that have so far been shown to have two main mechanisms of antitumor activity: (i) cytotoxicity due to incorporation into RNA and/or DNA, leading to induction of DNA damage response and (ii) DNA hypomethylation through inhibition of DNA methyltransferase, enabling restoration of normal cell growth and differentiation. See, e.g., Diesch et al. (2016) "A clinical-molecular update on azanucleoside-based therapy for the treatment of hematologic cancers." *Clin Epigenet*, 8: 71; Sato et al. (2017) "DNA Hypomethylating Drugs in Cancer Therapy." *Cold Spring Harbor Perspectives in Medicine*, 7(5), a026948; and Datta et al. (2012) "Novel Insights into the Molecular Mechanism of Action of DNA Hypomethylating Agents: Role of Protein Kinase C δ in Decitabine-Induced Degradation of DNA Methyltransferase 1." *Genes &cancer*, 3(1), 71-81 for additional details regarding hypomethylation agents.

In some embodiments, the hypomethylating agent is azacitidine (also known as 5-aza-2'-deoxycytidine, 5-Azacytidine, Azacytidine, Ladakamycin, 4-Amino-1-β-D-ribofuranosyl-s-triazin-2(1H)-one, and U-18496). Azacitidine, a pyrimidine nucleoside analogue of cytidine, is a white crystalline powder with the empirical formula $C_8H_{12}N_4O_5$ and a molecular weight of 244.2 g/mol. Azacitidine is described chemically as 4-amino-1-[(2R,3R,4S,5R)-3,4-dihydroxy-5-(hydroxymethyl)oxolan-2-yl]-1,3,5-triazin-2-one and has the following chemical structure:

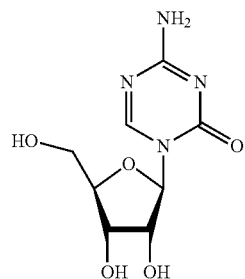

The CAS Registry Number for azacitidine is 320-67-2. Azacitidine is administered subcutaneously or intravenously and is sold under the trade names PREMIERPRO RX AZACITIDINE®, VIDAZA®, AZACITIDINE NOVAPLUS®, and others. Complete information about azacitidine preparation, dispensing, dosage, and administration schedule can be found in the local package insert (for the United States, see, e.g., www(dot)accessdata.fda(dot)gov/drugsatfda_docs/label/2008/050794s0111b1(dot)pdf; for Europe, see, e.g., www(dot)ema(dot)Europa(dot)eu/en/documents/product-information/vidaza-epar-product-information_en(dot)pdf. In some embodiments, the azacitidine is administered in accordance with the dosing and frequency recommended in the local package insert.

In some embodiments, the hypomethylating agent is decitabine (also known as 5-Aza-2'-deoxycytidine, 4-amino-1-(2-deoxy-β-D-erythro-pentofuranosyl)-s-triazin-2(1H)-one, and 5-azadeoxycytidine). Decitabine is also pyrimidine nucleoside analogue of cytidine. Decitabine has the empirical formula $C_8H_{12}N_4O_4$ and a molecular weight of 218.21 g/mol. Decitabine is described chemically as 4-amino-1-[(2R,4S,5R)-4-hydroxy-5-(hydroxymethyl)oxolan-2-yl]-1,3,5-triazin-2-one and has the following chemical structure:

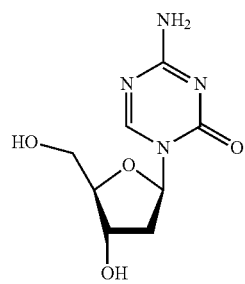 [SMILES: Nc1ncn([C@H]2C[C@@H](O)[C@@H](CO)O2)c(=O)n1]

The CAS Registry Number for decitabine is 2353-33-5. Decitabine is administered intravenously and is sold under the trade name DACOGEN® (and others). Complete information about decitabine preparation, dispensing, dosage, and administration schedule can be found in the local package insert (for the United States, see, e.g., www(dot)accessdata(dot)fda.gov/drugsatfda_docs/label/2010/021790s0061b1(dot)pdf, for Europe, see, e.g., www(dot)ema(dot)europa(dot)eu/en/documents/product-information/dacogen-epar-product-information_en(dot)pdf. In some embodiments, decitabine is administered in accordance with the dosing and frequency recommended in the local package insert.

In some embodiments, the hypomethylating agent is FdCyd (5-fluoro-2'-deoxycytidine), zebularine, CP-4200 (i.e., an elaidic acid derivative of azacitidine), RG108, nanaomycin A, guadecitabine, RX-3117, EPI01, antroquinonol, CC-486, or ASTX727 (see, e.g., astx(dot)com/research-development/clinical-pipeline/astx727-oral-dnmt-inhibitor-hematological-malignancies/). Other exemplary hypomethylating agents that find use in the present methods are described in, e.g., Sato et al. (2017). "DNA Hypomethylating Drugs in Cancer Therapy." *Cold Spring Harbor perspectives in medicine,* 7(5), a026948 and Duchmann, et al. (2019). "Clinical update on hypomethylating agents." *Int J Hematol* 110, 161-169.

Bcl-2 Inhibitors

Bcl-2 inhibitors are a class of anticancer drugs that are believed to exert their cytotoxic effects by competing with proapoptotic Bcl2s to occupy BH3 docking grooves on the surfaces of antiapoptotic family members. By binding to one or more Bcl2 family members, these inhibitors induce apoptosis by mimicking the activity of natural antagonists of BCL-2 and other related proteins and restore apoptosis in tumor cells.

In some embodiments, the Bcl-2 inhibitor is venetoclax (also known as GDC-0199, ABT-199, and RG7601) is an exemplary selective Bcl2 inhibitor used in the methods described herein. Venetoclax is a light yellow to dark yellow solid with the empirical formula $C_{45}H_{50}ClN_7O_7S$ and a molecular weight of 868.44 g/mol. Venetoclax has very low aqueous solubility. Venetoclax is described chemically as 4-(4-{[2-(4-chlorophenyl)-4,4dimethylcyclohex-1-en-1-yl]methyl}piperazin-1-yl)-N-({3-nitro-4-[(tetrahydro-2H-pyran-4ylmethyl)amino]phenyl}sulfonyl)-2-(1H-pyrrolo[2,3-b]pyridin-5-yloxy)benzamide) and has the following chemical structure:

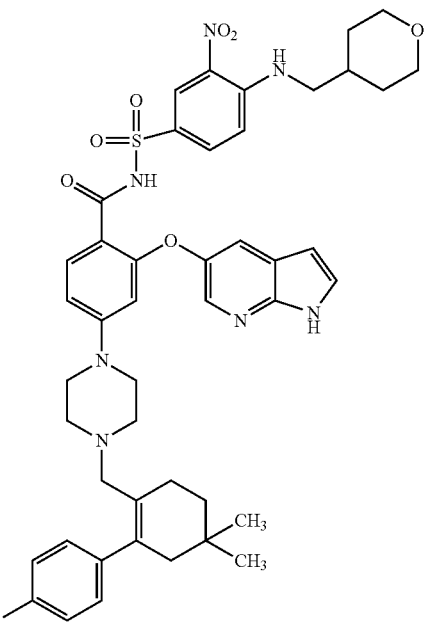

The CAS Registry Number for venetoclax is 1257044-40-8. Venetoclax is administered orally and is sold under the trade names Venclexta and Venclyxto. Complete information about venetoclax preparation, dispensing, dosage, and administration schedule can be found in the local package insert (for the United States, see, e.g., www(dot)accessdata(dot)fda(dot)gov/drugsatfda_docs/label/2016/208573s000lbl (dot) pdf; for Europe, see, e.g., www(dot)ema(dot)europa(dot)eu/en/medicines/human/EPAR/venclyxto#product-information-section). In some embodiments, the venetoclax is administered in accordance with the dosing and frequency recommended in the local package insert.

In some embodiments, the Bcl-2 inhibitor is ABT-737. ABT-737 is another exemplary selective Bcl2 inhibitor used in the methods described herein. ABT-737, which inhibits both Bcl2 and Bcl-xL, has the empirical formula $C_{42}H_{45}ClN_6O_5S_2$ and a molecular weight of 813.43 g/mol. The CAS Registry Number for ABT-737 is 852-808-04-9. ABT-737 is described chemically as 4-{4-[(4'-Chloro-2-biphenylyl)methyl]-1-piperazinyl}-N-[(4-{[(2R)-4-(dimethylamino)-1-(phenylsulfanyl)-2-butanyl]amino}-3-nitrophenyl) sulfonyl]benzamide and has the following chemical structure:

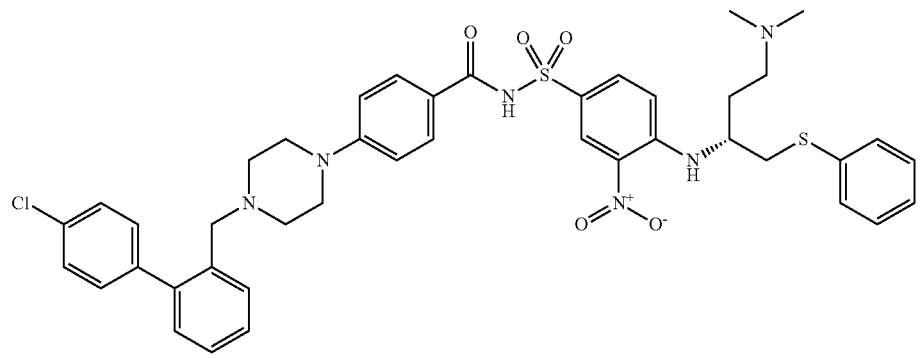 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]

In some embodiments, the Bcl-2 inhibitor used in the methods described herein is navitoclax. Navitoclax (also known as ABT-263), which inhibits both Bcl2, Bcl-xL, and Bcl-w, has the empirical formula $C_{47}H_{55}ClF_3N_5O_6S_3$ and a molecular weight of 974.6 g/mol. The CAS Registry Number for navitoclax is 923564-51-6. ABT-263 is described chemically as 4-[4-[[2-(4-chlorophenyl)-5,5-dimethylcyclohexen-1-yl]methyl]piperazin-1-yl]-N-[4-[[(2R)-4-morpholin-4-yl-1-phenylsulfanylbutan-2-yl]amino]-3-(trifluoromethylsulfonyl)phenyl]sulfonylbenzamide and has the chemical structure provided below. Additional details regarding navitoclax are provided in, e.g., Tse et al. (2008) *Cancer Res.* 68(9): 3421-3429.

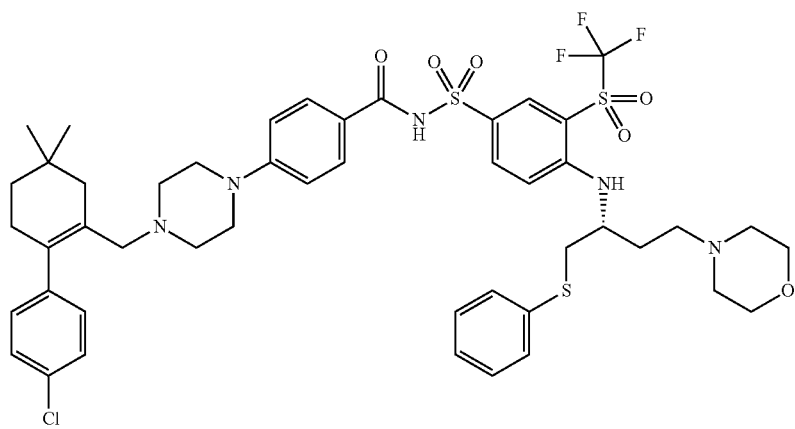 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]

In some embodiments, the Bcl2 inhibitor used in the methods described herein is S55746 (also known as BCL201 and Servier-1). S55746 occupies the hydrophobic groove of BCL-2. Its selectivity profile demonstrates no significant binding to MCL-1, BFL-1 S55746 occupies the hydrophobic groove of BCL-2. Its selectivity profile demonstrates no significant binding to MCL-1, BFL-1 (BCL2A1/A1) and poor affinity for BCL-XL. S55746 has no cytotoxic activity on BCL-XL-dependent cells, such as platelets (see, e.g., Casara et al. (2008) Oncotarget. 9(28): 29975-20088). S55746 has the empirical formula $C_{43}H_{42}N_4O_6$ and a molecular weight of 710.82 g/mol. The CAS Registry Number for S55746 is 1448584-12-0. S55746 is described chemically as(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-phenyl-5,6,7,8-tetrahydroindolizine-1-carboxamide and has the following chemical structure:

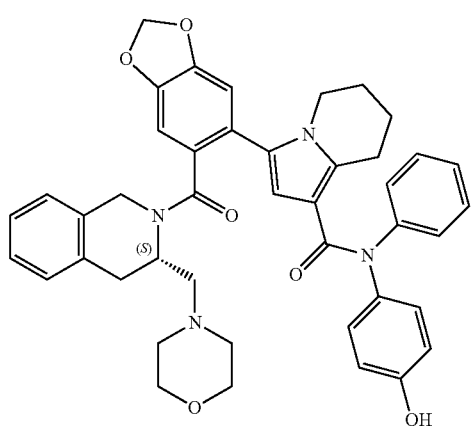

In some embodiments, the polypeptide (e.g., fusion polypeptide) and the hypomethylating agent (e.g., azacitidine) are administered simultaneously, concurrently, or sequentially. In some embodiments, the polypeptide (e.g., fusion polypeptide), the hypomethylating agent (e.g., azacitidine), and the Bcl-2 inhibitor (e.g., venetoclax) are administered simultaneously, concurrently, or sequentially. In some embodiments, the fusion polypeptide is administered via intravenous infusion. In some embodiments, the fusion polypeptide is administered (e.g., via intravenous infusion) at a dose of up to 60 mg/kg. In some embodiments, the fusion polypeptide is administered (e.g., via intravenous infusion) at a dose of 60 mg/kg once every 4 weeks (i.e., q4w) or once every 28 days. In some embodiments, the hypomethylating agent (e.g., azacitidine) is administered via intravenous infusion or subcutaneously. In some embodiments, the azacitidine is administered in one or more 28-day cycles. In some embodiments, the azacitidine is administered at a dose of 75 mg/m² daily for 7 days of each 28 day cycle. In some embodiments, the azacitidine is administered to the individual during each 28-day cycle at a dose of 75 mg/m² daily for 5 days, followed by 2 days without azacitidine administration, and then administered to the individual at a dose of 75 mg/m² for 2 additional days. In some embodiments, the Bcl-2 inhibitor (e.g., venetoclax) is administered orally In some embodiments, the venetoclax is administered at a dose of In some embodiments, the venetoclax is administered at a dose of 100 mg of Day 1 of treatment, 200 mg on Day 2 of treatment, and 400 mg every day following Day 3 of treatment. In some embodiments, the venetoclax is administered at a dose of 100 mg of Day 1 of treatment, 200 mg on Day 2 of treatment, 400 mg on Day 3 of treatment, and 600 mg every day following Day 3. In some embodiments, the venetoclax is administered 400 mg orally once daily of each 28-day cycle in combination with a hypomethylating agent (e.g., azacitidine or decitabine).

In some embodiments, the fusion polypeptide is supplied for use (e.g., intravenous administration) in a 100 mg/5 ml Type I clear glass vial sealed with a 20 mm Teflon coated rubber septum stopper and aluminum seal. In some embodiments, the fusion polypeptide is supplied for use (e.g., intravenous administration) in a 400 mg/20 ml Type I clear glass vial sealed with a 20 mm Teflon coated rubber septum stopper and aluminum seal. In some embodiments, the fusion polypeptide is stored in its original container at 2-8° C. (36-46° F.) until use (e.g., intravenous administration).

Combination Therapies for Treating Cancer

In some embodiments, provided is a method of treating cancer in an individual (e.g., a human individual) that comprises administering to the individual an effective amount of a polypeptide (e.g., a fusion polypeptide) comprising a SIRPα D1 domain variant (e.g., a SIRPα D1 domain variant described herein) and an Fc domain variant (e.g., an Fc domain variant described herein), wherein the polypeptide (e.g., fusion polypeptide) is administered to the individual (e.g., via intravenous infusion) at a dose of up to about 60 mg/kg (e.g., such as about any one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 mg/kg, including any range between these values). In some embodiments, provided is a method of treating cancer in an individual (e.g., a human individual) that comprises administering to the individual an effective amount of a polypeptide (e.g., fusion polypeptide) comprising a SIRPα D1 domain variant (e.g., a SIRPα D1 domain variant described herein) and an Fc domain variant (e.g., an Fc domain variant described herein), wherein the polypeptide (e.g., fusion polypeptide) is administered to the individual at a dose of about 60 mg/kg. In some embodiments the polypeptide (e.g., fusion polypeptide) is administered at a dose of about 60 mg/kg (e.g., via intravenous infusion) once every four weeks (e.g., q4w), or once every 28 days. In some embodiments, provided is a method of treating cancer in an individual (e.g., a human individual) that comprises administering to the individual an effective amount of a polypeptide (e.g., fusion polypeptide) comprising a SIRPα D1 domain variant (e.g., a SIRPα D1 domain variant described herein) and an Fc domain variant (e.g., an Fc domain variant described herein), wherein the polypeptide (e.g., fusion polypeptide) is administered to the individual (e.g., via intravenous infusion) at a dose of about 45 mg/kg. In some embodiments the polypeptide (e.g., fusion polypeptide) is administered to the individual (e.g., via intravenous infusion) at a dose of about 45 mg/kg once every three weeks (e.g., q3w), or once every 21 days. In some embodiments, C-terminus of the SIRPα D1 domain variant of the polypeptide (e.g., fusion polypeptide) is fused to the N-terminus of the Fc domain variant. In some embodiments, the polypeptide (e.g., fusion polypeptide) comprises a SIRPα D1 domain variant that comprises the amino acid sequence of SEQ ID NO: 81 or SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat (e.g., wherein the C-terminus of the SIRPα D1 domain variant is fused to the N-terminus of the Fc domain variant). In some embodiments, the polypeptide (e.g., fusion polypeptide) administered to the individual comprises the amino acid sequence of SEQ ID NO: 136 or SEQ ID NO: 135. In some embodiments, the polypeptide (e.g., fusion polypeptide) forms a homodimer. In some embodiments, the individual is human.

In some embodiments, the method comprises administering the polypeptide (e.g., fusion polypeptide) comprising a SIRPα D1 domain variant (e.g., a SIRPα D1 domain variant described herein) and an Fc domain variant (e.g., an Fc domain variant described herein) in combination with at least one additional agent (e.g., anti-cancer agent), such as at least two, three, four, or five additional agents (e.g., anti-cancer agents). In some embodiments, the exemplary anti-cancer agent(s) that find use with the methods herein include, without limitation, therapeutic antibodies, antibody-drug conjugates (ADC), small molecule inhibitors, peptide inhibitors, corticosteroids, methotrexate, immunomodulatory agents, anti-tumor antibiotics, immunotherapeutic agents, anti-cancer vaccines, oncolytic viruses, cytokines, or chemotherapeutic agents (e.g., topoisomerase inhibitors, antimetabolites, anti-mitotic drugs, hypomethylating agents, platinum-based compounds, anthracyclines, alkylating agents, plant alkaloids, and others), and combinations thereof.

Additionally or alternatively, in some embodiments, the method comprises administering the polypeptide comprising a SIRPα D1 domain variant (e.g., a SIRPα D1 domain variant described herein) and an Fc domain variant (e.g., an Fc domain variant described herein) in conjunction with at least one additional mode of therapy. In some embodiments, the exemplary mode(s) of therapies that are performed in conjunction with the administration of a fusion polypeptide include, without limitation, adoptive cell therapy (e.g., chimeric antigen receptor T-cell therapy (CAR-T), tumor infiltrating lymphocytes (TILs), TCR engineered T cells, TCR engineered NK cell, and macrophage cell products), autologous stem cell transplant, allogenic stem cell transplant, radiation, surgery, gene therapy, cryoablation, and bone marrow transplant.

In some embodiments, the cancer treated by a method provided herein is a solid tumor. Exemplary cancers treated by a method provided herein include, without limitation, e.g., breast cancer, lung cancer, adenocarcinoma of the lung, squamous cell lung cancer, small cell lung cancer (SCLC), non-small cell lung cancer (NSCLC), head and neck cancer, mesothelioma, brain cancer, brain tumor, abdominal cancer, colon cancer, colorectal cancer, esophageal cancer, parapharyngeal cancer, gastrointestinal cancer, glioma, liver cancer, gastric cancer, oral cancer, tongue cancer, neuroblastoma, osteosarcoma, ovarian cancer, renal cancer, urinary bladder cancer, urinary tract cancer, pancreatic cancer, retinoblastoma, cervical cancer, uterine cancer, Wilm's tumor, multiple myeloma, skin cancer, lymphoma, leukemia, blood cancer, thyroid cancer, bone cancer, adenocystic tumor, chondrosar-coma, pancreatic islet cell tumor, neuroendocrine tumor, prostate cancer, glioblastoma, endometrial carcinoma, endometrial cancer, leiomyosarcoma, gall bladder cancer, hepatocellular cancer, a melanoma, or other solid tumor.

In some embodiments, the cancer treated by a method provided herein is a hematological cancer. Exemplary cancers treated by a method provided herein include, without limitation, e.g., multiple myeloma, or a leukemia, including, but not limited to, e.g., acute or chronic myelogenous leukemia acute or chronic lymphoblastic leukemia, acute lymphocytic leukemia (ALL) chronic lymphocytic leukemia (CLL), small lymphocytic lymphoma (SLL), acute myeloid leukemia (AML), myelodysplastic syndrome (MDS), chronic myeloid leukemia (CML), hairy cell leukemia, chronic myelomonocytic leukemia (CMML), Juvenile myelomonocytic leukemia (JMML), large granular lymphocytic (LGL) leukemia, plasmacytoma, blastic plasmacytoid dendritic cell neoplasm (BPDCN), B-cell prolymphocytic leukemia (B-PLL), T-cell prolymphocytic leukemia (T-PLL), multiple myeloma (MM), and Non-Hodgkin lymphomas (such as diffuse large B-cell lymphoma (DLBCL), Burkitt lymphoma, mantle cell lymphoma (MCL), peripheral T-cell lymphoma (PTCL), lymphoplasmacytic lymphoma, Waldenstrom macroglobulinemia, marginal zone lymphoma (MZL) and follicular lymphoma (FL).

Kits and Articles of Manufacture

In another embodiment of the invention, provided is an article of manufacture or a kit is comprising a polypeptide (e.g., a fusion polypeptide described herein) comprising a SIRPα D1 domain variant and an Fc domain variant. In some embodiments, the SIRPα D1 domain variant is for use in combination with a hypomethylating agent (e.g., azacitidine) for the treatment of myelodysplastic disorder (MDS) or acute myeloid leukemia (AML) in an individual (e.g., human individual). In some embodiments, the SIRPα D1 domain variant is for use in combination with a hypomethylating agent (e.g., azacitidine) and a Bcl-2 inhibitor (e.g., veneotclax) for the treatment of AML in an individual (e.g., human individual). In some embodiments, the SIRPα D1 domain variant comprises the amino acid sequence selected from the group consisting of: SEQ ID NO: 81 and SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the Fc domain variant comprises the amino acid sequence of SEQ ID NO: 91. In some embodiments the polypeptide comprises the amino acid sequence of SEQ ID NO: 135 or SEQ ID NO: 136. In some embodiments, the polypeptide comprising a SIRPα D1 domain variant and an Fc domain variant forms a homodimer. In some embodiments, the kit or article of manufacture is for use according to a method of treatment provided herein.

In some embodiments, the kit or article of manufacture further comprises a hypomethylating agent. In some embodiments, the hypomethylating agent is azacitidine. In some embodiments, the kit comprises a package insert or label with instructions for using the polypeptide (e.g., fusion polypeptide) in combination with the hypomethylating agent (e.g., azacitidine) to treat or delay progression of cancer (e.g., a myeloid cancer such as myelodysplastic syndrome (MDS) or acute myeloid leukemia (AML)) in an individual (such as a human individual). In some embodiment, the kit or article of manufacture is for use in the treatment of AML, e.g., TP53-mutated AML and/or FLT3-mutated AML. In some embodiments, the kit or article of manufacture is for use in the treatment of MDS, e.g., higher risk MDS. In some embodiments, the polypeptide (e.g., fusion polypeptide) and the hypomethylating agent (e.g., azacitidine) are provided together in the kit. In some embodiments, the polypeptide (e.g., fusion polypeptide) and the hypomethylating agent (e.g., azacitidine) are provided in the same container or separate containers.

In some embodiments, the kit or article of manufacture further comprises a Bcl-2 inhibitor. In some embodiments, the Bcl-2 inhibitor is venetoclax. In some embodiments, the kit comprises a package insert or label with instructions for using the polypeptide (e.g., fusion polypeptide) in combination with the hypomethylating agent (e.g., azacitidine) and the Bcl-2 inhibitor (e.g., venetoclax) to treat or delay progression of cancer (e.g., a myeloid cancer such acute myeloid leukemia (AML)) in an individual (such as a human individual). In some embodiment, the kit or article of manufacture is for use in the treatment of AML, e.g., TP53-mutated AML and/or FLT3-mutated AML. In some embodiments, the polypeptide (e.g., fusion polypeptide), the hypomethylating agent (e.g., azacitidine), and the Bcl-2 inhibitor (e.g., venetoclax) are provided together in the kit. In some embodiments, the polypeptide (e.g., fusion polypeptide), the hypomethylating agent (e.g., azacitidine), and the Bcl-2 inhibitor (e.g., venetoclax) are provided in the same container or separate containers.

In another embodiment of the invention, an article of manufacture or a kit is provided comprising a polypeptide (e.g., a fusion polypeptide described herein) comprising a SIRPα D1 domain variant and an Fc domain variant. In some embodiments, the SIRPα D1 domain variant comprises the amino acid sequence selected from the group consisting of: SEQ ID NO: 81 and SEQ ID NO: 85. In some embodiments, the Fc domain variant is (i) a human IgG1 Fc region comprising L234A, L235A, G237A, and N297A mutations, wherein numbering is according to the EU index of Kabat; (ii) a human IgG2 Fc region comprising A330S, P331S, and N297A mutations, wherein numbering is according to the EU index of Kabat; (iii) a human IgG4 Fc region comprising S228P, E233P, F234V, L235A, and delG236 mutations, wherein numbering is according to the EU index of Kabat; or (iv) a human IgG4 Fc region comprising S228P, E233P, F234V, L235A, delG236, and N297A mutations, wherein numbering is according to the EU index of Kabat. In some embodiments, the Fc domain variant comprises the amino acid sequence of SEQ ID NO: 91. In some embodiments the polypeptide comprises the amino acid sequence of SEQ ID NO: 135 or SEQ ID NO: 136. In some embodiments, the polypeptide comprising a SIRPα D1 domain variant and an Fc domain variant forms a homodimer. In some embodiments, the kit comprises a package insert or label with instructions for using the polypeptide (e.g., fusion polypeptide) for the treatment of cancer (e.g., a cancer described elsewhere herein) in an individual (such as a human individual). In some embodiments, the package insert or label provides instructions to administer the polypeptide (e.g., fusion polypeptide) to the individual in need thereof at a dose of up to 60 mg/kg. In some embodiments, the package insert or label provides instructions to administer the polypeptide (e.g., fusion polypeptide) to the individual at a dose of 60 mg/kg once every 4 weeks (q4w), or once every 28 days. In some embodiments, the package insert or label provides instructions to administer the polypeptide (e.g., fusion polypeptide) to the individual in need thereof at a dose of 45 mg/kg once every 3 weeks (q3w), or once every 21 days. In some embodiments, the kit further comprises at least one additional anti-cancer agent (e.g., an anti-cancer agent described elsewhere herein). In some embodiments, the kit comprises a package insert or label with instructions for using the polypeptide (e.g., fusion polypeptide) in combination with the at least one additional anti-cancer agent to treat or delay progression of cancer (e.g., a cancer described herein) in an individual (such as a human individual). In some embodiments, the polypeptide (e.g., fusion polypeptide) and the at least one additional anti-cancer agent are provided in the same container or separate containers. Additionally or alternatively, in some embodiments, the kit comprises a package insert or label with instructions for using the polypeptide (e.g., fusion polypeptide) in conjunction with at least one additional mode of therapy (e.g., a mode of therapy described herein).

Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, an antineoplastic agent, a therapeutic antibody, etc.). Suitable containers for the one or more agents include, for example, bottles, vials, bags and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Materials and Methods for Examples 2A-2E

Peripheral Blood Mononuclear Cell (PBMC) Isolation

Trima residuals from Blood Centers of the Pacific or plateletpheresis leukoreduction filter (LRS chamber) (Vitalant) were diluted with PBS (Life Technologies). Diluted blood was split into two tubes and underlayed with 15 mL Ficoll-Paque Plus (GE Healthcare). Tubes were centrifuged for 30 minutes at 400×g. Peripheral blood mononuclear cells (PBMCs) were collected from the interface, washed twice by addition of 40 mL PBS, centrifuged for 10 minutes at 400×g, and resuspended in MACS buffer (PBS with 0.5% BSA (Thermo Fisher Scientific), 2 mM EDTA (Teknova)).

Derivation and Culture of Human Monocyte-Derived Macrophages for Phagocytosis $CD14^+$ monocytes were purified by negative selection using the Classical Monocytes Isolation Kit, human (Miltenyi Biotec) and LS columns (Miltenyi Biotec) according to the manufacturer's protocol. $CD14^+$ monocytes were seeded into 150 mm tissue culture dishes (Corning) at 6 million cells per dish in 25 mL medium comprised of RPMI complete media, supplemented with 50 ng/mL M-CSF (Miltenyi Biotec), 10% FBS (Thermo Fisher Scientific), 1% penicillin/streptomycin, and 1% GlutaMAX. Cells were cultured for seven to eleven days.

In Vitro Phagocytosis Assays

Target cells, HL60 and OCI-AML3 cells, were washed once in PBS and labeled with the Celltrace CFSE Cell Proliferation kit (Thermo Fisher Scientific) in suspension with 300 nM CFSE (carboxyfluorescein succinimidyl ester) according to the manufacturer's instructions and resuspended in RPMI complete media. Target cells were incubated overnight with two-fold serial dilutions of azacitidine between 39 nM to 2.5 µM in RPMI complete media. Prior to incubation with macrophages, cells were resuspended in RPMI. Macrophages were detached from culture plates by washing once with PBS and incubation in TrypLE Select for 20 minutes at 37° C. Cells were removed with a cell scraper (Corning), washed in PBS, and resuspended in RPMI.

CFSE-labeled target cells treated with azacitidine for 48 hours were spun and added to ultra-low attachment U-bottom 96 well plates (Corning) at 100,000 cells per well. Drug A was then added. Plates were incubated 30 minutes at 37° C. in a humidified incubator with 5% carbon dioxide, then 50,000 macrophages were added. Plates were incubated two hours at 37° C. in a humidified incubator with 5% carbon dioxide. Cells were pelleted by centrifugation for five minutes at 400×g and stained at 4° C. for 30 minutes in Fixable Viability Dye eFluor 780 (ebioscience) diluted 1:4000 in PBS. Cells were washed in FACS buffer (PBS with 0.5% BSA) and stained at 4° C. for 45 minutes in FACS buffer containing human FcR Blocking Reagent (Miltenyi Biotec), BV421 anti-CD33 (Biolegend), APC anti-CD14 (Biolegend) and PE-Cyanine7 anti-CD11b (Invitrogen). Cells were washed twice in FACS buffer and fixed overnight at 4 degrees C. in 0.5% paraformaldehyde diluted in PBS. Cells were analyzed on a FACS Canto II (BD Biosciences), with subsequent data analysis by Flowjo 10.6.1 (Becton Dickinson & Company). Dead cells were excluded by gating on the e780-negative population. Macrophages were identified as cell positive for the lineage markers CD33, CD11b and CD14. Of this population, macrophages that had phagocytosed tumor cells were identified as cells positive for CFSE.

Human PBMC Viability Assay

PBMCs were counted and plated in complete RPMI. Drug A alone or in combination azacitidine was added to the PBMCs. Following 72-hour or five day incubation at 37° C., cells were stained with a fixable viability dye followed by staining with cell surface markers: CD3, CD19, CD14, CD56, CD16, CD11c, and HLADR (Biolegend). Cells were processed for flow cytometry by Attune NxT and analyzed by FlowJo 10.3. Viability gating strategy included double singlet exclusion by FSC height and FSC width followed by cell type surface marker then viability gate. CD11c DCs were identified as lineage negative (CD3, CD19, CD14, CD16 and CD56) HLADR$^+$ CD11c$^+$. Percent viable cells were tabulated using GraphPad Prism 8.

Analysis of Calreticulin Expression

To detect changes in calreticulin expression levels in human acute myeloid leukemia cell lines HL60, OCI-AML3 and MV4-11, cells were incubated with either 2.5 pM or 75 nM of azacitidine (Selleckchem) in complete growth medium (RPMI1640, 10% FBS) in a 37° C. 5% $CO_2$ incubator for 72 hrs. Cells grown in complete growth medium was used as a control for calreticulin baseline expression. After incubation, cells were harvested and washed once in staining buffer (PBS, 2% FBS), stained in PBS with fixable live/dead stain (Invitrogen) for 1 hour at 4° C., washed once in staining buffer and incubated with 500 ng/mL of calreticulin-AF647 (clone 1G6A7, Novus). After a 1 hour incubation at 4° C., cells were washed twice in staining buffer and fixed in 0.5% paraformaldehyde. Cells were analyzed on an Attune (ThermoScientific), and subsequent data analysis using Flowjo 10.6.

In Vivo Anti-Tumor Activity

Subcutaneous tumor xenografts were induced by injecting HL60 (ATCC), MV4-11 (ATCC), OCI-AML3 (DSMZ) acute myeloid leukemia cell into the right flank of NOD-SCID female mice at a concentration of $5 \times 10^6$ cells per mouse using a 1:1 matrigel (Corning) and RPMI 1640 ratio. Tumors were monitored until average size of all tumors reached 105 mm$^3$ for HL60, 75 mm$^3$ for MV4-11 and 112 mm$^3$ for OCI-AML3. Mice were randomized into PBS, azacitidine (Selleckchem), Drug A and azacitidine+Drug A combination cohorts, with 4-5 mice per cohort for HL60 and OCI-AML3 and 10 mice per cohort for MV4-11. Mice in HL60 and OCI-AML3 tumor models were dosed intraperitoneally (IP) five times, three days apart at 5 mg/kg for azacitidine, and six times, three days apart at 10 mg/kg for Drug A. MV4-11 tumor bearing mice were dosed IP three times per week at 5 mg/kg for azacitidine and 10 mg/kg for Drug A. Tumors were measured in two dimensions with calipers and tumor volume was calculated as: length×width× width×0.5, where length was the larger of the two measurements. Animals were sacrificed when tumor reached a volume of ~2000 mm$^3$.

Serial BLI Imaging Systemic Leukemic Model

The HL60LUC2 (ATCC) cell line was injected through the tail vein of NOD-SCID female mice at a concentration of $7.5 \times 10^6$ cells per in RPMI 1640. Bioluminescence imaging (BLI) acquisition and analysis were performed using the IVIS Spectrum (Perkin Elmer) to monitor tumor growth. Firefly D-luciferin (Regis Technologies) was diluted to 15 mg/ml stock in phosphate-buffered saline and filtered before use. Groups of mice were placed in the specimen chamber and injected with 200 µl of D-luciferin intraperitoneally (IP). BLI whole-body signal was acquired at approximately 10 minutes post injection. BLI flux values were serially monitored twice a week with initial scans acquired three days post inoculation of mice. Living Image Software (Perkin Elmer) was used to quantify BLI average total flux values (photons/second, p/s) following the manual construction of regions of interest over the entire mouse body. At an average of 2.6E6 total flux (photons/sec), mice were randomized into PBS, azacitidine (Selleckchem), Drug A and azacitidine in combination with Drug A cohorts, with 10 mice per cohort. Formulation for azacitidine was 2% DMSO in PBS. Azacitidine-treated mice were dosed with 5 mg/kg of azacitidine by IP injection, five times total at three days apart. Drug A-treated mice were dosed by IP injection at 30 mg/kg, five times total at three days apart. Animals were sacrificed when the total flux reached 1E11 or loss in body weight of greater than 20%.

Example 2A: Effect of Drug a in Combination with Azacitidine on Phagocytosis by Macrophages in an In Vitro Model In this Example, the effects of Drug A alone, azacitidine alone, and Drug A in combination with azacitidine on the phagocytosis of HL60 and OCI-AML3 human acute myeloid leukemia cells by macrophages were assessed in an in vitro assay (see Example 1 for details). HL60 is a TP53null FLT3 wt cell line, and OCI-AML3 is TP53 wt and FLT3 wt.

Briefly HL60 cells and OCI-AML3 cells (i.e., "target cells") were labeled with CFSE (carboxyfluorescein succinimidyl ester) and treated with azacitidine (aza) for 48 hours. The target cells were then spun and added to wells of 96 well plates at 100,000 cells per well. Drug A was then added. Untreated control target cells, as well as control target cells that were treated only with azacitidine or only with Drug A, were prepared in parallel. Macrophages were added to the wells, and the plates were incubated two hours at 37° C. Macrophage cells were pelleted, stained, and analyzed via flow cytometry. Dead cells were excluded by gating on the e780-negative population. Macrophages were identified as cell positive for the lineage markers CD33, CD11b and CD14. Of this population, macrophages that had phagocytosed tumor cells were identified as cells positive for CFSE.

Figure 1B:
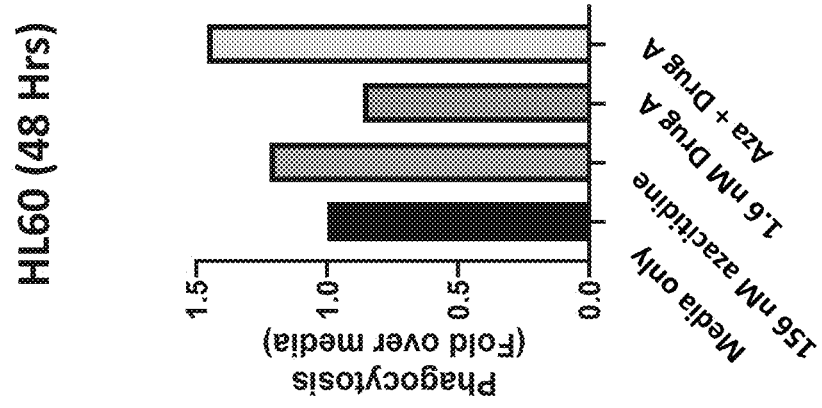
FIG. 1B provides results from experiments that were performed to assess the effects of Drug A, azacitidine, and Drug A+azacitidine on the phagocytosis of human OCI-AML3 cells by macrophages.

As shown in FIG. 1A, azacitidine (aza) as a single agent stimulated macrophage-mediated phagocytosis of HL60 cells slightly, whereas Drug A as a single agent had little effect on phagocytosis. (Compare Drug A treated cells to that of untreated cells.) The combination of 1.6 nM Drug A and 156 nM aza stimulated phagocytosis of HL60 cells by macrophages to a greater degree than either Drug A alone or aza alone. Similar results were observed with 40 nM Drug A and 2.5 pM aza in OCI-AML3 cells. See FIG. 1B.

Example 2B: Effect of Drug a in Combination with Azacitidine on the Viability of CD11c+ Dendritic Cells in Human PBMC Cultures In this Example, the effects of Drug A alone, azacitidine alone, and Drug A in combination with azacitidine on the viability of CD11c+ dendritic cells in human peripheral blood mononuclear cell cultures were assessed in an in vitro assay (see Example 1 for details). Dendritic cells (DCs) are antigen-presenting cells (also known as accessory cells) of the mammalian immune system. They are believed to act as messengers between the innate and the adaptive immune systems.

Figure 2:
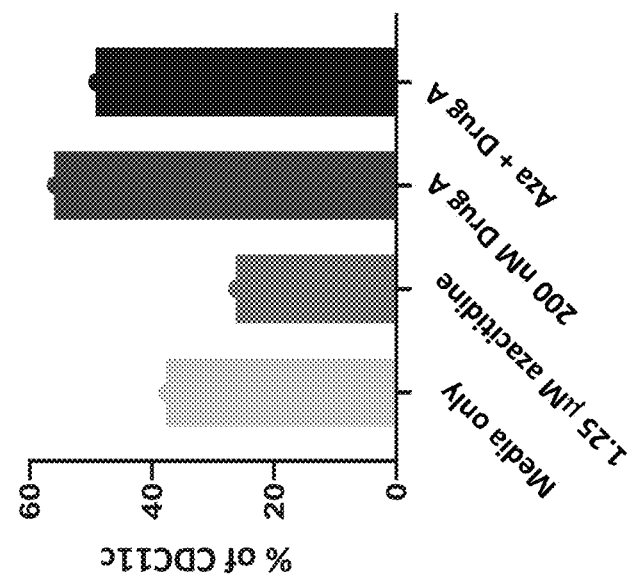
FIG. 2 provides results of experiments that were performed to assess the effects of Drug A, azacitidine, and Drug A+azacitidine on the viability of CD11c$^+$ dendritic cells in human peripheral blood mononuclear cell (PBMC) cultures.

The incubation of PMBC cells with 1.25 pM azacitidine (aza) alone reduced the viability of CD11c+ dendritic cells by about 40%, whereas the incubation of PBMC with 200 nM Drug A alone increased the viability of CD11c+ dendritic cells by about 40%. See FIG. 2. The viability of CD11c+ dendritic cells in PBMC cultures incubated with both 1.25 pM aza and 200 nM Drug A was almost comparable to that the viability of CD11c+ dendritic cells in PBMC cultures incubated with Drug A alone. See FIG. 2. Such result indicates that Drug A rescues the effects of azacitidine on CD11c+ dendritic cells.

Example 2C: Effect of Azacitidine or Venetoclax on Calreticulin Expression on Human Acute Myeloid Leukemia Cell Lines In this Example, the effect azacitidine on the expression levels of calreticulin on the cell surfaces of HL60, OCI-AML3, and MV4-11 human acute myeloid leukemia (AML) cells was assessed in an in vitro assay (see Example 1 for details). HL60 is a TP53null FLT3 wt cell line; OCI-AML3 is TP53 wt and FLT3 wt; and MV4-11 is TP53 wt and FLT3-ITD.

Figure 3A:
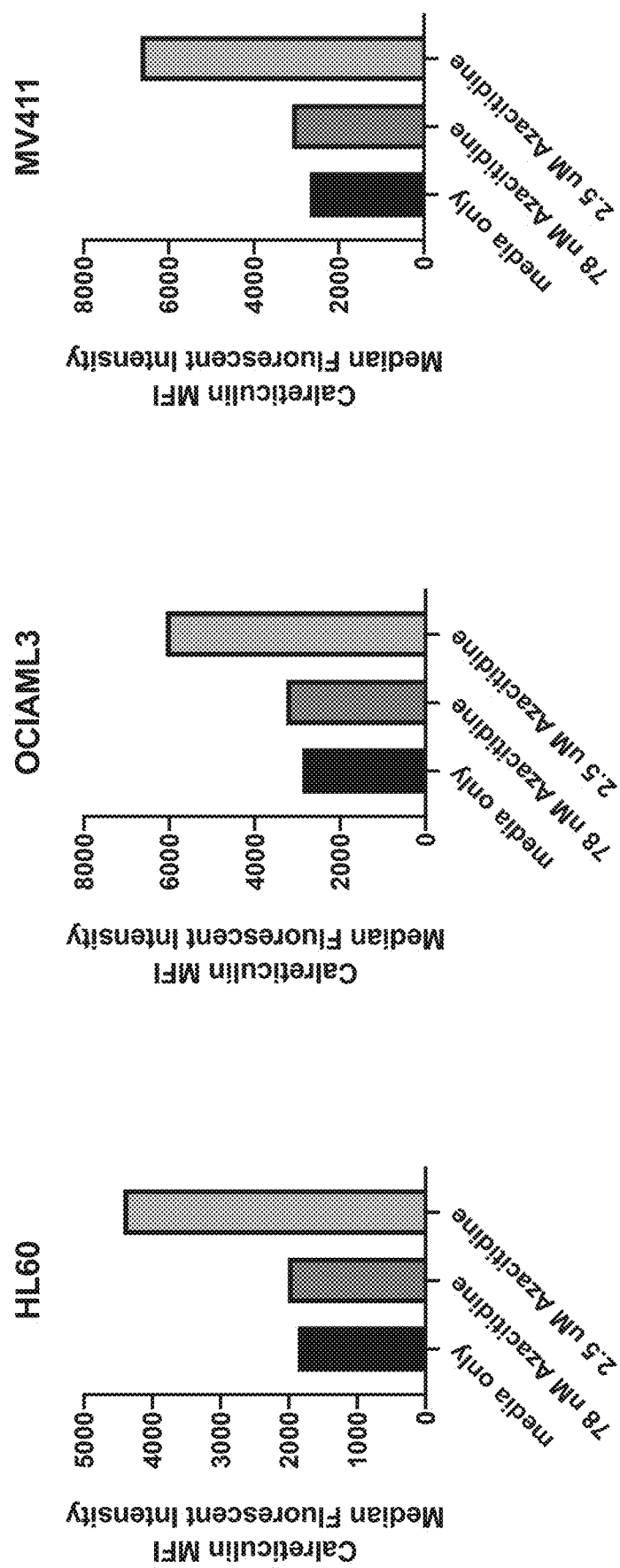
FIG. 3A provides the results of in vitro experiments that were performed to assess the effect of azacitidine on the expression of calreticulin on the surface of HL60, OCI-AML3, and MV4-11 human acute myeloid leukemia cell lines.

Calreticulin is a multifunctional protein involved in $Ca^{2+}$ binding and storage found in the endoplasmic reticulum. Calreticulin is also a cell-surface pro-phagocytic marker that has been previously described in acute myeloid leukemia (AML). As shown in FIG. 3A, the expression of calreticulin on the surface of HL60, OCI-AML3, and MV4-11 cells increased with increased concentrations of azacitidine. Baseline cell-surface calreticulin expression is shown in cells incubated in media alone.

Figure 3B:
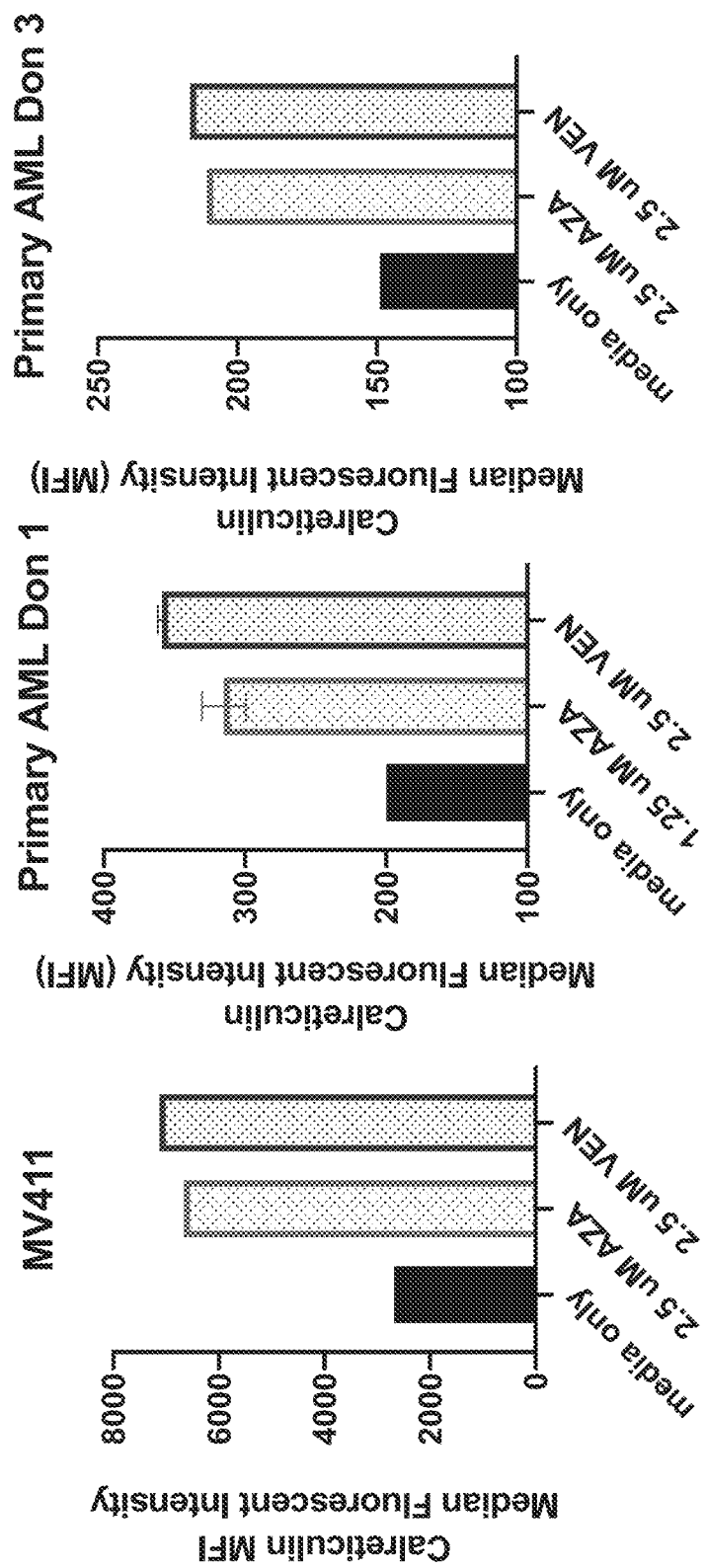
FIG. 3B provides the results of in vitro experiments that were performed to assess the effect of azacitidine or venetoclax on the expression of calreticulin on the surface of MV4-11 human acute myeloid leukemia cell lines and primary AML blasts from 2 human donors.

The effect of azacitidine or venetoclax on the expression levels of calreticulin on the cell surfaces of MV4-11 and primary AML cells from two different human patients was also tested. As shown in FIG. 3B, both azacitidine and venetoclax increase the expression of the pro-phagocytic signal calreticulin in both the MV411 AML cell line and in primary AML blasts.

In another set of assays, the effect of azacitidine or venetoclax on the expression levels of CD47 on the cell surfaces of MV4-11 and primary AML cells from two different human patients was tested. As shown in FIG. 3C, both azacitidine and venetoclax increase the expression of the anti-phagocytic signal CD47 in both the MV411 AML cell line and in primary AML blasts.

Figure 7A:
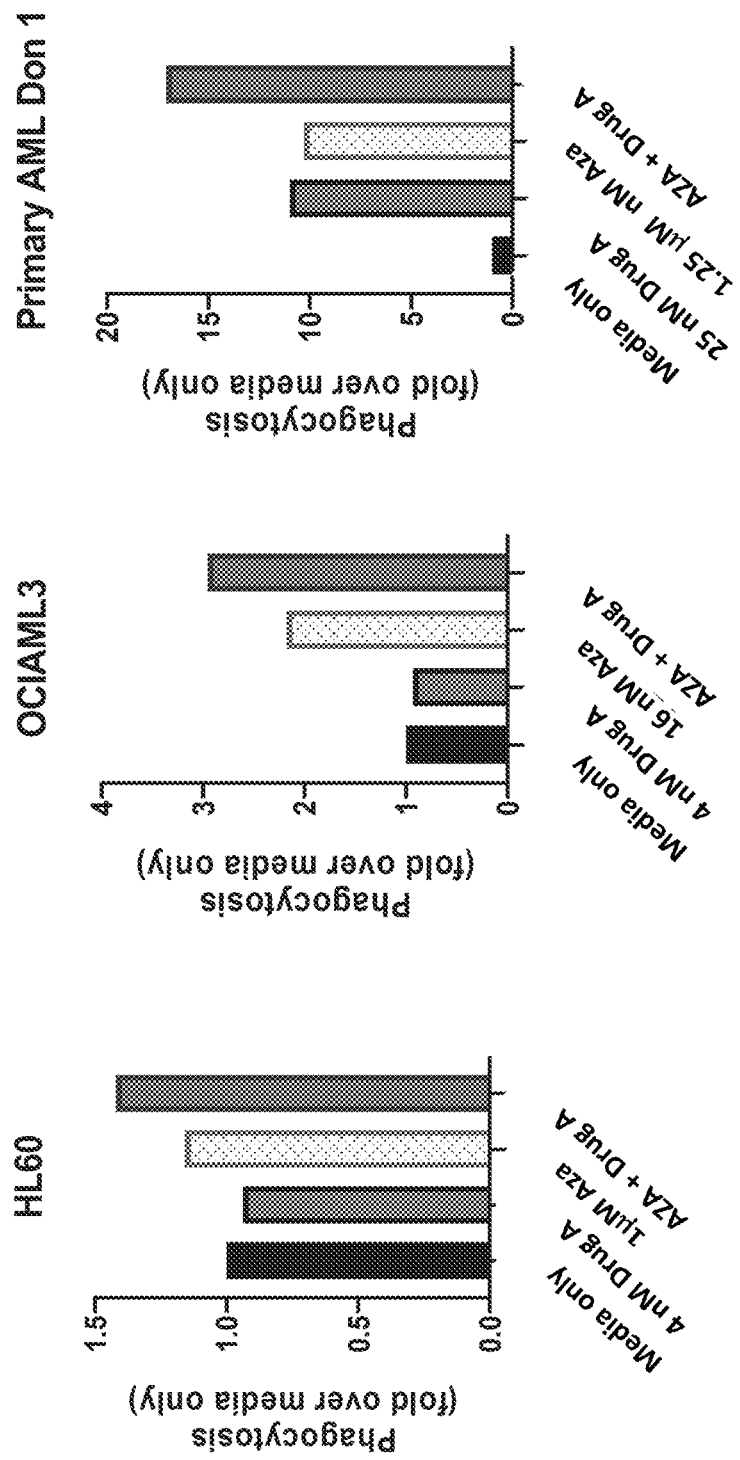
FIG. 7A provides results of experiments that were performed to assess the effects of Drug A, azacitidine, and Drug A+azacitidine on the phagocytosis of AML cells by human monocyte-derived macrophages.

Example 2D: The Effect of Drug a in Combination with Azacitidine or Venetoclax Ion the Phagocytosis of AML Cell Lines and Primary AML Blasts In Vitro AML cells (HL60, OCIAML3, or primary AML blasts from a human donor) were incubated with azacitidine or venetoclax for 24-48 hours and then co-cultured for 2 hours with human monocyte-derived macrophages in the presence or absence of Drug A. Phagocytosis of AML cells was determined by flow cytometry as the number of macrophages that have engulfed AML cells (CFSE+) vs. total macrophages. As shown in FIGS. 7A and 7B, Drug A in combination with azacitidine (7A) or venetoclax (7B) enhanced phagocytic elimination of AML cells by human macrophages compared to single agent treatment with Drug A, azacitidine, or venetoclax.

Example 2E: Anti-Tumor Activity of Drug a in Combination with Azacitidine in a Leukemia Xenograft Model In this Example, the anti-tumor activity of Drug A in combination with azacitidine (aza) was assessed mice bearing either HL60, OCI-AML3 and MV4-11 human leukemia tumor xenografts. (See Example 1 for experimental details.) HL60 is a TP53null FLT3 wt cell line; OCI-AML3 is TP53 wt and FLT3 wt; and MV4-11 is TP53 wt and FLT3-ITD.

Mice bearing HL60 xenografted tumors were randomized to 4 groups of 4-5 mice each. One group of mice was given (a) Drug A at 10 mg/kg IP (Q3D, 6 doses total), (b) aza at 5 mg/kg IP (Q3D, 5 doses total), (c) both Drug A and aza (at the doses and administration schedule for each single agent), or (d) vehicle. Mice bearing OCI-AML3 xenografts were similarly randomized and treated.

Mice bearing MV4-11 xenografts were randomized into 4 groups of 9-10 each. One group of mice was given Drug A at 10 mg/kg IP (3 times per week), the second group of mice was given aza at 5 mg/kg IP (three times per week), the third group was given both Drug A and aza (at the doses and administration schedule for each single agent, and the fourth group was given vehicle.

Figure 4B:
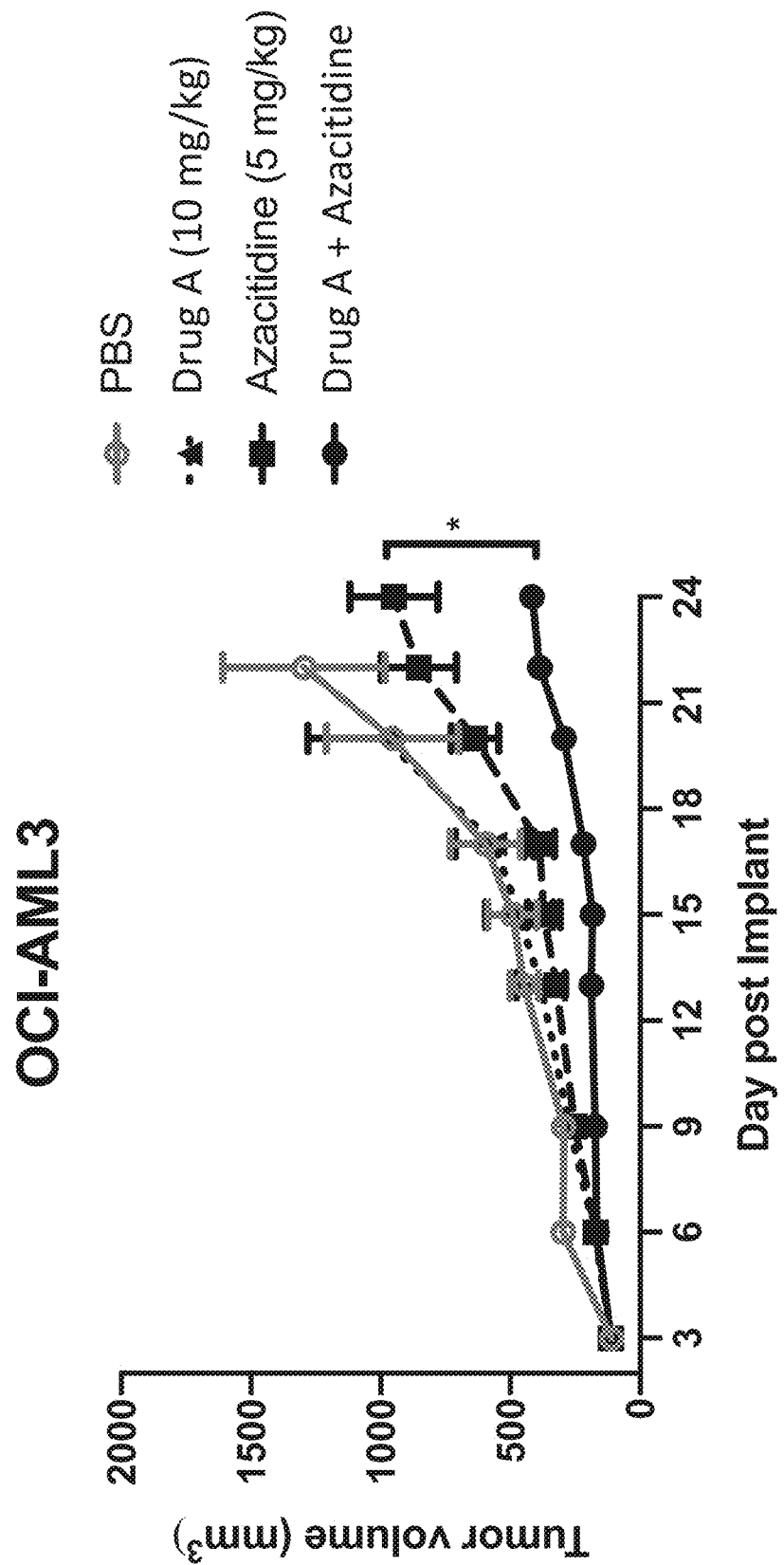
FIG. 4B provides results of experiments that were performed to assess the effects of Drug A, azacitidine, and Drug A+azacitidine on tumor growth in mice bearing OCI-AML3 tumor xenografts.

The % tumor growth inhibition (TGI) was calculated as follows: (1−(mean volume of treated tumors)/(mean volume of control tumors))×100%. At day 20, HL60 tumor growth in mice treated with single agent aza was minimally inhibited (i.e., as compared to mice that were given vehicle control), whereas treatment with Drug A did not have an appreciable effect of tumor growth in mice (i.e., as compared to treatment with vehicle). See FIG. 4A. Treatment with aza in combination with Drug A delayed HL60 tumor growth in mice to a greater degree than either drug alone. At day 20, 42% TGI was observed in mice treated with aza alone; 10% TGI was observed in mice treated with Drug A alone, and 67% TGI was observed in mice treated with Drug A in combination with aza. Similar results were observed in the OCI-AML3 model in that treatment with aza in combination with Drug A delayed OCI-AML3 tumor growth in mice to a greater degree than either drug alone. See FIG. 4B (*p<0.05, Tukey's Ordinary one-way ANOVA). At day 20, 33% TGI was observed in mice treated with aza alone; −3.7% TGI was observed in mice treated with Drug A alone, and 69% TGI was observed in mice treated with Drug A in combination with aza.

Figure 4D:
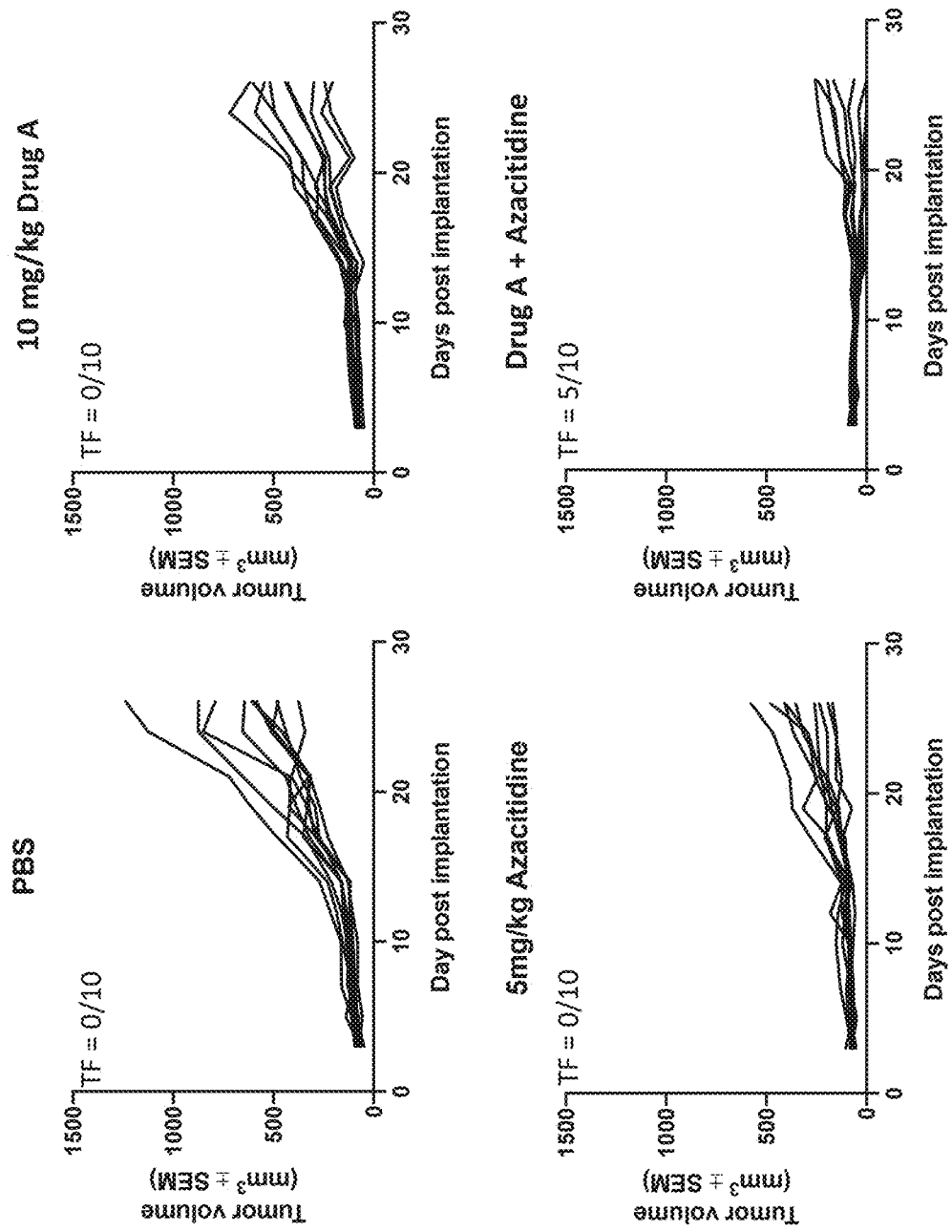
FIG. 4D shows the number of MV4-11 xenografted mice in each treatment group that demonstrated tumor regression.

Administration of Drug A at 10 mg/kg in combination with azacitidine at 5 mg/kg eradicated tumor growth in MV4-11 xenografts when compared to treatment with each single agent or vehicle control. At day 26, 49% TGI was observed in mice treated with aza alone, 35% TGI was observed in mice treated with Drug A alone, and 86% TGI was observed in mice treated with Drug A in combination with aza. See FIG. 4C (***p=0.001, Tukey's Ordinary one-way ANOVA on day 26). 5/10 mice treated with Drug A+aza demonstrated complete tumor eradication. See FIG. 4D.

Example 2F: Anti-Tumor Activity of Drug a in Combination with Azacitidine in a Systemic Leukemic Model Anti-tumor activity of Drug A alone and in combination with azacitidine was tested in a disseminated HL60-LUC2 acute myeloid leukemic models. After transplantation of HL60-LUC2 cells by intravenous tail injection into immunodeficient NSG mice (7.5E6 cells/animal), engraftment was confirmed by bioluminescence imaging and mice were randomized into 4 groups (10 mice/group). Treatment was performed as shown Table A below.

TABLE A1

Treatment Groups - Doses and Schedules

| Treatment Group | Dose level | Schedule of Administration (starting Day 4 post IV inoculation with tumor cells) |
| --- | --- | --- |
| Vehicle Control | N/A | Q3D, 5 doses total |
| Drug A | 30 mg/kg | Q3D, 5 doses total |
| Azacitidine | 5 mg/kg | Q3D, 5 doses total |
| Drug A + azacitidine | Drug A: 30 mg/kg azacitidine: 5 mg/kg | Drug A: Q3D, 5 doses total azacitidine: Q3D, 5 doses total |

Figure 5B:
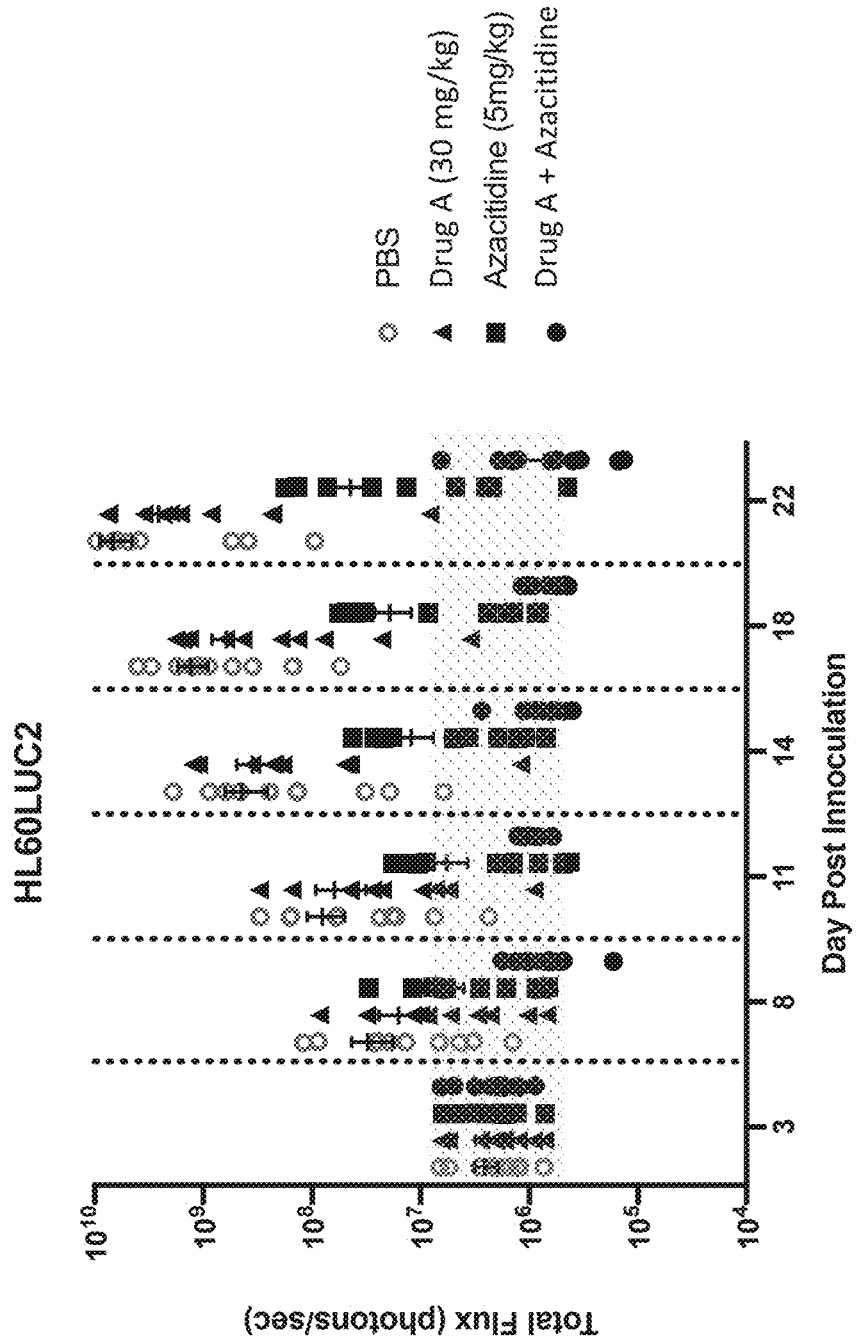
FIG. 5B provides data regarding total flux (luminescence) vs. time (i.e., tumor size vs. time) in mice that were imaged on Days 3, 8, 11, 14, 18, and 22 post-inoculation. Treatment began Day 4 post-IV inoculation.

Mice were imaged twice a week for bioluminescent signal starting Day 3. As shown in FIGS. 5A and 5B, administration of Drug A at 30 mg/kg in combination with azacitidine at 5 mg/kg eliminated tumor growth when compared to treatment with each single agent or vehicle control.

Treatment was continued until mice received 14 doses of single agent Drug A, single agent azacitidine, or Drug A in combination with azacitidine. Drug A monotherapy and azacitidine monotherapy produced moderate tumor growth inhibition, but all mice given Drug A monotherapy or azacitidine monotherapy succumbed to disease by Day 85 of treatment. See FIG. 5C. By contrast, the combination of Drug A and azacitidine completely eliminated tumor growth with 100% animal survival up to study termination on Day 147. See FIG. 5C.

In a second set of experiments performed in a disseminated HL60-LUC2 acute myeloid leukemic model, azacitidine and Drug A therapies were initiated 4 days post engraftment and dosed intraperitoneally every 3 days for a total of 14 doses. See Table A2 below.

TABLE A2

Treatment Groups - Doses and Schedules

| Treatment Group | Dose level | Schedule of Administration (starting Day 4 post IV inoculation with tumor cells) |
| --- | --- | --- |
| Vehicle Control | N/A | Q3D, 14 doses total |
| Drug A | 30 mg/kg | Q3D, 14 doses total |
| Azacitidine | 5 mg/kg | Q3D, 14 doses total |
| Drug A + azacitidine | Drug A: 30 mg/kg azacitidine: 5 mg/kg | Drug A: Q3D, 14 doses total azacitidine: Q3D, 14 doses total |

In half of the mice receiving Drug A+azacitidine, Drug A monotherapy was continued for an additional 16 doses. As shown in FIG. 5D, all mice treated with single agent azacitidine succumbed to treatment by about Day 85. In mice treated with 14 doses of Drug A+azacitidine, tumor inhibition was observed until Day 105. By contrast, tumor inhibition was observed until study termination (Day 147) in 3 of 4 mice treated with 14 doses of Drug A+azacitidine followed by 16 additional doses of Drug A monotherapy. See FIG. 5D.

Example 3: Anti-Tumor Activity of Drug a in Combination with Venetoclax in a Systemic Leukemic Model Anti-tumor activity of Drug A alone and in combination with venetoclax was tested in a disseminated HL60-LUC2 acute myeloid leukemic models, as described in Example 2. Venetoclax and Drug A therapies were initiated 4 days post engraftment and dosed every 3 days for a total of 5 doses. See Table B below.

TABLE B

Treatment Groups - Doses and Schedules

| Treatment Group | Dose level | Schedule of Administration (starting Day 4 post IV inoculation with tumor cells) |
| --- | --- | --- |
| Vehicle Control | N/A | Q3D, 5 doses total |
| Drug A | 30 mg/kg (intraperitoneally) | Q3D, 5 doses total |
| Venetoclax | 100 mg/kg (oral gavage) | Q3D, 5 doses total |
| Drug A + venetoclax | Drug A: 30 mg/kg (IP) venetoclax: 100 mg/kg (oral gavage) | Drug A: Q3D, 5 doses total venetoclax: Q3D, 5 doses total |

Figure 8:
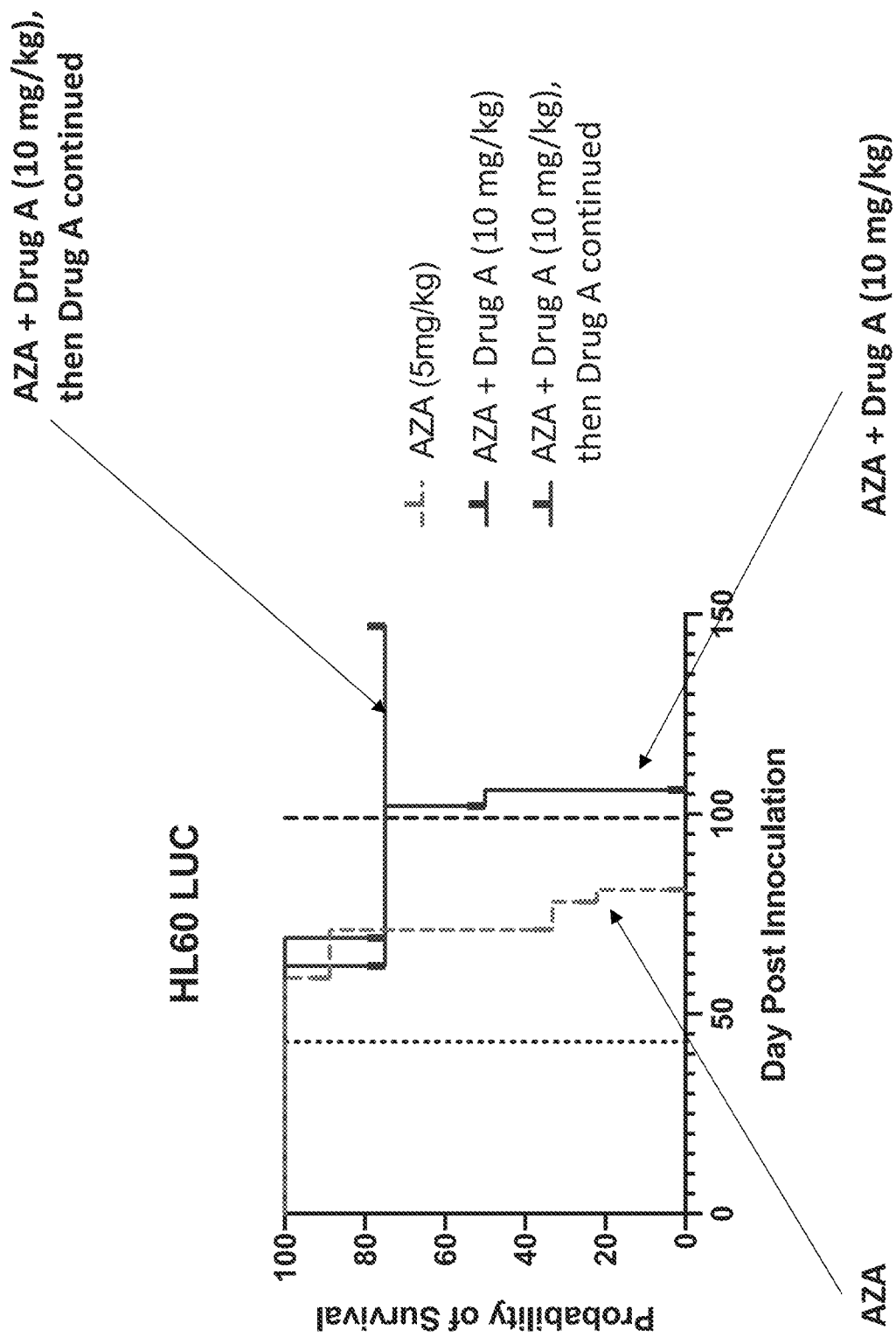
FIG. 8 provides results of experiments that were performed to assess the effects of Drug A, venetoclax, or Drug A+venetoclax on tumor growth in mice engrafted with HL60-LUC2 in an 80 day evaluation period.

Venetoclax monotherapy and Drug A monotherapy each produced moderate tumor growth inhibition, but did not maintain durable responses. All mice given venetoclax monotherapy or Drug A monotherapy succumbed to disease by Day 40. See FIG. 8. By contrast, tumor growth was completely eliminated in 6 out of 8 mice treated with venetoclax in combination with Drug A within an 80 day evaluation period.

Example 4: Anti-Tumor Activity of Drug a in Combination with Azacitidine and Venetoclax in a Systemic Leukemic Model The effect of Drug A in combination with azacitidine and venetoclax on the inhibition of tumor growth in mice bearing xenografted human HL-60Luc2 leukemia tumors. Female NODSCID (Charles River) mice at 6 weeks of age were used in the xenograft experiments. HL-60Luc2 cells ($10 \times 10^6$ cells per mouse) were injected intravenously into the tail vein each mouse. Tumor progression was monitored using an IVIS Caliper (Perkin Elmer) starting on Day 4 post inoculation. When leukemia burdens reached about $1 \times 10^6$ photons/second, mice were randomly grouped and intraperitoneally dosed with (a) PBS (control), (b) azacitidine, (c) venetoclax, (d) Drug A, (e) azacitidine+venetoclax, or (f) azacitidine+venetoclax+drug A. Azacitidine was administered intraperitoneally at a dose of 5 mg/kg every three days for a total of 5 doses; Drug A was administered intraperitoneally at a dose of 30 mg/kg every 3 days for a total of 5 doses; and venetoclax was administered at a dose of 100 mg/kg by oral gavage every day for 14 days. Every 3-4 days following the start of treatment, mice were injected with D-luciferin (Regis), and tumor bioluminescence was measured and recorded using a small animal in vivo imaging system (IVIS). Regions of interest were gated on the whole mouse through the IVIS software (Caliper Life Sciences) and reported as area flux (photons/second), defined by the radiance (photons/s/cm$^2$/steradian).

Figure 6B:
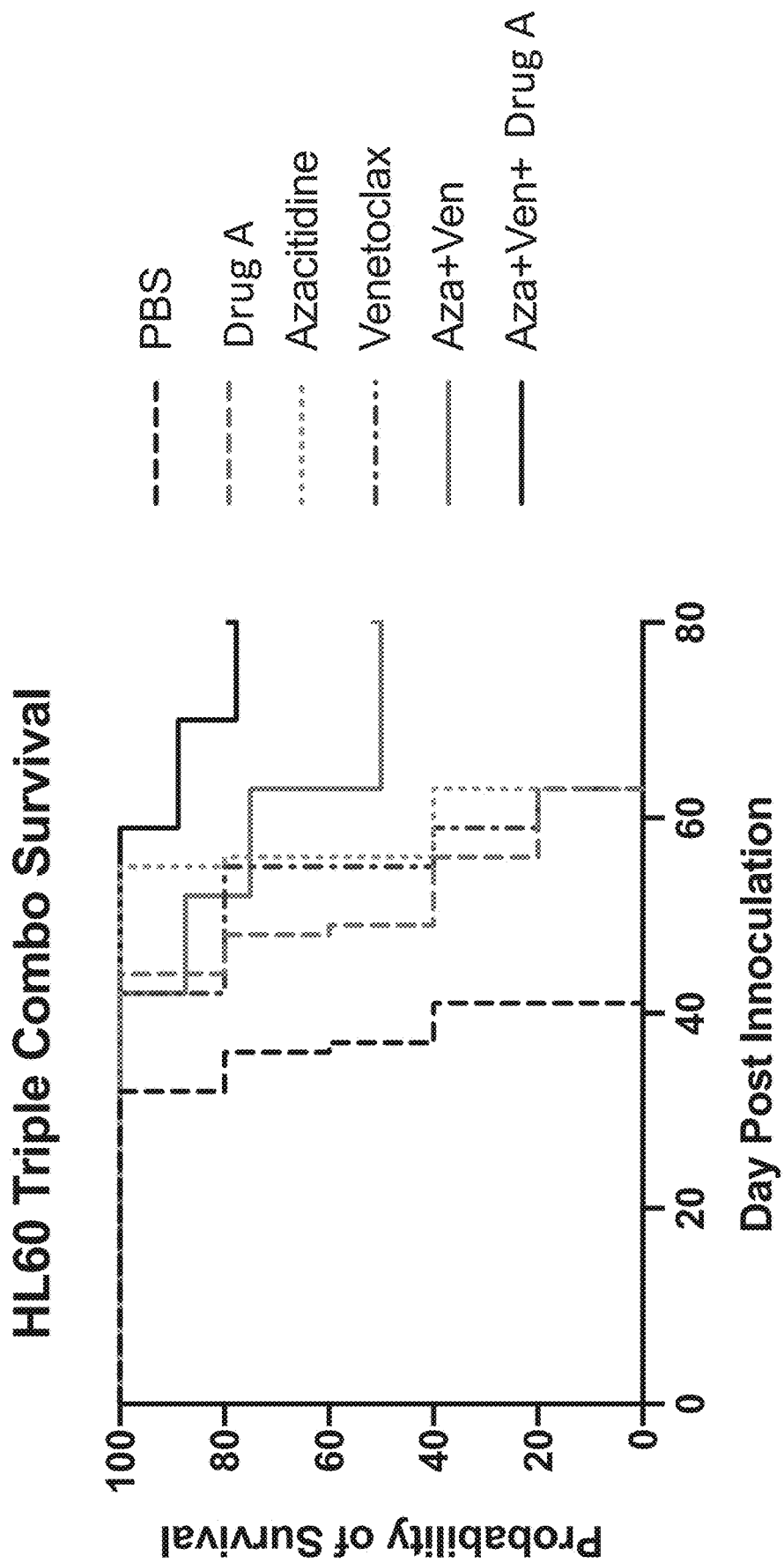
FIG. 6B shows the probability of survival (in days) of mice bearing xenografted human HL-60LUC2 tumors that that received treatment with PBS (control), azacitidine, venetoclax, Drug A, azacitidine+venetoclax, or azacitidine+venetoclax+Drug A.

As shown in FIG. 6A, Drug A in combination with venetoclax and azacitidine inhibited tumor growth to a greater extent than Drug A alone, azacitidine alone, venetoclax alone, or azacitidine in combination with venetoclax. As shown in FIG. 6B, mice treated with Drug A in combination with venetoclax and azacitidine demonstrated increased survival over mice treated with azacitidine alone, venetoclax alone, or azacitidine in combination with venetoclax. Drug A in combination with venetoclax and azacitidine completely eliminated tumor growth in 7 of 9 mince within an 80 day evaluation period. See FIG. 6B.

Example 5: Drug a Enhances the Depth and Durability of Response to Multiple Acute Myeloid Leukemia Therapies Acute myeloid leukemia (AMIL) is an aggressive hematologic malignancy with most patients relapsing even after standard therapies. Despite recent advances in treatment, the development of efficacious novel treatments remains an unmet need.

CD47 is a myeloid checkpoint upregulated by tumor cells to evade the host immune response, and its blockade enhances anti-tumor immunity (Weiskopf (2017) *Eur J Cancer,* 76:100-109). Drug A is an engineered fusion protein comprised of a high affinity CD47 blocker linked to an inactive human immunoglobulin Fc region. In preclinical studies, Drug A bridges innate and adaptive immunity by promoting macrophage phagocytosis, dendritic cell activation and a shift of tumor-associated macrophages towards an inflammatory phenotype, leading to increased anti-tumor activity when combined with various anti-cancer therapeutics (Kauder et al. (2018) *PLoS ONE* 13(8): e0201832). Drug A has previously been shown to be well tolerated in patients with solid tumor, as well as an patients with hematological malignancies. Encouraging anti-tumor responses have been reported with Drug A in combination with anti-cancer therapeutics (Kim et al. Abstract #EP1247, poster presented at the 25th Congress of the European Hematology Association (EHA) 2020 and Chow et al. Abstract #3056, poster presented at 2020 American Society of Clinical Oncology Virtual Scientific Program). Recently, the combination of azacitidine with venetoclax, a BCL2 inhibitor, has shown increased efficacy compared to azacitidine alone in patients with AML (DiNardo et al. (2019) *Blood,* 133 (1): 7-17. In vitro treatment with azacitidine or venetoclax increased the cell surface expression of both CD47 and calreticulin, a pro-phagocytic marker, in leukemic malignancies.

Experiments were performed to test the hypothesis that combining Drug A with either azacitidine or venetoclax would enhance the therapeutic efficacy against AML. In vitro treatment with Drug A led to enhanced phagocytic engulfment by human monocyte-derived macrophages across multiple AML cell lines treated with azacitidine or venetoclax, including those harboring TP53 and FLT3 mutations, compared to either treatment alone. See Examples 2B-2C. In vitro findings correlated with enhanced in vivo antileukemic activity in several murine AML xenograft models. See Examples 2C-2D. Mice were inoculated via tail vein or implanted subcutaneously with AML cells, and when tumors reached exponential growth, mice were randomized to receive the following: vehicle control, azacitidine, venetoclax, Drug A alone or Drug A in combination with the chemotherapeutics. Cohorts receiving Drug A combination therapies demonstrated significantly greater inhibition of tumor progression with evidence of tumor eradication, leading to markedly enhanced survival over any single agent therapy.

Example 6: Exemplary Clinical Trial to Assess the Safety, Tolerability, and Efficacy of Drug a in Combination with Azacitidine in Human Patients with Higher Risk Myelodysplastic Syndrome (MDS)

A Phase 1/2 clinical trial is performed to assess the safety, tolerability, and efficacy of the combination of Drug A and azacitidine (aza) in patients with higher risk myelodysplastic syndrome (MDS). Phase 1 includes a dose escalation of Drug A in combination with standard dose aza to evaluate safety and identify the Phase 2 recommended dose, and Phase 2 evaluates the efficacy of the Drug A+aza combination in patients with higher risk MDS.

About 63 patients are enrolled. Exemplary inclusion criteria are: (a) Phase 1: diagnosis of higher risk MDS that is either previously untreated or relapsed/refractory; Phase 2: diagnosis of higher risk MDS that is previously untreated; (b) adequate renal and liver function; (c) age of ≥18 years; and (d) adequate performance status (e.g., according to the Eastern Cooperative Oncology Group (ECOG) scale, see ecog-acrin(dot)org/resources/ecog-performance-status). Exemplary exclusion criteria are: (a) previous allogenic hematopoietic stem cell transplant (allo-HSCT) for MDS or acute myeloid leukemia (AML); (b) prior treatment with any anti-CD47 or anti-SIRPα agent; (c) known active viral infections, including hepatitis B and C, human immunodeficiency virus (HIV), acquired immunodeficiency syndrome (AIDS) related illness, or SARS-CoV-2.

For Phase 1, Drug A is administered up to 60 mg/kg, e.g., 60 mg/kg once every 4 weeks (Q4W), in combination with aza. Aza is administered intravenously or subcutaneously at a dose of 75 mg/m$^2$ daily for 7 days of each 28 day cycle (typically referred to as the "7-0 regimen") or at a dose of 75 mg/m$^2$ daily for 5 days, followed by 2 days without treatment (i.e., without azacitidine administration), and then 75 mg/m$^2$ daily for 2 days in each 28-day cycle (typically referred to as the "5-2-2 regimen"). For Phase 2, Drug A is administered at the Phase 2 recommended dose in combination with aza (administered intravenously or subcutaneously at a dose of 75 mg/m$^2$ daily for the first 7 days of each 28 day cycle).

The primary outcome measure for Phase 1 is the number of study participants with dose limiting toxicities (DLTs). The primary outcome measure for Phase 2 is the objective response rate (ORR), which is the number of study participants achieving a response (e.g., complete response "CR) or partial response "PR) per International Working Group (IWG) criteria (see, e.g., Cheson et al. *Blood.* 2000; 96: 3671 3674 and Cheson et al. *Blood.* 2006; 108: 419-425).

Example 7: Exemplary Clinical Trial to Assess the Safety, Tolerability, and Efficacy of Drug a in Combination with Venetoclax and Azacitidine in Human Patients with Acute Myeloid Leukemia (AML)

A phase 1/2 clinical trial is performed to assess the safety, tolerability, and efficacy of the combination of drug A, venetoclax and azacitidine (Aza) in patients with acute myeloid leukemia (AML). In Phase 1a, participants receive escalating doses of Drug A in combination with venetoclax and azacitidine. The primary outcome measure of phase i is the number of participants experiencing dose-limiting toxicities. In phase 1b/2, participants receive Drug A at the recommended Phase 2 dose in combination with venetoclax and azacitidine. The primary outcome measure of Phase 1b/2 is the number of participants achieving a complete remission (CR) and complete remission with incomplete hematologic recovery (CRi) per European Leukemia Net (ELN) 2017 criteria. These studies identify safety and efficacy of the combination, and recommended dose.

Exemplary inclusion criteria include, but are not limited to: (a) cytological or histologically confirmed diagnosis of relapsed/refractory or newly diagnosed AML per WHO 2016 classification; (b) for Phase 1a: AML that is relapsed/refractory or that is previously untreated in patients not considered suitable for intensive induction therapy; (c) for Phase 1b: AML that is relapsed/refractory after prior treatment with a HMA-based regimen; (d) for Phase 2: previously untreated AML in patients who are not considered suitable candidates for intensive induction therapy; (e) adequate renal and liver function; (f) age≥18 years; and (g) adequate performance status.

Exemplary exclusion criteria include, but are not limited to: (a) for Phase 1a and 1b, patients that have undergone prior allo-HSCT must be at least 3 months post-HCST, without uncontrolled graft-versus-host disease (GVHD); (b) for Phase 2, patients that have undergone prior allo-HSCT are excluded; (c) patients with newly diagnosed AML with favorable risk cytogenetics such as t(8; 21), inv(16), or t(16; 16) as per the NCCN guidelines version 3, 2019 for AML; (d) patients with acute promyelocytic leukemia (APL); (e) prior treatment with any anti-CD47 or anti-SIRPα (signal regulatory protein alpha) agent; (f) known active viral infections, including hepatitis B and C, human immunodeficiency virus (HIV), acquired immunodeficiency syndrome (AIDS) related illness, or sars-cov-2 (severe acute respiratory syndrome coronavirus 2).

The preceding examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

The invention claimed is:

1. A method of treating a myeloid cancer in an individual having a myeloid cancer, comprising administering to the individual an effective amount of: (a) a fusion polypeptide comprising a SIRPα D1 domain variant and an Fc domain variant, and (b) azacitidine;
   wherein the SIRPα D1 domain variant of the fusion polypeptide comprises the amino acid sequence of SEQ ID NO: 81 or SEQ ID NO: 85;
   wherein the Fc domain variant of the fusion polypeptide is
      (i) a human IgG1 Fc region comprising L234A, L235A, G237A, and N297A mutations, wherein numbering is according to the EU index of Kabat;
      (ii) a human IgG2 Fc region comprising A330S, P331S, and N297A mutations, wherein numbering is according to the EU index of Kabat;
      (iii) a human IgG4 Fc region comprising S228P, E233P, F234V, L235A, and delG236 mutations, wherein numbering is according to the EU index of Kabat; or
      (iv) a human IgG4 Fc region comprising S228P, E233P, F234V, L235A, delG236, and N297A mutations, wherein numbering is according to the EU index of Kabat; and
   wherein the C-terminus of the SIRPα D1 domain variant of the fusion polypeptide is linked to the N-terminus of the Fc-domain variant.

2. A method of treating a myeloid cancer in an individual having a myeloid cancer, comprising administering to the individual an effective amount of: (a) a fusion polypeptide comprising a SIRPα D1 domain variant and an Fc domain variant, (b) azacitidine, and (c) venetoclax;
   wherein the SIRPα D1 domain variant of the fusion polypeptide comprises the amino acid sequence of SEQ ID NO: 81 or SEQ ID NO: 85;
   wherein the Fc domain variant of the fusion polypeptide is
      (i) a human IgG1 Fc region comprising L234A, L235A, G237A, and N297A mutations, wherein numbering is according to the EU index of Kabat;
      (ii) a human IgG2 Fc region comprising A330S, P331S, and N297A mutations, wherein numbering is according to the EU index of Kabat;
      (iii) a human IgG4 Fc region comprising S228P, E233P, F234V, L235A, and delG236 mutations, wherein numbering is according to the EU index of Kabat; or
      (iv) a human IgG4 Fc region comprising S228P, E233P, F234V, L235A, delG236, and N297A mutations, wherein numbering is according to the EU index of Kabat; and
   wherein the C-terminus of the SIRPα D1 domain variant of the fusion polypeptide is linked to the N-terminus of the Fc-domain variant.

3. The method of claim 1, wherein the myeloid cancer is myelodysplastic syndrome (MDS).

4. The method of claim 3, wherein the MDS is higher risk MDS.

5. The method of claim 1, wherein the individual has (a) received prior therapy for MDS or (b) has not received prior therapy for MDS.

6. The method of claim 1, wherein treatment comprises an induction phase and a maintenance phase, wherein the induction phase comprises administering (a) the fusion polypeptide comprising a SIRPα D1 domain variant and an Fc domain variant, and (b) azacitidine, and wherein the maintenance phase comprises administering the fusion polypeptide comprising a SIRPα D1 domain variant and an Fc domain variant without azacitidine.

7. The method of claim 2, wherein the myeloid cancer is acute myeloid leukemia (AML).

8. The method of claim 7, wherein the individual has one or more of the following characteristics:
   (a) cytological or histologically confirmed diagnosis of relapsed/refractory or newly diagnosed AML;
   (b) AML that is relapsed/refractory or that is previously untreated and not considered suitable for intensive induction therapy;
   (c) AML that is relapsed/refractory after prior treatment with a HMA-based regimen;
   (d) previously untreated AML and is not considered suitable candidate for intensive induction therapy; and
   (e) adequate renal and liver function.

9. The method of claim 2, wherein venetoclax is administered at a dose of 100 mg on day 1, at a dose of 200 mg on day 2, and at a dose of 400 mg every day following day 2.

10. The method of claim 1, wherein the fusion polypeptide is administered at a dose up to about 60 mg/kg.

11. The method of claim 10, wherein the fusion polypeptide is administered at a dose of about 60 mg/kg once every four weeks (q4w).

12. The method of claim 1, wherein the Fc domain variant (a) is a human IgG1 Fc region comprising L234A, L235A, G237A, and N297A mutations, wherein numbering is according to the EU index of Kabat or (b) comprises the amino acid sequence of SEQ ID NO: 91.

13. The method of claim 1, wherein the fusion polypeptide comprises the amino acid sequence of SEQ ID NO: 135 or SEQ ID NO: 136.

14. The method of claim 1, wherein the fusion polypeptide forms a homodimer.

15. The method of claim 1, wherein the individual is a human.

16. The method of claim 2, wherein the Fc domain variant (a) is a human IgG1 Fc region comprising L234A, L235A, G237A, and N297A mutations, wherein numbering is according to the EU index of Kabat or (b) comprises the amino acid sequence of SEQ ID NO: 91.

17. The method of claim 2, wherein the fusion polypeptide comprises the amino acid sequence of SEQ ID NO: 135 or SEQ ID NO: 136.

* * * * *

UNITED STATES PATENT AND TRADEMARK OFFICE
CERTIFICATE OF CORRECTION

PATENT NO. : 12,343,377 B2
APPLICATION NO. : 17/334151
DATED : July 1, 2025
INVENTOR(S) : Jaume Pons et al.

It is certified that error appears in the above-identified patent and that said Letters Patent is hereby corrected as shown below:

On the Title Page

Column 2, under item (56) Other Publication, Line 20, please replace "(Suplement_1)" with -- (Supplement_1) --;

On page 2, Column 1, under item (56) Other Publication, Line 2, please replace "retrieved retrieved" with -- retrieved --;

On page 3, Column 1, under item (56) Other Publication, Line 29, please replace "retrieved retrieved" with -- retrieved --;

On page 3, Column 1, under item (56) Other Publication, Line 37, please replace "CD47-SIRPa" with -- CD47-SIRPα --;

In the Specification

At Column 1, Line number 15, please replace "entirety" with -- entirety. --;

At Column 1, Line number 24, please replace "KB)" with -- KB). --;

At Column 7, Line numbers 11-12, please replace "that that" with -- that --;

At Column 9, Line number 37, please replace "20 pM 10 pM" with -- 20 pM, 10 pM --;

At Column 10, Line number 15, please replace "20 pM 10 pM" with -- 20 pM, 10 pM --;

At Column 10, Line numbers 59-60, please replace "20 pM 10 pM" with -- 20 pM, 10 pM --;

At Column 11, Line number 19, please replace "20 pM 10 pM" with -- 20 pM, 10 pM --;

Signed and Sealed this
Seventh Day of October, 2025

John A. Squires
*Director of the United States Patent and Trademark Office*

CERTIFICATE OF CORRECTION (continued)
U.S. Pat. No. 12,343,377 B2

At Column 11, Line number 39, please replace "hSIRPT)." with -- hSIRPγ). --;

At Column 11, Line number 61, please replace "20 pM 10 pM" with -- 20 pM, 10 pM --;

At Column 12, Line number 29, please replace "Fe" with -- Fc --;

At Column 15, Line number 6, please replace "(NIP)," with -- (NHP), --;

At Column 16, Line number 64, please replace "of" with -- of: --;

At Column 16, Line number 67, please replace "FSJRIGNJ" with -- DFSIRIGNI --;

At Column 17, Line number 10, please replace "TD" with -- ID --;

At Column 17, Line number 12, please replace "IL" with -- I. --;

At Column 17, Line number 37, please replace "less $5\times10^{-10}$" with -- less than $5\times10^{-10}$ --;

At Column 18, Line numbers 17-18, please replace "less $5\times10^{-10}$" with -- less than $5\times10^{-10}$ --;

At Column 19, Line number 13, please replace "less $5\times10^{-10}$" with -- less than $5\times10^{-10}$ --;

At Column 25, Line number 57, please replace "SIRPα~" with -- SIRPα --;

At Column 25, Line number 61, please replace "iRNNMDJ" with -- RNNMD --;

At Column 27, Line numbers 29-39, please replace "less $5\times10^{-10}$" with -- less than $5\times10^{-10}$ --;

At Column 28, Line numbers 23-24, please replace "less $5\times10^{-10}$" with -- less than $5\times10^{-10}$ --;

At Column 29, Line number 40, please replace "less $5\times10^{-10}$" with -- less than $5\times10^{-10}$ --;

At Column 29, Line number 66, please replace "ID" with -- D --;

At Column 30, Line numbers 45-46, please replace "less $5\times10^{-10}$" with -- less than $5\times10^{-10}$ --;

At Column 31, Line numbers 38-39, please replace "less $5\times10^{-10}$" with -- less than $5\times10^{-10}$ --;

At Column 31, Line number 52, please replace "ID" with -- D --;

At Column 32, Line numbers 55-56, please replace "less $5\times10^{-10}$" with -- less than $5\times10^{-10}$ --;

At Column 33, Line number 3, please replace "L SVR" with -- LSVR --;

At Column 34, Line number 16, please replace "less $5\times10^{-10}$" with -- less than $5\times10^{-10}$ --;

CERTIFICATE OF CORRECTION (continued)
U.S. Pat. No. 12,343,377 B2

At Column 34, Line number 30, please replace "L SVRAKP" with -- LSVRAKP --;

At Column 35, Line number 43, please replace "less $5\times10^{-10}$" with -- less than $5\times10^{-10}$ --;

At Column 35, Line number 56, please replace "ID" with -- D --;

At Column 36, Line number 47, please replace "$1\times10^{-8}$M," and insert -- $1\times10^{-8}$ M, --;

At Column 43, Line number 67, please replace "Fe" with -- Fc --;

At Column 44, Line number 3, please replace "Fe" with -- Fc --;

At Column 44, Line number 59, please replace "MD" with -- MD. --;

At Column 45, Line number 64, please replace "Fe" with -- Fc --;

At Column 47 & 48, Line number 41 (Table 7), please replace "EI" with -- H --;

At Column 51, Line number 42, please replace "Fc" with -- Fcγ --;

At Column 51, Line number 46, please replace "Fc" with -- Fcγ --;

At Column 51, Line number 55, please replace "Fc" with -- Fcγ --;

At Column 51, Line number 61, please replace "5×10-6" with -- $5\times10^{-6}$ --;

At Column 52, Line number 26, please replace "Fe" with -- Fc --;

At Column 52, Line number 59, please replace "Fe" with -- Fc --;

At Column 53 & 54, Line number 24 (Table 8), please replace "EI" with -- H --;

At Column 55 & 56, Line number 35 (Table 8), please replace "E" with -- F --;

At Column 55 & 56, Line number 46 (Table 8), please replace "EI" with -- H --;

At Column 55 & 56, Line number 53 (Table 8), please replace "EI" with -- H --;

At Column 59 & 60, Line number 21 (Table 8), please replace "EI" with -- H --;

At Column 59 & 60, Line number 35 (Table 8), please replace "EI" with -- H --;

At Column 59 & 60, Line number 38 (Table 8), please replace "VES" with -- VFS --;

At Column 63, Line number 31, please replace "9500, 9600, 97%, 980%, 9900, or 10000" with -- 95%, 96%, 97%, 98%, 99%, or 100% --;

CERTIFICATE OF CORRECTION (continued)
U.S. Pat. No. 12,343,377 B2

At Column 63, Line number 35, please replace "SIRPα~" with -- SIRPα --;

At Column 65 & 66, Line number 19 (Table 10), please replace "EI" with -- H --;

At Column 65 & 66, Line number 31 (Table 10), please replace "EI" with -- H --;

At Column 67 & 68, Line number 10 (Table 10), please replace "EI" with -- H --;

At Column 67 & 68, Line number 45 (Table 10), please replace "EI" with -- H --;

At Column 70, Line number 25, please replace "Fe" with -- Fc --;

At Column 72, Line number 2, please replace "TD" with -- ID --;

At Column 75, Line number 3, please replace "CRL7030," with -- CRL7O3O, --;

At Column 75, Line number 35, please replace "lividans." with -- viridans. --;

At Column 76, Line number 35, after "e.g.," please delete "an";

At Column 80, Line number 30, please replace "/050794s011lb1" with -- /050794s011lbl --;

At Column 81, Line number 8, please replace "021790s0061bl(dot)pdf," with -- 021790s0061bl(dot)pdf; --;

At Column 82, Line number 34, please replace "208573s000lbl (dot) pdf;" with -- 208573s000lbl(dot)pdf; --;

At Column 82, Line numbers 47-48, please replace "nitrophenyl) sulfonyl]benzamide" with -- nitrophenyl)sulfonyl]benzamide --;

At Column 83, Line number 62, please replace "as(S)" with -- as (S) --;

At Column 87, Line number 26, please replace "chondrosar-coma," with -- chondrosarcoma, --;

At Column 87, Line number 64, please replace "veneotclax)" with -- venetoclax) --;

At Column 91, Line number 34, please replace "pM" with -- μM --;

At Column 92, Line number 4, after "Imaging" please insert -- in --;

At Column 92, Line number 34, please replace "a" with -- A --;

At Column 93, Line number 2, please replace "pM" with -- μM --;

At Column 93, Line number 4, please replace "a" with -- A --;

CERTIFICATE OF CORRECTION (continued)
U.S. Pat. No. 12,343,377 B2

At Column 93, Line number 16, please replace "pM" with -- µM --;

At Column 93, Line number 22, please replace "pM" with -- µM --;

At Column 93, Line number 61, please replace "a" with -- A --;

At Column 94, Line number 13, please replace "a" with -- A --;

At Column 94, Line number 36, please replace "agent," with -- agent), --;

At Column 95, Line number 5, please replace "a" with -- A --;

At Column 96, Line number 7, please replace "a" with -- A --;

At Column 94, Line number 42, please replace "a" with -- A --;

At Column 97, Line number 16, please replace "a" with -- A --;

At Column 97, Line number 20, please replace "(AMIL)" with -- (AML) --;

At Column 98, Line number 8, please replace "a" with -- A --;

At Column 98, Line number 59, please replace "a" with -- A --; and

At Column 99, Line number 22, please replace "age≥18" with -- age ≥18 --.

SEQUENCE LISTING

```
<160> NUMBER OF SEQ ID NOS: 222

<210> SEQ ID NO 1
<211> LENGTH: 119
<212> TYPE: PRT
<213> ORGANISM: Homo sapiens

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 2
<211> LENGTH: 118
<212> TYPE: PRT
<213> ORGANISM: Homo sapiens

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45
```

```
Ile Tyr Asn Gln Lys Glu Gly His Phe Pro Arg Val Thr Thr Val Ser
    50                  55                  60
Glu Ser Thr Lys Arg Glu Asn Met Asp Phe Ser Ile Ser Ile Ser Asn
65                  70                  75                  80
Ile Thr Pro Ala Asp Ala Gly Thr Tyr Tyr Cys Val Lys Phe Arg Lys
                85                  90                  95
Gly Ser Pro Asp Thr Glu Phe Lys Ser Gly Ala Gly Thr Glu Leu Ser
                100                 105                 110
Val Arg Ala Lys Pro Ser
        115
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 119
<212> TYPE: PRT
<213> ORGANISM: Homo sapiens
<220> FEATURE:
<221> NAME/KEY: VARIANT

```
<222> LOCATION: 3
<223> OTHER INFORMATION: Xaa = E or G
<220> FEATURE:
<221> NAME/KEY: VARIANT
<222> LOCATION: 12
<223> OTHER INFORMATION: Xaa = S or F
<220> FEATURE:
<221> NAME/KEY: VARIANT
<222> LOCATION: 14
<223> OTHER INFORMATION: Xaa = L or S
<220> FEATURE:
<221> NAME/KEY: VARIANT
<222> LOCATION: 20
<223> OTHER INFORMATION: Xaa = T or S
<220> FEATURE:
<221> NAME/KEY: VARIANT
<222> LOCATION: 22
<223> OTHER INFORMATION: Xaa = T or I
<220> FEATURE:
<221> NAME/KEY: VARIANT
<222> LOCATION: 24
<223> OTHER INFORMATION: Xaa = R, H, or L
<220> FEATURE:
<221> NAME/KEY: VARIANT
<222> LOCATION: 27
<223> OTHER INFORMATION: Xaa = A or V
<220> FEATURE:
<221> NAME/KEY: VARIANT
<222> LOCATION: 45
<223> OTHER INFORMATION: Xaa = G or A
<220> FEATURE:
<221> NAME/KEY: VARIANT
<222> LOCATION: 65
<223> OTHER INFORMATION: Xaa = D or E
<220> FEATURE:
<221> NAME/KEY: VARIANT
<222> LOCATION: 66
<223> OTHER INFORMATION: Xaa = L or S
<220> FEATURE:
<221> NAME/KEY: VARIANT
<222> LOCATION: 70
<223> OTHER INFORMATION: Xaa = N, E, or D
<220> FEATURE:
<221> NAME/KEY: VARIANT
<222> LOCATION: 75
<223> OTHER INFORMATION: Xaa = S or P
<220> FEATURE:
<221> NAME/KEY: VARIANT
<222> LOCATION: 77
<223> OTHER INFORMATION: Xaa = R or S
<220> FEATURE:
<221> NAME/KEY: VARIANT
<222> LOCATION: 79
<223> OTHER INFORMATION: Xaa = G or S
<220> FEATURE:
<221> NAME/KEY: VARIANT
<222> LOCATION: 99
<223> OTHER INFORMATION: Xaa = P or absent
<220> FEATURE:
<221> NAME/KEY: VARIANT
<222> LOCATION: 100
<223> OTHER INFORMATION: Xaa = D or P
<220> FEATURE:
<221> NAME/KEY: VARIANT
<222> LOCATION: 102
<223> OTHER INFORMATION: Xaa = V or T
<220> FEATURE:
<221> NAME/KEY: VARIANT
<222> LOCATION: 116
<223> OTHER INFORMATION: Xaa = A or G

<400> SEQUENCE: 11

Glu Glu Xaa Leu Gln Val Ile Gln Pro Asp Lys Xaa Val Xaa Val Ala
1               5                   10                  15

Ala Gly Glu Xaa Ala Xaa Leu Xaa Cys Thr Xaa Thr Ser Leu Ile Pro
            20                  25                  30
```

```
Val Gly Pro Ile Gln Trp Phe Arg Gly Ala Gly Pro Xaa Arg Glu Leu
         35                  40                  45

Ile Tyr Asn Gln Lys Glu Gly His Phe Pro Arg Val Thr Thr Val Ser
 50                  55                  60

Xaa Xaa Thr Lys Arg Xaa Asn Met Asp Phe Xaa Ile Xaa Ile Xaa Asn
 65                  70                  75                  80

Ile Thr Pro Ala Asp Ala Gly Thr Tyr Tyr Cys Val Lys Phe Arg Lys
                 85                  90                  95

Gly Ser Xaa Xaa Asp Xaa Glu Phe Lys Ser Gly Ala Gly Thr Glu Leu
         100                 105                 110

Ser Val Arg Xaa Lys Pro Ser
         115
```

<210> SEQ ID NO 12

<400> SEQUENCE: 12

000

<210> SEQ ID NO 13
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, or V
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 21
<223> OTHER INFORMATION: Xaa = A or V
<220> FEATURE:
<221> NAME/KEY: VARIANT
<222> LOCATION: 27
<223> OTHER INFORMATION: Xaa = A, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 66
<223> OTHER INFORMATION: Xaa = L, T, or G
<220> FEATURE:
<221> NAME/KEY: VARIANT
<222> LOCATION: 68
<223> OTHER INFORMATION: Xaa = K or R
<220> FEATURE:
<221> NAME/KEY: VARIANT
<222> LOCATION: 92

```
<223> OTHER INFORMATION: Xaa = V or I
<220> FEATURE:
<221> NAME/KEY: VARIANT
<222> LOCATION: 94
<223> OTHER INFORMATION: Xaa = F, L, or V
<220> FEATURE:
<221> NAME/KEY: VARIANT
<222> LOCATION: 104
<223> OTHER INFORMATION: Xaa = F or V

<400> SEQUENCE: 13

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Asn
65              70                  75                  80

Ile Thr Pro Ala Asp Ala Gly Thr Tyr Tyr Cys Xaa Lys Xaa Arg Lys
                85                  90                  95

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 14
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, or V
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 21
<223> OTHER INFORMATION: Xaa = A or V
<220> FEATURE:
<221> NAME/KEY: VARIANT
<222> LOCATION: 27
<223> OTHER INFORMATION: Xaa = V, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
```

```
<220> FEATURE:
<221> NAME/KEY: VARIANT
<222> LOCATION: 66
<223> OTHER INFORMATION: Xaa = S, T, or G
<220> FEATURE:
<221> NAME/KEY: VARIANT
<222> LOCATION: 68
<223> OTHER INFORMATION: Xaa = K or R
<220> FEATURE:
<221> NAME/KEY: VARIANT
<222> LOCATION: 92
<223> OTHER INFORMATION: Xaa = V or I
<220> FEATURE:
<221> NAME/KEY: VARIANT
<222> LOCATION: 94
<223> OTHER INFORMATION: Xaa = F, L, or V
<220> FEATURE:
<221> NAME/KEY: VARIANT
<222> LOCATION: 103
<223> OTHER INFORMATION: Xaa = F or V

<400> SEQUENCE: 14
```

Glu Glu Glu Xaa Gln Xaa Ile Gln Pro Asp Lys Ser Val Ser Val Ala
1               5                   10                  15

Ala Gly Glu Ser Xaa Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Xaa Arg Glu Asn Met Asp Phe Ser Ile Ser Ile Ser Asn
65              70                  75                  80

Ile Thr Pro Ala Asp Ala Gly Thr Tyr Tyr Cys Xaa Lys Xaa Arg Lys
            85                  90                  95

Gly Ser Pro Asp Thr Glu Xaa Lys Ser Gly Ala Gly Thr Glu Leu Ser
            100                 105                 110

Val Arg Ala Lys Pro Ser
        115

```
<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000
```

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E or G
<220> FEATURE:
<221> NAME/KEY: VARIANT
<222> LOCATION: 4
<223> OTHER INFORMATION: Xaa = L, I, or V
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 12
<223> OTHER INFORMATION: Xaa = S or F
<220> FEATURE:
<221> NAME/KEY: VARIANT
<222> LOCATION: 14
<223> OTHER INFORMATION: Xaa = L or S
<220> FEATURE:
<221> NAME/KEY: VARIANT
<222> LOCATION: 20
<223> OTHER INFORMATION: Xaa = S or T
<220> FEATURE:
<221> NAME/KEY: VARIANT
<222> LOCATION: 21
<223> OTHER INFORMATION: Xaa = A or V
<220> FEATURE:
<221> NAME/KEY: VARIANT
<222> LOCATION: 22
<223> OTHER INFORMATION: Xaa = I or T
<220> FEATURE:
<221> NAME/KEY: VARIANT
<222> LOCATION: 24
<223> OTHER INFORMATION: Xaa = H or R
<220> FEATURE:
<221> NAME/KEY: VARIANT
<222> LOCATION: 27
<223> OTHER INFORMATION: Xaa = A, V, I, or L
<220> FEATURE:
<221> NAME/KEY: VARIANT
<222> LOCATION: 31

```
-continued

<223> OTHER INFORMATION: Xaa = I, T, S, or F
<220> FEATURE:
<221> NAME/KEY: VARIANT
<222> LOCATION: 45
<223> OTHER INFORMATION: Xaa = A or G
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 65
<223> OTHER INFORMATION: Xaa = D or E
<220> FEATURE:
<221> NAME/KEY: VARIANT
<222> LOCATION: 66
<223> OTHER INFORMATION: Xaa = S, L, T, or G
<220> FEATURE:
<221> NAME/KEY: VARIANT
<222> LOCATION: 68
<223> OTHER INFORMATION: Xaa = K or R
<220> FEATURE:
<221> NAME/KEY: VARIANT
<222> LOCATION: 70
<223> OTHER INFORMATION: Xaa = E or D
<220> FEATURE:
<221> NAME/KEY: VARIANT
<222> LOCATION: 75
<223> OTHER INFORMATION: Xaa = S or P
<220> FEATURE:
<221> NAME/KEY: VARIANT
<222> LOCATION: 77
<223> OTHER INFORMATION: Xaa = S or R
<220> FEATURE:
<221> NAME/KEY: VARIANT
<222> LOCATION: 79
<223> OTHER INFORMATION: Xaa = S or G
<220> FEATURE:
<221> NAME/KEY: VARIANT
<222> LOCATION: 92
<223> OTHER INFORMATION: Xaa = V or I
<220> FEATURE:
<221> NAME/KEY: VARIANT
<222> LOCATION: 94
<223> OTHER INFORMATION: Xaa = F, L, or V
<220> FEATURE:
<221> NAME/KEY: VARIANT
<222> LOCATION: 101
<223> OTHER INFORMATION: Xaa = D or absent
<220> FEATURE:
<221> NAME/KEY: VARIANT
<222> LOCATION: 102
<223> OTHER INFORMATION: Xaa = T or V
<220> FEATURE:
<221> NAME/KEY: VARIANT
<222> LOCATION: 104
<223> OTHER INFORMATION: Xaa = F or V
<220> FEATURE:
<221> NAME/KEY: VARIANT
<222> LOCATION: 116
<223> OTHER INFORMATION: Xaa = A or G

<400> SEQUENCE: 23

Glu Glu Xaa Xaa Gln Xaa Ile Gln Pro Asp Lys Xaa Val Xaa Val Ala
 1               5                  10                  15
```

```
Ala Gly Glu Xaa Xaa Xaa Leu Xaa Cys Thr Xaa Thr Ser Leu Xaa Pro
              20                  25                  30

Val Gly Pro Ile Gln Trp Phe Arg Gly Ala Gly Pro Xaa Arg Xaa Leu
         35                  40                  45

Ile Tyr Asn Gln Xaa Xaa Gly Xaa Phe Pro Arg Val Thr Thr Val Ser
 50                  55                  60

Xaa Xaa Thr Xaa Arg Xaa Asn Met Asp Phe Xaa Ile Xaa Ile Xaa Asn
65                  70                  75                  80

Ile Thr Pro Ala Asp Ala Gly Thr Tyr Tyr Cys Xaa Lys Xaa Arg Lys
              85                  90                  95

Gly Ser Pro Asp Xaa Xaa Glu Xaa Lys Ser Gly Ala Gly Thr Glu Leu
             100                 105                 110

Ser Val Arg Xaa Lys Pro Ser
         115
```

<210> SEQ ID NO 24
<211> LENGTH: 102
<212> TYPE: PRT
<213> ORGANISM: Artificial Sequence
<220> FEATURE:
<223> OTHER INFORMATION: Synthetic Construct

<400> SEQUENCE: 24

```
Ala Pro Val Val Ser Gly Pro Ala Ala Arg Ala Thr Pro Gln His Thr
 1               5                  10                  15

Val Ser Phe Thr Cys Glu Ser His Gly Phe Ser Pro Arg Asp Ile Thr
             20                  25                  30

Leu Lys Trp Phe Lys Asn Gly Asn Glu Leu Ser Asp Phe Gln Thr Asn
         35                  40                  45

Val Asp Pro Val Gly Glu Ser Val Ser Tyr Ser Ile His Ser Thr Ala
 50                  55                  60

Lys Val Val Leu Thr Arg Glu Asp Val His Ser Gln Val Ile Cys Glu
65                  70                  75                  80

Val Ala His Val Thr Leu Gln Gly Asp Pro Leu Arg Gly Thr Ala Asn
              85                  90                  95

Leu Ser Glu Thr Ile Arg
            100
```

<210> SEQ ID NO 25
<211> LENGTH: 99
<212> TYPE: PRT
<213> ORGANISM: Artificial Sequence
<220> FEATURE:
<223> OTHER INFORMATION: Synthetic Construct

<400> SEQUENCE: 25

```
Val Pro Pro Thr Leu Glu Val Thr Gln Gln Pro Val Arg Ala Glu Asn
 1               5                  10                  15

Gln Val Asn Val Thr Cys Gln Val Arg Lys Phe Tyr Pro Gln Arg Leu
             20                  25                  30

Gln Leu Thr Trp Leu Glu Asn Gly Asn Val Ser Arg Thr Glu Thr Ala
         35                  40                  45

Ser Thr Val Thr Glu Asn Lys Asp Gly Thr Tyr Asn Trp Met Ser Trp
 50                  55                  60

Leu Leu Val Asn Val Ser Ala His Arg Asp Asp Val Lys Leu Thr Cys
65                  70                  75                  80
```

Gln Val Glu His Asp Gly Gln Pro Ala Val Ser Lys Ser His Asp Leu
                85                  90                  95

Lys Val Ser

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Arg Glu Gly His Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
                100                 105                 110

Val Arg Ala Lys Pro Ser
            115

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct

<400> SEQUENCE: 27

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
                20                  25                  30

Val Gly Pro Ile Gln Trp Phe Arg Gly Ala Gly Pro Ala Arg Val Leu
            35                  40                  45

Ile Tyr Asn Gln Arg Gln Gly His Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 28
<211> LENGTH: 118
<212> TYPE: PRT
<213> ORGANISM: Artificial Sequence

```
<220> FEATURE:
<223> OTHER INFORMATION: Synthetic Construct

<400> SEQUENCE: 28

Glu Glu Glu Val Gln Ile Ile Gln Pro Asp Lys Ser Val Ser Val Ala
1               5                   10                  15

Ala Gly Glu Ser Val Ile Leu His Cys Thr Ile Thr Ser Leu Thr Pro
            20                  25                  30

Val Gly Pro Ile Gln Trp Phe Arg Gly Ala Gly Pro Ala Arg Leu Leu
        35                  40                  45

Ile Tyr Asn Gln Arg Glu Gly Pro Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic Construct

<400> SEQUENCE: 29

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ser Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic Construct

<400> SEQUENCE: 30

Glu Glu Glu Ile Gln Val Ile Gln Pro Asp Lys Ser Val Ser Val Ala
1               5                   10                  15

Ala Gly Glu Ser Val Ile Ile His Cys Thr Val Thr Ser Leu Phe Pro
            20                  25                  30
```

-continued

Val Gly Pro Ile Gln Trp Phe Arg Gly Ala Gly Pro Ala Arg Val Leu
            35                  40                  45

Ile Tyr Asn Gln Arg Gln Gly Arg Phe Pro Arg Val Thr Thr Val Ser
 50                  55                  60

Glu Gly Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Val Arg Lys
                 85                  90                  95

Gly Ser Pro Asp Thr Glu Val Lys Ser Gly Ala Gly Thr Glu Leu Ser
                100                 105                 110

Val Arg Ala Lys Pro Ser
            115

<210> SEQ ID NO 31
<211> LENGTH: 118
<212> TYPE: PRT
<213> ORGANISM: Artificial Sequence
<220> FEATURE:
<223> OTHER INFORMATION: Synthetic Construct

<400> SEQUENCE: 31

Glu Glu Glu Val Gln Ile Ile Gln Pro Asp Lys Ser Val Ser Val Ala
 1               5                  10                  15

Ala Gly Glu Ser Ile Ile Leu His Cys Thr Val Thr Ser Leu Phe Pro
             20                  25                  30

Val Gly Pro Ile Gln Trp Phe Arg Gly Ala Gly Pro Ala Arg Val Leu
            35                  40                  45

Ile Tyr Asn Gln Arg Glu Gly Arg Phe Pro Arg Val Thr Thr Val Ser
 50                  55                  60

Glu Gly Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Leu Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 32
<211> LENGTH: 118
<212> TYPE: PRT
<213> ORGANISM: Artificial Sequence
<220> FEATURE:
<223> OTHER INFORMATION: Synthetic Construct

<400> SEQUENCE: 32

Glu Glu Glu Val Gln Leu Ile Gln Pro Asp Lys Ser Val Ser Val Ala
 1               5                  10                  15

Ala Gly Glu Ser Ala Ile Leu His Cys Thr Val Thr Ser Leu Phe Pro
             20                  25                  30

Val Gly Pro Ile Gln Trp Phe Arg Gly Ala Gly Pro Ala Arg Val Leu
            35                  40                  45

Ile Tyr Asn Gln Arg Glu Gly Pro Phe Pro Arg Val Thr Thr Val Ser
 50                  55                  60

Glu Gly Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

```
Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 33
<211> LENGTH: 119
<212> TYPE: PRT
<213> ORGANISM: Artificial Sequence
<220> FEATURE:
<223> OTHER INFORMATION: Synthetic Construct

<400> SEQUENCE: 33

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 34
<211> LENGTH: 118
<212> TYPE: PRT
<213> ORGANISM: Artificial Sequence
<220> FEATURE:
<223> OTHER INFORMATION: Synthetic Construct

<400> SEQUENCE: 34

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Leu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 35
<211> LENGTH: 118
<212> TYPE: PRT
```

<213> ORGANISM: Artificial Sequence
<220> FEATURE:
<223> OTHER INFORMATION: Synthetic Construct

<400> SEQUENCE: 35

```
Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Lys Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 36
<211> LENGTH: 118
<212> TYPE: PRT
<213> ORGANISM: Artificial Sequence
<220> FEATURE:
<223> OTHER INFORMATION: Synthetic Construct

<400> SEQUENCE: 36

```
Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115
```

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, or V
<220> FEATURE:
<221> NAME/KEY: VARIANT
<222> LOCATION: 6
<223> OTHER INFORMATION: Xaa = V, L, or I -continued

```
<220> FEATURE:
<221> NAME/KEY: VARIANT
<222> LOCATION: 21
<223> OTHER INFORMATION: Xaa = A or V
<220> FEATURE:
<221> NAME/KEY: VARIANT
<222> LOCATION: 27
<223> OTHER INFORMATION: Xaa = A, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 66
<223> OTHER INFORMATION: Xaa = L, T, or G
<220> FEATURE:
<221> NAME/KEY: VARIANT
<222> LOCATION: 68
<223> OTHER INFORMATION: Xaa = K or R
<220> FEATURE:
<221> NAME/KEY: VARIANT
<222> LOCATION: 80
<223> OTHER INFORMATION: Xaa = N, A, C, D, E, F, G, H, I, K,
      L, M, P, Q, R, S, T, V, W, or Y
<220> FEATURE:
<221> NAME/KEY: VARIANT
<222> LOCATION: 83
<223> OTHER INFORMATION: Xaa = P, A, C, D, E, F, G, H, I, K,
      L, M, N, Q, R, S, T, V, W, or Y
<220> FEATURE:
<221> NAME/KEY: VARIANT
<222> LOCATION: 92
<223> OTHER INFORMATION: Xaa = V or I
<220> FEATURE:
<221> NAME/KEY: VARIANT
<222> LOCATION: 94
<223> OTHER INFORMATION: Xaa = F, L, or V
<220> FEATURE:
<221> NAME/KEY: VARIANT
<222> LOCATION: 104
<223> OTHER INFORMATION: Xaa = F or V

<400> SEQUENCE: 37

Glu Glu Glu Xaa Gln Xaa Ile Gln Pro Asp Lys Ser Val Leu Val Ala
1               5                   10                  15

Ala Gly Glu Thr Xaa Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Xaa Arg Asn Asn Met Asp Phe Ser Ile Arg Ile Gly Xaa
65                  70                  75                  80

Ile Thr Xaa Ala Asp Ala Gly Thr Tyr Tyr Cys Xaa Lys Xaa Arg Lys
            85                  90                  95
```

Gly Ser Pro Asp Asp Val Glu Xaa Lys Ser Gly Ala Gly Thr Glu Leu
            100                 105                 110

Ser Val Arg Ala Lys Pro Ser
        115

<210> SEQ ID NO 38
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = L, I, or V
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 21
<223> OTHER INFORMATION: Xaa = A or V
<220> FEATURE:
<221> NAME/KEY: VARIANT
<222> LOCATION: 27
<223> OTHER INFORMATION: Xaa = V, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 66
<223> OTHER INFORMATION: Xaa = S, T, or G
<220> FEATURE:
<221> NAME/KEY: VARIANT
<222> LOCATION: 68
<223> OTHER INFORMATION: Xaa = K or R
<220> FEATURE:
<221> NAME/KEY: VARIANT
<222> LOCATION: 80
<223> OTHER INFORMATION: Xaa = N, A, C, D, E, F, G, H, I, K,
      L, M, P, Q, R, S, T, V, W, or Y
<220> FEATURE:
<221> NAME/KEY: VARIANT
<222> LOCATION: 83
<223> OTHER INFORMATION: Xaa = P, A, C, D, E, F, G, H, I, K,
      L, M, N, Q, R, S, T, V, W, or Y
<220> FEATURE:
<221> NAME/KEY: VARIANT
<222> LOCATION: 92
<223> OTHER INFORMATION: Xaa = V or I
<220> FEATURE:
<221> NAME/KEY: VARIANT
<222> LOCATION: 94
<223> OTHER INFORMATION: Xaa = F, L, or V
<220> FEATURE:
<221> NAME/KEY: VARIANT
<222> LOCATION: 103
<223> OTHER INFORMATION: Xaa = F or V

<400> SEQUENCE: 38

```
Glu Glu Glu Xaa Gln Xaa Ile Gln Pro Asp Lys Ser Val Ser Val Ala
1               5                   10                  15
Ala Gly Glu Ser Xaa Ile Leu His Cys Thr Xaa Thr Ser Leu Xaa Pro
            20                  25                  30
Val Gly Pro Ile Gln Trp Phe Arg Gly Ala Gly Pro Ala Arg Xaa Leu
        35                  40                  45
Ile Tyr Asn Gln Xaa Xaa Gly Xaa Phe Pro Arg Val Thr Thr Val Ser
    50                  55                  60
Glu Xaa Thr Xaa Arg Glu Asn Met Asp Phe Ser Ile Ser Ile Ser Xaa
65              70                  75                  80
Ile Thr Xaa Ala Asp Ala Gly Thr Tyr Tyr Cys Xaa Lys Xaa Arg Lys
            85                  90                  95
Gly Ser Pro Asp Thr Glu Xaa Lys Ser Gly Ala Gly Thr Glu Leu Ser
            100                 105                 110
Val Arg Ala Lys Pro Ser
            115
```

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = E or G
<220> FEATURE:
<221> NAME/KEY: VARIANT
<222> LOCATION: 4
<223> OTHER INFORMATION: Xaa = L, I, or V
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 12
<223> OTHER INFORMATION: Xaa = S or F
<220> FEATURE:
<221> NAME/KEY: VARIANT
<222> LOCATION: 14
<223> OTHER INFORMATION: Xaa = L or S
<220> FEATURE:
<221> NAME/KEY: VARIANT
<222> LOCATION: 20
<223> OTHER INFORMATION: Xaa = S or T
<220> FEATURE:
<221> NAME/KEY: VARIANT
<222> LOCATION: 21
<223> OTHER INFORMATION: Xaa = A or V
<220> FEATURE:
<221> NAME/KEY: VARIANT
<222> LOCATION: 22
<223> OTHER INFORMATION: Xaa = I or T
<220> FEATURE:
<221> NAME/KEY: VARIANT
<222> LOCATION: 24
<223> OTHER INFORMATION: Xaa = H, R, or L
<220> FEATURE:
<221> NAME/KEY: VARIANT
<222> LOCATION: 27
<223> OTHER INFORMATION: Xaa = A, V, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 45
<223> OTHER INFORMATION: Xaa = A or G
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 65
<223> OTHER INFORMATION: Xaa = D or E

```
<220> FEATURE:
<221> NAME/KEY: VARIANT
<222> LOCATION: 66
<223> OTHER INFORMATION: Xaa = S, L, T, or G
<220> FEATURE:
<221> NAME/KEY: VARIANT
<222> LOCATION: 68
<223> OTHER INFORMATION: Xaa = K or R
<220> FEATURE:
<221> NAME/KEY: VARIANT
<222> LOCATION: 70
<223> OTHER INFORMATION: Xaa = E or N
<220> FEATURE:
<221> NAME/KEY: VARIANT
<222> LOCATION: 75
<223> OTHER INFORMATION: Xaa = S or P
<220> FEATURE:
<221> NAME/KEY: VARIANT
<222> LOCATION: 77
<223> OTHER INFORMATION: Xaa = S or R
<220> FEATURE:
<221> NAME/KEY: VARIANT
<222> LOCATION: 79
<223> OTHER INFORMATION: Xaa = S or G
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 92
<223> OTHER INFORMATION: Xaa = V or I
<220> FEATURE:
<221> NAME/KEY: VARIANT
<222> LOCATION: 94
<223> OTHER INFORMATION: Xaa = F, L, or V
<220> FEATURE:
<221> NAME/KEY: VARIANT
<222> LOCATION: 101
<223> OTHER INFORMATION: Xaa = D or absent
<220> FEATURE:
<221> NAME/KEY: VARIANT
<222> LOCATION: 102
<223> OTHER INFORMATION: Xaa = T or V
<220> FEATURE:
<221> NAME/KEY: VARIANT
<222> LOCATION: 104
<223> OTHER INFORMATION: Xaa = F or V
<220> FEATURE:
<221> NAME/KEY: VARIANT
<222> LOCATION: 116
<223> OTHER INFORMATION: Xaa = A or G

<400> SEQUENCE: 47

Glu Glu Xaa Xaa Gln Xaa Ile Gln Pro Asp Lys Xaa Val Xaa Val Ala
1               5                   10                  15

Ala Gly Glu Xaa Xaa Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
    50                  55                  60

Xaa Xaa Thr Xaa Arg Xaa Asn Met Asp Phe Xaa Ile Xaa Ile Xaa Xaa
65                  70                  75                  80

Ile Thr Xaa Ala Asp Ala Gly Thr Tyr Tyr Cys Xaa Lys Xaa Arg Lys
            85                  90                  95

Gly Ser Pro Asp Xaa Xaa Glu Xaa Lys Ser Gly Ala Gly Thr Glu Leu
            100                 105                 110
```

Ser Val Arg Xaa Lys Pro Ser
        115

<210> SEQ ID NO 48
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 14
<223> OTHER INFORMATION: Xaa = L or S
<220> FEATURE:
<221> NAME/KEY: VARIANT
<222> LOCATION: 20
<223> OTHER INFORMATION: Xaa = T or S
<220> FEATURE:
<221> NAME/KEY: VARIANT
<222> LOCATION: 22
<223> OTHER INFORMATION: Xaa = T or I
<220> FEATURE:
<221> NAME/KEY: VARIANT
<222> LOCATION: 24
<223> OTHER INFORMATION: Xaa = R or H
<220> FEATURE:
<221> NAME/KEY: VARIANT
<222> LOCATION: 27
<223> OTHER INFORMATION: Xaa = A, V, or I
<220> FEATURE:
<221> NAME/KEY: VARIANT
<222> LOCATION: 31
<223> OTHER INFORMATION: Xaa = I, R, Y, K, or F
<220> FEATURE:
<221> NAME/KEY: VARIANT
<222> LOCATION: 45
<223> OTHER INFORMATION: Xaa = G or A
<220> FEATURE:
<221> NAME/KEY: VARIANT
<222> LOCATION: 47
<223> OTHER INFORMATION: Xaa = E or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E, D, or Q
<220> FEATURE:
<221> NAME/KEY: VARIANT
<222> LOCATION: 56
<223> OTHER INFORMATION: Xaa = H or P
<220> FEATURE:
<221> NAME/KEY: VARIANT
<222> LOCATION: 65
<223> OTHER INFORMATION: Xaa = D or E
<220> FEATURE:
<221> NAME/KEY: VARIANT
<222> LOCATION: 66
<223> OTHER INFORMATION: Xaa = S, L, or T
<220> FEATURE:
<221> NAME/KEY: VARIANT
<222> LOCATION: 70
<223> OTHER INFORMATION: Xaa = N or E
<220> FEATURE:
<221> NAME/KEY: VARIANT
<222> LOCATION: 77
<223> OTHER INFORMATION: Xaa = R or S
<220> FEATURE:
<221> NAME/KEY: VARIANT
<222> LOCATION: 79
<223> OTHER INFORMATION: Xaa = G or S

```
<220> FEATURE:
<221> NAME/KEY: VARIANT
<222> LOCATION: 80
<223> OTHER INFORMATION: Xaa = N or A
<220> FEATURE:
<221> NAME/KEY: VARIANT
<222> LOCATION: 92
<223> OTHER INFORMATION: Xaa = V or I
<220> FEATURE:
<221> NAME/KEY: VARIANT
<222> LOCATION: 98
<223> OTHER INFORMATION: Xaa = S, I , or M
<220> FEATURE:
<221> NAME/KEY: VARIANT
<222> LOCATION: 99
<223> OTHER INFORMATION: Xaa = P or absent
<220> FEATURE:
<221> NAME/KEY: VARIANT
<222> LOCATION: 100
<223> OTHER INFORMATION: Xaa = D or P
<220> FEATURE:
<221> NAME/KEY: VARIANT
<222> LOCATION: 102
<223> OTHER INFORMATION: Xaa = V or T

<400> SEQUENCE: 48

Glu Glu Glu Leu Gln Xaa Ile Gln Pro Asp Lys Ser Val Xaa Val Ala
1               5                   10                  15

Ala Gly Glu Xaa Ala Xaa Leu Xaa Cys Thr Xaa Thr Ser Leu Xaa Pro
            20                  25                  30

Val Gly Pro Ile Gln Trp Phe Arg Gly Ala Gly Pro Xaa Arg Xaa Leu
        35                  40                  45

Ile Tyr Asn Gln Xaa Xaa Gly Xaa Phe Pro Arg Val Thr Thr Val Ser
50                  55                  60

Xaa Xaa Thr Lys Arg Xaa Asn Met Asp Phe Ser Ile Xaa Ile Xaa Xaa
65                  70                  75                  80

Ile Thr Pro Ala Asp Ala Gly Thr Tyr Tyr Cys Xaa Lys Phe Arg Lys
                85                  90                  95

Gly Xaa Xaa Xaa Asp Xaa Glu Phe Lys Ser Gly Ala Gly Thr Glu Leu
            100                 105                 110

Ser Val Arg Ala Lys Pro Ser
        115

<210> SEQ ID NO 49
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, I, or L
<220> FEATURE:
<221> NAME/KEY: VARIANT
<222> LOCATION: 27
<223> OTHER INFORMATION: Xaa = A, I, V, or L
<220> FEATURE:
<221> NAME/KEY: VARIANT
<222> LOCATION: 31
<223> OTHER INFORMATION: Xaa = I, F, S, or T
<220> FEATURE:
<221> NAME/KEY: VARIANT
<222> LOCATION: 47
<223> OTHER INFORMATION: Xaa = E, V, or L
<220> FEATURE:
<221> NAME/KEY: VARIANT
<222> LOCATION: 53
<223> OTHER INFORMATION: Xaa = K or R
<220> FEATURE:
```

```
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 66
<223> OTHER INFORMATION: Xaa = L, T, S, or G
<220> FEATURE:
<221> NAME/KEY: VARIANT
<222> LOCATION: 80
<223> OTHER INFORMATION: Xaa = A
<220> FEATURE:
<221> NAME/KEY: VARIANT
<222> LOCATION: 92
<223> OTHER INFORMATION: Xaa = V or I

<400> SEQUENCE: 49

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Xaa Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 27
<223> OTHER INFORMATION: Xaa = V or I
<220> FEATURE:
<221> NAME/KEY: VARIANT
<222> LOCATION: 31
<223> OTHER INFORMATION: Xaa = I or F
<220> FEATURE:
<221> NAME/KEY: VARIANT
<222> LOCATION: 47
<223> OTHER INFORMATION: Xaa = E or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
```

```
<222> LOCATION: 56
<223> OTHER INFORMATION: Xaa = H or P
<220> FEATURE:
<221> NAME/KEY: VARIANT
<222> LOCATION: 66
<223> OTHER INFORMATION: Xaa = S or T
<220> FEATURE:
<221> NAME/KEY: VARIANT
<222> LOCATION: 80
<223> OTHER INFORMATION: Xaa = N or A
<220> FEATURE:
<221> NAME/KEY: VARIANT
<222> LOCATION: 92
<223> OTHER INFORMATION: Xaa = V or I

<400> SEQUENCE: 50

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Xaa Leu
        35                  40                  45

Ile Tyr Asn Gln Xaa Xaa Gly Xaa Phe Pro Arg Val Thr Thr Val Ser
    50                  55                  60

Glu Xaa Thr Lys Arg Glu Asn Met Asp Phe Ser Ile Ser Ile Ser Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 27
<223> OTHER INFORMATION: Xaa = A or I
<220> FEATURE:
<221> NAME/KEY: VARIANT
<222> LOCATION: 31
<223> OTHER INFORMATION: Xaa = I or F
<220> FEATURE:
<221> NAME/KEY: VARIANT
<222> LOCATION: 47
<223> OTHER INFORMATION: Xaa = E or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H or P
<220> FEATURE:
<221> NAME/KEY: VARIANT
<222> LOCATION: 66
<223> OTHER INFORMATION: Xaa = L or T
<220> FEATURE:
<221> NAME/KEY: VARIANT
<222> LOCATION: 80
```

```
<223> OTHER INFORMATION: Xaa = N or A
<220> FEATURE:
<221> NAME/KEY: VARIANT
<222> LOCATION: 92
<223> OTHER INFORMATION: Xaa = V or I

<400> SEQUENCE: 51

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45

Ile Tyr Asn Gln Xaa Glu Gly Xaa Phe Pro Arg Val Thr Thr Val Ser
    50                  55                  60

Asp Xaa Thr Lys Arg Asn Asn Met Asp Phe Ser Ile Arg Ile Gly Xaa
65                  70                  75                  80

Ile Thr Pro Ala Asp Ala Gly Thr Tyr Tyr Cys Xaa Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H, P, or R
<220> FEATURE:
<221> NAME/KEY: VARIANT
<222> LOCATION: 66
<223> OTHER INFORMATION: Xaa = L, T, or G
<220> FEATURE:
<221> NAME/KEY: VARIANT
<222> LOCATION: 80
<223> OTHER INFORMATION: Xaa = N or A

<400> SEQUENCE: 52

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Glu Leu
        35                  40                  45
```

-continued

```
Ile Tyr Asn Gln Xaa Glu Gly Xaa Phe Pro Arg Val Thr Val Ser
    50              55                  60

Asp Xaa Thr Lys Arg Asn Asn Met Asp Phe Ser Ile Arg Ile Gly Xaa
 65              70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 53
<211> LENGTH: 118
<212> TYPE: PRT
<213> ORGANISM: Artificial Sequence
<220> FEATURE:
<223> OTHER INFORMATION: Synthetic Construct

<400> SEQUENCE: 53

Glu Glu Glu Leu Gln Ile Ile Gln Pro Asp Lys Ser Val Ser Val Ala
  1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Val Leu
             35                  40                  45

Ile Tyr Asn Gln Arg Gln Gly Pro Phe Pro Arg Val Thr Val Ser
    50              55                  60

Glu Thr Thr Lys Arg Glu Asn Met Asp Phe Ser Ile Ser Ile Ser Asn
 65              70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 54
<211> LENGTH: 118
<212> TYPE: PRT
<213> ORGANISM: Artificial Sequence
<220> FEATURE:
<223> OTHER INFORMATION: Synthetic Construct

<400> SEQUENCE: 54

Glu Glu Glu Leu Gln Val Ile Gln Pro Asp Lys Ser Val Ser Val Ala
  1               5                  10                  15

Ala Gly Glu Ser Ala Ile Leu His Cys Thr Val Thr Ser Leu Phe Pro
                 20                  25                  30

Val Gly Pro Ile Gln Trp Phe Arg Gly Ala Gly Pro Ala Arg Glu Leu
             35                  40                  45

Ile Tyr Asn Gln Arg Gln Gly Pro Phe Pro Arg Val Thr Val Ser
    50              55                  60

Glu Ser Thr Lys Arg Glu Asn Met Asp Phe Ser Ile Ser Ile Ser Asn
 65              70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110
```

```
Val Arg Ala Lys Pro Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic Construct

<400> SEQUENCE: 55

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 56
<211> LENGTH: 118
<212> TYPE: PRT
<213> ORGANISM: Artificial Sequence
<220> FEATURE:
<223> OTHER INFORMATION: Synthetic Construct

<400> SEQUENCE: 56

Glu Glu Glu Leu Gln Ile Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic Construct
```

<400> SEQUENCE: 57

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 58
<211> LENGTH: 118
<212> TYPE: PRT
<213> ORGANISM: Artificial Sequence
<220> FEATURE:
<223> OTHER INFORMATION: Synthetic Construct

<400> SEQUENCE: 58

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 59
<211> LENGTH: 118
<212> TYPE: PRT
<213> ORGANISM: Artificial Sequence
<220> FEATURE:
<223> OTHER INFORMATION: Synthetic Construct

<400> SEQUENCE: 59

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

```
Ile Tyr Asn Gln Lys Gln Gly Pro Phe Pro Arg Val Thr Thr Val Ser
        50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115
```

<210> SEQ ID NO 60
<211> LENGTH: 118
<212> TYPE: PRT
<213> ORGANISM: Artificial Sequence
<220> FEATURE:
<223> OTHER INFORMATION: Synthetic Construct

<400> SEQUENCE: 60

```
Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Val Leu
             35                  40                  45

Ile Tyr Asn Gln Arg Glu Gly Pro Phe Pro Arg Val Thr Thr Val Ser
        50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115
```

<210> SEQ ID NO 61
<211> LENGTH: 118
<212> TYPE: PRT
<213> ORGANISM: Artificial Sequence
<220> FEATURE:
<223> OTHER INFORMATION: Synthetic Construct

<400> SEQUENCE: 61

```
Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
                 20                  25                  30

Val Gly Pro Ile Gln Trp Phe Arg Gly Ala Gly Pro Ala Arg Val Leu
             35                  40                  45

Ile Tyr Asn Gln Arg Gln Gly His Phe Pro Arg Val Thr Thr Val Ser
        50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95
```

```
Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 62
<211> LENGTH: 118
<212> TYPE: PRT
<213> ORGANISM: Artificial Sequence
<220> FEATURE:
<223> OTHER INFORMATION: Synthetic Construct

<400> SEQUENCE: 62

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 63
<211> LENGTH: 118
<212> TYPE: PRT
<213> ORGANISM: Artificial Sequence
<220> FEATURE:
<223> OTHER INFORMATION: Synthetic Construct

<400> SEQUENCE: 63

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 64
<211> LENGTH: 118
<212> TYPE: PRT
```

<213> ORGANISM: Artificial Sequence
<220> FEATURE:
<223> OTHER INFORMATION: Synthetic Construct

<400> SEQUENCE: 64

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 65
<211> LENGTH: 118
<212> TYPE: PRT
<213> ORGANISM: Artificial Sequence
<220> FEATURE:
<223> OTHER INFORMATION: Synthetic Construct

<400> SEQUENCE: 65

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

<210> SEQ ID NO 66
<211> LENGTH: 118
<212> TYPE: PRT
<213> ORGANISM: Artificial Sequence
<220> FEATURE:
<223> OTHER INFORMATION: Synthetic Construct

<400> SEQUENCE: 66

```
Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30
```

```
Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
 50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
               100                 105                 110

Val Arg Ala Lys Pro Ser
            115

<210> SEQ ID NO 67
<211> LENGTH: 118
<212> TYPE: PRT
<213> ORGANISM: Artificial Sequence
<220> FEATURE:
<223> OTHER INFORMATION: Synthetic Construct

<400> SEQUENCE: 67

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
 50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
               100                 105                 110

Val Arg Ala Lys Pro Ser
            115

<210> SEQ ID NO 68
<211> LENGTH: 118
<212> TYPE: PRT
<213> ORGANISM: Artificial Sequence
<220> FEATURE:
<223> OTHER INFORMATION: Synthetic Construct

<400> SEQUENCE: 68

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
 50                  55                  60

Glu Ser Thr Lys Arg Glu Asn Met Asp Phe Ser Ile Ser Ile Ser Asn
65                  70                  75                  80
```

```
Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 69
<211> LENGTH: 118
<212> TYPE: PRT
<213> ORGANISM: Artificial Sequence
<220> FEATURE:
<223> OTHER INFORMATION: Synthetic Construct

<400> SEQUENCE: 69

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 70
<211> LENGTH: 118
<212> TYPE: PRT
<213> ORGANISM: Artificial Sequence
<220> FEATURE:
<223> OTHER INFORMATION: Synthetic Construct

<400> SEQUENCE: 70

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115
```

```
<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71
```

| Glu | Glu | Glu | Leu | Gln | Val | Ile | Gln | Pro | Asp | Lys | Ser | Val | Leu | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Gly | Glu | Thr | Ala | Thr | Leu | Arg | Cys | Thr | Ala | Thr | Ser | Leu | Phe | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Gly | Pro | Ile | Gln | Trp | Phe | Arg | Gly | Ala | Gly | Pro | Gly | Arg | Glu | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ile | Tyr | Asn | Gln | Arg | Gln | Gly | Pro | Phe | Pro | Arg | Val | Thr | Thr | Val | Ser |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Asp | Leu | Thr | Lys | Arg | Asn | Asn | Met | Asp | Phe | Ser | Ile | Arg | Ile | Gly | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Thr | Pro | Ala | Asp | Ala | Gly | Thr | Tyr | Tyr | Cys | Val | Lys | Phe | Arg | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Ser | Pro | Asp | Asp | Val | Glu | Phe | Lys | Ser | Gly | Ala | Gly | Thr | Glu | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Val | Arg | Ala | Lys | Pro | Ser |
|-----|-----|-----|-----|-----|-----|-----|
|     |     |     | 115 |     |     |     |

```
<210> SEQ ID NO 72
<211> LENGTH: 119
<212> TYPE: PRT
<213> ORGANISM: Artificial Sequence
<220> FEATURE:
<223> OTHER INFORMATION: Synthetic Construct

<400> SEQUENCE: 72
```

| Glu | Glu | Glu | Leu | Gln | Ile | Ile | Gln | Pro | Asp | Lys | Ser | Val | Leu | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Gly | Glu | Thr | Ala | Thr | Leu | Arg | Cys | Thr | Ile | Thr | Ser | Leu | Phe | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Gly | Pro | Ile | Gln | Trp | Phe | Arg | Gly | Ala | Gly | Pro | Gly | Arg | Glu | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ile | Tyr | Asn | Gln | Arg | Glu | Gly | Pro | Phe | Pro | Arg | Val | Thr | Thr | Val | Ser |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Asp | Leu | Thr | Lys | Arg | Asn | Asn | Met | Asp | Phe | Ser | Ile | Arg | Ile | Gly | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Thr | Pro | Ala | Asp | Ala | Gly | Thr | Tyr | Tyr | Cys | Val | Lys | Phe | Arg | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Ser | Pro | Asp | Asp | Val | Glu | Phe | Lys | Ser | Gly | Ala | Gly | Thr | Glu | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Val | Arg | Ala | Lys | Pro | Ser |
|-----|-----|-----|-----|-----|-----|-----|
|     |     |     | 115 |     |     |     |

```
<210> SEQ ID NO 73
<211> LENGTH: 119
<212> TYPE: PRT
<213> ORGANISM: Artificial Sequence
<220> FEATURE:
<223> OTHER INFORMATION: Synthetic Construct

<400> SEQUENCE: 73
```

| Glu | Glu | Glu | Leu | Gln | Val | Ile | Gln | Pro | Asp | Lys | Ser | Val | Leu | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 74
<211> LENGTH: 119
<212> TYPE: PRT
<213> ORGANISM: Artificial Sequence
<220> FEATURE:
<223> OTHER INFORMATION: Synthetic Construct

<400> SEQUENCE: 74

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 75
<211> LENGTH: 119
<212> TYPE: PRT
<213> ORGANISM: Artificial Sequence
<220> FEATURE:
<223> OTHER INFORMATION: Synthetic Construct

<400> SEQUENCE: 75

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 76
<211> LENGTH: 119
<212> TYPE: PRT
<213> ORGANISM: Artificial Sequence
<220> FEATURE:
<223> OTHER INFORMATION: Synthetic Construct

<400> SEQUENCE: 76

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 77
<211> LENGTH: 119
<212> TYPE: PRT
<213> ORGANISM: Artificial Sequence
<220> FEATURE:
<223> OTHER INFORMATION: Synthetic Construct

<400> SEQUENCE: 77

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

```
Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 79
<211> LENGTH: 119
<212> TYPE: PRT
<213> ORGANISM: Artificial Sequence
<220> FEATURE:
<223> OTHER INFORMATION: Synthetic Construct

<400> SEQUENCE: 79

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 80
<211> LENGTH: 119
<212> TYPE: PRT
```

<213> ORGANISM: Artificial Sequence
<220> FEATURE:
<223> OTHER INFORMATION: Synthetic Construct

<400> SEQUENCE: 80

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 81
<211> LENGTH: 119
<212> TYPE: PRT
<213> ORGANISM: Artificial Sequence
<220> FEATURE:
<223> OTHER INFORMATION: Synthetic Construct

<400> SEQUENCE: 81

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 82
<211> LENGTH: 119
<212> TYPE: PRT
<213> ORGANISM: Artificial Sequence
<220> FEATURE:
<223> OTHER INFORMATION: Synthetic Construct

<400> SEQUENCE: 82

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

-continued

```
Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 83
<211> LENGTH: 119
<212> TYPE: PRT
<213> ORGANISM: Artificial Sequence
<220> FEATURE:
<223> OTHER INFORMATION: Synthetic Construct

<400> SEQUENCE: 83

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 84
<211> LENGTH: 119
<212> TYPE: PRT
<213> ORGANISM: Artificial Sequence
<220> FEATURE:
<223> OTHER INFORMATION: Synthetic Construct

<400> SEQUENCE: 84

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80
```

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 85
<211> LENGTH: 119
<212> TYPE: PRT
<213> ORGANISM: Artificial Sequence
<220> FEATURE:
<223> OTHER INFORMATION: Synthetic Construct

<400> SEQUENCE: 85

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 86
<211> LENGTH: 119
<212> TYPE: PRT
<213> ORGANISM: Artificial Sequence
<220> FEATURE:
<223> OTHER INFORMATION: Synthetic Construct

<400> SEQUENCE: 86

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

```
<210> SEQ ID NO 87
<211> LENGTH: 119
<212> TYPE: PRT
<213> ORGANISM: Artificial Sequence
<220> FEATURE:
<223> OTHER INFORMATION: Synthetic Construct

<400> SEQUENCE: 87

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 88
<211> LENGTH: 232
<212> TYPE: PRT
<213> ORGANISM: Artificial Sequence
<220> FEATURE:
<223> OTHER INFORMATION: Synthetic Construct

<400> SEQUENCE: 88

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 89
<211> LENGTH: 325
<212> TYPE: PRT
<213> ORGANISM: Artificial Sequence
<220> FEATURE:
<223> OTHER INFORMATION: Synthetic Construct

<400> SEQUENCE: 89

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

```
Leu Ser Pro Gly Lys
            325

<210> SEQ ID NO 90
<211> LENGTH: 227
<212> TYPE: PRT
<213> ORGANISM: Artificial Sequence
<220> FEATURE:
<223> OTHER INFORMATION: Synthetic Construct

<400> SEQUENCE: 90

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 91
<211> LENGTH: 226
<212> TYPE: PRT
<213> ORGANISM: Artificial Sequence
<220> FEATURE:
<223> OTHER INFORMATION: Synthetic Construct

<400> SEQUENCE: 91

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Ala Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 92
<211> LENGTH: 223
<212> TYPE: PRT
<213> ORGANISM: Artificial Sequence
<220> FEATURE:
<223> OTHER INFORMATION: Synthetic Construct

<400> SEQUENCE: 92

Val Glu Cys Pro Pro Cys Pro Ala Pro Pro Val Ala Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Ala Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 93
<211> LENGTH: 222
<212> TYPE: PRT
<213> ORGANISM: Artificial Sequence
<220> FEATURE:
<223> OTHER INFORMATION: Synthetic Construct

<400> SEQUENCE: 93

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Ala Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 94
<211> LENGTH: 228
<212> TYPE: PRT
<213> ORGANISM: Artificial Sequence
<220> FEATURE:
<223> OTHER INFORMATION: Synthetic Construct

<400> SEQUENCE: 94

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
            50                  55                  60

Val His Asn Ala Lys Thr Lys Pro Arg Glu Glu Gln Phe Ala Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ser Ser
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225

<210> SEQ ID NO 95
<211> LENGTH: 227
<212> TYPE: PRT
<213> ORGANISM: Artificial Sequence
<220> FEATURE:
<223> OTHER INFORMATION: Synthetic Construct

<400> SEQUENCE: 95

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
            50                  55                  60

Val His Asn Ala Lys Thr Lys Pro Arg Glu Glu Gln Phe Ala Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ser Ser
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

```
Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly
225

<210> SEQ ID NO 96
<211> LENGTH: 346
<212> TYPE: PRT
<213> ORGANISM: Artificial Sequence
<220> FEATURE:
<223> OTHER INFORMATION: Synthetic Construct

<400> SEQUENCE: 96

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300
```

-continued

```
Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 97
<211> LENGTH: 346
<212> TYPE: PRT
<213> ORGANISM: Artificial Sequence
<220> FEATURE:
<223> OTHER INFORMATION: Synthetic Construct

<400> SEQUENCE: 97

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320
```

```
Val Phe Ser Cys Ser Val Met His Glu Ala Leu His Asn His Tyr Thr
            325                 330                 335

Gln Lys Ser Leu Ser Leu Ser Pro Gly Lys
        340                 345

<210> SEQ ID NO 98
<211> LENGTH: 346
<212> TYPE: PRT
<213> ORGANISM: Artificial Sequence
<220> FEATURE:
<223> OTHER INFORMATION: Synthetic Construct

<400> SEQUENCE: 98

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335
```

<210> SEQ ID NO 99
<211> LENGTH: 346
<212> TYPE: PRT
<213> ORGANISM: Artificial Sequence
<220> FEATURE:
<223> OTHER INFORMATION: Synthetic Construct

<400> SEQUENCE: 99

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

<210> SEQ ID NO 100
<211> LENGTH: 346
<212> TYPE: PRT
<213> ORGANISM: Artificial Sequence
<220> FEATURE:
<223> OTHER INFORMATION: Synthetic Construct

<400> SEQUENCE: 100

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 101

<211> LENGTH: 346
<212> TYPE: PRT
<213> ORGANISM: Artificial Sequence
<220> FEATURE:
<223> OTHER INFORMATION: Synthetic Construct

<400> SEQUENCE: 101

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 102
<211> LENGTH: 346
<212> TYPE: PRT
<213> ORGANISM: Artificial Sequence
<220> FEATURE:
<223> OTHER INFORMATION: Synthetic Construct

<400> SEQUENCE: 102

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 103
<211> LENGTH: 346
<212> TYPE: PRT
<213> ORGANISM: Artificial Sequence
<220> FEATURE:
<223> OTHER INFORMATION: Synthetic Construct

<400> SEQUENCE: 103

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Asp Lys Thr His Thr Cys Pro Pro Cys
        115                 120                 125
Pro Ala Pro Glu Ala Ala Gly Ala Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
            180                 185                 190
Glu Gln Tyr Ala Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345
```

<210> SEQ ID NO 104
<211> LENGTH: 346
<212> TYPE: PRT
<213> ORGANISM: Artificial Sequence
<220> FEATURE:
<223> OTHER INFORMATION: Synthetic Construct

<400> SEQUENCE: 104

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 105
<211> LENGTH: 342
<212> TYPE: PRT
<213> ORGANISM: Artificial Sequence
<220> FEATURE:
<223> OTHER INFORMATION: Synthetic Construct

<400> SEQUENCE: 105

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Val Glu Cys Pro Pro Cys Pro Ala Pro
        115                 120                 125
Pro Val Ala Gly Pro Ser Val Phe Leu Phe Pro Pro Lys Pro Lys Asp
    130                 135                 140
Thr Leu Met Ile Ser Arg Thr Pro Glu Val Thr Cys Val Val Val Asp
145                 150                 155                 160
Val Ser His Glu Asp Pro Glu Val Gln Phe Asn Trp Tyr Val Asp Gly
                165                 170                 175
Val Glu Val His Asn Ala Lys Thr Lys Pro Arg Glu Glu Gln Phe Ala
            180                 185                 190
Ser Thr Phe Arg Val Val Ser Val Leu Thr Val Val His Gln Asp Trp
        195                 200                 205
Leu Asn Gly Lys Glu Tyr Lys Cys Lys Val Ser Asn Lys Gly Leu Pro
    210                 215                 220
Ser Ser Ile Glu Lys Thr Ile Ser Lys Thr Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
            260                 265                 270
Ala Val Glu Trp Glu Ser Asn Gly Gln Pro Glu Asn Asn Tyr Lys Thr
        275                 280                 285
Thr Pro Pro Met Leu Asp Ser Asp Gly Ser Phe Phe Leu Tyr Ser Lys
    290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
            340
```

<210> SEQ ID NO 106
<211> LENGTH: 342
<212> TYPE: PRT
<213> ORGANISM: Artificial Sequence
<220> FEATURE:
<223> OTHER INFORMATION: Synthetic Construct

<400> SEQUENCE: 106

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 107
<211> LENGTH: 342
<212> TYPE: PRT
<213> ORGANISM: Artificial Sequence
<220> FEATURE:
<223> OTHER INFORMATION: Synthetic Construct

<400> SEQUENCE: 107

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 108
<211> LENGTH: 342
<212> TYPE: PRT
<213> ORGANISM: Artificial Sequence
<220> FEATURE:
<223> OTHER INFORMATION: Synthetic Construct

<400> SEQUENCE: 108

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Gln Gly Pro Phe Pro Arg Val Thr Thr Val Ser
    50                  55                  60
Asp Leu Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Val Glu Cys Pro Pro Cys Pro Ala Pro
        115                 120                 125
Pro Val Ala Gly Pro Ser Val Phe Leu Phe Pro Pro Lys Pro Lys Asp
    130                 135                 140
Thr Leu Met Ile Ser Arg Thr Pro Glu Val Thr Cys Val Val Val Asp
145                 150                 155                 160
Val Ser His Glu Asp Pro Glu Val Gln Phe Asn Trp Tyr Val Asp Gly
                165                 170                 175
Val Glu Val His Asn Ala Lys Thr Lys Pro Arg Glu Glu Gln Phe Ala
            180                 185                 190
Ser Thr Phe Arg Val Val Ser Val Leu Thr Val Val His Gln Asp Trp
        195                 200                 205
Leu Asn Gly Lys Glu Tyr Lys Cys Lys Val Ser Asn Lys Gly Leu Pro
    210                 215                 220
Ser Ser Ile Glu Lys Thr Ile Ser Lys Thr Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
            260                 265                 270
Ala Val Glu Trp Glu Ser Asn Gly Gln Pro Glu Asn Asn Tyr Lys Thr
        275                 280                 285
Thr Pro Pro Met Leu Asp Ser Asp Gly Ser Phe Phe Leu Tyr Ser Lys
    290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
            340
```

<210> SEQ ID NO 109
<211> LENGTH: 342
<212> TYPE: PRT
<213> ORGANISM: Artificial Sequence
<220> FEATURE:
<223> OTHER INFORMATION: Synthetic Construct

<400> SEQUENCE: 109

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
50                  55                  60
Asp Leu Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Val Glu Cys Pro Pro Cys Pro Ala Pro
        115                 120                 125
Pro Val Ala Gly Pro Ser Val Phe Leu Phe Pro Pro Lys Pro Lys Asp
130                 135                 140
Thr Leu Met Ile Ser Arg Thr Pro Glu Val Thr Cys Val Val Val Asp
145                 150                 155                 160
Val Ser His Glu Asp Pro Glu Val Gln Phe Asn Trp Tyr Val Asp Gly
                165                 170                 175
Val Glu Val His Asn Ala Lys Thr Lys Pro Arg Glu Glu Gln Phe Ala
            180                 185                 190
Ser Thr Phe Arg Val Val Ser Val Leu Thr Val Val His Gln Asp Trp
        195                 200                 205
Leu Asn Gly Lys Glu Tyr Lys Cys Lys Val Ser Asn Lys Gly Leu Pro
210                 215                 220
Ser Ser Ile Glu Lys Thr Ile Ser Lys Thr Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
            260                 265                 270
Ala Val Glu Trp Glu Ser Asn Gly Gln Pro Glu Asn Asn Tyr Lys Thr
        275                 280                 285
Thr Pro Pro Met Leu Asp Ser Asp Gly Ser Phe Phe Leu Tyr Ser Lys
290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
            340
```

<210> SEQ ID NO 110
<211> LENGTH: 342
<212> TYPE: PRT
<213> ORGANISM: Artificial Sequence
<220> FEATURE:
<223> OTHER INFORMATION: Synthetic Construct

<400> SEQUENCE: 110

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
            115                 120                 125

Pro Val Ala Gly Pro Ser Val Phe Leu Phe Pro Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 111
<211> LENGTH: 342
<212> TYPE: PRT
<213> ORGANISM: Artificial Sequence
<220> FEATURE:
<223> OTHER INFORMATION: Synthetic Construct

<400> SEQUENCE: 111

| | | | | | | | | | | | | | | |
|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | | |5| | | | |10| | | | |15| |

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Ala Gly Thr Glu Leu
            100                 105                 110

Ser Val Arg Ala Lys Pro Ser Val Glu Cys Pro Pro Cys Pro Ala Pro
            115                 120                 125

Pro Val Ala Gly Pro Ser Val Phe Leu Phe Pro Pro Lys Pro Lys Asp
            130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
            195                 200                 205

Leu Asn Gly Lys Glu Tyr Lys Cys Lys Val Ser Asn Lys Gly Leu Pro
            210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
            275                 280                 285

Thr Pro Pro Met Leu Asp Ser Asp Gly Ser Phe Phe Leu Tyr Ser Lys
            290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 112
<211> LENGTH: 342
<212> TYPE: PRT
<213> ORGANISM: Artificial Sequence
<220> FEATURE:
<223> OTHER INFORMATION: Synthetic Construct

<400> SEQUENCE: 112

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Val Glu Cys Pro Pro Cys Pro Ala Pro
            115                 120                 125
Pro Val Ala Gly Pro Ser Val Phe Leu Phe Pro Pro Lys Pro Lys Asp
        130                 135                 140
Thr Leu Met Ile Ser Arg Thr Pro Glu Val Thr Cys Val Val Val Asp
145                 150                 155                 160
Val Ser His Glu Asp Pro Glu Val Gln Phe Asn Trp Tyr Val Asp Gly
                165                 170                 175
Val Glu Val His Asn Ala Lys Thr Lys Pro Arg Glu Glu Gln Phe Ala
            180                 185                 190
Ser Thr Phe Arg Val Val Ser Val Leu Thr Val Val His Gln Asp Trp
        195                 200                 205
Leu Asn Gly Lys Glu Tyr Lys Cys Lys Val Ser Asn Lys Gly Leu Pro
    210                 215                 220
Ser Ser Ile Glu Lys Thr Ile Ser Lys Thr Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
            260                 265                 270
Ala Val Glu Trp Glu Ser Asn Gly Gln Pro Glu Asn Asn Tyr Lys Thr
        275                 280                 285
Thr Pro Pro Met Leu Asp Ser Asp Gly Ser Phe Phe Leu Tyr Ser Lys
    290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly Lys
            340
```

<210> SEQ ID NO 113
<211> LENGTH: 342
<212> TYPE: PRT
<213> ORGANISM: Artificial Sequence
<220> FEATURE:
<223> OTHER INFORMATION: Synthetic Construct

<400> SEQUENCE: 113

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Val Glu Cys Pro Pro Cys Pro Ala Pro
        115                 120                 125

Pro Val Ala Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Gln Phe Asn Trp Tyr Val Asp Gly
                165                 170                 175

Val Glu Val His Asn Ala Lys Thr Lys Pro Arg Glu Glu Gln Phe Ala
            180                 185                 190

Ser Thr Phe Arg Val Val Ser Val Leu Thr Val Val His Gln Asp Trp
        195                 200                 205

Leu Asn Gly Lys Glu Tyr Lys Cys Lys Val Ser Asn Lys Gly Leu Pro
    210                 215                 220

Ser Ser Ile Glu Lys Thr Ile Ser Lys Thr Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Met Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 114
<211> LENGTH: 347
<212> TYPE: PRT
<213> ORGANISM: Artificial Sequence
<220> FEATURE:
<223> OTHER INFORMATION: Synthetic Construct

<400> SEQUENCE: 114

| | | | | | | | | | | | | | | |
|---|---|---|---|---|---|---|---|---|---|---|---|---|---|---|
| Glu | Glu | Glu | Leu | Gln | Ile | Ile | Gln | Pro | Asp | Lys | Ser | Val | Leu | Val | Ala |
| 1 | | | | 5 | | | | | 10 | | | | | 15 | |
| Ala | Gly | Glu | Thr | Ala | Thr | Leu | Arg | Cys | Thr | Ile | Thr | Ser | Leu | Phe | Pro |
| | | | 20 | | | | | 25 | | | | | 30 | | |
| Val | Gly | Pro | Ile | Gln | Trp | Phe | Arg | Gly | Ala | Gly | Pro | Gly | Arg | Val | Leu |
| | | 35 | | | | | 40 | | | | | 45 | | | |
| Ile | Tyr | Asn | Gln | Arg | Gln | Gly | Pro | Phe | Pro | Arg | Val | Thr | Thr | Val | Ser |
| 50 | | | | | 55 | | | | | 60 | | | | | |
| Asp | Thr | Thr | Lys | Arg | Asn | Asn | Met | Asp | Phe | Ser | Ile | Arg | Ile | Gly | Asn |
| 65 | | | | | 70 | | | | | 75 | | | | | 80 |
| Ile | Thr | Pro | Ala | Asp | Ala | Gly | Thr | Tyr | Tyr | Cys | Ile | Lys | Phe | Arg | Lys |
| | | | | 85 | | | | | 90 | | | | | 95 | |
| Gly | Ser | Pro | Asp | Asp | Val | Glu | Phe | Lys | Ser | Gly | Ala | Gly | Thr | Glu | Leu |
| | | | 100 | | | | | 105 | | | | | 110 | | |
| Ser | Val | Arg | Ala | Lys | Pro | Ser | Glu | Arg | Lys | Ser | Ser | Val | Glu | Cys | Pro |
| | | | 115 | | | | | 120 | | | | | 125 | | |
| Pro | Cys | Pro | Ala | Pro | Val | Ala | Gly | Pro | Ser | Val | Phe | Leu | Phe | Pro |
| | | 130 | | | | | 135 | | | | | 140 | | | |
| Pro | Lys | Pro | Lys | Asp | Thr | Leu | Met | Ile | Ser | Arg | Thr | Pro | Glu | Val | Thr |
| 145 | | | | | 150 | | | | | 155 | | | | | 160 |
| Cys | Val | Val | Val | Asp | Val | Ser | His | Glu | Asp | Pro | Glu | Val | Gln | Phe | Asn |
| | | | | 165 | | | | | 170 | | | | | 175 | |
| Trp | Tyr | Val | Asp | Gly | Val | Glu | Val | His | Asn | Ala | Lys | Thr | Lys | Pro | Arg |
| | | | 180 | | | | | 185 | | | | | 190 | | |
| Glu | Glu | Gln | Phe | Ala | Ser | Thr | Phe | Arg | Val | Val | Ser | Val | Leu | Thr | Val |
| | | | 195 | | | | | 200 | | | | | 205 | | |
| Val | His | Gln | Asp | Trp | Leu | Asn | Gly | Lys | Glu | Tyr | Lys | Cys | Lys | Val | Ser |
| | | 210 | | | | | 215 | | | | | 220 | | | |
| Asn | Lys | Gly | Leu | Pro | Ser | Ser | Ile | Glu | Lys | Thr | Ile | Ser | Lys | Thr | Lys |
| 225 | | | | | 230 | | | | | 235 | | | | | 240 |
| Gly | Gln | Pro | Arg | Glu | Pro | Gln | Val | Tyr | Thr | Leu | Pro | Pro | Ser | Arg | Glu |
| | | | | 245 | | | | | 250 | | | | | 255 | |
| Glu | Met | Thr | Lys | Asn | Gln | Val | Ser | Leu | Thr | Cys | Leu | Val | Lys | Gly | Phe |
| | | | 260 | | | | | 265 | | | | | 270 | | |
| Tyr | Pro | Ser | Asp | Ile | Ala | Val | Glu | Trp | Glu | Ser | Asn | Gly | Gln | Pro | Glu |
| | | 275 | | | | | 280 | | | | | 285 | | | |
| Asn | Asn | Tyr | Lys | Thr | Thr | Pro | Pro | Met | Leu | Asp | Ser | Asp | Gly | Ser | Phe |
| 290 | | | | | 295 | | | | | 300 | | | | | |
| Phe | Leu | Tyr | Ser | Lys | Leu | Thr | Val | Asp | Lys | Ser | Arg | Trp | Gln | Gln | Gly |
| 305 | | | | 310 | | | | | 315 | | | | | | 320 |
| Asn | Val | Phe | Ser | Cys | Ser | Val | Met | His | Glu | Ala | Leu | His | Asn | His | Tyr |
| | | | | 325 | | | | | 330 | | | | | 335 | |
| Thr | Gln | Lys | Ser | Leu | Ser | Leu | Ser | Pro | Gly | Lys |
| | | | 340 | | | | | 345 | | |

<210> SEQ ID NO 115
<211> LENGTH: 347
<212> TYPE: PRT
<213> ORGANISM: Artificial Sequence
<220> FEATURE:
<223> OTHER INFORMATION: Synthetic Construct

<400> SEQUENCE: 115

| Glu | Glu | Glu | Leu | Gln | Val | Ile | Gln | Pro | Asp | Lys | Ser | Val | Leu | Val | Ala |
|---|---|---|---|---|---|---|---|---|---|---|---|---|---|---|---|
| 1 | | | | 5 | | | | | 10 | | | | | 15 | |

Ala Gly Glu Thr Ala Thr Leu Arg Cys Thr Ala Thr Ser Leu Phe Pro
            20              25              30

Val Gly Pro Ile Gln Trp Phe Arg Gly Ala Gly Pro Gly Arg Glu Leu
          35              40              45

Ile Tyr Asn Gln Arg Gln Gly Pro Phe Pro Arg Val Thr Thr Val Ser
    50                  55              60

Asp Leu Thr Lys Arg Asn Asn Met Asp Phe Ser Ile Arg Ile Gly Asn
65                    70              75              80

Ile Thr Pro Ala Asp Ala Gly Thr Tyr Tyr Cys Val Lys Phe Arg Lys
          85              90              95

Gly Ser Pro Asp Asp Val Glu Phe Lys Ser Gly Ala Gly Thr Glu Leu
          100            105           110

Ser Val Arg Ala Lys Pro Ser Glu Arg Lys Ser Ser Val Glu Cys Pro
        115            120           125

Pro Cys Pro Ala Pro Val Ala Gly Pro Ser Val Phe Leu Phe Pro
130                 135              140

Pro Lys Pro Lys Asp Thr Leu Met Ile Ser Arg Thr Pro Glu Val Thr
145                 150            155           160

Cys Val Val Val Asp Val Ser His Glu Asp Pro Glu Val Gln Phe Asn
            165            170           175

Trp Tyr Val Asp Gly Val Glu Val His Asn Ala Lys Thr Lys Pro Arg
        180            185           190

Glu Glu Gln Phe Ala Ser Thr Phe Arg Val Val Ser Val Leu Thr Val
        195            200           205

Val His Gln Asp Trp Leu Asn Gly Lys Glu Tyr Lys Cys Lys Val Ser
    210                215              220

Asn Lys Gly Leu Pro Ser Ser Ile Glu Lys Thr Ile Ser Lys Thr Lys
225                    230              235           240

Gly Gln Pro Arg Glu Pro Gln Val Tyr Thr Leu Pro Pro Ser Arg Glu
          245              250              255

Glu Met Thr Lys Asn Gln Val Ser Leu Thr Cys Leu Val Lys Gly Phe
        260            265           270

Tyr Pro Ser Asp Ile Ala Val Glu Trp Glu Ser Asn Gly Gln Pro Glu
    275                280              285

Asn Asn Tyr Lys Thr Thr Pro Pro Met Leu Asp Ser Asp Gly Ser Phe
    290                295              300

Phe Leu Tyr Ser Lys Leu Thr Val Asp Lys Ser Arg Trp Gln Gln Gly
305                    310            315           320

Asn Val Phe Ser Cys Ser Val Met His Glu Ala Leu His Asn His Tyr
          325              330           335

Thr Gln Lys Ser Leu Ser Leu Ser Pro Gly Lys
        340            345

<210> SEQ ID NO 116
<211> LENGTH: 347
<212> TYPE: PRT
<213> ORGANISM: Artificial Sequence
<220> FEATURE:
<223> OTHER INFORMATION: Synthetic Construct

<400> SEQUENCE: 116

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Ser Ser Val Glu Cys Pro
        115                 120                 125
Pro Cys Pro Ala Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 117
<211> LENGTH: 347
<212> TYPE: PRT
<213> ORGANISM: Artificial Sequence
<220> FEATURE:
<223> OTHER INFORMATION: Synthetic Construct

<400> SEQUENCE: 117

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 118
<211> LENGTH: 347
<212> TYPE: PRT
<213> ORGANISM: Artificial Sequence
<220> FEATURE:
<223> OTHER INFORMATION: Synthetic Construct

<400> SEQUENCE: 118

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345
```

<210> SEQ ID NO 119
<211> LENGTH: 347
<212> TYPE: PRT
<213> ORGANISM: Artificial Sequence
<220> FEATURE:
<223> OTHER INFORMATION: Synthetic Construct

<400> SEQUENCE: 119

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65              70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
            115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
            195                 200                 205

Val His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 120
<211> LENGTH: 347
<212> TYPE: PRT
<213> ORGANISM: Artificial Sequence
<220> FEATURE:
<223> OTHER INFORMATION: Synthetic Construct

<400> SEQUENCE: 120

| | | | | | | | | | | | | | | |
|---|---|---|---|---|---|---|---|---|---|---|---|---|---|---|
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 121
<211> LENGTH: 347
<212> TYPE: PRT
<213> ORGANISM: Artificial Sequence
<220> FEATURE:
<223> OTHER INFORMATION: Synthetic Construct

<400> SEQUENCE: 121

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Ser Ser Val Glu Cys Pro
        115                 120                 125

Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 122
<211> LENGTH: 347
<212> TYPE: PRT
<213> ORGANISM: Artificial Sequence
<220> FEATURE:
<223> OTHER INFORMATION: Synthetic Construct

<400> SEQUENCE: 122

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Ser Ser Val Glu Cys Pro
        115                 120                 125
Pro Cys Pro Ala Pro Val Ala Gly Pro Ser Val Phe Leu Phe Pro
130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Ala Ser Thr Phe Arg Val Val Ser Val Leu Thr Val
        195                 200                 205
Val His Gln Asp Trp Leu Asn Gly Lys Glu Tyr Lys Cys Lys Val Ser
210                 215                 220
Asn Lys Gly Leu Pro Ser Ser Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 123
<211> LENGTH: 346
<212> TYPE: PRT
<213> ORGANISM: Artificial Sequence
<220> FEATURE:
<223> OTHER INFORMATION: Synthetic Construct

<400> SEQUENCE: 123

| | | | | | | | | | | | | | | |
|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | | |5| | | | |10| | | | |15| |
|Ala|Gly|Glu|Thr|Ala|Thr|Leu|Arg|Cys|Thr|Ile|Thr|Ser|Leu|Phe|Pro|
| | | |20| | | | |25| | | | |30| | |
|Val|Gly|Pro|Ile|Gln|Trp|Phe|Arg|Gly|Ala|Gly|Pro|Gly|Arg|Val|Leu|
| | |35| | | | |40| | | | |45| | | |
|Ile|Tyr|Asn|Gln|Arg|Gln|Gly|Pro|Phe|Pro|Arg|Val|Thr|Thr|Val|Ser|
| |50| | | | |55| | | | |60| | | | |
|Asp|Thr|Thr|Lys|Arg|Asn|Asn|Met|Asp|Phe|Ser|Ile|Arg|Ile|Gly|Asn|
|65| | | | |70| | | | |75| | | | |80|
|Ile|Thr|Pro|Ala|Asp|Ala|Gly|Thr|Tyr|Tyr|Cys|Ile|Lys|Phe|Arg|Lys|
| | | | |85| | | | |90| | | | |95| |
|Gly|Ser|Pro|Asp|Asp|Val|Glu|Phe|Lys|Ser|Gly|Ala|Gly|Thr|Glu|Leu|
| | | |100| | | | |105| | | | |110| | |
|Ser|Val|Arg|Ala|Lys|Pro|Ser|Asp|Lys|Thr|His|Thr|Cys|Pro|Pro|Cys|
| | |115| | | | |120| | | | |125| | | |
|Pro|Ala|Pro|Glu|Leu|Leu|Gly|Gly|Pro|Ser|Val|Phe|Leu|Phe|Pro|Pro|
| |130| | | | |135| | | | |140| | | | |
|Lys|Pro|Lys|Asp|Thr|Leu|Met|Ile|Ser|Arg|Thr|Pro|Glu|Val|Thr|Cys|
|145| | | | |150| | | | |155| | | | |160|
|Val|Val|Val|Asp|Val|Ser|His|Glu|Asp|Pro|Glu|Val|Lys|Phe|Asn|Trp|
| | | | |165| | | | |170| | | | |175| |
|Tyr|Val|Asp|Gly|Val|Glu|Val|His|Asn|Ala|Lys|Thr|Lys|Pro|Arg|Glu|
| | | |180| | | | |185| | | | |190| | |
|Glu|Gln|Tyr|Asn|Ser|Thr|Tyr|Arg|Val|Val|Ser|Val|Leu|Thr|Val|Leu|
| | |195| | | | |200| | | | |205| | | |
|His|Gln|Asp|Trp|Leu|Asn|Gly|Lys|Glu|Tyr|Lys|Cys|Lys|Val|Ser|Asn|
| |210| | | | |215| | | | |220| | | | |
|Lys|Ala|Leu|Pro|Ala|Pro|Ile|Glu|Lys|Thr|Ile|Ser|Lys|Ala|Lys|Gly|
|225| | | | |230| | | | |235| | | | |240|
|Gln|Pro|Arg|Glu|Pro|Gln|Val|Tyr|Thr|Leu|Pro|Pro|Ser|Arg|Glu|Glu|
| | | | |245| | | | |250| | | | |255| |
|Met|Thr|Lys|Asn|Gln|Val|Ser|Leu|Thr|Cys|Leu|Val|Lys|Gly|Phe|Tyr|
| | | |260| | | | |265| | | | |270| | |
|Pro|Ser|Asp|Ile|Ala|Val|Glu|Trp|Glu|Ser|Asn|Gly|Gln|Pro|Glu|Asn|
| | |275| | | | |280| | | | |285| | | |
|Asn|Tyr|Lys|Thr|Thr|Pro|Pro|Val|Leu|Asp|Ser|Asp|Gly|Ser|Phe|Phe|
| |290| | | | |295| | | | |300| | | | |
|Leu|Tyr|Ser|Lys|Leu|Thr|Val|Asp|Lys|Ser|Arg|Trp|Gln|Gln|Gly|Asn|
|305| | | | |310| | | | |315| | | | |320|
|Val|Phe|Ser|Cys|Ser|Val|Met|His|Glu|Ala|Leu|His|Asn|His|Tyr|Thr|
| | | | |325| | | | |330| | | | |335| |
|Gln|Lys|Ser|Leu|Ser|Leu|Ser|Pro|Gly|Lys| | | | | | |
| | | |340| | | | |345| | | | | | | |

<210> SEQ ID NO 124
<211> LENGTH: 346
<212> TYPE: PRT
<213> ORGANISM: Artificial Sequence
<220> FEATURE:
<223> OTHER INFORMATION: Synthetic Construct

<400> SEQUENCE: 124

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 125
<211> LENGTH: 346
<212> TYPE: PRT
<213> ORGANISM: Artificial Sequence
<220> FEATURE:
<223> OTHER INFORMATION: Synthetic Construct

<400> SEQUENCE: 125

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 126
<211> LENGTH: 347
<212> TYPE: PRT
<213> ORGANISM: Artificial Sequence
<220> FEATURE:
<223> OTHER INFORMATION: Synthetic Construct

<400> SEQUENCE: 126

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Glu Arg Lys Cys Cys Val Glu Cys Pro
        115                 120                 125
Pro Cys Pro Ala Pro Val Ala Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser His Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Asn Ser Thr Phe Arg Val Val Ser Val Leu Thr Val
        195                 200                 205
Val His Gln Asp Trp Leu Asn Gly Lys Glu Tyr Lys Cys Lys Val Ser
    210                 215                 220
Asn Lys Gly Leu Pro Ala Pro Ile Glu Lys Thr Ile Ser Lys Thr Lys
225                 230                 235                 240
Gly Gln Pro Arg Glu Pro Gln Val Tyr Thr Leu Pro Pro Ser Arg Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Met Leu Asp Ser Asp Gly Ser Phe
    290                 295                 300
Phe Leu Tyr Ser Lys Leu Thr Val Asp Lys Ser Arg Trp Gln Gln Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Pro Gly Lys
            340                 345
```

<210> SEQ ID NO 127
<211> LENGTH: 347
<212> TYPE: PRT
<213> ORGANISM: Artificial Sequence
<220> FEATURE:
<223> OTHER INFORMATION: Synthetic Construct

<400> SEQUENCE: 127

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Cys Cys Val Glu Cys Pro
        115                 120                 125

Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345
```

<210> SEQ ID NO 128
<211> LENGTH: 347
<212> TYPE: PRT
<213> ORGANISM: Artificial Sequence
<220> FEATURE:
<223> OTHER INFORMATION: Synthetic Construct

<400> SEQUENCE: 128

| | | | | | | | | | | | | | | |
|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | |  |5| | | | |10| | | | |15| |
|Ala|Gly|Glu|Thr|Ala|Thr|Leu|Arg|Cys|Thr|Ile|Thr|Ser|Leu|Phe|Pro|
| | | |20| | | | |25| | | | |30| | |
|Val|Gly|Pro|Ile|Gln|Trp|Phe|Arg|Gly|Ala|Gly|Pro|Gly|Arg|Val|Leu|
| | | |35| | | | |40| | | | |45| | |
|Ile|Tyr|Asn|Gln|Arg|Gln|Gly|Pro|Phe|Pro|Arg|Val|Thr|Thr|Val|Ser|
| |50| | | | |55| | | | |60| | | | |
|Asp|Thr|Thr|Lys|Arg|Asn|Asn|Met|Asp|Phe|Ser|Ile|Arg|Ile|Gly|Asn|
|65| | | | |70| | | | |75| | | | |80|
|Ile|Thr|Pro|Ala|Asp|Ala|Gly|Thr|Tyr|Tyr|Cys|Ile|Lys|Phe|Arg|Lys|
| | | | |85| | | | |90| | | | |95| |
|Gly|Ser|Pro|Asp|Asp|Val|Glu|Phe|Lys|Ser|Gly|Ala|Gly|Thr|Glu|Leu|
| | | |100| | | | |105| | | | |110| | |
|Ser|Val|Arg|Ala|Lys|Pro|Ser|Glu|Arg|Lys|Cys|Cys|Val|Glu|Cys|Pro|
| | | |115| | | | |120| | | | |125| | |
|Pro|Cys|Pro|Ala|Pro|Pro|Val|Ala|Gly|Pro|Ser|Val|Phe|Leu|Phe|Pro|
| | | |130| | | | |135| | | | |140| | |
|Pro|Lys|Pro|Lys|Asp|Thr|Leu|Met|Ile|Ser|Arg|Thr|Pro|Glu|Val|Thr|
|145| | | | |150| | | | |155| | | | |160|
|Cys|Val|Val|Val|Asp|Val|Ser|His|Glu|Asp|Pro|Glu|Val|Gln|Phe|Asn|
| | | | |165| | | | |170| | | | |175| |
|Trp|Tyr|Val|Asp|Gly|Val|Glu|Val|His|Asn|Ala|Lys|Thr|Lys|Pro|Arg|
| | | |180| | | | |185| | | | |190| | |
|Glu|Glu|Gln|Phe|Ala|Ser|Thr|Phe|Arg|Val|Val|Ser|Val|Leu|Thr|Val|
| | | |195| | | | |200| | | | |205| | |
|Val|His|Gln|Asp|Trp|Leu|Asn|Gly|Lys|Glu|Tyr|Lys|Cys|Lys|Val|Ser|
| | | |210| | | | |215| | | | |220| | |
|Asn|Lys|Gly|Leu|Pro|Ala|Pro|Ile|Glu|Lys|Thr|Ile|Ser|Lys|Thr|Lys|
|225| | | | |230| | | | |235| | | | |240|
|Gly|Gln|Pro|Arg|Glu|Pro|Gln|Val|Tyr|Thr|Leu|Pro|Pro|Ser|Arg|Glu|
| | | | |245| | | | |250| | | | |255| |
|Glu|Met|Thr|Lys|Asn|Gln|Val|Ser|Leu|Thr|Cys|Leu|Val|Lys|Gly|Phe|
| | | |260| | | | |265| | | | |270| | |
|Tyr|Pro|Ser|Asp|Ile|Ala|Val|Glu|Trp|Glu|Ser|Asn|Gly|Gln|Pro|Glu|
| | | |275| | | | |280| | | | |285| | |
|Asn|Asn|Tyr|Lys|Thr|Thr|Pro|Pro|Met|Leu|Asp|Ser|Asp|Gly|Ser|Phe|
| |290| | | | |295| | | | |300| | | | |
|Phe|Leu|Tyr|Ser|Lys|Leu|Thr|Val|Asp|Lys|Ser|Arg|Trp|Gln|Gln|Gly|
|305| | | | |310| | | | |315| | | | |320|
|Asn|Val|Phe|Ser|Cys|Ser|Val|Met|His|Glu|Ala|Leu|His|Asn|His|Tyr|
| | | |325| | | | |330| | | | |335| | |
|Thr|Gln|Lys|Ser|Leu|Ser|Leu|Ser|Pro|Gly|Lys| | | | | |
| | | |340| | | | |345| | | | | | | |

<210> SEQ ID NO 129
<211> LENGTH: 347
<212> TYPE: PRT
<213> ORGANISM: Artificial Sequence
<220> FEATURE:
<223> OTHER INFORMATION: Synthetic Construct

<400> SEQUENCE: 129

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Arg Lys Cys Cys Val Glu Cys Pro
        115                 120                 125

Pro Cys Pro Ala Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Ala Ser Thr Phe Arg Val Val Ser Val Leu Thr Val
        195                 200                 205

Val His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Met Leu Asp Ser Asp Gly Ser Phe
    290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 130
<211> LENGTH: 347
<212> TYPE: PRT
<213> ORGANISM: Artificial Sequence
<220> FEATURE:
<223> OTHER INFORMATION: Synthetic Construct

<400> SEQUENCE: 130

```
Glu Glu Glu Leu Gln Val Ile Gln Pro Asp Lys Ser Val Ser Val Ala
1               5                   10                  15
Ala Gly Glu Ser Ala Ile Leu His Cys Thr Val Thr Ser Leu Ile Pro
            20                  25                  30
Val Gly Pro Ile Gln Trp Phe Arg Gly Ala Gly Pro Ala Arg Glu Leu
        35                  40                  45
Ile Tyr Asn Gln Lys Glu Gly His Phe Pro Arg Val Thr Thr Val Ser
    50                  55                  60
Glu Ser Thr Lys Arg Glu Asn Met Asp Phe Ser Ile Ser Ile Ser Asn
65                  70                  75                  80
Ile Thr Pro Ala Asp Ala Gly Thr Tyr Tyr Cys Val Lys Phe Arg Lys
                85                  90                  95
Gly Ser Pro Asp Thr Glu Phe Lys Ser Gly Ala Gly Thr Glu Leu Ser
            100                 105                 110
Val Arg Ala Lys Pro Ser Glu Ser Lys Tyr Gly Pro Pro Cys Pro Ser
        115                 120                 125
Cys Pro Ala Pro Glu Phe Leu Gly Gly Pro Ser Val Phe Leu Phe Pro
    130                 135                 140
Pro Lys Pro Lys Asp Thr Leu Met Ile Ser Arg Thr Pro Glu Val Thr
145                 150                 155                 160
Cys Val Val Val Asp Val Ser Gln Glu Asp Pro Glu Val Gln Phe Asn
                165                 170                 175
Trp Tyr Val Asp Gly Val Glu Val His Asn Ala Lys Thr Lys Pro Arg
            180                 185                 190
Glu Glu Gln Phe Asn Ser Thr Tyr Arg Val Val Ser Val Leu Thr Val
        195                 200                 205
Leu His Gln Asp Trp Leu Asn Gly Lys Glu Tyr Lys Cys Lys Val Ser
    210                 215                 220
Asn Lys Gly Leu Pro Ser Ser Ile Glu Lys Thr Ile Ser Lys Ala Lys
225                 230                 235                 240
Gly Gln Pro Arg Glu Pro Gln Val Tyr Thr Leu Pro Pro Ser Gln Glu
                245                 250                 255
Glu Met Thr Lys Asn Gln Val Ser Leu Thr Cys Leu Val Lys Gly Phe
            260                 265                 270
Tyr Pro Ser Asp Ile Ala Val Glu Trp Glu Ser Asn Gly Gln Pro Glu
        275                 280                 285
Asn Asn Tyr Lys Thr Thr Pro Pro Val Leu Asp Ser Asp Gly Ser Phe
    290                 295                 300
Phe Leu Tyr Ser Arg Leu Thr Val Asp Lys Ser Arg Trp Gln Glu Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Leu Gly Lys
            340                 345
```

<210> SEQ ID NO 131
<211> LENGTH: 348
<212> TYPE: PRT
<213> ORGANISM: Artificial Sequence
<220> FEATURE:
<223> OTHER INFORMATION: Synthetic Construct

<400> SEQUENCE: 131

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345
```

<210> SEQ ID NO 132
<211> LENGTH: 348
<212> TYPE: PRT
<213> ORGANISM: Artificial Sequence
<220> FEATURE:
<223> OTHER INFORMATION: Synthetic Construct

<400> SEQUENCE: 132

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Glu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 133
<211> LENGTH: 347
<212> TYPE: PRT
<213> ORGANISM: Artificial Sequence
<220> FEATURE:
<223> OTHER INFORMATION: Synthetic Construct

<400> SEQUENCE: 133

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Pro Val Ala Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 134
<211> LENGTH: 346
<212> TYPE: PRT
<213> ORGANISM: Artificial Sequence
<220> FEATURE:
<223> OTHER INFORMATION: Synthetic Construct

<400> SEQUENCE: 134

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Ala Ala Ala Pro Pro Cys Pro Pro Cys
        115                 120                 125
Pro Ala Pro Glu Phe Leu Gly Gly Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser Gln Glu Asp Pro Glu Val Gln Phe Asn Trp
                165                 170                 175
Tyr Val Asp Gly Val Glu Val His Asn Ala Lys Thr Lys Pro Arg Glu
            180                 185                 190
Glu Gln Phe Asn Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Gly Leu Pro Ser Ser Ile Glu Lys Thr Ile Ser Lys Ala Lys Gly
225                 230                 235                 240
Gln Pro Arg Glu Pro Gln Val Tyr Thr Leu Pro Pro Ser Gln Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Arg Leu Thr Val Asp Lys Ser Arg Trp Gln Glu Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345
```

<210> SEQ ID NO 135
<211> LENGTH: 345
<212> TYPE: PRT
<213> ORGANISM: Artificial Sequence
<220> FEATURE:
<223> OTHER INFORMATION: Synthetic Construct

<400> SEQUENCE: 135

```
Glu Glu Glu Leu Gln Val Ile Gln Pro Asp Lys Ser Val Leu Val Ala
1               5                   10                  15
Ala Gly Glu Thr Ala Thr Leu Arg Cys Thr Ala Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Leu Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Asp Lys Thr His Thr Cys Pro Pro Cys
        115                 120                 125
Pro Ala Pro Glu Ala Ala Gly Ala Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
            180                 185                 190
Glu Gln Tyr Ala Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly
            340                 345
```

<210> SEQ ID NO 136
<211> LENGTH: 345
<212> TYPE: PRT
<213> ORGANISM: Artificial Sequence
<220> FEATURE:
<223> OTHER INFORMATION: Synthetic Construct

<400> SEQUENCE: 136

```
Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Glu Leu
        35                  40                  45
Ile Tyr Asn Gln Arg Glu Gly Pro Phe Pro Arg Val Thr Thr Val Ser
    50                  55                  60
Asp Thr Thr Lys Arg Asn Asn Met Asp Phe Ser Ile Arg Ile Gly Ala
65                  70                  75                  80
Ile Thr Pro Ala Asp Ala Gly Thr Tyr Tyr Cys Val Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Asp Lys Thr His Thr Cys Pro Pro Cys
        115                 120                 125
Pro Ala Pro Glu Ala Ala Gly Ala Pro Ser Val Phe Leu Phe Pro Pro
    130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
            180                 185                 190
Glu Gln Tyr Ala Ser Thr Tyr Arg Val Val Ser Val Leu Thr Val Leu
        195                 200                 205
His Gln Asp Trp Leu Asn Gly Lys Glu Tyr Lys Cys Lys Val Ser Asn
    210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
        275                 280                 285
Asn Tyr Lys Thr Thr Pro Pro Val Leu Asp Ser Asp Gly Ser Phe Phe
    290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly
            340                 345
```

<210> SEQ ID NO 137
<211> LENGTH: 345
<212> TYPE: PRT
<213> ORGANISM: Artificial Sequence
<220> FEATURE:
<223> OTHER INFORMATION: Synthetic Construct

<400> SEQUENCE: 137

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly
            340                 345

<210> SEQ ID NO 138
<211> LENGTH: 346
<212> TYPE: PRT
<213> ORGANISM: Artificial Sequence
<220> FEATURE:
<223> OTHER INFORMATION: Synthetic Construct

<400> SEQUENCE: 138

| | | | | | | | | | | | | | | |
|---|---|---|---|---|---|---|---|---|---|---|---|---|---|---|
|Glu|Glu|Glu|Leu|Gln|Ile|Ile|Gln|Pro|Asp|Lys|Ser|Val|Leu|Val|Ala|
|1| | | |5| | | | |10| | | | |15| |

Ala Gly Glu Thr Ala Thr Leu Arg Cys Thr Ile Thr Ser Leu Phe Pro
        20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly Lys
            340                 345

<210> SEQ ID NO 139
<211> LENGTH: 227
<212> TYPE: PRT
<213> ORGANISM: Artificial Sequence
<220> FEATURE:
<223> OTHER INFORMATION: Synthetic Construct

<400> SEQUENCE: 139

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 140
<211> LENGTH: 346
<212> TYPE: PRT
<213> ORGANISM: Artificial Sequence
<220> FEATURE:
<223> OTHER INFORMATION: Synthetic Construct

<400> SEQUENCE: 140

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

```
Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 141
<211> LENGTH: 227
<212> TYPE: PRT
<213> ORGANISM: Artificial Sequence
<220> FEATURE:
<223> OTHER INFORMATION: Synthetic Construct

<400> SEQUENCE: 141

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125
```

```
Tyr Thr Leu Pro Pro Ser Arg Glu Glu Met Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 142
<211> LENGTH: 346
<212> TYPE: PRT
<213> ORGANISM: Artificial Sequence
<220> FEATURE:
<223> OTHER INFORMATION: Synthetic Construct

<400> SEQUENCE: 142

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255
```

```
Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 143
<211> LENGTH: 346
<212> TYPE: PRT
<213> ORGANISM: Artificial Sequence
<220> FEATURE:
<223> OTHER INFORMATION: Synthetic Construct

<400> SEQUENCE: 143

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270
```

```
Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 144
<211> LENGTH: 449
<212> TYPE: PRT
<213> ORGANISM: Artificial Sequence
<220> FEATURE:
<223> OTHER INFORMATION: Synthetic Construct

<400> SEQUENCE: 144

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Arg Lys
    210                 215                 220

Thr His Thr Cys Pro Arg Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 145
<211> LENGTH: 346
<212> TYPE: PRT
<213> ORGANISM: Artificial Sequence
<220> FEATURE:
<223> OTHER INFORMATION: Synthetic Construct

<400> SEQUENCE: 145

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Lys Thr His Thr Cys Pro Glu Cys
        115                 120                 125

Pro Ala Pro Glu Ala Ala Gly Ala Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190
```

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
            245                 250                 255

Met Thr Lys Asn Gln Val Ser Leu Thr Cys Glu Val Lys Gly Phe Tyr
        260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly Lys
            340                 345

<210> SEQ ID NO 146
<211> LENGTH: 346
<212> TYPE: PRT
<213> ORGANISM: Artificial Sequence
<220> FEATURE:
<223> OTHER INFORMATION: Synthetic Construct

<400> SEQUENCE: 146

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
            165                 170                 175

Tyr Val Asp Gly Val Glu Val His Asn Ala Lys Thr Lys Pro Arg Glu
        180                 185                 190

Glu Gln Tyr Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 147
<211> LENGTH: 227
<212> TYPE: PRT
<213> ORGANISM: Artificial Sequence
<220> FEATURE:
<223> OTHER INFORMATION: Synthetic Construct

<400> SEQUENCE: 147

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 148
<211> LENGTH: 346
<212> TYPE: PRT
<213> ORGANISM: Artificial Sequence
<220> FEATURE:
<223> OTHER INFORMATION: Synthetic Construct

<400> SEQUENCE: 148

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Ser Cys Ala Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Val Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

```
<210> SEQ ID NO 149
<211> LENGTH: 227
<212> TYPE: PRT
<213> ORGANISM: Artificial Sequence
<220> FEATURE:
<223> OTHER INFORMATION: Synthetic Construct

<400> SEQUENCE: 149
```

Asp Lys Thr His Thr Cys Pro Pro Cys Pro Ala Pro Glu Ala Ala Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

```
<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153
```

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161
<211> LENGTH: 226
<212> TYPE: PRT
<213> ORGANISM: Homo sapiens

<400> SEQUENCE: 161

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
    115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly
225

<210> SEQ ID NO 162
<211> LENGTH: 227
<212> TYPE: PRT
<213> ORGANISM: Homo sapiens

<400> SEQUENCE: 162

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205
```

Met His Glu Ala Leu His Asn His Tyr Thr Gln Lys Ser Leu Ser Leu
    210                 215                 220

Ser Pro Gly
225

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct

<400> SEQUENCE: 163

Gly Gly Gly Gly Ser
1               5

<210> SEQ ID NO 164
<211> LENGTH: 4
<212> TYPE: PRT
<213> ORGANISM: Artificial Sequence
<220> FEATURE:
<223> OTHER INFORMATION: Synthetic Construct

<400> SEQUENCE: 164

Gly Gly Ser Gly
1

<210> SEQ ID NO 165
<211> LENGTH: 4
<212> TYPE: PRT
<213> ORGANISM: Artificial Sequence
<220> FEATURE:
<223> OTHER INFORMATION: Synthetic Construct

<400> SEQUENCE: 165

Ser Gly Gly Gly
1

<210> SEQ ID NO 166
<211> LENGTH: 4
<212> TYPE: PRT
<213> ORGANISM: Artificial Sequence
<220> FEATURE:
<223> OTHER INFORMATION: Synthetic Construct

<400> SEQUENCE: 166

Gly Ser Gly Ser
1

<210> SEQ ID NO 167
<211> LENGTH: 6
<212> TYPE: PRT
<213> ORGANISM: Artificial Sequence
<220> FEATURE:
<223> OTHER INFORMATION: Synthetic Construct

<400> SEQUENCE: 167

Gly Ser Gly Ser Gly Ser
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Gly Ser Gly Ser Gly Ser Gly Ser
1               5

<210> SEQ ID NO 169
<211> LENGTH: 10
<212> TYPE: PRT
<213> ORGANISM: Artificial Sequence
<220> FEATURE:
<223> OTHER INFORMATION: Synthetic Construct

<400> SEQUENCE: 169

Gly Ser Gly Ser Gly Ser Gly Ser Gly Ser
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Synthetic Construct

<400> SEQUENCE: 170

Gly Ser Gly Ser Gly Ser Gly Ser Gly Ser Gly Ser
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Synthetic Construct

<400> SEQUENCE: 171

Gly Gly Ser Gly Gly Ser
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Gly Gly Ser Gly Gly Ser Gly Gly Ser
1               5

<210> SEQ ID NO 173
<211> LENGTH: 12
<212> TYPE: PRT
<213> ORGANISM: Artificial Sequence
<220> FEATURE:
<223> OTHER INFORMATION: Synthetic Construct

<400> SEQUENCE: 173

Gly Gly Ser Gly Gly Ser Gly Gly Ser Gly Gly Ser
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 174

Gly Gly Ser Gly Gly Gly Ser Gly
1               5

<210> SEQ ID NO 175
<211> LENGTH: 12
<212> TYPE: PRT
<213> ORGANISM: Artificial Sequence
<220> FEATURE:
<223> OTHER INFORMATION: Synthetic Construct

<400> SEQUENCE: 175

Gly Gly Ser Gly Gly Gly Ser Gly Gly Gly Ser Gly
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Synthetic Construct

<400> SEQUENCE: 176

Gly Gly Gly Gly Ser Gly Gly Gly Gly Ser Gly Gly Gly Gly Ser
1               5                   10                  15

<210> SEQ ID NO 177
<211> LENGTH: 3
<212> TYPE: PRT
<213> ORGANISM: Artificial Sequence
<220> FEATURE:
<223> OTHER INFORMATION: Synthetic Construct

<400> SEQUENCE: 177

Ala Ala Ser
1

<210> SEQ ID NO 178
<211> LENGTH: 4
<212> TYPE: PRT
<213> ORGANISM: Artificial Sequence
<220> FEATURE:
<223> OTHER INFORMATION: Synthetic Construct

<400> SEQUENCE: 178

Ala Ala Ala Leu
1

<210> SEQ ID NO 179
<211> LENGTH: 4
<212> TYPE: PRT
<213> ORGANISM: Artificial Sequence
<220> FEATURE:
<223> OTHER INFORMATION: Synthetic Construct

<400> SEQUENCE: 179

Ala Ala Ala Lys
1

<210> SEQ ID NO 180
<211> LENGTH: 4
<212> TYPE: PRT
<213> ORGANISM: Artificial Sequence
<220> FEATURE:
<223> OTHER INFORMATION: Synthetic Construct
```

<400> SEQUENCE: 180

Ala Ala Ala Arg
1

<210> SEQ ID NO 181
<211> LENGTH: 14
<212> TYPE: PRT
<213> ORGANISM: Artificial Sequence
<220> FEATURE:
<223> OTHER INFORMATION: Synthetic Construct

<400> SEQUENCE: 181

Glu Gly Lys Ser Ser Gly Ser Gly Ser Glu Ser Lys Ser Thr
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Synthetic Construct

<400> SEQUENCE: 182

Gly Ser Ala Gly Ser Ala Ala Gly Ser Gly Glu Phe
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Construct

<400> SEQUENCE: 183

Ala Glu Ala Ala Ala Lys Glu Ala Ala Ala Lys Ala
1               5                   10

<210> SEQ ID NO 184
<211> LENGTH: 18
<212> TYPE: PRT
<213> ORGANISM: Artificial Sequence
<220> FEATURE:
<223> OTHER INFORMATION: Synthetic Construct

<400> SEQUENCE: 184

Lys Glu Ser Gly Ser Val Ser Ser Glu Gln Leu Ala Gln Phe Arg Ser
1               5                   10                  15

Leu Asp

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Gly Gly Gly Gly Ala Gly Gly Gly Gly
1               5

<210> SEQ ID NO 186
<211> LENGTH: 10
<212> TYPE: PRT
<213> ORGANISM: Artificial Sequence
<220> FEATURE:

```
<223> OTHER INFORMATION: Synthetic Construct

<400> SEQUENCE: 186

Gly Glu Asn Leu Tyr Phe Gln Ser Gly Gly
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Ser Ala Cys Tyr Cys Glu Leu Ser
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic Construct

<400> SEQUENCE: 188

Arg Ser Ile Ala Thr
1               5

<210> SEQ ID NO 189
<211> LENGTH: 17
<212> TYPE: PRT
<213> ORGANISM: Artificial Sequence
<220> FEATURE:
<223> OTHER INFORMATION: Synthetic Construct

<400> SEQUENCE: 189

Arg Pro Ala Cys Lys Ile Pro Asn Asp Leu Lys Gln Lys Val Met Asn
1               5                   10                  15

His

<210> SEQ ID NO 190
<211> LENGTH: 36
<212> TYPE: PRT
<213> ORGANISM: Artificial Sequence
<220> FEATURE:
<223> OTHER INFORMATION: Synthetic Construct

<400> SEQUENCE: 190

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35

<210> SEQ ID NO 191
<211> LENGTH: 17
<212> TYPE: PRT
<213> ORGANISM: Artificial Sequence
<220> FEATURE:
<223> OTHER INFORMATION: Synthetic Construct
```

-continued

<400> SEQUENCE: 191

Ala Ala Ala Asn Ser Ser Ile Asp Leu Ile Ser Val Pro Val Asp Ser
1               5                   10                  15

Arg

<210> SEQ ID NO 192
<211> LENGTH: 36
<212> TYPE: PRT
<213> ORGANISM: Artificial Sequence
<220> FEATURE:
<223> OTHER INFORMATION: Synthetic Construct

<400> SEQUENCE: 192

Gly Gly Ser Gly Gly Gly Ser Glu Gly Gly Gly Ser Glu Gly Gly Gly
1               5                   10                  15

Ser Glu Gly Gly Gly Ser Glu Gly Gly Gly Ser Glu Gly Gly Gly Ser
                20                  25                  30

Gly Gly Gly Ser
        35

<210> SEQ ID NO 193
<211> LENGTH: 5
<212> TYPE: PRT
<213> ORGANISM: Artificial Sequence
<220> FEATURE:
<223> OTHER INFORMATION: Synthetic Construct

<400> SEQUENCE: 193

Glu Ala Ala Ala Lys
1               5

<210> SEQ ID NO 194
<211> LENGTH: 5
<212> TYPE: PRT
<213> ORGANISM: Artificial Sequence
<220> FEATURE:
<223> OTHER INFORMATION: Synthetic Construct

<400> SEQUENCE: 194

Pro Ala Pro Ala Pro
1               5

<210> SEQ ID NO 195
<211> LENGTH: 119
<212> TYPE: PRT
<213> ORGANISM: Artificial Sequence
<220> FEATURE:
<223> OTHER INFORMATION: Synthetic Construct

<400> SEQUENCE: 195

Glu Glu Glu Leu Gln Ile Ile Gln Pro Asp Lys Ser Val Leu Val Ala
1               5                   10                  15

Ala Gly Glu Thr Ala Thr Leu Arg Cys Thr Met Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
        50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 196
<211> LENGTH: 119
<212> TYPE: PRT
<213> ORGANISM: Artificial Sequence
<220> FEATURE:
<223> OTHER INFORMATION: Synthetic Construct

<400> SEQUENCE: 196

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Lys Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 197
<211> LENGTH: 119
<212> TYPE: PRT
<213> ORGANISM: Artificial Sequence
<220> FEATURE:
<223> OTHER INFORMATION: Synthetic Construct

<400> SEQUENCE: 197

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
            115

-continued

```
<210> SEQ ID NO 198
<211> LENGTH: 119
<212> TYPE: PRT
<213> ORGANISM: Artificial Sequence
<220> FEATURE:
<223> OTHER INFORMATION: Synthetic Construct

<400> SEQUENCE: 198

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 199
<211> LENGTH: 119
<212> TYPE: PRT
<213> ORGANISM: Artificial Sequence
<220> FEATURE:
<223> OTHER INFORMATION: Synthetic Construct

<400> SEQUENCE: 199

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Glu Glu Leu Gln Ile Ile Gln Pro Asp Lys Ser Val Leu Val Ala
1               5                   10                  15
```

```
Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
            115

<210> SEQ ID NO 201
<211> LENGTH: 119
<212> TYPE: PRT
<213> ORGANISM: Artificial Sequence
<220> FEATURE:
<223> OTHER INFORMATION: Synthetic Construct

<400> SEQUENCE: 201

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Met Pro Asp Asp Val Glu Phe Lys Ser Gly Ala Gly Thr Glu Leu
            100                 105                 110

Ser Val Arg Ala Lys Pro Ser
            115

<210> SEQ ID NO 202
<211> LENGTH: 118
<212> TYPE: PRT
<213> ORGANISM: Artificial Sequence
<220> FEATURE:
<223> OTHER INFORMATION: Synthetic Construct

<400> SEQUENCE: 202

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60
```

-continued

```
Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Val Glu Phe Lys Ser Gly Ala Gly Thr Glu Leu Ser
            100                 105                 110

Val Arg Ala Lys Pro Ser
        115

<210> SEQ ID NO 203
<211> LENGTH: 120
<212> TYPE: PRT
<213> ORGANISM: Artificial Sequence
<220> FEATURE:
<223> OTHER INFORMATION: Synthetic Construct

<400> SEQUENCE: 203

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Ser Glu Pro Asp Val Glu Phe Lys Ser Gly Ala Gly Thr Glu
            100                 105                 110

Leu Ser Val Arg Ala Lys Pro Ser
        115                 120

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

<400> SEQUENCE: 204

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95
```

```
Gly Ser Pro Asp Asp Val Glu Phe Lys Ser Gly Ala Gly Thr Glu Leu
                100                 105                 110

Ser Val Arg Ala Lys Pro Ser
        115

<210> SEQ ID NO 205
<211> LENGTH: 119
<212> TYPE: PRT
<213> ORGANISM: Artificial Sequence
<220> FEATURE:
<223> OTHER INFORMATION: Synthetic Construct

<400> SEQUENCE: 205

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
                100                 105                 110

Ser Val Arg Ala Lys Pro Ser
        115

<210> SEQ ID NO 206
<211> LENGTH: 119
<212> TYPE: PRT
<213> ORGANISM: Artificial Sequence
<220> FEATURE:
<223> OTHER INFORMATION: Synthetic Construct

<400> SEQUENCE: 206

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
                100                 105                 110

Ser Val Arg Ala Lys Pro Ser
        115

<210> SEQ ID NO 207
<211> LENGTH: 119
<212> TYPE: PRT
```

<213> ORGANISM: Artificial Sequence
<220> FEATURE:
<223> OTHER INFORMATION: Synthetic Construct

<400> SEQUENCE: 207

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Asp Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ile Pro Asp Asp Val Glu Phe Lys Ser Gly Ala Gly Thr Glu Leu
            100                 105                 110

Ser Val Arg Ala Lys Pro Ser
            115

<210> SEQ ID NO 209
<211> LENGTH: 119
<212> TYPE: PRT
<213> ORGANISM: Artificial Sequence
<220> FEATURE:
<223> OTHER INFORMATION: Synthetic Construct

<400> SEQUENCE: 209

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Tyr Pro
            20                  25                  30

```
Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ile Pro Asp Asp Val Glu Phe Lys Ser Gly Ala Gly Thr Glu Leu
                100                 105                 110

Ser Val Arg Ala Lys Pro Ser
        115

<210> SEQ ID NO 210
<211> LENGTH: 119
<212> TYPE: PRT
<213> ORGANISM: Artificial Sequence
<220> FEATURE:
<223> OTHER INFORMATION: Synthetic Construct

<400> SEQUENCE: 210

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                 85                  90                  95

Gly Ile Pro Asp Asp Val Glu Phe Lys Ser Gly Ala Gly Thr Glu Leu
                100                 105                 110

Ser Val Arg Ala Lys Pro Ser
        115

<210> SEQ ID NO 211
<211> LENGTH: 345
<212> TYPE: PRT
<213> ORGANISM: Artificial Sequence
<220> FEATURE:
<223> OTHER INFORMATION: Synthetic Construct

<400> SEQUENCE: 211

Glu Glu Glu Leu Gln Ile Ile Gln Pro Asp Lys Ser Val Leu Val Ala
 1               5                  10                  15

Ala Gly Glu Thr Ala Thr Leu Arg Cys Thr Ile Thr Ser Leu Arg Pro
            20                  25                  30

Val Gly Pro Ile Gln Trp Phe Arg Gly Ala Gly Pro Gly Arg Glu Leu
            35                  40                  45

Ile Tyr Asn Gln Arg Asp Gly Pro Phe Pro Arg Val Thr Thr Val Ser
 50                  55                  60

Asp Thr Thr Lys Arg Asn Asn Met Asp Phe Ser Ile Arg Ile Gly Ala
 65                  70                  75                  80
```

```
Ile Thr Pro Ala Asp Ala Gly Thr Tyr Tyr Cys Val Lys Phe Arg Lys
            85                  90                  95

Gly Ile Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
            165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
            245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Pro Gly
            340                 345

<210> SEQ ID NO 212
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = V, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H, P, or R
```

```
<220> FEATURE:
<221> NAME/KEY: VARIANT
<222> LOCATION: 66
<223> OTHER INFORMATION: Xaa = S, T, or G
<220> FEATURE:
<221> NAME/KEY: VARIANT
<222> LOCATION: 80
<223> OTHER INFORMATION: Xaa = N or A

<400> SEQUENCE: 212

Glu Glu Glu Leu Gln Xaa Ile Gln Pro Asp Lys Ser Val Ser Val Ala
1               5                   10                  15

Ala Gly Glu Ser Ala Ile Leu His Cys Thr Xaa Thr Ser Leu Xaa Pro
            20                  25                  30

Val Gly Pro Ile Gln Trp Phe Arg Gly Ala Gly Pro Ala Arg Glu Leu
        35                  40                  45

Ile Tyr Asn Gln Xaa Glu Gly Xaa Phe Pro Arg Val Thr Thr Val Ser
    50                  55                  60

Glu Xaa Thr Lys Arg Glu Asn Met Asp Phe Ser Ile Ser Ile Ser Xaa
65              70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 213
<211> LENGTH: 119
<212> TYPE: PRT
<213> ORGANISM: Artificial Sequence
<220> FEATURE:
<223> OTHER INFORMATION: Synthetic Construct

<400> SEQUENCE: 213

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65              70                  75                  80

Ile Thr Val Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 214
<211> LENGTH: 346
<212> TYPE: PRT
<213> ORGANISM: Artificial Sequence
<220> FEATURE:
<223> OTHER INFORMATION: Synthetic Construct
```

<400> SEQUENCE: 214

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Glu Arg Lys Ser Ser Val Glu Cys Pro
            115                 120                 125

Pro Cys Pro Ala Pro Val Ala Gly Pro Ser Val Phe Leu Phe Pro
130                 135                 140

Pro Lys Pro Lys Asp Thr Leu Met Ile Ser Arg Thr Pro Glu Val Thr
145                 150                 155                 160

Cys Val Val Val Asp Val Ser His Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Ala Ser Thr Phe Arg Val Val Ser Val Leu Thr Val
            195                 200                 205

Val His Gln Asp Trp Leu Asn Gly Lys Glu Tyr Lys Cys Lys Val Ser
210                 215                 220

Asn Lys Gly Leu Pro Ser Ser Ile Glu Lys Thr Ile Ser Lys Thr Lys
225                 230                 235                 240

Gly Gln Pro Arg Glu Pro Gln Val Tyr Thr Leu Pro Pro Ser Arg Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Met Leu Asp Ser Asp Gly Ser Phe
290                 295                 300

Phe Leu Tyr Ser Lys Leu Thr Val Asp Lys Ser Arg Trp Gln Gln Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly
            340                 345
```

<210> SEQ ID NO 215
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2

```
<223> OTHER INFORMATION: Xaa = Any Amino Acid except P
<220> FEATURE:
<221> NAME/KEY: VARIANT
<222> LOCATION: 3
<223> OTHER INFORMATION: Xaa = Any Amino Acid except T, S, or C
<220> FEATURE:
<221> NAME/KEY: VARIANT
<222> LOCATION: 4
<223> OTHER INFORMATION: Xaa = Any Amino Acid except P

<400> SEQUENCE: 215

Asn Xaa Xaa Xaa
1

<210> SEQ ID NO 216
<211> LENGTH: 346
<212> TYPE: PRT
<213> ORGANISM: Artificial Sequence
<220> FEATURE:
<223> OTHER INFORMATION: Synthetic Construct

<400> SEQUENCE: 216

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285
```

```
Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
                340                 345

<210> SEQ ID NO 217
<211> LENGTH: 346
<212> TYPE: PRT
<213> ORGANISM: Artificial Sequence
<220> FEATURE:
<223> OTHER INFORMATION: Synthetic Construct

<400> SEQUENCE: 217

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Glu Leu
            35                  40                  45

Ile Tyr Asn Gln Arg Glu Gly Pro Phe Pro Arg Val Thr Thr Val Ser
50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Lys Thr His Thr Cys Pro Glu Cys
        115                 120                 125

Pro Ala Pro Glu Ala Ala Gly Ala Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Ala Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Glu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300
```

```
Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 218
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, V, L, or I
<220> FEATURE:
<221> NAME/KEY: VARIANT
<222> LOCATION: 31
<223> OTHER INFORMATION: Xaa = I, S, T, or F
<220> FEATURE:
<221> NAME/KEY: VARIANT
<222> LOCATION: 47
<223> OTHER INFORMATION: Xaa = E, L, or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, R, or P
<220> FEATURE:
<221> NAME/KEY: VARIANT
<222> LOCATION: 66
<223> OTHER INFORMATION: Xaa = S, G, L, or T
<220> FEATURE:
<221> NAME/KEY: VARIANT
<222> LOCATION: 80
<223> OTHER INFORMATION: Xaa = Any Amino Acid
<220> FEATURE:
<221> NAME/KEY: VARIANT
<222> LOCATION: 81
<223> OTHER INFORMATION: Xaa = Any Amino Acid
<220> FEATURE:
<221> NAME/KEY: VARIANT
<222> LOCATION: 82
<223> OTHER INFORMATION: Xaa = Any Amino Acid
<220> FEATURE:
<221> NAME/KEY: VARIANT
<222> LOCATION: 83
<223> OTHER INFORMATION: Xaa = Any Amino Acid
<220> FEATURE:
<221> NAME/KEY: VARIANT
<222> LOCATION: 92
<223> OTHER INFORMATION: Xaa = V or I

<400> SEQUENCE: 218

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
        35                  40                  45
```

-continued

Ile Tyr Asn Gln Xaa Xaa Gly Xaa Phe Pro Arg Val Thr Val Ser
    50              55                  60

Asp Xaa Thr Lys Arg Asn Asn Met Asp Phe Ser Ile Arg Ile Gly Xaa
65              70                  75                  80

Xaa Xaa Xaa Ala Asp Ala Gly Thr Tyr Tyr Cys Xaa Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 219
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, V, L, or I
<220> FEATURE:
<221> NAME/KEY: VARIANT
<222> LOCATION: 31
<223> OTHER INFORMATION: Xaa = I, S, T, or F
<220> FEATURE:
<221> NAME/KEY: VARIANT
<222> LOCATION: 47
<223> OTHER INFORMATION: Xaa = E, L, or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 54
<223> OTHER INFORMATION: Xaa = E or Q
<220> FEATURE:
<221> NAME/KEY: VARIANT
<222> LOCATION: 56
<223> OTHER INFORMATION: Xaa = H, R, or P
<220> FEATURE:
<221> NAME/KEY: VARIANT
<222> LOCATION: 66
<223> OTHER INFORMATION: Xaa = S, G, L, or T
<220> FEATURE:
<221> NAME/KEY: VARIANT
<222> LOCATION: 80
<223> OTHER INFORMATION: Xaa = N
<220> FEATURE:
<221> NAME/KEY: VARIANT
<222> LOCATION: 83
<223> OTHER INFORMATION: Xaa = Any Amino Acid except P
<220> FEATURE:
<221> NAME/KEY: VARIANT
<222> LOCATION: 92
<223> OTHER INFORMATION: Xaa = V or I

<400> SEQUENCE: 219

Glu Glu Glu Leu Gln Xaa Ile Gln Pro Asp Lys Ser Val Leu Val Ala
1               5                   10                  15

Ala Gly Glu Thr Ala Thr Leu Arg Cys Thr Xaa Thr Ser Leu Xaa Pro
            20                  25                  30

Val Gly Pro Ile Gln Trp Phe Arg Gly Ala Gly Pro Gly Arg Xaa Leu
            35                  40                  45

-continued

```
Ile Tyr Asn Gln Xaa Xaa Gly Xaa Phe Pro Arg Val Thr Val Ser
    50              55                  60

Asp Xaa Thr Lys Arg Asn Asn Met Asp Phe Ser Ile Arg Ile Gly Xaa
 65              70                  75                  80

Ile Thr Xaa Ala Asp Ala Gly Thr Tyr Tyr Cys Xaa Lys Phe Arg Lys
             85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

<210> SEQ ID NO 220

<400> SEQUENCE: 220

000

<210> SEQ ID NO 221
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V or I
<220> FEATURE:
<221> NAME/KEY: VARIANT
<222> LOCATION: 27
<223> OTHER INFORMATION: Xaa = A or I
<220> FEATURE:
<221> NAME/KEY: VARIANT
<222> LOCATION: 31
<223> OTHER INFORMATION: Xaa = I or F
<220> FEATURE:
<221> NAME/KEY: VARIANT
<222> LOCATION: 47
<223> OTHER INFORMATION: Xaa = E or V
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H or P
<220> FEATURE:
<221> NAME/KEY: VARIANT
<222> LOCATION: 66
<223> OTHER INFORMATION: Xaa = L or T
<220> FEATURE:
<221> NAME/KEY: VARIANT
<222> LOCATION: 80
<223> OTHER INFORMATION: Xaa = Any Amino Acid except N
<220> FEATURE:
<221> NAME/KEY: VARIANT
<222> LOCATION: 92
<223> OTHER INFORMATION: Xaa = V or I

<400> SEQUENCE: 221

```
Glu Glu Glu Leu Gln Xaa Ile Gln Pro Asp Lys Ser Val Leu Val Ala
 1               5                  10                  15

Ala Gly Glu Thr Ala Thr Leu Arg Cys Thr Xaa Thr Ser Leu Xaa Pro
             20                  25                  30

Val Gly Pro Ile Gln Trp Phe Arg Gly Ala Gly Pro Gly Arg Xaa Leu
            35                  40                  45

Ile Tyr Asn Gln Xaa Glu Gly Xaa Phe Pro Arg Val Thr Val Ser
    50              55                  60
```

```
Asp Xaa Thr Lys Arg Asn Asn Met Asp Phe Ser Ile Arg Ile Gly Xaa
 65                  70                  75                  80

Ile Thr Pro Ala Asp Ala Gly Thr Tyr Tyr Cys Xaa Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 222
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = V, L, or I
<220> FEATURE:
<221> NAME/KEY: VARIANT
<222> LOCATION: 27
<223> OTHER INFORMATION: Xaa = A, I, or L
<220> FEATURE:
<221> NAME/KEY: VARIANT
<222> LOCATION: 31
<223> OTHER INFORMATION: Xaa = I, T, S, or F
<220> FEATURE:
<221> NAME/KEY: VARIANT
<222> LOCATION: 53
<223> OTHER INFORMATION: Xaa = K or R
<220> FEATURE:
<221> NAME/KEY: VARIANT
<222> LOCATION: 56
<223> OTHER INFORMATION: Xaa = H or P
<220> FEATURE:
<221> NAME/KEY: VARIANT
<222> LOCATION: 66
<223> OTHER INFORMATION: Xaa = L, T, or G
<220> FEATURE:
<221> NAME/KEY: VARIANT
<222> LOCATION: 80
<223> OTHER INFORMATION: Xaa = N or A

<400> SEQUENCE: 222

Glu Glu Glu Leu Gln Xaa Ile Gln Pro Asp Lys Ser Val Leu Val Ala
 1               5                  10                  15

Ala Gly Glu Thr Ala Thr Leu Arg Cys Thr Xaa Thr Ser Leu Xaa Pro
                 20                  25                  30

Val Gly Pro Ile Gln Trp Phe Arg Gly Ala Gly Pro Gly Arg Glu Leu
             35                  40                  45

Ile Tyr Asn Gln Xaa Glu Gly Xaa Phe Pro Arg Val Thr Thr Val Ser
 50                  55                  60

Asp Xaa Thr Lys Arg Asn Asn Met Asp Phe Ser Ile Arg Ile Gly Xaa
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```